United States Patent
Ausubel et al.

(10) Patent No.: US 7,186,816 B2
(45) Date of Patent: Mar. 6, 2007

(54) PHOTOLYASE NUCLEIC ACIDS

(75) Inventors: Frederick M. Ausubel, Newton, MA (US); Stephen B. Calderwood, Wellesley, MA (US); Danielle A. Garsin, Houston, TX (US); Eleftherios Mylonakis, Boston, MA (US); Costi D. Sifri, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 37 days.

(21) Appl. No.: 10/758,979

(22) Filed: Jan. 16, 2004

(65) Prior Publication Data

US 2004/0214208 A1   Oct. 28, 2004

Related U.S. Application Data

(63) Continuation of application No. PCT/US02/22979, filed on Jul. 18, 2002.

(60) Provisional application No. 60/306,212, filed on Jul. 18, 2001.

(51) Int. Cl.
*C07H 21/02* (2006.01)

(52) U.S. Cl. .................. 536/23.1; 536/23.1; 435/6; 435/69.1; 435/320.1; 435/325; 530/350

(58) Field of Classification Search .............. None
See application file for complete search history.

(56) References Cited

FOREIGN PATENT DOCUMENTS

WO      WO 9850555      * 11/1998

OTHER PUBLICATIONS

Seffernick et al., J. Bacteriology, vol. 183, pp. 2405-2410, 2001.*
Tuddenham et al., Nucleic Acids Research, vol. 22, No. 17, pp. 3511-3533, 1994.*
Heim et al., PNAS, vol. 91, pp. 12501-12504, 1994.*
Ferretti, et al., "Complete Genome Sequence of an M1 Strain of Streptococcus Pyogenes," *PNAS* 98:4658-4663, (2001).
Glaser et al., "Comparative Genomics of Listeria Species," *Science* 294:849-852, (2001).

* cited by examiner

*Primary Examiner*—Kathleen M. Kerr
*Assistant Examiner*—Hope Robinson
(74) *Attorney, Agent, or Firm*—Clark & Elbing, LLP

(57) ABSTRACT

The invention generally provides a novel approach to identifying Enterococcal virulence factors and for identifying compounds for treating bacterial pathogenesis. The invention further provides Enterococcal virulence factors, which serve as targets for drug discovery.

2 Claims, 55 Drawing Sheets

Figure 5A

Photolyase
```
gaaattgacc gtaaagtcaa tatttacaac attttaagcc tgaatgcgct aggtacgcta  60
tacgaactgg aaaaagatat gagaaaagcg caagtgtatt acgaaaaatc attacaagaa 120
ttggaacaat ttaaattaga atgttccttg gagcgttgta gaatttatta taattctgct 180
aaattctact cggaaatgaa agactaccaa aaaagtgtca ttttaagcga aaagggatt  240
cagatttgtc gtgacaaaca ctccatttat ttgctagatt atcttttata tgaaaaagcc 300
tttaacaaac aaatgctcgg ggaagacaca gccgatgact atcgccaagc ctattatttt 360
acacaatttt ttggcaatac ggaagtcctg caatatattg agaaagatat gaaagctttt 420
aatatttcct attaatttaa tcaaaaagcc gataaagct gaaaactcag ttttaccgg   480
cttttgaaa  aatataggca agttgctttt aaaaatcagc agtcacggtt acgataagca 540
agacgaagta tttaggagga tttaaaagtg aaaagagtaa tatggtttag acgtgattta 600
cgattacagg ataataaagc attagcacac gcgttacaaa attctgcagc tgatgaattg 660
attttattat tccaaatgaa tcctcaacaa tttattcaag aaagtgctaa tcataacgct 720
ttttttgcaa gcttagcctc gttcaaagaa cgaatcgatc aagaggcaca tttacaaatc 780
atggtcggcg aaccattaga tttatttca  cgtttgaaac gcaaattacc cgattggcag 840
gccatttatt ttaatgaaga tacttgtggc tttggggcaa agcgggacca gcaagctatg 900
cgctttttg  aagaaaataa tattcagtct ttctctttc  aagatgccta tttgcatggc 960
tctgaagaaa ttaagaagaa cgatggcagc aagtaccaag tgtttacgcc ctattacaat 1020
aaatggaaag aggcgcctaa agaaacaccg attcctgttt cctatacagc tgaaaaaatt 1080
tttagtgcgt gtcttttcc  agaagaggaa gcagcttatc gtgaacagat tgcgaggatt 1140
cctttaacac actatagtgt cggcgaagaa acagccagaa ggcgcttaaa tactttatt  1200
gatcaaaaac ttcaatccta tgaaaataag cgtgatttc  cttatcagga tcaaacgagt 1260
catctgtcta ctttttaag  aacgggagaa ctttcgattc gcaccatttg gcaagagctt 1320
gcatctgtgc cttctagctt aagtaaagaa accttcaaaa aagaattagc ttggcgcgac 1380
ttttacaata tgatctatag tgcgtttcca caacaaaaag aggaagctat tcaagaaaaa 1440
tttcgttata ttcaatggac aaatgaccca gaaatgtttg tcaagtggca aaaagggag  1500
acggggtacc ctataattga tgccgcaatg cgacaactga atcaaactgg ttggatgcac 1560
aatcgcttaa gaatgattac tgcctctttt ttagttaaaa atttacacat cgattggcgt 1620
tggggtgaaa aatactttca aaaaatgttg attgactatg atgctgccaa taatatcggt 1680
ggctggcaat gggctgcttc aacaggaacg gacgctgtcc cttatttcg  gattttaat  1740
ccaattatcc agtcaaaaaa atttgataat gacggccagt tcatcaaaaa atatgttcca 1800
gaacttaagc aagtgccaca aaagtatatt catcaaccaa atctaatgaa cgaagcctta 1860
caaacgcaat atcatgtaca tttaggagaa aattatccaa aacccattgt cgattatgca 1920
tcaagtaaaa aacaaacatt gtttctatat gaagcgagca aagaaattca tcaagaaatg 1980
aacaatccaa ggtttcaata aacagtaaac ccaactagct tagcaaacaa cttgtaaggt 2040
tagttgggca aattaattag tcgaaagaga agtgcaattt atcggctaaa gttttttatt 2100
ctattctagt taacataata tacattatac aaagtagagt aaaaagcatt gaaaagcaaa 2160
caaaaccagt ctttagttta tctagactgg ttttgtcacg tacgttatat aaattatgct 2220
tgttgcttga tggcttgtgc gacacgtgct ccatattctg gatttac             2267
```

Figure 5B

Photolyase

| | | | | | | | | | | | | |
|---|---|---|---|---|---|---|---|---|---|---|---|---|
| Met | Lys | Arg | Val | Ile | Trp | Phe | Arg | Arg | Asp | Leu | Arg | Leu | Gln | Asp | Asn |
| 1 | | | | 5 | | | | | 10 | | | | | | |
| Lys | Ala | Leu | Ala | His | Ala | Leu | Gln | Asn | Ser | Ala | Ala | Asp | Glu | Leu | Ile |
| | | | 20 | | | | | 25 | | | | | 30 | | |
| Leu | Leu | Phe | Gln | Met | Asn | Pro | Gln | Gln | Phe | Ile | Gln | Glu | Ser | Ala | Asn |
| | | 35 | | | | | 40 | | | | | 45 | | | |
| His | Asn | Ala | Phe | Phe | Ala | Ser | Leu | Ala | Ser | Phe | Lys | Glu | Arg | Ile | Asp |
| | 50 | | | | | 55 | | | | | 60 | | | | |
| Gln | Glu | Ala | His | Leu | Gln | Ile | Met | Val | Gly | Glu | Pro | Leu | Asp | Leu | Phe |
| 65 | | | | | 70 | | | | 75 | | | | | | 80 |
| Ser | Arg | Leu | Lys | Arg | Lys | Leu | Pro | Asp | Trp | Gln | Ala | Ile | Tyr | Phe | Asn |
| | | | | 85 | | | | | 90 | | | | | 95 | |
| Glu | Asp | Thr | Cys | Gly | Phe | Gly | Ala | Lys | Arg | Asp | Gln | Gln | Ala | Met | Arg |
| | | | 100 | | | | | 105 | | | | | 110 | | |
| Phe | Phe | Glu | Glu | Asn | Asn | Ile | Gln | Ser | Phe | Ser | Phe | Gln | Asp | Ala | Tyr |
| | | 115 | | | | | 120 | | | | | 125 | | | |
| Leu | His | Gly | Ser | Glu | Glu | Ile | Lys | Lys | Asn | Asp | Gly | Ser | Lys | Tyr | Gln |
| | 130 | | | | | 135 | | | | | 140 | | | | |
| Val | Phe | Thr | Pro | Tyr | Tyr | Asn | Lys | Trp | Lys | Glu | Ala | Pro | Lys | Glu | Thr |
| 145 | | | | | 150 | | | | | 155 | | | | | 160 |
| Pro | Ile | Pro | Val | Ser | Tyr | Thr | Ala | Glu | Lys | Ile | Phe | Ser | Ala | Cys | Leu |
| | | | | 165 | | | | | 170 | | | | | 175 | |
| Phe | Pro | Glu | Glu | Glu | Ala | Ala | Tyr | Arg | Glu | Gln | Ile | Ala | Arg | Ile | Pro |
| | | | 180 | | | | | 185 | | | | | 190 | | |
| Leu | Thr | His | Tyr | Ser | Val | Gly | Glu | Glu | Thr | Ala | Arg | Arg | Arg | Leu | Asn |
| | | 195 | | | | | 200 | | | | | 205 | | | |
| Thr | Phe | Ile | Asp | Gln | Lys | Leu | Gln | Ser | Tyr | Glu | Asn | Lys | Arg | Asp | Phe |
| | 210 | | | | | 215 | | | | | 220 | | | | |
| Pro | Tyr | Gln | Asp | Gln | Thr | Ser | His | Leu | Ser | Thr | Phe | Leu | Arg | Thr | Gly |
| 225 | | | | 230 | | | | | 235 | | | | | | 240 |
| Glu | Leu | Ser | Ile | Arg | Thr | Ile | Trp | Gln | Glu | Leu | Ala | Ser | Val | Pro | Ser |
| | | | | 245 | | | | | 250 | | | | | 255 | |
| Ser | Leu | Ser | Lys | Glu | Thr | Phe | Lys | Lys | Glu | Leu | Ala | Trp | Arg | Asp | Phe |
| | | | 260 | | | | | 265 | | | | | 270 | | |
| Tyr | Asn | Met | Ile | Tyr | Ser | Ala | Phe | Pro | Gln | Gln | Lys | Glu | Glu | Ala | Ile |
| | | 275 | | | | | 280 | | | | | 285 | | | |
| Gln | Glu | Lys | Phe | Arg | Tyr | Ile | Gln | Trp | Thr | Asn | Asp | Pro | Glu | Met | Phe |
| | 290 | | | | | 295 | | | | | 300 | | | | |
| Val | Lys | Trp | Gln | Lys | Gly | Glu | Thr | Gly | Tyr | Pro | Ile | Ile | Asp | Ala | Ala |
| 305 | | | | | 310 | | | | | 315 | | | | | 320 |
| Met | Arg | Gln | Leu | Asn | Gln | Thr | Gly | Trp | Met | His | Asn | Arg | Leu | Arg | Met |
| | | | | 325 | | | | | 330 | | | | | 335 | |
| Ile | Thr | Ala | Ser | Phe | Leu | Val | Lys | Asn | Leu | His | Ile | Asp | Trp | Arg | Trp |
| | | | 340 | | | | | 345 | | | | | 350 | | |
| Gly | Glu | Lys | Tyr | Phe | Gln | Lys | Met | Leu | Ile | Asp | Tyr | Asp | Ala | Ala | Asn |
| | | 355 | | | | | 360 | | | | | 365 | | | |
| Asn | Ile | Gly | Gly | Trp | Gln | Trp | Ala | Ala | Ser | Thr | Gly | Thr | Asp | Ala | Val |
| | 370 | | | | | 375 | | | | | 380 | | | | |
| Pro | Tyr | Phe | Arg | Ile | Phe | Asn | Pro | Ile | Ile | Gln | Ser | Lys | Lys | Phe | Asp |
| 385 | | | | | 390 | | | | | 395 | | | | | 400 |
| Asn | Asp | Gly | Gln | Phe | Ile | Lys | Lys | Tyr | Val | Pro | Glu | Leu | Lys | Gln | Val |
| | | | | 405 | | | | | 410 | | | | | 415 | |
| Pro | Gln | Lys | Tyr | Ile | His | Gln | Pro | Asn | Leu | Met | Asn | Glu | Ala | Leu | Gln |
| | | | 420 | | | | | 425 | | | | | 430 | | |
| Thr | Gln | Tyr | His | Val | His | Leu | Gly | Glu | Asn | Tyr | Pro | Lys | Pro | Ile | Val |
| | | 435 | | | | | 440 | | | | | 445 | | | |
| Asp | Tyr | Ala | Ser | Ser | Lys | Lys | Gln | Thr | Leu | Phe | Leu | Tyr | Glu | Ala | Ser |
| | 450 | | | | | 455 | | | | | 460 | | | | |
| Lys | Glu | Ile | His | Gln | Glu | Met | Asn | Asn | Pro | Arg | Phe | Gln | | | |
| 465 | | | | 470 | | | | | | 475 | | | | | |

Figure 6A

ScrR

```
cctttgaaa atttagatga aggatttgat gtctacgcca ctcaagcctt taatgcgcca 60
gatggtcgtg cacttgcggt cagttggatt gggttgccag aaatcactta cccaagtgat 120
gtggagggtt gggcaaatgg cttaagtctg gttaaagaac tcacaattca aacgggaaa 180
ctatttcaat atccagtttc tgaaacagaa atgcttcgtc aatccgctac tactttatca 240
aatggctgcc atttcttatc tactgcttct tttgaattag aagtggatat tcccaaaaat 300
gagattgctt ttattcggct tttagcgaac gaaacgggtt caaaaggact tttaattaca 360
attgatacga ttcatggtaa aataacccct gatcgaacat ttgctggcca atcttttgct 420
gaaaagtatg gcacaattcg tgaaactaaa attaggaaaa ataagtcagt tcagttaact 480
atttttgttg attgctctgt tgcagaaatc tatgtaaata aaggtgaaaa aacgatgact 540
ggtcgcttct tccagataa agcgaacag tatcttcatc tatccaagac ggcaaaagct 600
tgttttatg agctggaaaa tacgaataat taggaatgat ggtgaatttt gatggtggtt 660
aaattaacgg atgtagcaaa gcttgctggg gtgagcccga caacggtaag ccgcgtgatt 720
aataattatg gttatcttag tcaaaaaaca attgataaag ttcatcaagc gatggaagaa 780
ttaaattatc aacctaatgg attagccaga agcctccaag gaaaaagtac gcagctgatt 840
ggtttagtct tcccttctgt tagtcatcca ttttttggtg aattaattga aacactggaa 900
agaaagctct ttgttcaagg atataaagtg attttatgtg atagtgaaaa agatccagaa 960
aaagagcgcg cctatttacg aatgctcgct gcaaataaag tggacggtgt aatcactggt 1020
agccataact tagctattaa cgaatatgaa aatgtttcac tacctattgt ttcctttgac 1080
cgtttcttgg cacctggcat tccaattgtc tcttcgcaaa actttcaagg gggccaaaaa 1140
gccactgaag ccttatttgc aagtggtgca caaagattg caattattac tggtgctaat 1200
aacacaggcg cacctagcga ttatcgattg gctggttata aacaaacaat ggaaaaatat 1260
ggcgcagaaa aaacgattct acaaattgat aatgggacct caacaacatt aaaaaatcta 1320
gaaatcgaac gtttgcttca aaataaaact gtagacggca tcttttgtac agatgatttg 1380
acagcaatta cagttatgaa tattgctcaa aaattgaaga tatccattcc tgaagaatta 1440
aaagtaattg gttatgatgg gacaaaatta atcaaagaa ttgccccaca actatcaacc 1500
attgtcagc caatcgacga gatgtgtgac gttatgattg acttactgct tcgtagaatg 1560
aaggatcctg atgttgcact tgaggaaaat tatcctattc cgattcagct atcattgtct 1620
gaatcctgtt aaaaaagaca cctttcagg tgtcttttt tattcttaat tcctcatttg 1680
cctatttcc cttaattcca aagcacagag attaaataat acaacaacat gatccctaca 1740
aatacaccga gcattagtaa aacataccac caattttgg cgctataggt ttcatttta 1800
tttttttcgg ttcgtttccc ggcagcccat ttcataaat cgtaattatt catctctctc 1860
accacctta atgggtttat taacttaagc ctaacacgga atgagagaac ttgaaaacaa 1920
aaggatcacc cgcttatgca atggatgatc ctttttggg cactattctt ctgataaccc 1980
attatttta ataactgatt ggtaccaata aaaactatct tttaatgc gtcgtaaatc 2040
ttttaactca tggtcttcac gattaacgta aataaaaccg tagcgttttt tgaatccttg 2100
atgggaactt aaaatatcca tgaccgacca agggcaatag ccaaacaact caacaccgtc 2160
agaaatagcc gcatgacaag cagcaatatg atcatgcaaa tacgcaattc gataatcatc 2220
atgaattttt ccgtcctctg ttaggtgatc tggtgtgcct aagccgtttt ctgtaatgat 2280
taacggcaaa cggtattgac gataataatc atttaaaact aaacgtagac cagttggatc 2340
aatttgggca ccatacttag aggtttttaa atgttgattt ttttcgattt taaaataacc 2400
gtatagatca aaatcaatgt cctttttcttt cgtacccaat gggtgttgct catctgtcgg 2460
taaatagcta gcgactaacg tccgataata attaagagcg ataaaatctg gtttagcggc 2520
tttcaaaatt gcttgatctt ctg                                        2543
```

Figure 6B

ScrR

| | | | | | | | | | | | | | | |
|---|---|---|---|---|---|---|---|---|---|---|---|---|---|---|
| Met | Val | Val | Lys | Leu | Thr | Asp | Val | Ala | Lys | Leu | Ala | Gly | Val | Ser | Pro |
| 1 | | | | 5 | | | | | 10 | | | | | 15 | |
| Thr | Thr | Val | Ser | Arg | Val | Ile | Asn | Asn | Tyr | Gly | Tyr | Leu | Ser | Gln | Lys |
| | | | 20 | | | | | 25 | | | | | 30 | | |
| Thr | Ile | Asp | Lys | Val | His | Gln | Ala | Met | Glu | Glu | Leu | Asn | Tyr | Gln | Pro |
| | | 35 | | | | | 40 | | | | | 45 | | | |
| Asn | Gly | Leu | Ala | Arg | Ser | Leu | Gln | Gly | Lys | Ser | Thr | Gln | Leu | Ile | Gly |
| | 50 | | | | | 55 | | | | | 60 | | | | |
| Leu | Val | Phe | Pro | Ser | Val | Ser | His | Pro | Phe | Phe | Gly | Glu | Leu | Ile | Glu |
| 65 | | | | | 70 | | | | | 75 | | | | | 80 |
| Thr | Leu | Glu | Arg | Lys | Leu | Phe | Val | Gln | Gly | Tyr | Lys | Val | Ile | Leu | Cys |
| | | | | 85 | | | | | 90 | | | | | 95 | |
| Asp | Ser | Glu | Lys | Asp | Pro | Glu | Lys | Glu | Arg | Ala | Tyr | Leu | Arg | Met | Leu |
| | | | 100 | | | | | 105 | | | | | 110 | | |
| Ala | Ala | Asn | Lys | Val | Asp | Gly | Val | Ile | Thr | Gly | Ser | His | Asn | Leu | Ala |
| | | 115 | | | | | 120 | | | | | 125 | | | |
| Ile | Asn | Glu | Tyr | Glu | Asn | Val | Ser | Leu | Pro | Ile | Val | Ser | Phe | Asp | Arg |
| | 130 | | | | | 135 | | | | | 140 | | | | |
| Phe | Leu | Ala | Pro | Gly | Ile | Pro | Ile | Val | Ser | Ser | Gln | Asn | Phe | Gln | Gly |
| 145 | | | | | 150 | | | | | 155 | | | | | 160 |
| Gly | Gln | Lys | Ala | Thr | Glu | Ala | Leu | Phe | Ala | Ser | Gly | Ala | Gln | Lys | Ile |
| | | | | 165 | | | | | 170 | | | | | 175 | |
| Ala | Ile | Ile | Thr | Gly | Ala | Asn | Asn | Thr | Gly | Ala | Pro | Ser | Asp | Tyr | Arg |
| | | | 180 | | | | | 185 | | | | | 190 | | |
| Leu | Ala | Gly | Tyr | Lys | Gln | Thr | Met | Glu | Lys | Tyr | Gly | Ala | Glu | Lys | Thr |
| | | 195 | | | | | 200 | | | | | 205 | | | |
| Ile | Leu | Gln | Ile | Asp | Asn | Gly | Thr | Ser | Thr | Thr | Leu | Lys | Asn | Leu | Glu |
| | 210 | | | | | 215 | | | | | 220 | | | | |
| Ile | Glu | Arg | Leu | Leu | Gln | Asn | Lys | Thr | Val | Asp | Gly | Ile | Phe | Cys | Thr |
| 225 | | | | | 230 | | | | | 235 | | | | | 240 |
| Asp | Asp | Leu | Thr | Ala | Ile | Thr | Val | Met | Asn | Ile | Ala | Gln | Lys | Leu | Lys |
| | | | | 245 | | | | | 250 | | | | | 255 | |
| Ile | Ser | Ile | Pro | Glu | Glu | Leu | Lys | Val | Ile | Gly | Tyr | Asp | Gly | Thr | Lys |
| | | | 260 | | | | | 265 | | | | | 270 | | |
| Leu | Ile | Lys | Arg | Ile | Ala | Pro | Gln | Leu | Ser | Thr | Ile | Val | Gln | Pro | Ile |
| | | 275 | | | | | 280 | | | | | 285 | | | |
| Asp | Glu | Met | Cys | Asp | Val | Met | Ile | Asp | Leu | Leu | Leu | Arg | Arg | Met | Lys |
| | 290 | | | | | 295 | | | | | 300 | | | | |
| Asp | Pro | Asp | Val | Ala | Leu | Glu | Glu | Asn | Tyr | Pro | Ile | Pro | Ile | Gln | Leu |
| 305 | | | | | 310 | | | | | 315 | | | | | 320 |
| Ser | Leu | Ser | Glu | Ser | Cys | | | | | | | | | | |
| | | | | 325 | | | | | | | | | | | |

Figure 7A

OppA

```
ctgcggcgtg caagcgattt tgtttatcac gctttgtcgg attgcaggga taccagccaa 60
atggcaatcg ggattatatg tttctacaca ttatacaggc tgtcatgatt gggcacaatt 120
ttatataaaa ccgtacggct ggctctttgc ggatttgtct tttggcggag gtgcttaccg 180
agacggggat agacagcggt ggaatcatta tttcggcaat ttagatgttt ttagaatggt 240
cgcaaatagt gagatccagg cagactttca gccggcaaaa atgcaattgc gtgcagaccc 300
aattgacaac cagcggggag aatttgagta cgaaaatgag ggcttgccct acgcatgctt 360
gatagtttcg caagaacggc tttccatgga agagttgccg tttgattgac acatagggg 420
aatagtatga aaaagttaaa aatgatgggg attatgttat tgttagtac ggtcttggta 480
ggttgtggca caacagcaga aacaaaaata gacgagaaag caactgagaa aaccagtgtc 540
tcgaaaaaag ttttaaattt aatggagaac tcggaaatcg gttcaatgga ttctatttt 600
acacaagatg aagccagtat taacgcacag tccaatgtct ttgaagggtt atatcaattg 660
gatgaaaaag atcaactaat acctgctgct gctaaagaga tgccagaaat ttctgaggat 720
ggcaaacgat ataccattaa actaagagaa gatggcaagt ggtccaatgg tgatgctgta 780
acagccaatg atttcgtttt tgcttggcgt aaattagcga atcccaaaaa ccaagccaat 840
tacttttct tgttagaagg aacgattctg aacggaacag ctattacaaa agaggaaaaa 900
gcaccagagg aattgggtgt caaagcgctt gatgattata ctttggaggt tactttagaa 960
aagcctgtac catattttac gtcgttattg gcattttctc cattttccc acaaaacgaa 1020
gcattcgtga aagaaaaagg acaagcctat ggcacttcta gtgaaatgat tgtatctaat 1080
ggtccgtttt taatgaaaaa ttgggatcag tcagcgatgt cgtgggattt tgtgcgtaat 1140
ccctactatt acgataaaga aaagtaaaa tcagaaacga ttcatttga agttcttaaa 1200
gaaaccaata ccgtttataa tttgtacgaa tcaggtgaat tagatgtggc tgtcttaaca 1260
ggagatttg ctaaacaaaa tcgagacaac ccagactatg aagcaatcga acggtcaaaa 1320
gtctattcct tacgtttaaa ccaaaaaaga aacgaaaaac catccatttt tgcaaatgag 1380
aatgtccgca aagctttagc ttatgctttg gataaaaaaa gtttagtcga taatatttta 1440
gcagatggct caaaagaaat ttatgggtac attccagaaa aatttgtata taccccagaa 1500
acgaatgaag attttcgtca agaagcaggc gctcttgtca aaacagacgc caaaaaagcc 1560
aaagagtatt tagataaagc aaaagcagag ctaaacggag atgtagccat tgaacttctt 1620
tcaagagatg gtgatagtga ccgaaaagtt gctgaattta tccaaggcca gttacaagaa 1680
acgttgcctg gtctcactat taatgtcaaa acagttcctt taaataatgc aattgaatta 1740
atgagaaaag gggattatga attgtctgtt ggcatgtggg gacccgatta tcaggatcca 1800
atgactttct tagaaagctc agttagtggt aaccgtatga actattctag cccaacgttt 1860
gatcaactaa ttgaagaagc aacaactaaa tacgcaaatg agcctgaaac tcgttggcaa 1920
acattaatta aagctgaaaa agtattggtg gaagaagatg ccgctttaat tcctttatac 1980
caagaggccc gtagtcagct tgtacgacca ggtgtcaaag gtattcagta tcataacttc 2040
ggtgcaacga gcacatataa gtatgcctat aaagaataaa ttagtgaaca aaagtacctt 2100
tagctgaagg tactttttt ccgataagag cttctttttt gttaatagtc aacaattaat 2160
aaaaaaataa ttgaaaaagg ttgacaaaaa taatgatact cgttagaata agcactgtta 2220
acaaatgaat agcgttttca tgtgactaga taatactagg catggaagaa tttcgtaata 2280
caatgtggtg tacaatggtt acgcaacatg tttaacggga ttgttctatg cttttttgt 2340
tgttttcact gaaaatgtta gaattactc tgcagaagag ggtcattat gaaaattaaa 2400
aaggtgctaa atcaaaatgc tgtacttgtt cttgacgaag gacaggagaa agtagctgtc 2460
ggtaaaggcg tcgggttaa taagactaaa aatgatgtct tatctcgaca ttggtggag 2520
cggatgtttg tgatggagcc agaaggactg aaaaaacttc aagtactgct atcacaaatt 2580
gaagacaaat actttttagg agtgaagaaa ttatccaaca tgctgaaacg gtattgggtg 2640
aaaagttgaa tgaacatatt aatattgggt tgagtgatca cattgctttt gcagctgaaa 2700
atattcaaaa taatattatt gttcggaaca agcttttaag tgaaattgag atttatata 2760
gtgaagaatt tgctattgct caatgggctg tagaatattt aacacaaacc ttagagattc 2820
catttagtta tgatgaagcg gggtatattg cgattcatat ccatagtgct cgcagcgggc 2880
gtactgataa tagtaaaagt atccgtgaag ttacaatcgt ttctgaaatt attcatttaa 2940
tcgagcagga attggctatt gatattcatg atgataaaaa tagtctcagt tattcacgtt 3000
tggtgaatca tttacgtttg tttattcatc gcttccaaca aaatcaatac gctgttttag 3060
atga                                                                3064
```

Figure 7B

OppA

```
Met Lys Lys Leu Lys Met Met Gly Ile Met Leu Phe Val Ser Thr Val
 1            5                   10                  15
Leu Val Gly Cys Gly Thr Thr Ala Glu Thr Lys Ile Asp Glu Lys Ala
            20                  25                  30
Thr Glu Lys Thr Ser Val Ser Lys Lys Val Leu Asn Leu Met Glu Asn
            35                  40                  45
Ser Glu Ile Gly Ser Met Asp Ser Ile Phe Thr Gln Asp Glu Ala Ser
            50                  55                  60
Ile Asn Ala Gln Ser Asn Val Phe Glu Gly Leu Tyr Gln Leu Asp Glu
 65                  70                  75                  80
Lys Asp Gln Leu Ile Pro Ala Ala Lys Glu Met Pro Glu Ile Ser
                85                  90                  95
Glu Asp Gly Lys Arg Tyr Thr Ile Lys Leu Arg Glu Asp Gly Lys Trp
                100                 105                 110
Ser Asn Gly Asp Ala Val Thr Ala Asn Asp Phe Val Phe Ala Trp Arg
            115                 120                 125
Lys Leu Ala Asn Pro Lys Asn Gln Ala Asn Tyr Phe Phe Leu Leu Glu
        130                 135                 140
Gly Thr Ile Leu Asn Gly Thr Ala Ile Thr Lys Glu Glu Lys Ala Pro
145                 150                 155                 160
Glu Glu Leu Gly Val Lys Ala Leu Asp Tyr Thr Leu Glu Val Thr
                165                 170                 175
Leu Glu Lys Pro Val Pro Tyr Phe Thr Ser Leu Leu Ala Phe Ser Pro
            180                 185                 190
Phe Phe Pro Gln Asn Glu Ala Phe Val Lys Glu Lys Gly Gln Ala Tyr
        195                 200                 205
Gly Thr Ser Ser Glu Met Ile Val Ser Asn Gly Pro Phe Leu Met Lys
    210                 215                 220
Asn Trp Asp Gln Ser Ala Met Ser Trp Asp Phe Val Arg Asn Pro Tyr
225                 230                 235                 240
Tyr Tyr Asp Lys Glu Lys Val Lys Ser Glu Thr Ile His Phe Glu Val
            245                 250                 255
Leu Lys Glu Thr Asn Thr Val Tyr Asn Leu Tyr Glu Ser Gly Glu Leu
            260                 265                 270
Asp Val Ala Val Leu Thr Gly Asp Phe Ala Lys Gln Asn Arg Asp Asn
            275                 280                 285
Pro Asp Tyr Glu Ala Ile Glu Arg Ser Lys Val Tyr Ser Leu Arg Leu
    290                 295                 300
Asn Gln Lys Arg Asn Glu Lys Pro Ser Ile Phe Ala Asn Glu Asn Val
305                 310                 315                 320
Arg Lys Ala Leu Ala Tyr Ala Leu Asp Lys Lys Ser Leu Val Asp Asn
            325                 330                 335
Ile Leu Ala Asp Gly Ser Lys Glu Ile Tyr Gly Tyr Ile Pro Glu Lys
            340                 345                 350
Phe Val Tyr Asn Pro Glu Thr Asn Glu Asp Phe Arg Gln Glu Ala Gly
        355                 360                 365
Ala Leu Val Lys Thr Asp Ala Lys Lys Ala Lys Glu Tyr Leu Asp Lys
        370                 375                 380
Ala Lys Ala Glu Leu Asn Gly Asp Val Ala Ile Glu Leu Leu Ser Arg
385                 390                 395                 400
Asp Gly Asp Ser Asp Arg Lys Val Ala Glu Phe Ile Gln Gly Gln Leu
                405                 410                 415
Gln Glu Thr Leu Pro Gly Leu Thr Ile Asn Val Lys Thr Val Pro Leu
            420                 425                 430
Asn Asn Ala Ile Glu Leu Met Arg Lys Gly Asp Tyr Glu Leu Ser Val
            435                 440                 445
Gly Met Trp Gly Pro Asp Tyr Gln Asp Pro Met Thr Phe Leu Glu Ser
450                 455                 460
Ser Val Ser Gly Asn Arg Met Asn Tyr Ser Ser Pro Thr Phe Asp Gln
```

```
465                     470                     475                     480
Leu Ile Glu Glu Ala Thr Thr Lys Tyr Ala Asn Glu Pro Glu Thr Arg
                485                     490                     495
Trp Gln Thr Leu Ile Lys Ala Glu Lys Val Leu Val Glu Glu Asp Ala
                500                     505                     510
Ala Leu Ile Pro Leu Tyr Gln Glu Ala Arg Ser Gln Leu Val Arg Pro
                515                     520                     525
Gly Val Lys Gly Ile Gln Tyr His Asn Phe Gly Ala Thr Ser Thr Tyr
        530                     535                     540
Lys Tyr Ala Tyr Lys Glu
545                 550
```

Fig. 7B
Page 2 of 2

Figure 8A

TcaA

```
aatcaatgaa atttaataaa aaagcttagt tagttgcatt cattgttcaa atcggttaca 60
ctaagtaagt aaaaaaatat aatacaaggt tcgtcttcag gggcagggtg taattcccga 120
ccggtggtta tagtccacga ctcgttttta acgattgaat tggtgtaatt ccaataccga 180
cagtatagtc tggataaaga agatagggct tatttgagac gcttttcat cagataatcc 240
tactctattt ttccctgcag aaaaatagg ttttttgta tgacaaagaa gcgaatcaaa 300
aagttcgttg aagatgggtc cttaattgga ggatttcaga tgaacaacaa ggtacaaaaa 360
atggtcagca ttgcaatgtt ggccgcaatc ggtacagtat tacaatttgt ggcatttccg 420
attatgccgg cgtttagttt tttgaaaatc gattttagtg atattccgat tctactcgga 480
atgttcttgt acggaccgtt agcaggagta attactgctt ttgttgcttc gttgctacac 540
ctgttcttaa ccggactagc accgcaaaat atggtggag atttcgctag cttttagca 600
agtagtatct tcaccttgcc aatttttat ttctttggta aaaagaaaaa tatccgtaca 660
aatcggatag tgggcttagt aagtgggatc ttagccttga caatttcat gagtattgcg 720
aattattttg tcattacacc catttactta caattatatg gtgtgaccac acaacaattt 780
ttaggaacat ctttagcaag ctatgtggcg attggtattg tgccattcaa ccttattaaa 840
ggcctcttag tcagtggtgt ttttctagta ctacatgcga agttattgcc atggctatca 900
aaaaaacaac atactattca gaaaaaaaca ccgttaacaa aataaatgat aaaaaacctg 960
ctgttgaaca atgtttgaca gtgggttttt aaaatttacg cctaaaagaa aagaggttgt 1020
cataatctgt catcattctg ttaaaaaata ctaaaccatc tgcattgtaa tttaacttt 1080
cccttggtat gatagaaatc atcaaagaaa gaggagtttt cctgagtgaa aaagtgtaaa 1140
aattgtcgtc acgtgaatcg tgatacggag tcctttgtg aagaatgcgg cgctccgcta 1200
atgaatgaat caatgcatca agaggaaaac caagcacaac catcaatgaa taaagggaac 1260
gaatctactc ctctcagatc aaaaagaagc tggatctggg cgtttctttt tgtgttcatc 1320
gttcttggag cgggtagcta tttctcggg acgcattatt tttctaagga acaacaaatt 1380
tcttatttta ttgaagcgat tgagaatggt gatgcccaag aattaagtaa aaaaatgagg 1440
acgaacgagt ctgaatttca agtgaatccg caaagcatta agcctttaat cacttattat 1500
caaaaaaatc caactgagct aaaaaaatta gaaaagcgc tattaaagga taaaagtta 1560
catggtttaa ctattcgtga aacaagtcaa acagcatttt tctttcaccg ttatcaattc 1620
attttaacgc ctgtttctgt tcagttaacg acgaatcagc gcggtgtgac gctggcaatg 1680
aacgggcggg aagtgggcac ttccgactca accacttatc aaaaggaatt gggcccctta 1740
gcgccaggac aatatacttt tacagccaca gtgaaagata gcaccggcga acctgttatc 1800
acagaagagt accgtttatt agaagaggaa aattatattt ctagtattcc tttagatttt 1860
aaacgaatga attttgttgt ggaaagcaat ctgccagacg cagatattta tattaatgat 1920
cggaaagttg gtacgctaac gaatggaagc aaaacgattg gcccttgtt ctggtccaaa 1980
gggatgacga ttcaacttaa aaagacgatt aatggagaag aaattcaaac atcaaaagaa 2040
acgattggtg aaaatgattt tgtcgaagcg ctctccgata atccaacgct acaattgaat 2100
tttccgttag ctagcgacta tgatgcccgc aaagcgctag aaaccttta tcaagcattt 2160
gccaaacaag tgaaaagtca tacggatagt acagaatttg ctaaaaaata tctcgttggt 2220
ggggaaaata atcctcaatt tccttctttt atagaagcac ttgaacgatt acgtgaaaag 2280
aaatcgaccg atggttcacc agatttgaa gtgaccatta atacgctaca attggatggt 2340
aaagaaaatt accatgtcaa ttattattta gaagccaaaa attctaaagc aaaagaaaat 2400
ggtcttcgtt atgaatggat caatggccta aatgatcaaa ttcatttagt caaagaaccg 2460
ttaaaagaag gacaattaca gtttgtttcg atagatgaac aaacacttgc ttggctcgaa 2520
aagatactc aagcaaaaat gagtgctaaa ttatttagca ctcatttttg cttatttcta 2580
ttgcacgcgt gggacattg cgctacgctt ttaacacatt ctcgcgttcg ttttctggaa 2640
taaattgttg tcgagcatgc ggctcgtctt taaaaggac aatcccatga tcatcataat 2700
caaatatatt aggcgcataa acttgacaaa gtccacaagc aatacatttt tcaggaacta 2760
aacgtgattg cataaacagt gacacatcct atctaaaaga ggtttactat ggaagcaact 2820
tttattttag cgttattatc tcatggatac aaggtacgtg catcaacttt gtatcatctt 2880
ttaaaaggca aacggactag ctctgttttg atttatggtt ttttatatga ttgtttacgg 2940
ttcattggct ggtggccaac gatttccgaa caagcctatt ttcaatttct tgaaaaactt 3000
tcgaaggcga aacaattca gtatcacgaa gagacaaatg agattcaact aacaaaagaa 3060
gggcaactat ttttaaagga gcaccatttt tcgttgctgg attatcctgc aattgatctt 3120
tatcgttttg gcagaagtga tcgagaaagt tggcaactca ttcaatttgc cgtgcaagtg 3180
acttcatatt tatcatttga ggaaaaacag tatattccac ttttatcaac accgattccg 3240
caactatatt tgaaacgatg gttacaacaa gacaagaaag agcagcgcgt tcaatcaatc 3300
aaagaagaac tgttgcgagg gtttgagtta ctacctgaag cagaaagcga ctatttggtt 3360
gcgcaacttt ctggttatca gcaaactggc aaagttcctc agcaattaac aagccataag 3420
acagctcttg aacagcgttt gtggcacacg caagcggttc atcatttact gcagttgata 3480
```
atgtacggag gaaattat

Figure 8A
Page 2 of 2

Figure 8B

TcaA

| | | | | | | | | | | | | | | |
|---|---|---|---|---|---|---|---|---|---|---|---|---|---|---|
| Met 1 | Asn | Glu | Ser | Met 5 | His | Gln | Glu | Glu | Asn 10 | Gln | Ala | Gln | Pro | Ser 15 | Met |
| Asn | Lys | Gly | Asn 20 | Glu | Ser | Thr | Pro | Leu 25 | Arg | Ser | Lys | Arg | Ser 30 | Trp | Ile |
| Trp | Ala | Phe 35 | Leu | Phe | Val | Phe | Ile 40 | Val | Leu | Gly | Ala | Gly 45 | Ser | Tyr | Phe |
| Leu | Gly 50 | Thr | His | Tyr | Phe | Ser 55 | Lys | Glu | Gln | Gln | Ile 60 | Ser | Tyr | Phe | Ile |
| Glu 65 | Ala | Ile | Glu | Asn | Gly 70 | Asp | Ala | Gln | Glu | Leu 75 | Ser | Lys | Lys | Met | Arg 80 |
| Thr | Asn | Glu | Ser | Glu 85 | Phe | Gln | Val | Asn | Pro 90 | Gln | Ser | Ile | Lys | Pro 95 | Leu |
| Ile | Thr | Tyr | Tyr 100 | Gln | Lys | Asn | Pro | Thr 105 | Glu | Leu | Lys | Lys | Leu 110 | Glu | Lys |
| Ala | Leu | Leu 115 | Lys | Asp | Lys | Lys | Leu 120 | His | Gly | Leu | Thr | Ile 125 | Arg | Glu | Thr |
| Ser | Gln 130 | Thr | Ala | Phe | Phe | Phe 135 | His | Arg | Tyr | Gln | Phe 140 | Ile | Leu | Thr | Pro |
| Val 145 | Ser | Val | Gln | Leu | Thr 150 | Thr | Asn | Gln | Arg | Gly 155 | Val | Thr | Leu | Ala | Met 160 |
| Asn | Gly | Arg | Glu | Val 165 | Gly | Thr | Ser | Asp | Ser 170 | Thr | Thr | Tyr | Gln | Lys 175 | Glu |
| Leu | Gly | Pro | Leu 180 | Ala | Pro | Gly | Gln | Tyr 185 | Thr | Phe | Thr | Ala | Thr 190 | Val | Lys |
| Asp | Ser | Thr 195 | Gly | Glu | Pro | Val | Ile 200 | Thr | Glu | Glu | Tyr | Arg 205 | Leu | Leu | Glu |
| Glu 210 | Glu | Asn | Tyr | Ile | Ser 215 | Ser | Ile | Pro | Leu | Asp 220 | Phe | Lys | Arg | Met | Asn |
| Phe 225 | Val | Val | Glu | Ser | Asn 230 | Leu | Pro | Asp | Ala | Asp 235 | Ile | Tyr | Ile | Asn | Asp 240 |
| Arg | Lys | Val | Gly | Thr 245 | Leu | Thr | Asn | Gly | Ser 250 | Lys | Thr | Ile | Gly | Pro 255 | Leu |
| Phe | Trp | Ser | Lys 260 | Gly | Met | Thr | Ile | Gln 265 | Leu | Lys | Lys | Thr | Ile 270 | Asn | Gly |
| Glu | Glu | Ile 275 | Gln | Thr | Ser | Lys | Glu 280 | Thr | Ile | Gly | Glu | Asn 285 | Asp | Phe | Val |
| Glu | Ala 290 | Leu | Ser | Asp | Asn | Pro 295 | Thr | Leu | Gln | Leu | Asn 300 | Phe | Pro | Leu | Ala |
| Ser 305 | Asp | Tyr | Asp | Ala | Arg 310 | Lys | Ala | Leu | Glu | Thr 315 | Phe | Tyr | Gln | Ala | Phe 320 |
| Ala | Lys | Gln | Val | Lys 325 | Ser | His | Thr | Asp | Ser 330 | Thr | Glu | Phe | Ala | Lys 335 | Lys |
| Tyr | Leu | Val | Gly 340 | Gly | Glu | Asn | Asn | Pro 345 | Gln | Phe | Pro | Ser | Phe 350 | Ile | Glu |
| Ala | Leu | Glu 355 | Arg | Leu | Arg | Glu | Lys 360 | Lys | Ser | Thr | Asp | Gly 365 | Ser | Pro | Asp |
| Phe | Glu 370 | Val | Thr | Ile | Asn | Thr 375 | Leu | Gln | Leu | Asp | Gly 380 | Lys | Glu | Asn | Tyr |
| His 385 | Val | Asn | Tyr | Tyr | Leu 390 | Glu | Ala | Lys | Asn | Ser 395 | Lys | Ala | Lys | Glu | Asn 400 |
| Gly | Leu | Arg | Tyr | Glu 405 | Trp | Ile | Asn | Gly | Leu 410 | Asn | Asp | Gln | Ile | His 415 | Leu |
| Val | Lys | Glu | Pro 420 | Leu | Lys | Glu | Gly | Gln 425 | Leu | Gln | Phe | Val | Ser 430 | Ile | Asp |
| Glu | Gln | Thr 435 | Leu | Ala | Trp | Leu | Glu 440 | Lys | Ile | Leu | | | | | |

Figure 9A

ScrB
```
aatttagata attgacgccg gccgcttcgg caactgtgac aatatcaaag ccagcaaaag   60
cttttctttt taattcgttc agaaagtcac tcattcctgg catgtttcta ctagcttttg  120
ttactttggc taattgatct gccccatcag caggtaagtt tgtccaagtc aaatctttct  180
taataaaatt aatcgcatct acacgaaaac cagcaattcc tttgtttaac caaaaacgaa  240
tcatttgata gatttctttg cgtagttcag gatttccca atttaaatcc ggctgttttt  300
tatgaaaggc atgaaagtag taggcatctt ccccaggtaa ttttccccaa acactaccac  360
cgaagttaga ccgccaattt gtaggtgctt ctcgtccttc ttttataata taaaagtctc  420
gaaaacgact ttgaggatttt tttaaaacat cttgaaacca agcatgttca tcagatgtat  480
ggtttaccac caaatctaaa ataactttta tgtttcgttt ttttgcttct tcaatgagtt  540
catcgaagtc tgccattgta ccaaaatcgc tagaaatacc ataatagtct gaaatatcat  600
atccattgtc agccattggc gacgggtaca ttggactcag ccaaatcagc gtaattccta  660
aattttctaa gtaatccagt ttttgaataa tgccttgtaa atcaccaatt ccgtcattat  720
tactatccga aaagctacgt ggataaattt gataggccac ttcttttttgc caccaatttc  780
tgttcattct ggttctcctc actcttaaac tagtcctgtt aatttttttct gtaaccgttt  840
ttacattttg tatgatactc gtttttgcgt aatatgtcaa acgtttatca taaataaatg  900
taaattataa tattcttttg atttaaatag atttatatat gttatacgtt tgactttttt  960
ctgatttgtt tatactatta gactaactac tattttctaa taaggagac attacttatg 1020
tcaagcatca tgaaccaatg gacggatgaa ttacgttatg cgccttattc ttcttggaca 1080
tctgctcacc tcgaaaatct aacttctatt atcgcgcaat ctagttggcg ttttaagtat 1140
catattcaac cacagacagg actactaaat gatcccaacg gttttcgta tttcaataac 1200
cagtggcatt tattttatca agcgtttcct ttcgggagtg ttcacggact aaaaagttgg 1260
gcccacttaa cttcctccga cttaattcac tgggattatg aaggaattgc cctttatccc 1320
gactctgaat atgattctca tggcgtctat tcaggctcag ctttaacaat agataaccaa 1380
ctatgtttat tttatacagg aaatgttcgt gatcaaactt ggcaacgatt tgcatatcaa 1440
aatattgcat ggctgaattc tttaggtgcg atcacaaagg aatcaacacc attcctacct 1500
attgacccca attattcttc ccattttcgt gatccgatgg tatttcctta tcaagaagga 1560
cttgtttttat taattggtgc tagtgattta aatggacaag gaaaaattgt ggtctatttt 1620
tctaaagatc gaaatgtaca caattttcat caacttggcg aattgacgtt caccaaccaa 1680
gaattaggct acatggttga atgccccaat ttggtattta ttgatggcca gcctgtctta 1740
ttatttgcc cacaaggtct atctccatct gtaaaaagtt atcagaatat ctatccgaat 1800
atgtacacat tggccgaaac gtttgatttg gagaatcttt ctttagttca ggctgggcct 1860
tttgaaaatt tagatgaagg atttgatgtc tacgccactc aagcctttaa tgcgccagat 1920
ggtcgtgcac ttgcggtcag ttggattggg ttgccagaaa tcacttaccc aagtgatgtg 1980
gagggttggg caaatggctt aagtctggtt aaagaactca caattcacaa cgggaaacta 2040
tttcaatatc cagtttctga aacagaaatg cttcgtcaat ccgctactac tttatcaaat 2100
ggctgccatt tcttatctac tgcttctttt gaattagaag tggatattcc caaaaatgag 2160
attgctttta ttcggctttt agcgaacgaa acgggttcaa aaggactttt aattacaatt 2220
gatacgattc atggtaaaat aacccttgat cgaacatttg ctggccaatc ttttgctgaa 2280
aagtatggca caattcgtga aactaaaatt aggaaaaata agtcagttca gttaactatt 2340
tttgttgatt gctctgttgc agaaatctat gtaaataaag gtgaaaaaac gatgactggt 2400
cgcttctttc cagataaagc gcaacagtat cttcatctat ccaagacggc aaaagcttgt 2460
ttttatgagc tggaaaatac gaataattag gaatgatggt gaatttgat ggtggttaaa 2520
ttaacggatg tagcaaagct tgctggggtg agcccgacaa cggtaagccg cgtgattaat 2580
aattatggtt atcttagtca aaaacaatt gataaagttc atcaagcgat ggaagaatta 2640
aattatcaac ctaatggatt agccagaagc ctccaagaa aaagtacgca gctgattggt 2700
ttagtcttcc cttctgttag tcatccattt tttggtgaat taattgaaac actggaaaga 2760
aagctctttg ttcaaggata taaagtgatt ttatgtgata gtgaaaaaga tccagaaaaa 2820
gagcgcgcct atttacgaat gctcgctgca aataaagtgg acggtgtaat cactggtagc 2880
cataacttag ctattaacga atatgaaaat gtttcactac ctattgtttc ctttgaccgt 2940
ttcttggcac ctggcattcc aattgtctct tcgcaaaact ttcaaggggg ccaaaaagcc 3000
actgaagcct tatttgcaag tggtgcacaa aagattgcaa ttattactgg tgctaataac 3060
acaggcgcac ctagcgatta tcgattggct ggttataaac aaacaatgga aaaatatggc 3120
gcagaaaaaa cgattctaca aattgataat gggacctcaa caacattaaa aaatctagaa 3180
atcgaacgtt tgcttcaaaa taaaactgta gacggcatct tttgtacaga tgatttgaca 3240
gcaattacag ttatgaatat tgctcaaaaa ttgaagatat ccattcctga agaattaaaa 3300
gtaattggtt atgatgggac aaaattaatc aaaagaattg ccccacaact atcaaccatt 3360
gtgcagccaa tcgacgagat gtgtgacgtt atgattgact              3400
```

Figure 9B

ScrB

| | | | | | | | | | | | | | | |
|---|---|---|---|---|---|---|---|---|---|---|---|---|---|---|
| Met | Ser | Ser | Ile | Met | Asn | Gln | Trp | Thr | Asp | Glu | Leu | Arg | Tyr | Ala | Pro |
| 1 | | | | 5 | | | | | 10 | | | | | 15 |
| Tyr | Ser | Ser | Trp | Thr | Ser | Ala | His | Leu | Glu | Asn | Leu | Thr | Ser | Ile | Ile |
| | | | 20 | | | | | 25 | | | | | 30 | |
| Ala | Gln | Ser | Ser | Trp | Arg | Phe | Lys | Tyr | His | Ile | Gln | Pro | Gln | Thr | Gly |
| | | 35 | | | | | 40 | | | | | 45 | | | |
| Leu | Leu | Asn | Asp | Pro | Asn | Gly | Phe | Ser | Tyr | Phe | Asn | Asn | Gln | Trp | His |
| | 50 | | | | | 55 | | | | | 60 | | | | |
| Leu | Phe | Tyr | Gln | Ala | Phe | Pro | Phe | Gly | Ser | Val | His | Gly | Leu | Lys | Ser |
| 65 | | | | | 70 | | | | | 75 | | | | | 80 |
| Trp | Ala | His | Leu | Thr | Ser | Ser | Asp | Leu | Ile | His | Trp | Asp | Tyr | Glu | Gly |
| | | | | 85 | | | | | 90 | | | | | 95 | |
| Ile | Ala | Leu | Tyr | Pro | Asp | Ser | Glu | Tyr | Asp | Ser | His | Gly | Val | Tyr | Ser |
| | | | | 100 | | | | | 105 | | | | | 110 | |
| Gly | Ser | Ala | Leu | Thr | Ile | Asp | Asn | Gln | Leu | Cys | Leu | Phe | Tyr | Thr | Gly |
| | | | 115 | | | | | 120 | | | | | 125 | | |
| Asn | Val | Arg | Asp | Gln | Thr | Trp | Gln | Arg | Phe | Ala | Tyr | Gln | Asn | Ile | Ala |
| | 130 | | | | | 135 | | | | | 140 | | | | |
| Trp | Leu | Asn | Ser | Leu | Gly | Ala | Ile | Thr | Lys | Glu | Ser | Thr | Pro | Phe | Leu |
| 145 | | | | | 150 | | | | | 155 | | | | | 160 |
| Pro | Ile | Asp | Pro | Asn | Tyr | Ser | Ser | His | Phe | Arg | Asp | Pro | Met | Val | Phe |
| | | | | 165 | | | | | 170 | | | | | 175 | |
| Pro | Tyr | Gln | Glu | Gly | Leu | Val | Leu | Leu | Ile | Gly | Ala | Ser | Asp | Leu | Asn |
| | | | 180 | | | | | 185 | | | | | 190 | | |
| Gly | Gln | Gly | Lys | Ile | Val | Val | Tyr | Phe | Ser | Lys | Asp | Arg | Asn | Val | His |
| | | 195 | | | | | 200 | | | | | 205 | | | |
| Asn | Phe | His | Gln | Leu | Gly | Glu | Leu | Thr | Phe | Thr | Asn | Gln | Glu | Leu | Gly |
| | | 210 | | | | | 215 | | | | | 220 | | | |
| Tyr | Met | Val | Glu | Cys | Pro | Asn | Leu | Val | Phe | Ile | Asp | Gly | Gln | Pro | Val |
| 225 | | | | | 230 | | | | | 235 | | | | | 240 |
| Leu | Leu | Phe | Cys | Pro | Gln | Gly | Leu | Ser | Pro | Ser | Val | Lys | Ser | Tyr | Gln |
| | | | | 245 | | | | | 250 | | | | | 255 | |
| Asn | Ile | Tyr | Pro | Asn | Met | Tyr | Thr | Leu | Ala | Glu | Thr | Phe | Asp | Leu | Glu |
| | | | 260 | | | | | 265 | | | | | 270 | | |
| Asn | Leu | Ser | Leu | Val | Gln | Ala | Gly | Pro | Phe | Glu | Asn | Leu | Asp | Glu | Gly |
| | | 275 | | | | | 280 | | | | | 285 | | | |
| Phe | Asp | Val | Tyr | Ala | Thr | Gln | Ala | Phe | Asn | Ala | Pro | Asp | Gly | Arg | Ala |
| | 290 | | | | | 295 | | | | | 300 | | | | |
| Leu | Ala | Val | Ser | Trp | Ile | Gly | Leu | Pro | Glu | Ile | Thr | Tyr | Pro | Ser | Asp |
| 305 | | | | | 310 | | | | | 315 | | | | | 320 |
| Val | Glu | Gly | Trp | Ala | Asn | Gly | Leu | Ser | Leu | Val | Lys | Glu | Leu | Thr | Ile |
| | | | | 325 | | | | | 330 | | | | | 335 | |
| His | Asn | Gly | Lys | Leu | Phe | Gln | Tyr | Pro | Val | Ser | Glu | Thr | Glu | Met | Leu |
| | | | 340 | | | | | 345 | | | | | 350 | | |
| Arg | Gln | Ser | Ala | Thr | Thr | Leu | Ser | Asn | Gly | Cys | His | Phe | Leu | Ser | Thr |
| | | | 355 | | | | | 360 | | | | | 365 | | |
| Ala | Ser | Phe | Glu | Leu | Glu | Val | Asp | Ile | Pro | Lys | Asn | Glu | Ile | Ala | Phe |
| | | 370 | | | | | 375 | | | | | 380 | | | |
| Ile | Arg | Leu | Leu | Ala | Asn | Glu | Thr | Gly | Ser | Lys | Gly | Leu | Leu | Ile | Thr |
| 385 | | | | | 390 | | | | | 395 | | | | | 400 |
| Ile | Asp | Thr | Ile | His | Gly | Lys | Ile | Thr | Leu | Asp | Arg | Thr | Phe | Ala | Gly |
| | | | | 405 | | | | | 410 | | | | | 415 | |
| Gln | Ser | Phe | Ala | Glu | Lys | Tyr | Gly | Thr | Ile | Arg | Glu | Thr | Lys | Ile | Arg |
| | | | 420 | | | | | 425 | | | | | 430 | | |
| Lys | Asn | Lys | Ser | Val | Gln | Leu | Thr | Ile | Phe | Val | Asp | Cys | Ser | Val | Ala |
| | | 435 | | | | | 440 | | | | | 445 | | | |
| Glu | Ile | Tyr | Val | Asn | Lys | Gly | Glu | Lys | Thr | Met | Thr | Gly | Arg | Phe | Phe |
| 450 | | | | | 455 | | | | | 460 | | | | | |
| Pro | Asp | Lys | Ala | Gln | Gln | Tyr | Leu | His | Leu | Ser | Lys | Thr | Ala | Lys | Ala |

```
        465                 470              475              480
    Cys Phe Tyr Glu Leu Glu Asn Thr Asn Asn
                        485              490
```

Fig. 9B
Page 2 of 2

Figure 10A

RecQ
```
ccgcggctgt gggtgtatcg ggattggcga gcgcaagaag cgacgctttc ttatttagat  60
tttcggttat atcaaatcca acaaatttgg caagaaaagg agtgagtgtt gttgacatta 120
gaacaagaat tattcactca atttggttac gcagcgttta agcctggtca aaaagaagtg 180
attacaaact tacttgacgg tatgaataca ttggctgttt tgccaacagg gactggaaaa 240
tcattgtgtt atcaatttgt gggccagaag ttagagggac taacggtaat tgtttctccc 300
ttactttcgt taatggaaga tcagatgcgt caattacaaa gacaaggaat taaaggtgcg 360
gttgccttaa acagtacgtt acagtattca gaaaagcgtt atattttagc gaaaatgttc 420
caatacgatt atctgttttt aagcccagaa atgcttttgc agcaagaagt acttagtgtg 480
ttacaacgcc aaaaaattgc attatttgtg gtggatgaag cccattgtgt ttatcagtgg 540
ggcgtcgatt ttcgccctga atatagtaaa ttagatctgg tccaaaaaca gctagacttt 600
cctttgacct tggcgttaac tgccacagcg acacccgttg tacagcacgc aattataaaa 660
caattatttt ctcatggcag ctatcaagaa gttctttctt cagtgaatcg aaaaaatatt 720
ggcttgttcg tgaaggaaac gtcagaaaaa gaagaagtgt tactagatta cttatctaaa 780
acggctggta aaatcattat ctattgcgcc acgcgcaaca aaacagaaca aatcagtcaa 840
cttattcagg caaaaaccag ttttaaggta gcctatatc atgggggctt ggaggctagt 900
gaacgtagtc gcttgcaaga acaatttatt gataatcaaa tcgatattct ttgtgcaacg 960
aatgcttttg ggatgggaat cgacaaacct gatgttcgtg gagtgattca ttttgatttg 1020
cctgatagct tagaaaatta cctgcaagaa atcgggcgag ctggacgtga tggtcaaaaa 1080
agttgggcgc tattattgta taaaaaaggg gatgaattta ttcatcggtt tttcttagaa 1140
gagacaagag cgaatcgagc gaccttaaaa tcgctgattg aaggagaaga acaagcaggt 1200
ttgctagaaa atgccaccga gttacaacaa aaatgggtcc aaggctattt agccaaggat 1260
tattcttttg aagagctaga gcatcgttta gaggagaaag aaaaagatcg ccaagcacaa 1320
ttaagaggga tgctgacgta tattgaaacc acaacctgtc gaagaacgtt gattcaaact 1380
tattttcaag aaccgattgt caaacaatca ccggaaactt gttgtgataa ttgtgcgtta 1440
ttctttgaca tttaccaaga ttcaatagta aaatcgaaca agaccagcaa tcaaaatgaa 1500
gaaggttggc gttctaaatt tctaaaatta tttaaagaac gtgattaatt cattttttta 1560
gtcggcagtt ggcaaaagct atgatataat aacaagcgag agaagtttag gaggaaatta 1620
gcagtgagta aaaggacaa aaagaaaaac caagctcgtg agccatggga acaatcaatt 1680
tatgaacctg atcaaaatgg tggtggttct cgtttagcaa aacgccaaca gcaacgagga 1740
aattcattat ttctaactgt tttagttatt ttgctattat taattattgc cattccaatt 1800
gggactttct tatggatgat gcaagacaag aaaccgaacg aaagtgctag caaaaatagc 1860
cagccatctt cttcattagt ccaatcatca tcaaaagaga agaaaaaaga aagtacgtca 1920
aaatcagtgg aaagctcaga accagcaagc agccaaccag ctgaaaatac aacaccttca 1980
agttcagatg ctgctgcaca gcaacaacag gaccaacaag cacaacaaca gcaacagcaa 2040
caacaagagc agcaacaaca acaagaagct caaaatcaac aacagcaac       2089
```

Figure 10B

RecQ

| | | | | | | | | | | | | | | |
|---|---|---|---|---|---|---|---|---|---|---|---|---|---|---|
| Met | Asn | Thr | Leu | Ala | Val | Leu | Pro | Thr | Gly | Thr | Gly | Lys | Ser | Leu | Cys |
| 1 | | | | 5 | | | | | 10 | | | | | 15 |
| Tyr | Gln | Phe | Val | Gly | Gln | Lys | Leu | Glu | Gly | Leu | Thr | Val | Ile | Val | Ser |
| | | | 20 | | | | | 25 | | | | | 30 | | |
| Pro | Leu | Leu | Ser | Leu | Met | Glu | Asp | Gln | Met | Arg | Gln | Leu | Gln | Arg | Gln |
| | | 35 | | | | | 40 | | | | | 45 | | | |
| Gly | Ile | Lys | Gly | Ala | Val | Ala | Leu | Asn | Ser | Thr | Leu | Gln | Tyr | Ser | Glu |
| | 50 | | | | | 55 | | | | | 60 | | | | |
| Lys | Arg | Tyr | Ile | Leu | Ala | Lys | Met | Phe | Gln | Tyr | Asp | Tyr | Leu | Phe | Leu |
| 65 | | | | | 70 | | | | | 75 | | | | | 80 |
| Ser | Pro | Glu | Met | Leu | Leu | Gln | Gln | Glu | Val | Leu | Ser | Val | Leu | Gln | Arg |
| | | | | 85 | | | | | 90 | | | | | 95 | |
| Gln | Lys | Ile | Ala | Leu | Phe | Val | Val | Asp | Glu | Ala | His | Cys | Val | Tyr | Gln |
| | | | 100 | | | | | 105 | | | | | 110 | | |
| Trp | Gly | Val | Asp | Phe | Arg | Pro | Glu | Tyr | Ser | Lys | Leu | Asp | Leu | Val | Gln |
| | | 115 | | | | | 120 | | | | | 125 | | | |
| Lys | Gln | Leu | Asp | Phe | Pro | Leu | Thr | Leu | Ala | Leu | Thr | Ala | Thr | Ala | Thr |
| | 130 | | | | | 135 | | | | | 140 | | | | |
| Pro | Val | Val | Gln | His | Ala | Ile | Ile | Lys | Gln | Leu | Phe | Ser | His | Gly | Ser |
| 145 | | | | | 150 | | | | | 155 | | | | | 160 |
| Tyr | Gln | Glu | Val | Leu | Ser | Ser | Val | Asn | Arg | Lys | Asn | Ile | Gly | Leu | Phe |
| | | | | 165 | | | | | 170 | | | | | 175 | |
| Val | Lys | Glu | Thr | Ser | Glu | Lys | Glu | Glu | Val | Leu | Leu | Asp | Tyr | Leu | Ser |
| | | | 180 | | | | | 185 | | | | | 190 | | |
| Lys | Thr | Ala | Gly | Lys | Ile | Ile | Ile | Tyr | Cys | Ala | Thr | Arg | Asn | Lys | Thr |
| | | 195 | | | | | 200 | | | | | 205 | | | |
| Glu | Gln | Ile | Ser | Gln | Leu | Ile | Gln | Ala | Lys | Thr | Ser | Phe | Lys | Val | Ala |
| | 210 | | | | | 215 | | | | | 220 | | | | |
| Tyr | Tyr | His | Gly | Gly | Leu | Glu | Ala | Ser | Glu | Arg | Ser | Arg | Leu | Gln | Glu |
| 225 | | | | | 230 | | | | | 235 | | | | | 240 |
| Gln | Phe | Ile | Asp | Asn | Gln | Ile | Asp | Ile | Leu | Cys | Ala | Thr | Asn | Ala | Phe |
| | | | | 245 | | | | | 250 | | | | | 255 | |
| Gly | Met | Gly | Ile | Asp | Lys | Pro | Asp | Val | Arg | Gly | Val | Ile | His | Phe | Asp |
| | | | 260 | | | | | 265 | | | | | 270 | | |
| Leu | Pro | Asp | Ser | Leu | Glu | Asn | Tyr | Leu | Gln | Glu | Ile | Gly | Arg | Ala | Gly |
| | | 275 | | | | | 280 | | | | | 285 | | | |
| Arg | Asp | Gly | Gln | Lys | Ser | Trp | Ala | Leu | Leu | Leu | Tyr | Lys | Lys | Gly | Asp |
| | 290 | | | | | 295 | | | | | 300 | | | | |
| Glu | Phe | Ile | His | Arg | Phe | Phe | Leu | Glu | Glu | Thr | Arg | Ala | Asn | Arg | Ala |
| 305 | | | | | 310 | | | | | 315 | | | | | 320 |
| Thr | Leu | Lys | Ser | Leu | Ile | Glu | Gly | Glu | Glu | Gln | Ala | Gly | Leu | Leu | Glu |
| | | | | 325 | | | | | 330 | | | | | 335 | |
| Asn | Ala | Thr | Glu | Leu | Gln | Gln | Lys | Trp | Val | Gln | Gly | Tyr | Leu | Ala | Lys |
| | | | 340 | | | | | 345 | | | | | 350 | | |
| Asp | Tyr | Ser | Phe | Glu | Glu | Leu | Glu | His | Arg | Leu | Glu | Glu | Lys | Glu | Lys |
| | | 355 | | | | | 360 | | | | | 365 | | | |
| Asp | Arg | Gln | Ala | Gln | Leu | Arg | Gly | Met | Leu | Thr | Tyr | Ile | Glu | Thr | Thr |
| | 370 | | | | | 375 | | | | | 380 | | | | |
| Thr | Cys | Arg | Arg | Thr | Leu | Ile | Gln | Thr | Tyr | Phe | Gln | Glu | Pro | Ile | Val |
| 385 | | | | | 390 | | | | | 395 | | | | | 400 |
| Lys | Gln | Ser | Pro | Glu | Thr | Cys | Cys | Asp | Asn | Cys | Ala | Leu | Phe | Phe | Asp |
| | | | | 405 | | | | | 410 | | | | | 415 | |
| Ile | Tyr | Gln | Asp | Ser | Ile | Val | Lys | Ser | Asn | Lys | Thr | Ser | Asn | Gln | Asn |
| | | | 420 | | | | | 425 | | | | | 430 | | |
| Glu | Glu | Gly | Trp | Arg | Ser | Lys | Phe | Leu | Lys | Leu | Phe | Lys | Glu | Arg | Asp |
| | | 435 | | | | | 440 | | | | | 445 | | | |

Figure 11A

LysR
```
tactttagct tctcaaaagc tccatacgag tcaaccttat ttaagtaccc agctcaagga   60
gttggaacgt gaattaggtg cttcattaat tttaagagac aagaaacatt gtcggctttc  120
tccagcaggc gaagtcgtcg ccaagcgaac agaaatgatt tttgcactca ttaaggaagc  180
gcaagaagag attaatgaat tagtgaccca aggatcgaca acgaccattc ggattggaac  240
aaacttaatt gatatagata aagcatttgg agaagtcttg ttgttattta atcaatccta  300
tccgtatgta agtattgatt ttaagtatta ttacgatctt gaaacagcct tggaaacaga  360
tttaattgac attgggattg ggatattttt ggatacctcg attccattag agaaagaatt  420
aatttataca gaaagctatc tcctttgtgt caataaaaat catcctttag cccatgccga  480
tagcgtgacg attgacgaaa ttcgttcttt acctttttgct gcatattccg atcaagtata  540
tgaaaaaaaa gtgttcaaac gttgggaacg taaaatcaat tgggaaaatc ggcaaatcgt  600
catcgaactt ccttctcttc atttagtctt agacatggtc caacgagaaa aagcctgtag  660
catccttccc tattcactca ctgatgaact aaacagacgt aacttagttg gtattcctct  720
ggaagatagt ccagaacgag ccatctattt agttcagaat aatcatcacg gacattgtga  780
agcacaccgt tatttattcg aacaattacg ttatttattc taggaataga aaaaggagga  840
attcccatgg aactatttcg tttacattat tttttagagt tatgcaaagt gaaacaattt  900
actaaagcag ccgaaaattt agcaatttct caagctgcat taagtaagca aataaaaatt  960
cttgaagcaa cgttaggcgc ggaactttt aatcgccaag gccaaactac caccttaacg 1020
ccagctggat taattttaga aaaatattgt tggcgcatca ccaatgagtt ggtctcaatt 1080
gaagaagagc taaaagaaat taatcattct tccaaccata tttatgtggc cacttatctc 1140
tgtgatttag aatataaatt gaatgactta ctaatgacaa cattaacgga tcgttcatcc 1200
aacttacaag tccacactat tattacagaa aatattcttc aatccttgga acaatggat  1260
gcagattttg gtatttcctt tgctgactta ccattacctg aacatattgg taaaattgat 1320
ttatttacag caaattatca attcatttta agaaacgatc atccagctt ggcaaaagcc 1380
acgacggaag aaattttaaa agaactaaca atgtacccct tcgtccgttt aaataccgaa 1440
ttttccgagc aaaacaaatt aaccaattgg ctagatacta cgttttctaa ttttctcca  1500
gagaaagtca ttcaagtgga tactctttca cttattactc acttggtgtc tcattccgat 1560
agtttcgcta ttgtccccga atacacaaat attcaacttt tagacaattc gatccataca 1620
ctaacttacc aagaactacc taaacgaaac atggcagttt attatttaaa agaacgttac 1680
atgagtcgac aacttcaaca acttttggct gaatgccaaa aacaatttca atagtaaaaa 1740
ccaagactag agcttgtcgg caagcgagtt ccagtcttgg ttttttatttg tgttttcagg 1800
tagcggcttc tcttcctttg acaaatccta aagaagtgat agccatcact aacgaagtgc 1860
ctccttgact taaaaacgga agcggaatac cttttaacgg caacagtcca atcaccgcac 1920
cgatattctc caccgtttga aagaccagcg aaaaaatgag ggcgacacag atgtacatac 1980
aaaaacgcga attgctccgc aagccagcta ctaaaacttg ataaaacaag taaaaataga 2040
gaaaaacaac ggtggcactg cccacaaagc cccaggcttc cccgataaaa gtaaaa      2096
```

Figure 11B
LysR

| | | | | | | | | | | | | | | |
|---|---|---|---|---|---|---|---|---|---|---|---|---|---|---|
|Met|Glu|Leu|Phe|Arg|Leu|His|Tyr|Phe|Leu|Glu|Leu|Cys|Lys|Val|Lys|
|1| | | |5| | | | |10| | | | |15|
|Gln|Phe|Thr|Lys|Ala|Ala|Glu|Asn|Leu|Ala|Ile|Ser|Gln|Ala|Ala|Leu|
| | | |20| | | |25| | | | |30| | |
|Ser|Lys|Gln|Ile|Lys|Ile|Leu|Glu|Ala|Thr|Leu|Gly|Ala|Glu|Leu|Phe|
| | |35| | | |40| | | | |45| | | |
|Asn|Arg|Gln|Gly|Gln|Thr|Thr|Thr|Leu|Thr|Pro|Ala|Gly|Leu|Ile|Leu|
| |50| | | |55| | | | |60| | | | |
|Glu|Lys|Tyr|Cys|Trp|Arg|Ile|Thr|Asn|Glu|Leu|Val|Ser|Ile|Glu|Glu|
|65| | | |70| | | | |75| | | | |80|
|Glu|Leu|Lys|Glu|Ile|Asn|His|Ser|Ser|Asn|His|Ile|Tyr|Val|Ala|Thr|
| | | |85| | | | |90| | | | |95|
|Tyr|Leu|Cys|Asp|Leu|Glu|Tyr|Lys|Leu|Asn|Asp|Leu|Leu|Met|Thr|Thr|
| | |100| | | |105| | | | |110| | | |
|Leu|Thr|Asp|Arg|Ser|Ser|Asn|Leu|Gln|Val|His|Thr|Ile|Ile|Thr|Glu|
| |115| | | | |120| | | | |125| | | |
|Asn|Ile|Leu|Gln|Ser|Leu|Glu|Thr|Met|Asp|Ala|Asp|Phe|Gly|Ile|Ser|
|130| | | | |135| | | | |140| | | | |
|Phe|Ala|Asp|Leu|Pro|Leu|Pro|Glu|His|Ile|Gly|Lys|Ile|Asp|Leu|Phe|
|145| | | |150| | | | |155| | | | |160|
|Thr|Ala|Asn|Tyr|Gln|Phe|Ile|Leu|Arg|Asn|Asp|His|Pro|Ala|Leu|Ala|
| | | |165| | | | |170| | | | |175| |
|Lys|Ala|Thr|Thr|Glu|Glu|Ile|Leu|Lys|Glu|Leu|Thr|Met|Tyr|Pro|Phe|
| | |180| | | | |185| | | | |190| | |
|Val|Arg|Leu|Asn|Thr|Glu|Phe|Ser|Glu|Gln|Asn|Lys|Leu|Thr|Asn|Trp|
| |195| | | | |200| | | | |205| | | |
|Leu|Asp|Thr|Thr|Phe|Ser|Asn|Phe|Ser|Pro|Glu|Lys|Val|Ile|Gln|Val|
|210| | | | |215| | | | |220| | | | |
|Asp|Thr|Leu|Ser|Leu|Ile|Thr|His|Leu|Val|Ser|His|Ser|Asp|Phe|Ala|
|225| | | | |230| | | | |235| | | | |240|
|Ile|Val|Pro|Glu|Tyr|Thr|Asn|Ile|Gln|Leu|Leu|Asp|Asn|Ser|Ile|His|
| | | |245| | | | |250| | | | |255| |
|Thr|Leu|Thr|Tyr|Gln|Glu|Leu|Pro|Lys|Arg|Asn|Met|Ala|Val|Tyr|Tyr|
| | |260| | | | |265| | | | |270| | |
|Leu|Lys|Glu|Arg|Tyr|Met|Ser|Arg|Gln|Leu|Gln|Gln|Leu|Leu|Ala|Glu|
| |275| | | | |280| | | | |285| | | |
|Cys|Gln|Lys|Gln|Phe|Gln| | | | | | | | | | |
|290| | | | | | | | | | | | | | |

Figure 12A

XAA-His Dipeptidase

```
acaaaaatta ccttcagaat atgatttagc taaagaatat aactgcagtc gcttgaccat 60
ccgtaaagcg attgatgatt tgatccgcaa aaatattttg gtaaaacgac atggtaaagg 120
tagttatgtg atgtcgcaag cgaaaattca aagtggtcgc gctggcttac aaggttttac 180
tgaggcagcc aaagcttacg ggaaaaaaag ccagacagaa gtcatttcct ttgaagaagt 240
agtacatccc gctgagaaaa ttcgggaggc gctccaagta ggcaaaaatg aggcaattta 300
tgaactgatt cgccgccgaa tgttagacgg cgaaccaatg acagttgaaa aaatttatt 360
gccacaggca tacgtacaag gccatacgaa gcaagacttc gagggctctc ttttctgctt 420
aatcgagaag aacgtcgaga ttgcttattc gcatcaagaa attgaagcaa tcttagttga 480
agcggaaatt tcagaattat tgaatgttcc tgtgggccaa ccacttttac aagtccactc 540
tatcacctat gcgcttgatg caactcctat tttatatgat gtctctttat atcgagcaga 600
tcggtacacg tttaaaaaca cactgacccg ctatagcccg tctgaaaaca accaagtgga 660
gctaggaggt tcttggaacg aatgaagatc aagaagaaa tagccgctca aaaagattta 720
ttttatgaag acttaaacaa aattatcgcg attcgaagtg tgaaagggtc gcctaaaaaa 780
gaggcacctt ttggcgaagg accgaaaaga gccttggaag aaacgctgaa acttgcagag 840
cgttatggtt ttcaaactgg gattgtcaat gacgcagttg gctatgcgca atggggaaca 900
gcggaagaat atctgggaat tattggtcat ttagatgtag taccagaagg ttctggttgg 960
tcagtgccgc cctttcaatt aacgaaaaaa aatcaacgtt tgtatggtag aggaattcta 1020
gataataaag gtcctatctt ggcttgcctg tatggaatga aattactgaa agaacttggt 1080
taccaaccaa agaaaaccat tcgcttaatg tttggcacgg atgaagaaag tgggagtgga 1140
gatatcccct tatatttaga gaaggaaaac gcacccgttt ttggatttac tccagattgt 1200
aaatatccag tagtttatgg ggagcgaggg attgttaatt atgagatcac aacgaccatc 1260
ccagatgatt caagtgaaca aattggtcag attataggtg atcaagcaaa agaccacgta 1320
cctgatcaat taagtgtggt gattgcggga aaaacaacag caatcacggg aaaacgtgct 1380
ccttccaatg cgccagaact aggcaagaac gcgattactt tattggcaca gaaaattagc 1440
gaggaacagt tagtcaaagg aaatttatta cagtatttcg actggttaac cgctagtttt 1500
cacgaaaagc actatggcga aggagtagct ctggactta aggatcagga tagtgggcaa 1560
ttgattttaa cgccctatgc gttggaaaaa agaggacagc aattggtgtt atcattggcc 1620
gtgcgttatc ctgtttctat tacagaaaac gaagtaacca cgcagctaac gaaggcacta 1680
tttccagaaa gtgaagtgac cgtcatccgc cgcctcccta gtacgctgtt tccaaaagat 1740
gagcgcaatg ttcaaaaatt aaccaaggtt tatgaacaaa ttactggctt agatgggacg 1800
ccagtcacaa ctacaggtgc tacgtatgct cgctttatgc cgaatatcgt tgcttttggt 1860
ccatcatttc ctggtcaaaa aggcattgcg cataaccaag atgaatatat ggatgaaaaa 1920
gatttactgc ttaatctgga aatctatatg caagcgatga ttgcattaac agaagcataa 1980
aaccaataga agatacacgt atgagaagaa gacaatgtgt ttcgtagagg tcgcatacgt 2040
gtatcttcta tttttctgta taaaatttca ttttcagtat atacaaaaca gtatatacta 2100
gtttataatg gtggagaaat gtaagcgtta acgaaagggc ggatggaaaa tgacttgggg 2160
tgcaattgcg acatggcgga tgcacatga tgggttacta aaagctacag aagaattaca 2220
acaaggaggt gctgcaggca cggccgtgga acaattaatt aaagaagtag aagactatcc 2280
tttttataag tcagtgggct acggcggttt acctaatgag gaagggattt tagaaatgga 2340
```

Figure 12B

XAA-His Dipeptidase

```
Met Lys Ile Lys Glu Glu Ile Ala Ala Gln Lys Asp Leu Phe Tyr Glu
 1               5                  10                  15
Asp Leu Asn Lys Ile Ile Ala Ile Arg Ser Val Lys Gly Ser Pro Lys
                20                  25                  30
Lys Glu Ala Pro Phe Gly Glu Gly Pro Lys Arg Ala Leu Glu Glu Thr
            35                  40                  45
Leu Lys Leu Ala Glu Arg Tyr Gly Phe Gln Thr Gly Ile Val Asn Asp
        50                  55                  60
Ala Val Gly Tyr Ala Gln Trp Gly Thr Ala Glu Glu Tyr Leu Gly Ile
 65                 70                  75                  80
Ile Gly His Leu Asp Val Val Pro Glu Gly Ser Gly Trp Ser Val Pro
                85                  90                  95
Pro Phe Gln Leu Thr Lys Lys Asn Gln Arg Leu Tyr Gly Arg Gly Ile
            100                 105                 110
Leu Asp Asn Lys Gly Pro Ile Leu Ala Cys Leu Tyr Gly Met Lys Leu
            115                 120                 125
Leu Lys Glu Leu Gly Tyr Gln Pro Lys Lys Thr Ile Arg Leu Met Phe
        130                 135                 140
Gly Thr Asp Glu Glu Ser Gly Ser Gly Asp Ile Pro Leu Tyr Leu Glu
145                 150                 155                 160
Lys Glu Asn Ala Pro Val Phe Gly Phe Thr Pro Asp Cys Lys Tyr Pro
                165                 170                 175
Val Val Tyr Gly Glu Arg Gly Ile Val Asn Tyr Glu Ile Thr Thr Thr
            180                 185                 190
Ile Pro Asp Asp Ser Ser Glu Gln Ile Gly Gln Ile Ile Gly Asp Gln
            195                 200                 205
Ala Lys Asp His Val Pro Asp Gln Leu Ser Val Val Ile Ala Gly Lys
        210                 215                 220
Thr Thr Ala Ile Thr Gly Lys Arg Ala Pro Ser Asn Ala Pro Glu Leu
225                 230                 235                 240
Gly Lys Asn Ala Ile Thr Leu Leu Ala Gln Lys Ile Ser Glu Glu Gln
            245                 250                 255
Leu Val Lys Gly Asn Leu Leu Gln Tyr Phe Asp Trp Leu Thr Ala Ser
            260                 265                 270
Phe His Glu Lys His Tyr Gly Glu Gly Val Ala Leu Asp Phe Lys Asp
        275                 280                 285
Gln Asp Ser Gly Gln Leu Ile Leu Thr Pro Tyr Ala Leu Glu Lys Arg
        290                 295                 300
Gly Gln Gln Leu Val Leu Ser Leu Ala Val Arg Tyr Pro Val Ser Ile
305                 310                 315                 320
Thr Glu Asn Glu Val Thr Thr Gln Leu Thr Lys Ala Leu Phe Pro Glu
                325                 330                 335
Ser Glu Val Thr Val Ile Arg Arg Leu Pro Ser Thr Leu Phe Pro Lys
            340                 345                 350
Asp Glu Arg Asn Val Gln Lys Leu Thr Lys Val Tyr Glu Gln Ile Thr
        355                 360                 365
Gly Leu Asp Gly Thr Pro Val Thr Thr Thr Gly Ala Thr Tyr Ala Arg
    370                 375                 380
Phe Met Pro Asn Ile Val Ala Phe Gly Pro Ser Phe Pro Gly Gln Lys
385                 390                 395                 400
Gly Ile Ala His Asn Gln Asp Glu Tyr Met Asp Glu Lys Asp Leu Leu
                405                 410                 415
Leu Asn Leu Glu Ile Tyr Met Gln Ala Met Ile Ala Leu Thr Glu Ala
            420                 425                 430
```

Figure 13A

SacU

```
catttttat taaattacat atttgtaata ggaatttcct gtgaaatgag gtatcctaag   60
aaaggtgata aaacacagag gtaaaggagt gacacgatga gtcgtgtaga tcgttataaa  120
catattcatg aaaaatcgag accagcagag cataaaaaga cctttaatcc ccgaaaatca  180
atgggtgaac atagagaaga agaaccagaa gaactagctg aaagccttca agagccagtt  240
tacgaagaca gctatactga ggacagtcgc agaagtgaga ggcgacatca aacagattca  300
ggtggtggca acggttctga ccaaccaccc cgcggaaaaa aagacaagaa accaaaaaag  360
aaacgtaaaa aatcaaaaac aaaacgcttt ttcaaatggc tagtgatcct attgattctg  420
ttatttgcct atagtacagt catgttttta aaggaaaat ctgcagcaga acatgatgac   480
tcgttgcctc aagaaaaagt agaaacattt aatggtgtca aaagtagcaa cggggctaag  540
aatatttttaa ttcttggcag cgatacacgt ggggaagatg ctggacgagc cgacacaata  600
atggttctcc aactaaatgg accatcaaaa aaaccgaaat taatttcatt tatgcgtgat  660
acattcgtgg acattcctgg tgtcgggccg aataaaatta atgccgcata cgcttatggc  720
ggtgctgaat tggttcgtga aacgttaaaa caaaactta atttagatac gaaatattat   780
gctaaggtag atttccaatc atttgaaaaa attgttgact ctatgtttcc aaaaggtgtc  840
aaaatcgatg cagaaaaatc actgaattta gatggtgttg atattgaaaa agggcaacag  900
gtcatggatg gacatgtctt acttcaatac gctcgcttta ggatggatga agaaggcgac  960
tttggtcggg ttcgtcgcca acaacaagtt atgtcagctg taatgagcca aatgaaaaac 1020
ccaatgactt tattaagaac cccagaatca cttgggaaat tagtcggcta tatgtcgaca 1080
gatgtgcctg ttagtttcat gttaacgaat ggaccatcat tgttgattaa aggaaagca  1140
ggggttgagt cattatcggt tccggtacca gattcttgga attttggtga atcctcttat 1200
gcaggcagta ttttagaagt agatgaacaa aaaaatgctg acgccatcga aaaattcctg 1260
aacgaataag gaaagcattt taaaatatcc ttttttatgc tatattagaa acaacgtgga 1320
aaattagtga acgaggtta caaaatgaaa attgctattg tgacagatag tacagcttat 1380
ttacccgagc gcattaaaga tcatccgaat cttttttgtaa ttcccatccc agtcatttta 1440
gatggaaaaa tatacaacga aggcattgac attgaagcag atgaatatta tgcattgcta 1500
aataatagta aagaatttcc gacgacttca caacctgctt taggagaagt gttagagctt 1560
tacaaatcaa tcgctgaaca agggtacgac accatcatca gcattcatct ttcttcagga 1620
atctctggtt ttgttcatac attgcacgga cttaccgatg aaatcccagg cgttgctttg 1680
tatccatatg actcaaaaat tacaagtatg ccaatgggac acatggtaga agctgcttta 1740
gatttaacag aagaaaagc cagcttagaa gaaatttttg ccaaattaga tttaattcgt 1800
gacaatacgt atgcatatct aattgtagaa gatctgaaca acttagttcg tggcggtcgc 1860
ttaacgaatg gcgcagcctt gatcgctgga ctattgaaga ttaaacctat cttgactttt 1920
gaagatggaa agattgtatt atttgaaaaa atccgttcaa caaagaaagc ttttgctcgt 1980
gcagaaaaga ttattggtga acgaaacgca gggattgaag caccagttaa actgtatgtg 2040
attcatgcca ataaccgcat cgttgctgaa aagaacaag caaaattaca aaagctatac 2100
ccaaatgcag aaattgaaat tggtcatttt ggtccagtta tcgggaccca cctaggggaa 2160
aaagcaattg gtttagcgat ttcagctcaa taataaaaga tgagacaaaa gtaaactact 2220
tctgtctcat cttttattct attatttat cgttcgctgg tgttactcag ccgaacactt  2280
tttgttata agaaaatgta aaattactcc tttttattag aaaatatctt gcaaattaag  2340
caattcctta caaagtaatg ta                                          2362
```

Figure 13B

SacU

| | | | | | | | | | | | | | | |
|---|---|---|---|---|---|---|---|---|---|---|---|---|---|---|
| Met | Lys | Ile | Ala | Ile | Val | Thr | Asp | Ser | Thr | Ala | Tyr | Leu | Pro | Glu | Arg |
| 1 | | | | 5 | | | | | 10 | | | | | 15 | |
| Ile | Lys | Asp | His | Pro | Asn | Leu | Phe | Val | Ile | Pro | Ile | Pro | Val | Ile | Leu |
| | | | | 20 | | | | | 25 | | | | | 30 | |
| Asp | Gly | Lys | Ile | Tyr | Asn | Glu | Gly | Ile | Asp | Ile | Glu | Ala | Asp | Glu | Tyr |
| | | | 35 | | | | | 40 | | | | | 45 | | |
| Tyr | Ala | Leu | Leu | Asn | Asn | Ser | Lys | Glu | Phe | Pro | Thr | Thr | Ser | Gln | Pro |
| | 50 | | | | | 55 | | | | | 60 | | | | |
| Ala | Leu | Gly | Glu | Val | Leu | Glu | Leu | Tyr | Lys | Ser | Ile | Ala | Glu | Gln | Gly |
| 65 | | | | | 70 | | | | | 75 | | | | | 80 |
| Tyr | Asp | Thr | Ile | Ile | Ser | Ile | His | Leu | Ser | Ser | Gly | Ile | Ser | Gly | Phe |
| | | | | 85 | | | | | 90 | | | | | 95 | |
| Val | His | Thr | Leu | His | Gly | Leu | Thr | Asp | Glu | Ile | Pro | Gly | Val | Ala | Leu |
| | | | | 100 | | | | | 105 | | | | | 110 | |
| Tyr | Pro | Tyr | Asp | Ser | Lys | Ile | Thr | Ser | Met | Pro | Met | Gly | His | Met | Val |
| | | | 115 | | | | | 120 | | | | | 125 | | |
| Glu | Ala | Ala | Leu | Asp | Leu | Thr | Glu | Glu | Lys | Ala | Ser | Leu | Glu | Glu | Ile |
| | | 130 | | | | | 135 | | | | | 140 | | | |
| Phe | Ala | Lys | Leu | Asp | Leu | Ile | Arg | Asp | Asn | Thr | Tyr | Ala | Tyr | Leu | Ile |
| 145 | | | | | 150 | | | | | 155 | | | | | 160 |
| Val | Glu | Asp | Leu | Asn | Asn | Leu | Val | Arg | Gly | Gly | Arg | Leu | Thr | Asn | Gly |
| | | | | 165 | | | | | 170 | | | | | 175 | |
| Ala | Ala | Leu | Ile | Ala | Gly | Leu | Leu | Lys | Ile | Lys | Pro | Ile | Leu | Thr | Phe |
| | | | 180 | | | | | 185 | | | | | 190 | | |
| Glu | Asp | Gly | Lys | Ile | Val | Leu | Phe | Glu | Lys | Ile | Arg | Ser | Thr | Lys | Lys |
| | | 195 | | | | | 200 | | | | | 205 | | | |
| Ala | Phe | Ala | Arg | Ala | Glu | Lys | Ile | Ile | Gly | Glu | Arg | Asn | Ala | Gly | Ile |
| | 210 | | | | | 215 | | | | | 220 | | | | |
| Glu | Ala | Pro | Val | Lys | Leu | Tyr | Val | Ile | His | Ala | Asn | Asn | Arg | Ile | Val |
| 225 | | | | | 230 | | | | | 235 | | | | | 240 |
| Ala | Glu | Lys | Glu | Gln | Ala | Lys | Leu | Gln | Lys | Leu | Tyr | Pro | Asn | Ala | Glu |
| | | | | 245 | | | | | 250 | | | | | 255 | |
| Ile | Glu | Ile | Gly | His | Phe | Gly | Pro | Val | Ile | Gly | Thr | His | Leu | Gly | Glu |
| | | | 260 | | | | | 265 | | | | | 270 | | |
| Lys | Ala | Ile | Gly | Leu | Ala | Ile | Ser | Ala | Gln | | | | | | |
| | | | 275 | | | | 280 | | | | | | | | |

Figure 14A

Pai1

```
gagattatct aaagaaaagt aagcacaatt cgaggtttca atgtttttt caaagggatg   60
attttctaga atgtcacaag aaaagatcat tttatagtac tgaaatagtt gaggaatgtc  120
ttttcgttta tctgtatcat aaacagcaag caattctttt gctgtaacaa ctaagccagt  180
ttcttccaat acttcttttt caatattttc tttaggagag cagccaattt cggcatagcc  240
accaggtaat gaccattctt tggtccgtaa atcttcaact aataaaaaac gattctcttt  300
ttttatcaaa ccgcgaacat ctactttcgg tgttggataa ccttcttctt tagttaagat  360
ttttctaag tcgggcaaga cagtcgcttc gtgtccggtt gcgctaataa gttgtaacgt  420
aagttctcgt agttcttggt aacgttcttg atcaaaagca tctttcccgt aaaaaagacc  480
agcatctgcc aatgctagca accgcttata agtgttcaga taatccatat acgcacgctc  540
ctcatagact taatacgttt agtttaacag aaaaaaataa agaaagggca gatttagcga  600
gaaaaggcgt cgttttaagg aaataataaa gaataaatga ctaacttaca tttttaaact  660
acctatgcta ttatttaata aaaagattg ggtatacaat aattttgtta tgtaaacaaa  720
aaggaggttg taaattgaaa gaatttacaa ttataaggga aaaaatgca gataaaaga   780
ctcaggcagc acaagaagta ttgtttaatc ttccagaatg gtttggcctt gaaaaagaga  840
cccgcaagta tatcgatata gctagcactt tacctatgtg ggtggcaaag gatgtagaga  900
ataaaatact cggttttata acactttcag aaacaagtaa agatacagta gaaatccatt  960
gtatggcagt taaaagcgg tatcatcgca aaggtatcgg caagttattg atagaaagcg 1020
tggaaacgta ttctaaaaat aactatttt ttattcaagt caaaacagtt gacgaaggaa 1080
attattccgt gtacgatcat actattcgtt tttacgaatc attgggtttt aagcgccttg 1140
aggttttcc gacattatgg gacgcttga atccttgttt aattttaatt aaacagttga 1200
tttaatctac aaaggagttt tagtatgtca gtatttatta gagagtgtac cgtcgcagac 1260
gtaccagaat tagaggccat tgccaagag acttttgcag atacttatgg agatggcgaa 1320
aacgaaaagg atttacaggc acattatgag aggaaattta gtccagcagt tttagaaagc 1380
gaaatcttac ataaagattc gcaatatttc tttgcttttt ataataatga acttgcaggt 1440
tatgtgaaat taaatcacgg tgatgctcag attacctatc aacatccaca agcgttacaa 1500
gttgagcgca tttatattcg taaatctttt aagcgtttag cttaggcaa acatttgatt 1560
acgaaagcaa ttgaattagc ggaagaagca gaaaaagaga cggtttggtt aggtgtttgg 1620
gaacataatc atccagcgca aaaatttat caatcattgg gcttcgtcaa aacagatgaa 1680
catgattttt atatgggaaa tgaacgccat accgattata caatgacgaa acagttaaaa 1740
gagtcaacgg aaagcaaaaa caaggaaacg gacgcaatga agccgacgat tccttgtttt 1800
tttatcttaa aattgtgaag gagattttcc ataatatttt ttgaataatt tactgaaatg 1860
ataggcatct tcgtaaccaa ccgttttgc cacttctttg acacttaggg aatcattttt 1920
cagcaattct ttcgcatggt ttaagcggat ttgaattaaa taattgattg gcccaacgcc 1980
tgtggccgct ttaaaggttt tcgacaaata agtcggggtc acatatagca tttcagctaa 2040
ctgttccaaa gtaatttctt cgtcatggtg cgttccaga taataaatcg tatgattgac 2100
taaatttcgt tttcttttt ccgttttcga tagccgagtt tcaattttat tttcttgatc 2160
aactgctaag cttcttaaaa tatagaccaa tagttcaata act                   2203
```

Figure 14B

Pai1

| | | | | | | | | | | | | | | |
|---|---|---|---|---|---|---|---|---|---|---|---|---|---|---|
| Met | Ser | Val | Phe | Ile | Arg | Glu | Cys | Thr | Val | Ala | Asp | Val | Pro | Glu | Leu |
| 1 | | | | 5 | | | | | 10 | | | | | 15 | |
| Glu | Ala | Ile | Cys | Gln | Glu | Thr | Phe | Ala | Asp | Thr | Tyr | Gly | Asp | Gly | Glu |
| | | | 20 | | | | | 25 | | | | | 30 | | |
| Asn | Glu | Lys | Asp | Leu | Gln | Ala | His | Tyr | Glu | Arg | Lys | Phe | Ser | Pro | Ala |
| | | 35 | | | | | 40 | | | | | 45 | | | |
| Val | Leu | Glu | Ser | Glu | Ile | Leu | His | Lys | Asp | Ser | Gln | Tyr | Phe | Phe | Ala |
| | 50 | | | | | 55 | | | | | 60 | | | | |
| Phe | Tyr | Asn | Asn | Glu | Leu | Ala | Gly | Tyr | Val | Lys | Leu | Asn | His | Gly | Asp |
| 65 | | | | | 70 | | | | | 75 | | | | | 80 |
| Ala | Gln | Ile | Thr | Tyr | Gln | His | Pro | Gln | Ala | Leu | Gln | Val | Glu | Arg | Ile |
| | | | | 85 | | | | | 90 | | | | | 95 | |
| Tyr | Ile | Arg | Lys | Ser | Phe | Lys | Arg | Leu | Gly | Leu | Gly | Lys | His | Leu | Ile |
| | | | 100 | | | | | 105 | | | | | 110 | | |
| Thr | Lys | Ala | Ile | Glu | Leu | Ala | Glu | Glu | Ala | Glu | Lys | Glu | Thr | Val | Trp |
| | | 115 | | | | | 120 | | | | | 125 | | | |
| Leu | Gly | Val | Trp | Glu | His | Asn | His | Pro | Ala | Gln | Lys | Phe | Tyr | Gln | Ser |
| | 130 | | | | | 135 | | | | | 140 | | | | |
| Leu | Gly | Phe | Val | Lys | Thr | Asp | Glu | His | Asp | Phe | Tyr | Met | Gly | Asn | Glu |
| 145 | | | | | 150 | | | | | 155 | | | | | 160 |
| Arg | His | Thr | Asp | Tyr | Thr | Met | Thr | Lys | Gln | Leu | Lys | Glu | Ser | Thr | |
| | | | | 165 | | | | | 170 | | | | | 175 | |

Figure 15A

Enterococcal amino acid biosynthetic gene cluster

```
ccatgtagat ttaagaaaat ctatagtggc ttttatattg cttttttgta gggtattcac   60
tgtagatttt tcttaaaatt tactgtgaat atccttttttg tttggccaaa aattaggatt  120
tcagaaactt actaaaaaaa tttcgtaaag gagcacacag g atg aaa gaa ata act   176
                                              Met Lys Glu Ile Thr
                                                1               5
```

| | | | | | | | | | | | | | | | |
|--|--|--|--|--|--|--|--|--|--|--|--|--|--|--|--|
| gga | gcc | act | cgt | tta | gct | ggg | cta | ttc | gcg | aaa | ccc | agc | caa | cac | agt | 224
| Gly | Ala | Thr | Arg | Leu | Ala | Gly | Leu | Phe | Ala | Lys | Pro | Ser | Gln | His | Ser |
| | | | | 10 | | | | | 15 | | | | | 20 | |

```
att tca ccg ttg att cat aat aca gca ttt caa aat tta gga gtt gat   272
Ile Ser Pro Leu Ile His Asn Thr Ala Phe Gln Asn Leu Gly Val Asp
            25              30              35 gct cgg tat ctg gcg ttt gac gtt gga caa gag aca ttg cca caa gca   320
Ala Arg Tyr Leu Ala Phe Asp Val Gly Gln Glu Thr Leu Pro Gln Ala
            40              45              50 att gaa gcg att cga acg ttt cac atg tta ggg gcc aac tta tca atg   368
Ile Glu Ala Ile Arg Thr Phe His Met Leu Gly Ala Asn Leu Ser Met
 55              60              65 ccc aat aaa gtg gcg gct gta agt tat atg gat gaa cta agt cct acc   416
Pro Asn Lys Val Ala Ala Val Ser Tyr Met Asp Glu Leu Ser Pro Thr
 70              75              80              85 gct caa ctg gtt ggc gca att aat acg att gtc aac aaa gat gga aaa   464
Ala Gln Leu Val Gly Ala Ile Asn Thr Ile Val Asn Lys Asp Gly Lys
            90              95              100 ctt tac gga gac agc acg gat ggt act ggt ttt atg tgg agt ttg aaa   512
Leu Tyr Gly Asp Ser Thr Asp Gly Thr Gly Phe Met Trp Ser Leu Lys
            105             110             115 gag aaa aag gtt gac gtt ttt cag aat aaa atg acc atc tta gga aca   560
Glu Lys Lys Val Asp Val Phe Gln Asn Lys Met Thr Ile Leu Gly Thr
            120             125             130 ggt ggt gca gcc tta tca atc att gcc caa gct gct tta gat ggc gtg   608
Gly Gly Ala Ala Leu Ser Ile Ile Ala Gln Ala Ala Leu Asp Gly Val
 135             140             145 aaa gaa atc gcc gtt tac aac agg aaa agc gcg ggc ttt aac gac agt   656
Lys Glu Ile Ala Val Tyr Asn Arg Lys Ser Ala Gly Phe Asn Asp Ser
150             155             160             165 caa aaa aaa ctg gca aat ttc act gaa cga acc aac tgt gta att cat   704
Gln Lys Lys Leu Ala Asn Phe Thr Glu Arg Thr Asn Cys Val Ile His
            170             175             180 tta aac gat tta gcg gat act gaa aaa cta gca aaa gat gtt gct gaa   752
Leu Asn Asp Leu Ala Asp Thr Glu Lys Leu Ala Lys Asp Val Ala Glu
            185             190             195 agc gtc ttg tta gtt aat gca acg agt gtg ggt atg cat cca cat gcg   800
Ser Val Leu Leu Val Asn Ala Thr Ser Val Gly Met His Pro His Ala
 200             205             210 cat agt agt cct ata gaa aat tat gca atg att caa ccg aag tta ttt   848
```

```
    His Ser Ser Pro Ile Glu Asn Tyr Ala Met Ile Gln Pro Lys Leu Phe
        215             220             225 gtg tat gat gct att tat aat ccc aga gaa aca cag tta tta aaa gaa          896
Val Tyr Asp Ala Ile Tyr Asn Pro Arg Glu Thr Gln Leu Leu Lys Glu
230             235             240             245 gcc cgt tta cgt ggt gca gaa aca agc aac ggc ttg gac atg cta ctt          944
Ala Arg Leu Arg Gly Ala Glu Thr Ser Asn Gly Leu Asp Met Leu Leu
                250             255             260 tat caa ggc gct gct gct ttt gaa caa tgg aca gga caa aaa atg cct          992
Tyr Gln Gly Ala Ala Ala Phe Glu Gln Trp Thr Gly Gln Lys Met Pro
            265             270             275 gta tca gtc gta aaa cgt aaa att gaa aat aga taa aaagagcgcc              1038
Val Ser Val Val Lys Arg Lys Ile Glu Asn Arg  *
        280             285 gtttaaaggc atgaggagag aatata atg atc gta att atg aaa gaa aat gca        1091
                             Met Ile Val Ile Met Lys Glu Asn Ala
                                     290             295 acc gaa aag caa atg aaa caa gtc att gat tta gta aca ggt gca ggc         1139
Thr Glu Lys Gln Met Lys Gln Val Ile Asp Leu Val Thr Gly Ala Gly
        300             305             310 tta act act caa aca agt caa gat aat gga aaa aca gtg ata ggc ttg         1187
Leu Thr Thr Gln Thr Ser Gln Asp Asn Gly Lys Thr Val Ile Gly Leu
        315             320             325 att ggt gat aca gaa aaa tta gtt gaa gca gag tta aca gca tta gaa         1235
Ile Gly Asp Thr Glu Lys Leu Val Glu Ala Glu Leu Thr Ala Leu Glu
330             335             340             345 ggc gtg gag aaa agt gtc cgc att tcg ttg tct tac aaa cta acg agt         1283
Gly Val Glu Lys Ser Val Arg Ile Ser Leu Ser Tyr Lys Leu Thr Ser
                350             355             360 cgt tta ttt cat cca gag aat aca gtg gtt gat gtg aac ggt gtt aaa         1331
Arg Leu Phe His Pro Glu Asn Thr Val Val Asp Val Asn Gly Val Lys
            365             370             375 atc ggt gac ggc agt atg acc atg atg gcg ggc cct tgt tca atc gaa         1379
Ile Gly Asp Gly Ser Met Thr Met Met Ala Gly Pro Cys Ser Ile Glu
        380             385             390 agc tta gat cag att cgc gaa tgt gcg cga att gct aaa gct gga ggt         1427
Ser Leu Asp Gln Ile Arg Glu Cys Ala Arg Ile Ala Lys Ala Gly Gly
        395             400             405 gca aca att tta cga ggt ggt gca ttc aaa cct aga acg tcg cca tac         1475
Ala Thr Ile Leu Arg Gly Gly Ala Phe Lys Pro Arg Thr Ser Pro Tyr
410             415             420             425 gct ttc caa gga cta gaa gaa gaa gga cta aaa tac att cgc caa gcg         1523
Ala Phe Gln Gly Leu Glu Glu Glu Gly Leu Lys Tyr Ile Arg Gln Ala
                430             435             440 gct gat gaa tta gat atg caa gtc att aca gaa gtg atg gat gaa gcg         1571
Ala Asp Glu Leu Asp Met Gln Val Ile Thr Glu Val Met Asp Glu Ala
```

```
                445                     450                     455
aat tta gaa ctt gtc gca aaa tac agt gac att tta caa atc ggt gcg    1619
Asn Leu Glu Leu Val Ala Lys Tyr Ser Asp Ile Leu Gln Ile Gly Ala
        460                     465                     470 cgc aac atg caa aat ttc aag tta tta caa gcg gtt ggt aaa act gga    1667
Arg Asn Met Gln Asn Phe Lys Leu Leu Gln Ala Val Gly Lys Thr Gly
    475                     480                     485 aaa cct att ggc tta aaa cgc ggg att gct ggt acg att gat gaa tgg    1715
Lys Pro Ile Gly Leu Lys Arg Gly Ile Ala Gly Thr Ile Asp Glu Trp
490                     495                     500             505 cta aac gca gct gaa tac att gct gcg caa gga aat ttc aat gtg atc    1763
Leu Asn Ala Ala Glu Tyr Ile Ala Ala Gln Gly Asn Phe Asn Val Ile
            510                     515                     520 ttc att gaa cgt ggg att cgt acg tac gaa acc gct acg cgc aat aca    1811
Phe Ile Glu Arg Gly Ile Arg Thr Tyr Glu Thr Ala Thr Arg Asn Thr
        525                     530                     535 ctt gat tta agt gcg gtg cct tta att aaa aaa tta agt cat ttt cca    1859
Leu Asp Leu Ser Ala Val Pro Leu Ile Lys Lys Leu Ser His Phe Pro
        540                     545                     550 att att gtt gat ccg agt cat ggt gtt ggt atc tgg gat tta gta ccg    1907
Ile Ile Val Asp Pro Ser His Gly Val Gly Ile Trp Asp Leu Val Pro
555                     560                     565 cca atg gcc cga gca ggt gtt gct tca ggt gcg gac ggc ttg att gta    1955
Pro Met Ala Arg Ala Gly Val Ala Ser Gly Ala Asp Gly Leu Ile Val
570                     575                     580                     585 gaa att cat cca gat cca gcg aat gcg tgg tca gat ggg cca caa tcc    2003
Glu Ile His Pro Asp Pro Ala Asn Ala Trp Ser Asp Gly Pro Gln Ser
                590                     595                     600 ttg aat gaa aaa act tac cta cgt atg atg aaa gaa gtt cat atc atc    2051
Leu Asn Glu Lys Thr Tyr Leu Arg Met Met Lys Glu Val His Ile Ile
        605                     610                     615 gaa aaa gca atg aaa gaa att aat gct tta gaa gat tag taaagacaga    2100
Glu Lys Ala Met Lys Glu Ile Asn Ala Leu Glu Asp *
        620                     625 ggagtagagg ac atg aaa tta acc gta acg tta cct aca cat tca tat gat 2153
              Met Lys Leu Thr Val Thr Leu Pro Thr His Ser Tyr Asp
                    630                     635                     640 tta acc atc gaa aca ggt gcc tta gat aaa att ggc acc tgg gta cgt    2199
Leu Thr Ile Glu Thr Gly Ala Leu Asp Lys Ile Gly Thr Trp Val Arg
        645                     650                     655 agc ctg tgg cag cca caa cgg gta gcg att att acc gat gaa acg gtg    2247
Ser Leu Trp Gln Pro Gln Arg Val Ala Ile Ile Thr Asp Glu Thr Val
    660                     665                     670 aat aaa tta tat ggc gca gct gtt gag aaa gaa ttg caa gct gct ggt    2295
Asn Lys Leu Tyr Gly Ala Ala Val Glu Lys Glu Leu Gln Ala Ala Gly
675                     680                     685                     690
```

Fig. 15A
3 of 12

```
ttt gaa aca tca ttg att gct gta gcg gca ggt gaa caa agt aag agc    2343
Phe Glu Thr Ser Leu Ile Ala Val Ala Ala Gly Glu Gln Ser Lys Ser
                695                 700                 705 ctc gaa ata gct caa ctg ctt tat gat ttt tta gcg gaa cag caa ttg    2391
Leu Glu Ile Ala Gln Leu Leu Tyr Asp Phe Leu Ala Glu Gln Gln Leu
                710                 715                 720 act cga agt gat ggt cta att gct tta ggt gga ggc gtt gtg gga gat    2439
Thr Arg Ser Asp Gly Leu Ile Ala Leu Gly Gly Gly Val Val Gly Asp
                725                 730                 735 cta gct gga ttt gtc gct tca acc tat atg cgc ggt att cac ttt ttg    2487
Leu Ala Gly Phe Val Ala Ser Thr Tyr Met Arg Gly Ile His Phe Leu
        740                 745                 750 caa gta cca aca acc tta ctg gca caa gta gat agt agc att gga ggt    2535
Gln Val Pro Thr Thr Leu Leu Ala Gln Val Asp Ser Ser Ile Gly Gly
755                 760                 765                 770 aaa aca gcg gtt aat act aaa aaa gcc aaa aat ctt gtc ggt act ttt    2583
Lys Thr Ala Val Asn Thr Lys Lys Ala Lys Asn Leu Val Gly Thr Phe
                775                 780                 785 gcc caa cca gat ggg gtt tta att gat cct aat aca ctt aaa aca tta    2631
Ala Gln Pro Asp Gly Val Leu Ile Asp Pro Asn Thr Leu Lys Thr Leu
                790                 795                 800 gaa cct aga cgt gtg cgt gaa gga att gca gaa att gta aaa tca gca    2679
Glu Pro Arg Arg Val Arg Glu Gly Ile Ala Glu Ile Val Lys Ser Ala
                805                 810                 815 gct atc gct gat gtt gaa ttg tgg cac cgt tta tcc tct ttg gaa aat    2727
Ala Ile Ala Asp Val Glu Leu Trp His Arg Leu Ser Ser Leu Glu Asn
        820                 825                 830 gaa caa gat tta gtg gca cat gca gaa gaa att atc acg gcc tgt tgc    2775
Glu Gln Asp Leu Val Ala His Ala Glu Glu Ile Ile Thr Ala Cys Cys
835                 840                 845                 850 aag att aaa cgt gat gtc gtc gaa gaa gat gaa tta gat ttg ggc tta    2823
Lys Ile Lys Arg Asp Val Val Glu Glu Asp Glu Leu Asp Leu Gly Leu
                855                 860                 865 cgt ttg att ctg aat ttt ggg cat acg atc ggc cac gca tta gaa aat    2871
Arg Leu Ile Leu Asn Phe Gly His Thr Ile Gly His Ala Leu Glu Asn
                870                 875                 880 aca gct ggt tac ggg gtg att gct cac ggt gaa ggc gtt tct tta gga    2919
Thr Ala Gly Tyr Gly Val Ile Ala His Gly Glu Gly Val Ser Leu Gly
                885                 890                 895 atg att caa ata act caa gtc gca gaa caa caa ggg ctt tcc cca ctt    2967
Met Ile Gln Ile Thr Gln Val Ala Glu Gln Gln Gly Leu Ser Pro Leu
900                 905                 910 ggg act acc caa gag ttg gtc acc atg cta gaa aag ttc cat tta cca    3015
Gly Thr Thr Gln Glu Leu Val Thr Met Leu Glu Lys Phe His Leu Pro
915                 920                 925                 930
```

Fig. 15A

```
gta acc aca gat cgt tgg tca gaa gaa cgt ctc tat caa gca att aca    3063
Val Thr Thr Asp Arg Trp Ser Glu Glu Arg Leu Tyr Gln Ala Ile Thr
            935                 940                 945 cat gat aaa aaa aca cgt ggg gga cag att aaa atc att gtc tta gaa    3111
His Asp Lys Lys Thr Arg Gly Gly Gln Ile Lys Ile Ile Val Leu Glu
            950                 955                 960 aaa att ggt caa gcg aaa att gtc tct tta cca acg gaa gaa att cga    3159
Lys Ile Gly Gln Ala Lys Ile Val Ser Leu Pro Thr Glu Glu Ile Arg
            965                 970                 975 gca ttt tta aac aga gaa gga gga att taa g atg cgc ttt att aca gca  3208
Ala Phe Leu Asn Arg Glu Gly Gly Ile  *   Met Arg Phe Ile Thr Ala
            980                 985                 990 ggc gaa tca cat gga cct gaa tta act gct att att gaa ggc tta cca    3256
Gly Glu Ser His Gly Pro Glu Leu Thr Ala Ile Ile Glu Gly Leu Pro
            995                 1000                1005 gcc ggc ttg cct tta agt agc gaa gag att aac cga gaa tta gca aga    3304
Ala Gly Leu Pro Leu Ser Ser Glu Glu Ile Asn Arg Glu Leu Ala Arg
1010                1015                1020                1025 cgt caa ggc ggt tac ggt cgt ggg gga cgg atg aaa att gaa aaa gac    3352
Arg Gln Gly Gly Tyr Gly Arg Gly Gly Arg Met Lys Ile Glu Lys Asp
                    1030                1035                1040 caa gta cgt att act tcg ggt att cgg cat ggt aaa aca ctt ggc tca    3400
Gln Val Arg Ile Thr Ser Gly Ile Arg His Gly Lys Thr Leu Gly Ser
                1045                1050                1055 cca gta acg ttg att gtc gaa aac aaa gac tgg aaa aat tgg acc tcc    3448
Pro Val Thr Leu Ile Val Glu Asn Lys Asp Trp Lys Asn Trp Thr Ser
                1060                1065                1070 gtg atg tca gta gag cca gtt cct gaa aaa caa aag aaa atc cgc cgc    3496
Val Met Ser Val Glu Pro Val Pro Glu Lys Gln Lys Lys Ile Arg Arg
    1075                1080                1085 gtc agc aaa cca cgt cca gga cat gct gat tta gtc ggt ggc atg aaa    3544
Val Ser Lys Pro Arg Pro Gly His Ala Asp Leu Val Gly Gly Met Lys
1090                1095                1100                1105 tat caa cat gat gat tta cgg aat gtt tta gaa cgg tct tcg gca cga    3592
Tyr Gln His Asp Asp Leu Arg Asn Val Leu Glu Arg Ser Ser Ala Arg
                    1110                1115                1120 gaa aca acg atg cgt gtg gcg att ggt gcg gtt gct aaa aaa ctc tta    3640
Glu Thr Thr Met Arg Val Ala Ile Gly Ala Val Ala Lys Lys Leu Leu
                1125                1130                1135 gct gaa ctg gat atc caa gtc gct ggg cat gtc gcg gta tta ggt ggg    3688
Ala Glu Leu Asp Ile Gln Val Ala Gly His Val Ala Val Leu Gly Gly
                1140                1145                1150 att gaa gct acg atc cct gaa aat tta acg att cgt gaa att caa gaa    3736
Ile Glu Ala Thr Ile Pro Glu Asn Leu Thr Ile Arg Glu Ile Gln Glu
                1155                1160                1165 cga tct gaa caa tct gcc gtt cgc gta tta gat cct tcc gta gaa gaa    3784
```

```
            Arg Ser Glu Gln Ser Ala Val Arg Val Leu Asp Pro Ser Val Glu Glu
            1170            1175            1180            1185 aaa atg aaa gaa cta att gac caa acc aag aaa aat ggc gat aca att       3832
Lys Met Lys Glu Leu Ile Asp Gln Thr Lys Lys Asn Gly Asp Thr Ile
                1190            1195            1200 ggt ggg gta gta gaa gta ctt gtg ggt ggc gtt cca gct ggc tta ggt       3880
Gly Gly Val Val Glu Val Leu Val Gly Gly Val Pro Ala Gly Leu Gly
                1205            1210            1215 agc tat gtc caa tgg gat cgt aaa cta gat gcc aaa att gcg caa gca       3928
Ser Tyr Val Gln Trp Asp Arg Lys Leu Asp Ala Lys Ile Ala Gln Ala
                1220            1225            1230 gtt gta agc atc aac gct ttt aca ggt gct gag ttt ggc att gga ttt       3976
Val Val Ser Ile Asn Ala Phe Thr Gly Ala Glu Phe Gly Ile Gly Phe
                1235            1240            1245 gaa atg gca caa cgc cct ggt agt caa ctg atg gac gag att gtt tgg       4024
Glu Met Ala Gln Arg Pro Gly Ser Gln Leu Met Asp Glu Ile Val Trp
1250            1255            1260            1265 gac gaa agt act ggt tat acc aga act tcc aac aat tta ggc ggt ttt       4072
Asp Glu Ser Thr Gly Tyr Thr Arg Thr Ser Asn Asn Leu Gly Gly Phe
                1270            1275            1280 gaa gga gga atg acc aac gga atg cca atc atc gtt cgt ggt gtc atg       4120
Glu Gly Gly Met Thr Asn Gly Met Pro Ile Ile Val Arg Gly Val Met
                1285            1290            1295 aaa cct att cca acc ctt tat aaa cca tta caa agc gtg aat att gat       4168
Lys Pro Ile Pro Thr Leu Tyr Lys Pro Leu Gln Ser Val Asn Ile Asp
                1300            1305            1310 aca aaa gag cct tat aag gcc agt gtt gag cgc tct gat agc acg gcg       4216
Thr Lys Glu Pro Tyr Lys Ala Ser Val Glu Arg Ser Asp Ser Thr Ala
                1315            1320            1325 gta ccg gcc gct agc gtt gtt tgt gaa gcc gtt gtt gca acg gaa gta       4264
Val Pro Ala Ala Ser Val Val Cys Glu Ala Val Val Ala Thr Glu Val
1330            1335            1340            1345 gca aag gct atg ctc gaa aaa ttt gat agt gac tca ttt gaa caa atg       4312
Ala Lys Ala Met Leu Glu Lys Phe Asp Ser Asp Ser Phe Glu Gln Met
                1350            1355            1360 aaa gaa gca gtg aaa cgt tat cgt cta tat act caa aac ttt taa          4357
Lys Glu Ala Val Lys Arg Tyr Arg Leu Tyr Thr Gln Asn Phe *
                1365            1370            1375 tggaagaaag tcgcaagtat atggagggaa aaa atg aag aaa cgt att tta atc    4411
                                    Met Lys Lys Arg Ile Leu Ile
                                                        1380 gta gga tta ggg cta atc ggg agt tca ctg gct ttg tgt atc aaa aaa      4459
Val Gly Leu Gly Leu Ile Gly Ser Ser Leu Ala Leu Cys Ile Lys Lys
            1385            1390            1395 ggg cat cca aac agt gag att atc ggt ttc gat aat caa gcg gag gca      4507
Gly His Pro Asn Ser Glu Ile Ile Gly Phe Asp Asn Gln Ala Glu Ala
```

```
                1400                    1405                    1410
act gaa ttt gct aag aaa acg ggt cta att gat gag ata gct gaa tct    4555
Thr Glu Phe Ala Lys Lys Thr Gly Leu Ile Asp Glu Ile Ala Glu Ser
1415                1420                    1425                1430 tta aca agt ggg gca aga cga gca gag att att ttt ctt tgt tcc cca    4603
Leu Thr Ser Gly Ala Arg Arg Ala Glu Ile Ile Phe Leu Cys Ser Pro
                    1435                    1440                1445 gtt aaa gca act tta gta caa cta gaa gaa tta aac caa tta tca cta    4651
Val Lys Ala Thr Leu Val Gln Leu Glu Glu Leu Asn Gln Leu Ser Leu
                1450                    1455                1460 gaa act gct ctg atc aca gat gtg ggt agt acc aag gtg gaa att aat    4699
Glu Thr Ala Leu Ile Thr Asp Val Gly Ser Thr Lys Val Glu Ile Asn
            1465                    1470                1475 cag tta gca aca aag ctt aac atg aaa aat ttt att ggt ggt cat cca    4747
Gln Leu Ala Thr Lys Leu Asn Met Lys Asn Phe Ile Gly Gly His Pro
        1480                    1485                1490 atg gct ggt tca cat aaa tcc ggc gta aca gcc gct gat gaa cgt ttg    4795
Met Ala Gly Ser His Lys Ser Gly Val Thr Ala Ala Asp Glu Arg Leu
1495                1500                    1505                1510 ttt gaa aat gcc tac tat att ttt acc gat gac cat ggc gaa aaa aac    4843
Phe Glu Asn Ala Tyr Tyr Ile Phe Thr Asp Asp His Gly Glu Lys Asn
                    1515                    1520                1525 aaa cag att cag gag tta caa acg tta cta aaa gga acg cat gcg aag    4891
Lys Gln Ile Gln Glu Leu Gln Thr Leu Leu Lys Gly Thr His Ala Lys
                1530                    1535                1540 ttt att acg atg cct gca cag gaa cat gat gaa att act ggt gct cta    4939
Phe Ile Thr Met Pro Ala Gln Glu His Asp Glu Ile Thr Gly Ala Leu
            1545                    1550                1555 agt cac ttg cca cat att gtt gcc gca gcg tta gtg aac gaa agt cag    4987
Ser His Leu Pro His Ile Val Ala Ala Ala Leu Val Asn Glu Ser Gln
        1560                    1565                1570 caa ctg aat acc act tac cct aga gcg cag cag cta gcg gct gga gga    5035
Gln Leu Asn Thr Thr Tyr Pro Arg Ala Gln Gln Leu Ala Ala Gly Gly
1575                1580                    1585                1590 ttc aga gat att act cga att gct tcc tct gat gca acg atg tgg acg    5083
Phe Arg Asp Ile Thr Arg Ile Ala Ser Ser Asp Ala Thr Met Trp Thr
                    1595                    1600                1605 gat att tta tta agc aat cgc tta gta tta ttg gac tta cta gaa aat    5131
Asp Ile Leu Leu Ser Asn Arg Leu Val Leu Leu Asp Leu Leu Glu Asn
                1610                    1615                1620 tgg caa aaa gag atg act act gtt tgc caa tgg tta aca gaa aaa aat    5179
Trp Gln Lys Glu Met Thr Thr Val Cys Gln Trp Leu Thr Glu Lys Asn
            1625                    1630                1635 gcc cca gct att cgt aat ttt ttt gat aag gcc aaa gaa aca cgt gct    5227
Ala Pro Ala Ile Arg Asn Phe Phe Asp Lys Ala Lys Glu Thr Arg Ala
        1640                    1645                1650
```

```
caa ttg cct att cat aaa gaa ggc gca atc cca gct ttc tat gat ctg    5275
Gln Leu Pro Ile His Lys Glu Gly Ala Ile Pro Ala Phe Tyr Asp Leu
1655             1660             1665             1670 ttt gtt gat gta cca gat caa cca gga atc att gct gaa att acg caa    5323
Phe Val Asp Val Pro Asp Gln Pro Gly Ile Ile Ala Glu Ile Thr Gln
             1675             1680             1685 att tta ggc gaa gcg gac ctt tct ctt aca aat att aaa att tta gaa    5371
Ile Leu Gly Glu Ala Asp Leu Ser Leu Thr Asn Ile Lys Ile Leu Glu
         1690             1695             1700 acg aga gaa gaa atc tat ggg att ctt caa ttg tct ttt aaa aat caa    5419
Thr Arg Glu Glu Ile Tyr Gly Ile Leu Gln Leu Ser Phe Lys Asn Gln
     1705             1710             1715 cca gac tgc caa gct gca aaa caa att tta tct aaa aaa acg aac tat    5467
Pro Asp Cys Gln Ala Ala Lys Gln Ile Leu Ser Lys Lys Thr Asn Tyr
     1720             1725             1730 acg tgt tac gaa aaa taa gaggtg atg agg gtg caa cta cgt aca aat    5515
Thr Cys Tyr Glu Lys  *        Met Arg Val Gln Leu Arg Thr Asn
1735                              1740             1745 gtg aag cat tta caa ggg act ctg atg gtt cct agc gac aaa tcg att    5563
Val Lys His Leu Gln Gly Thr Leu Met Val Pro Ser Asp Lys Ser Ile
         1750             1755             1760 tcc cat aga agt att atg ttt gga gcg att tct tct gga aaa acg acg    5611
Ser His Arg Ser Ile Met Phe Gly Ala Ile Ser Ser Gly Lys Thr Thr
     1765             1770             1775 att aca aat ttt cta aga ggc gaa gat tgt tta agt acc tta gcg gcg    5659
Ile Thr Asn Phe Leu Arg Gly Glu Asp Cys Leu Ser Thr Leu Ala Ala
1780             1785             1790             1795 ttt cgt tct tta ggt gtg aac att gaa gat gac ggg acg aca atc acc    5707
Phe Arg Ser Leu Gly Val Asn Ile Glu Asp Asp Gly Thr Thr Ile Thr
             1800             1805             1810 gtt gag ggg cga gga ttt gca ggc tta aaa aag gcg aag aat aca att    5755
Val Glu Gly Arg Gly Phe Ala Gly Leu Lys Lys Ala Lys Asn Thr Ile
         1815             1820             1825 gat gtt gga aat tca ggg aca aca att cgt ctg atg ctg ggc att tta    5803
Asp Val Gly Asn Ser Gly Thr Thr Ile Arg Leu Met Leu Gly Ile Leu
     1830             1835             1840 gct ggc tgt ccc ttt gaa acg cgc cta gct ggt gat gcg tct att gcc    5851
Ala Gly Cys Pro Phe Glu Thr Arg Leu Ala Gly Asp Ala Ser Ile Ala
     1845             1850             1855 aaa cga cca atg aat cgt gta atg ctt cct tta aac caa atg gga gcg    5899
Lys Arg Pro Met Asn Arg Val Met Leu Pro Leu Asn Gln Met Gly Ala
1860             1865             1870             1875 gaa tgt caa ggg gtt cag caa acg gag ttt ccg cca att tct att cgc    5947
Glu Cys Gln Gly Val Gln Gln Thr Glu Phe Pro Pro Ile Ser Ile Arg
             1880             1885             1890
```

Fig. 15A

```
ggg act caa aat ttg caa ccg att gac tac aca atg cct gtt gca agt    5995
Gly Thr Gln Asn Leu Gln Pro Ile Asp Tyr Thr Met Pro Val Ala Ser
        1895            1900            1905 gct caa gtt aaa tcg gct att tta ttc gcc gct ttg caa gcc gag ggc    6043
Ala Gln Val Lys Ser Ala Ile Leu Phe Ala Ala Leu Gln Ala Glu Gly
    1910            1915            1920 act tct gta gtg gtt gag aaa gaa aag aca cgt gat cat aca gaa gag    6091
Thr Ser Val Val Val Glu Lys Glu Lys Thr Arg Asp His Thr Glu Glu
        1925            1930            1935 atg att cga caa ttt ggt ggg aca ctt gaa gta gac ggt aaa aaa att    6139
Met Ile Arg Gln Phe Gly Gly Thr Leu Glu Val Asp Gly Lys Lys Ile
1940            1945            1950            1955 atg tta act gga ccg caa caa tta aca ggt caa aat gtg gta gtt cct    6187
Met Leu Thr Gly Pro Gln Gln Leu Thr Gly Gln Asn Val Val Val Pro
            1960            1965            1970 ggt gat atc tct tct gca gct ttc ttt tta gtt gcg ggt tta gta gtc    6235
Gly Asp Ile Ser Ser Ala Ala Phe Phe Leu Val Ala Gly Leu Val Val
        1975            1980            1985 cca gat agc gag ata ctt ctg aaa aat gtt ggc tta aat caa acg cgg    6283
Pro Asp Ser Glu Ile Leu Leu Lys Asn Val Gly Leu Asn Gln Thr Arg
    1990            1995            2000 aca ggt att tta gat gtg att aaa aac atg ggc ggt tcc gtc act att    6331
Thr Gly Ile Leu Asp Val Ile Lys Asn Met Gly Gly Ser Val Thr Ile
    2005            2010            2015 tta aat gaa gat gag gcc aat cat tct ggc gat tta ctt gta aaa acg    6379
Leu Asn Glu Asp Glu Ala Asn His Ser Gly Asp Leu Leu Val Lys Thr
2020            2025            2030            2035 agt caa tta aca gct aca gag att ggt ggc gct att atc cca cgt tta    6427
Ser Gln Leu Thr Ala Thr Glu Ile Gly Gly Ala Ile Ile Pro Arg Leu
            2040            2045            2050 att gat gag tta ccg att att gct ttg tta gct act cag gct act ggc    6475
Ile Asp Glu Leu Pro Ile Ile Ala Leu Leu Ala Thr Gln Ala Thr Gly
        2055            2060            2065 acg aca atc att cga gat gca gaa gaa ttg aaa gtc aaa gaa acc aat    6523
Thr Thr Ile Ile Arg Asp Ala Glu Glu Leu Lys Val Lys Glu Thr Asn
    2070            2075            2080 cgg att gat gca gta gcg aaa gaa tta aca att tta ggc gcc gac atc    6571
Arg Ile Asp Ala Val Ala Lys Glu Leu Thr Ile Leu Gly Ala Asp Ile
    2085            2090            2095 acg cct act gat gat ggc tta att ata cat gga cca act tct tta cat    6619
Thr Pro Thr Asp Asp Gly Leu Ile Ile His Gly Pro Thr Ser Leu His
2100            2105            2110            2115 ggt gga aga gtt acc agt tat ggg gat cat cgt atc ggg atg atg tta    6667
Gly Gly Arg Val Thr Ser Tyr Gly Asp His Arg Ile Gly Met Met Leu
            2120            2125            2130 caa att gct gca tta ctt gta aaa gaa ggc act gtt gaa tta gat aag    6715
```

Fig. 15A

```
                Gln Ile Ala Ala Leu Leu Val Lys Glu Gly Thr Val Glu Leu Asp Lys
                                2135            2140            2145 gct gaa gca gtt tca gtt tct tat cca gca ttt ttt gac gac tta gaa     6763
Ala Glu Ala Val Ser Val Ser Tyr Pro Ala Phe Phe Asp Asp Leu Glu
        2150            2155            2160 cgt tta agt tgt taa cgaaggagga taacga acc atg gaa agc att gtt tta  6815
Arg Leu Ser Cys *                       Thr Met Glu Ser Ile Val Leu
        2165                                        2170 att ggt ttc atg ggt gcg ggt aaa aca act atc ggc caa agt ttg gcc    6863
Ile Gly Phe Met Gly Ala Gly Lys Thr Thr Ile Gly Gln Ser Leu Ala
2175            2180            2185            2190 aat aaa ctg aag atg cct cat ctt gat tta gat aca gcg tta att gaa    6911
Asn Lys Leu Lys Met Pro His Leu Asp Leu Asp Thr Ala Leu Ile Glu
                2195            2200            2205 aaa ata gga cgc tca att cct gac tat ttc gaa aaa tat ggt gaa gca    6959
Lys Ile Gly Arg Ser Ile Pro Asp Tyr Phe Glu Lys Tyr Gly Glu Ala
                2210            2215            2220 gct ttc cga gaa cag gaa acc caa ctt tta aag gag ctg tca aaa aat    7007
Ala Phe Arg Glu Gln Glu Thr Gln Leu Leu Lys Glu Leu Ser Lys Asn
        2225            2230            2235 aca gcc gtc ctt tca act ggg ggc ggg att gtt gtc gga cca gaa aat    7055
Thr Ala Val Leu Ser Thr Gly Gly Gly Ile Val Val Gly Pro Glu Asn
        2240            2245            2250 cgt agc tta tta aaa tct ttt cag caa gtg att tat tta cat gcg aca    7103
Arg Ser Leu Leu Lys Ser Phe Gln Gln Val Ile Tyr Leu His Ala Thr
2255            2260            2265            2270 cca gaa gag ctg tta aaa aga atc aca gaa gat act gaa aac caa cgg    7151
Pro Glu Glu Leu Leu Lys Arg Ile Thr Glu Asp Thr Glu Asn Gln Arg
                2275            2280            2285 ccc tta gct ata gaa cgt tct tca aaa gaa atc att act ttg ttt gag    7199
Pro Leu Ala Ile Glu Arg Ser Ser Lys Glu Ile Ile Thr Leu Phe Glu
        2290            2295            2300 tct cgt aaa aat ttt tat gaa gaa tgt gcg aag atg aca att gat acg    7247
Ser Arg Lys Asn Phe Tyr Glu Glu Cys Ala Lys Met Thr Ile Asp Thr
        2305            2310            2315 acc aat cgc tcg cca gaa gaa att atc aat gaa att ctg caa caa tta   7295
Thr Asn Arg Ser Pro Glu Glu Ile Ile Asn Glu Ile Leu Gln Gln Leu
        2320            2325            2330 aag gag tag agaaacg atg aaa gtt ggt tat tta ggt ccg att ggt tcc   7344
Lys Glu *        Met Lys Val Gly Tyr Leu Gly Pro Ile Gly Ser
2335                    2340            2345 ttt acg tac agt gca acg ttg gct gct ttt cct gaa gct acg ttg atg   7392
Phe Thr Tyr Ser Ala Thr Leu Ala Ala Phe Pro Glu Ala Thr Leu Met
        2350            2355            2360 ccg tac gca tcg att cca gct tgc ttg aaa gca att gaa cag caa gaa   7440
Pro Tyr Ala Ser Ile Pro Ala Cys Leu Lys Ala Ile Glu Gln Gln Glu
```

```
              2365                    2370                    2375
gtg gca tgg agc att atc cca ata gaa aac acg att gaa gga act gtt   7488
Val Ala Trp Ser Ile Ile Pro Ile Glu Asn Thr Ile Glu Gly Thr Val
2380            2385                    2390                    2395 aac gca tcg ata gat tat ttg tat cat caa gcg cag tta cct gtc caa   7536
Asn Ala Ser Ile Asp Tyr Leu Tyr His Gln Ala Gln Leu Pro Val Gln
                2400                    2405                    2410 gca gag tta gtt tta ccg att caa caa caa tta atg gtg gca aaa gag   7584
Ala Glu Leu Val Leu Pro Ile Gln Gln Gln Leu Met Val Ala Lys Glu
        2415                    2420                    2425 aat caa gcg atc tgg caa caa agt cag aaa att tta tca cat ccg caa   7632
Asn Gln Ala Ile Trp Gln Gln Ser Gln Lys Ile Leu Ser His Pro Gln
            2430                    2435                    2440 gca tta gct caa tcg cag atg ttt cta gag aaa aac ttt cca gaa gcg   7680
Ala Leu Ala Gln Ser Gln Met Phe Leu Glu Lys Asn Phe Pro Glu Ala
        2445                    2450                    2455 att tta gaa gca aca cct tca aca gct tac gcc gcc aaa tac att gca   7728
Ile Leu Glu Ala Thr Pro Ser Thr Ala Tyr Ala Ala Lys Tyr Ile Ala
2460            2465                    2470                    2475 gaa cat cca gaa tta cct ttt gca gct att gca cca aaa ctt tct gcg   7776
Glu His Pro Glu Leu Pro Phe Ala Ala Ile Ala Pro Lys Leu Ser Ala
                2480                    2485                    2490 gaa atg tat gat ttg acc att gtt gaa aaa aat ata caa gat tta tcg   7824
Glu Met Tyr Asp Leu Thr Ile Val Glu Lys Asn Ile Gln Asp Leu Ser
        2495                    2500                    2505 gta aat caa acc cga ttt tgg gtt ctt ggt tct gaa aat tta gcg att   7872
Val Asn Gln Thr Arg Phe Trp Val Leu Gly Ser Glu Asn Leu Ala Ile
            2510                    2515                    2520 tct ttc ccg cta tct gag aaa aaa ata aca ctg gcg att acg atg cca   7920
Ser Phe Pro Leu Ser Glu Lys Lys Ile Thr Leu Ala Ile Thr Met Pro
2525            2530                    2535 agt aat gtt cct ggc tct tta cac aaa gta tta agc gtg ttt agt tgg   7968
Ser Asn Val Pro Gly Ser Leu His Lys Val Leu Ser Val Phe Ser Trp
2540            2545                    2550                    2555 cga ggg att aat ctt agc aaa ata gaa tcg cgg ccg ttg aaa aca aag   8016
Arg Gly Ile Asn Leu Ser Lys Ile Glu Ser Arg Pro Leu Lys Thr Lys
                2560                    2565                    2570 cta gga gag tac ttc ttt tta atg gac tta gtg aaa gat caa cca gaa   8064
Leu Gly Glu Tyr Phe Phe Leu Met Asp Leu Val Lys Asp Gln Pro Glu
        2575                    2580                    2585 aaa tta att gaa gca gcc tta aca gaa ctg aaa ctc att ggt gca gaa   8112
Lys Leu Ile Glu Ala Ala Leu Thr Glu Leu Glu Leu Ile Gly Ala Glu
            2590                    2595                    2600 ata aaa att tta ggg gat tac ccg atc tat gtt ttg tcc aca ctt taa   8160
Ile Lys Ile Leu Gly Asp Tyr Pro Ile Tyr Val Leu Ser Thr Leu *
2605            2610                    2615
```

```
agagttaaaa atgaaaatga agcttactta ttagataaag tgagtttcat tttttattaa 8220
attacatatt tgtaatagga atttcctgtg aaatgaggta tcctaagaaa ggtgataaaa 8280
cacagaggta aaggagtgac acgatgagtc gtgtagatcg ttataaacat attcatgaaa 8340
tcttttc                                                          8347
```

ORF1

```
atgaaagaaa taactggagc cactcgttta gctgggctat tcgcgaaacc cagccaacac  60
agtatttcac cgttgattca taatacagca tttcaaaatt taggagttga tgctcggtat 120
ctggcgtttg acgttggaca agagacattg ccacaagcaa ttgaagcgat tcgaacgttt 180
cacatgttag gggccaactt atcaatgccc aataaagtgg cggctgtaag ttatatggat 240
gaactaagtc ctaccgctca actggttggc gcaattaata cgattgtcaa caaagatgga 300
aaactttacg gagacagcac ggatggtact ggttttatgt ggagtttgaa agagaaaaag 360
gttgacgttt ttcagaataa aatgaccatc ttaggaacag gtggtgcagc cttatcaatc 420
attgcccaag ctgctttaga tggcgtgaaa gaaatcgccg tttacaacag gaaaagcgcg 480
ggctttaacg acagtcaaaa aaaactggca aatttcactg aacgaaccaa ctgtgtaatt 540
catttaaacg atttagcgga tactgaaaaa ctagcaaaag atgttgctga aagcgtcttg 600
ttagttaatg caacgagtgt gggtatgcat ccacatgcgc atagtagtcc tatagaaaat 660
tatgcaatga ttcaaccgaa gttatttgtg tatgatgcta tttataatcc cagagaaaca 720
cagttattaa agaagcccg tttacgtggt gcagaaacaa gcaacggctt ggacatgcta 780
ctttatcaag gcgctgctgc ttttgaacaa tggacaggac aaaaaatgcc tgtatcagtc 840
gtaaaacgta aaattgaaaa tagataa                                     867
```

Figure 15C

ORF1

| | | | | | | | | | | | | | | |
|---|---|---|---|---|---|---|---|---|---|---|---|---|---|---|
| Met | Lys | Glu | Ile | Thr | Gly | Ala | Thr | Arg | Leu | Ala | Gly | Leu | Phe | Ala | Lys |
| 1 | | | | 5 | | | | | 10 | | | | | 15 |
| Pro | Ser | Gln | His | Ser | Ile | Ser | Pro | Leu | Ile | His | Asn | Thr | Ala | Phe | Gln |
| | | | 20 | | | | | 25 | | | | | 30 | | |
| Asn | Leu | Gly | Val | Asp | Ala | Arg | Tyr | Leu | Ala | Phe | Asp | Val | Gly | Gln | Glu |
| | | 35 | | | | | 40 | | | | | 45 | | | |
| Thr | Leu | Pro | Gln | Ala | Ile | Glu | Ala | Ile | Arg | Thr | Phe | His | Met | Leu | Gly |
| | 50 | | | | | 55 | | | | | 60 | | | | |
| Ala | Asn | Leu | Ser | Met | Pro | Asn | Lys | Val | Ala | Ala | Val | Ser | Tyr | Met | Asp |
| 65 | | | | | 70 | | | | | 75 | | | | | 80 |
| Glu | Leu | Ser | Pro | Thr | Ala | Gln | Leu | Val | Gly | Ala | Ile | Asn | Thr | Ile | Val |
| | | | | 85 | | | | | 90 | | | | | 95 | |
| Asn | Lys | Asp | Gly | Lys | Leu | Tyr | Gly | Asp | Ser | Thr | Asp | Gly | Thr | Gly | Phe |
| | | | 100 | | | | | 105 | | | | | 110 | | |
| Met | Trp | Ser | Leu | Lys | Glu | Lys | Lys | Val | Asp | Val | Phe | Gln | Asn | Lys | Met |
| | | | 115 | | | | | 120 | | | | | 125 | | |
| Thr | Ile | Leu | Gly | Thr | Gly | Gly | Ala | Ala | Leu | Ser | Ile | Ile | Ala | Gln | Ala |
| | | 130 | | | | | 135 | | | | | 140 | | | |
| Ala | Leu | Asp | Gly | Val | Lys | Glu | Ile | Ala | Val | Tyr | Asn | Arg | Lys | Ser | Ala |
| 145 | | | | | 150 | | | | | 155 | | | | | 160 |
| Gly | Phe | Asn | Asp | Ser | Gln | Lys | Lys | Leu | Ala | Asn | Phe | Thr | Glu | Arg | Thr |
| | | | | 165 | | | | | 170 | | | | | 175 | |
| Asn | Cys | Val | Ile | His | Leu | Asn | Asp | Leu | Ala | Asp | Thr | Glu | Lys | Leu | Ala |
| | | | 180 | | | | | 185 | | | | | 190 | | |
| Lys | Asp | Val | Ala | Glu | Ser | Val | Leu | Leu | Val | Asn | Ala | Thr | Ser | Val | Gly |
| | | 195 | | | | | 200 | | | | | 205 | | | |
| Met | His | Pro | His | Ala | His | Ser | Ser | Pro | Ile | Glu | Asn | Tyr | Ala | Met | Ile |
| | 210 | | | | | 215 | | | | | 220 | | | | |
| Gln | Pro | Lys | Leu | Phe | Val | Tyr | Asp | Ala | Ile | Tyr | Asn | Pro | Arg | Glu | Thr |
| 225 | | | | | 230 | | | | | 235 | | | | | 240 |
| Gln | Leu | Leu | Lys | Glu | Ala | Arg | Leu | Arg | Gly | Ala | Glu | Thr | Ser | Asn | Gly |
| | | | 245 | | | | | 250 | | | | | 255 | | |
| Leu | Asp | Met | Leu | Leu | Tyr | Gln | Gly | Ala | Ala | Ala | Phe | Glu | Gln | Trp | Thr |
| | | | 260 | | | | | 265 | | | | | 270 | | |
| Gly | Gln | Lys | Met | Pro | Val | Ser | Val | Val | Lys | Arg | Lys | Ile | Glu | Asn | Arg |
| | | 275 | | | | | 280 | | | | | 285 | | | |

Figure 15D

ORF2

```
atgatcgtaa ttatgaaaga aaatgcaacc gaaaagcaaa tgaaacaagt cattgattta 60
gtaacaggtg caggcttaac tactcaaaca agtcaagata atggaaaaac agtgataggc 120
ttgattggtg atacagaaaa attagttgaa gcagagttaa cagcattaga aggcgtggag 180
aaaagtgtcc gcatttcgtt gtcttacaaa ctaacgagtc gtttatttca tccagagaat 240
acagtggttg atgtgaacgg tgttaaaatc ggtgacggca gtatgaccat gatggcgggc 300
ccttgttcaa tcgaaagctt agatcagatt cgcgaatgtg cgcgaattgc taaagctgga 360
ggtgcaacaa ttttacgagg tggtgcattc aaacctagaa cgtcgccata cgctttccaa 420
ggactagaag aagaaggact aaaatacatt cgccaagcgg ctgatgaatt agatatgcaa 480
gtcattacag aagtgatgga tgaagcgaat ttagaacttg tcgcaaaata cagtgacatt 540
ttacaaatcg gtgcgcgcaa catgcaaaat ttcaagttat tacaagcggt tggtaaaact 600
ggaaaaccta ttggcttaaa acgcgggatt gctggtacga ttgatgaatg ctaaacgca 660
gctgaataca ttgctgcgca aggaaatttc aatgtgatct tcattgaacg tgggattcgt 720
acgtacgaaa ccgctacgcg caatacactt gatttaagtg cggtgccttt aattaaaaaa 780
ttaagtcatt ttccaattat tgttgatccg agtcatggtg ttggtatctg ggatttagta 840
ccgccaatgg cccgagcagg tgttgcttca ggtgcggacg gcttgattgt agaaattcat 900
ccagatccag cgaatgcgtg gtcagatggg ccacaatcct tgaatgaaaa aacttaccta 960
cgtatgatga agaagttca tatcatcgaa aaagcaatga agaaattaa tgctttagaa 1020
gattag                                                           1026
```

Figure 15E

ORF2

| | | | | | | | | | | | | | | |
|---|---|---|---|---|---|---|---|---|---|---|---|---|---|---|
| Met | Ile | Val | Ile | Met | Lys | Glu | Asn | Ala | Thr | Glu | Lys | Gln | Met | Lys | Gln |
| 1 | | | | 5 | | | | | 10 | | | | | 15 |
| Val | Ile | Asp | Leu | Val | Thr | Gly | Ala | Gly | Leu | Thr | Thr | Gln | Thr | Ser | Gln |
| | | | 20 | | | | | 25 | | | | | 30 | | |
| Asp | Asn | Gly | Lys | Thr | Val | Ile | Gly | Leu | Ile | Gly | Asp | Thr | Glu | Lys | Leu |
| | | 35 | | | | | 40 | | | | | 45 | | | |
| Val | Glu | Ala | Glu | Leu | Thr | Ala | Leu | Glu | Gly | Val | Glu | Lys | Ser | Val | Arg |
| | 50 | | | | | 55 | | | | | 60 | | | | |
| Ile | Ser | Leu | Ser | Tyr | Lys | Leu | Thr | Ser | Arg | Leu | Phe | His | Pro | Glu | Asn |
| 65 | | | | | 70 | | | | | 75 | | | | | 80 |
| Thr | Val | Val | Asp | Val | Asn | Gly | Val | Lys | Ile | Gly | Asp | Gly | Ser | Met | Thr |
| | | | | 85 | | | | | 90 | | | | | 95 | |
| Met | Met | Ala | Gly | Pro | Cys | Ser | Ile | Glu | Ser | Leu | Asp | Gln | Ile | Arg | Glu |
| | | | 100 | | | | | 105 | | | | | 110 | | |
| Cys | Ala | Arg | Ile | Ala | Lys | Ala | Gly | Gly | Ala | Thr | Ile | Leu | Arg | Gly | Gly |
| | | 115 | | | | | 120 | | | | | 125 | | | |
| Ala | Phe | Lys | Pro | Arg | Thr | Ser | Pro | Tyr | Ala | Phe | Gln | Gly | Leu | Glu | Glu |
| | 130 | | | | | 135 | | | | | 140 | | | | |
| Glu | Gly | Leu | Lys | Tyr | Ile | Arg | Gln | Ala | Ala | Asp | Glu | Leu | Asp | Met | Gln |
| 145 | | | | | 150 | | | | | 155 | | | | | 160 |
| Val | Ile | Thr | Glu | Val | Met | Asp | Glu | Ala | Asn | Leu | Glu | Leu | Val | Ala | Lys |
| | | | | 165 | | | | | 170 | | | | | 175 | |
| Tyr | Ser | Asp | Ile | Leu | Gln | Ile | Gly | Ala | Arg | Asn | Met | Gln | Asn | Phe | Lys |
| | | | 180 | | | | | 185 | | | | | 190 | | |
| Leu | Leu | Gln | Ala | Val | Gly | Lys | Thr | Gly | Lys | Pro | Ile | Gly | Leu | Lys | Arg |
| | | 195 | | | | | 200 | | | | | 205 | | | |
| Gly | Ile | Ala | Gly | Thr | Ile | Asp | Glu | Trp | Leu | Asn | Ala | Ala | Glu | Tyr | Ile |
| | 210 | | | | | 215 | | | | | 220 | | | | |
| Ala | Ala | Gln | Gly | Asn | Phe | Asn | Val | Ile | Phe | Ile | Glu | Arg | Gly | Ile | Arg |
| 225 | | | | | 230 | | | | | 235 | | | | | 240 |
| Thr | Tyr | Glu | Thr | Ala | Thr | Arg | Asn | Thr | Leu | Asp | Leu | Ser | Ala | Val | Pro |
| | | | | 245 | | | | | 250 | | | | | 255 | |
| Leu | Ile | Lys | Lys | Leu | Ser | His | Phe | Pro | Ile | Ile | Val | Asp | Pro | Ser | His |
| | | | | 260 | | | | | 265 | | | | | 270 | |
| Gly | Val | Gly | Ile | Trp | Asp | Leu | Val | Pro | Pro | Met | Ala | Arg | Ala | Gly | Val |
| | | 275 | | | | | 280 | | | | | 285 | | | |
| Ala | Ser | Gly | Ala | Asp | Gly | Leu | Ile | Val | Glu | Ile | His | Pro | Asp | Pro | Ala |
| | 290 | | | | | 295 | | | | | 300 | | | | |
| Asn | Ala | Trp | Ser | Asp | Gly | Pro | Gln | Ser | Leu | Asn | Glu | Lys | Thr | Tyr | Leu |
| 305 | | | | | 310 | | | | | 315 | | | | | 320 |
| Arg | Met | Met | Lys | Glu | Val | His | Ile | Ile | Glu | Lys | Ala | Met | Lys | Glu | Ile |
| | | | | 325 | | | | | 330 | | | | | 335 | |
| Asn | Ala | Leu | Glu | Asp | | | | | | | | | | | |
| | | | | 340 | | | | | | | | | | | |

Figure 15F

ORF3

```
atgaaattaa ccgtaacgtt acctacacat tcatatgatt taaccatcga aacaggtgcc   60
ttagataaaa ttggcacctg ggtacgtagc ctgtggcagc cacaacgggt agcgattatt  120
accgatgaaa cggtgaataa attatatggc gcagctgttg agaaagaatt gcaagctgct  180
ggttttgaaa catcattgat tgctgtagcg gcaggtgaac aaagtaagag cctcgaaata  240
gctcaactgc tttatgattt tttagcggaa cagcaattga ctcgaagtga tggtctaatt  300
gctttaggtg gaggcgttgt gggagatcta gctggatttg tcgcttcaac ctatatgcgc  360
ggtattcact ttttgcaagt accaacaacc ttactggcac aagtagatag tagcattgga  420
ggtaaaacag cggttaatac taaaaaagcc aaaaatcttg tcggtacttt tgcccaacca  480
gatggggttt taattgatcc taatacactt aaaacattag aacctagacg tgtgcgtgaa  540
ggaattgcag aaattgtaaa atcagcagct atcgctgatg ttgaattgtg gcaccgttta  600
tcctctttgg aaaatgaaca agatttagtg gcacatgcag aagaaattat cacggcctgt  660
tgcaagatta aacgtgatgt cgtcgaagaa gatgaattag atttgggctt acgtttgatt  720
ctgaattttg ggcatacgat cggccacgca ttagaaaata cagctggtta cggggtgatt  780
gctcacggtg aaggcgtttc tttaggaatg attcaaataa ctcaagtcgc agaacaacaa  840
gggctttccc cacttgggac tacccaagag ttggtcacca tgctagaaaa gttccattta  900
ccagtaacca cagatcgttg gtcagaagaa cgtctctatc aagcaattac acatgataaa  960
aaaacacgtg ggggacagat taaaatcatt gtcttagaaa aaattggtca agcgaaaatt 1020
gtctctttac caacggaaga aattcgagca tttttaaaca gagaaggagg aattaa     1077
```

Figure 15G

ORF3

| | | | | | | | | | | | | | | |
|---|---|---|---|---|---|---|---|---|---|---|---|---|---|---|
| Met 1 | Lys | Leu | Thr | Val 5 | Thr | Leu | Pro | Thr | His 10 | Ser | Tyr | Asp | Leu | Thr Ile 15 |
| Glu | Thr | Gly | Ala 20 | Leu | Asp | Lys | Ile | Gly 25 | Thr | Trp | Val | Arg | Ser 30 | Leu Trp |
| Gln | Pro | Gln 35 | Arg | Val | Ala | Ile | Ile 40 | Thr | Asp | Glu | Thr | Val 45 | Asn | Lys Leu |
| Tyr | Gly 50 | Ala | Ala | Val | Glu | Lys 55 | Glu | Leu | Gln | Ala | Ala 60 | Gly | Phe | Glu Thr |
| Ser 65 | Leu | Ile | Ala | Val 70 | Ala | Ala | Gly | Glu | Gln 75 | Ser | Lys | Ser | Leu | Glu Ile 80 |
| Ala | Gln | Leu | Leu | Tyr 85 | Asp | Phe | Leu | Ala | Glu 90 | Gln | Gln | Leu | Thr | Arg Ser 95 |
| Asp | Gly | Leu | Ile 100 | Ala | Leu | Gly | Gly | Val 105 | Val | Gly | Asp | Leu | Ala 110 | Gly |
| Phe | Val | Ala 115 | Ser | Thr | Tyr | Met | Arg 120 | Gly | Ile | His | Phe | Leu 125 | Gln | Val Pro |
| Thr | Thr 130 | Leu | Leu | Ala | Gln | Val 135 | Asp | Ser | Ser | Ile | Gly 140 | Gly | Lys | Thr Ala |
| Val Asn 145 | Thr | Lys | Lys | Ala 150 | Lys | Asn | Leu | Val | Gly 155 | Thr | Phe | Ala | Gln | Pro 160 |
| Asp | Gly | Val | Leu | Ile 165 | Asp | Pro | Asn | Thr | Leu 170 | Lys | Thr | Leu | Glu | Pro Arg 175 |
| Arg | Val | Arg | Glu 180 | Gly | Ile | Ala | Glu | Ile 185 | Val | Lys | Ser | Ala | Ala 190 | Ile Ala |
| Asp | Val | Glu 195 | Leu | Trp | His | Arg | Leu 200 | Ser | Ser | Leu | Glu | Asn 205 | Glu | Gln Asp |
| Leu | Val 210 | Ala | His | Ala | Glu | Glu 215 | Ile | Ile | Thr | Ala | Cys 220 | Cys | Lys | Ile Lys |
| Arg 225 | Asp | Val | Val | Glu | Glu 230 | Asp | Glu | Leu | Asp | Leu 235 | Gly | Leu | Arg | Leu Ile 240 |
| Leu | Asn | Phe | Gly | His 245 | Thr | Ile | Gly | His | Ala 250 | Leu | Glu | Asn | Thr | Ala Gly 255 |
| Tyr | Gly | Val | Ile 260 | Ala | His | Gly | Glu | Gly 265 | Val | Ser | Leu | Gly | Met 270 | Ile Gln |
| Ile | Thr | Gln 275 | Val | Ala | Glu | Gln | Gln 280 | Gly | Leu | Ser | Pro | Leu 285 | Gly | Thr Thr |
| Gln | Glu 290 | Leu | Val | Thr | Met | Leu 295 | Glu | Lys | Phe | His | Leu 300 | Pro | Val | Thr Thr |
| Asp 305 | Arg | Trp | Ser | Glu | Glu 310 | Arg | Leu | Tyr | Gln | Ala 315 | Ile | Thr | His | Asp Lys 320 |
| Lys | Thr | Arg | Gly | Gly 325 | Gln | Ile | Lys | Ile | Ile 330 | Val | Leu | Glu | Lys | Ile Gly 335 |
| Gln | Ala | Lys | Ile 340 | Val | Ser | Leu | Pro | Thr 345 | Glu | Glu | Ile | Arg | Ala 350 | Phe Leu |
| Asn | Arg | Glu 355 | Gly | Gly | Ile | | | | | | | | | |

Figure 15H

ORF4
```
atgcgcttta ttacagcagg cgaatcacat ggacctgaat taactgctat tattgaaggc  60
ttaccagccg gcttgccttt aagtagcgaa gagattaacc gagaattagc aagacgtcaa 120
ggcggttacg gtcgtggggg acggatgaaa attgaaaaag accaagtacg tattacttcg 180
ggtattcggc atggtaaaac acttggctca ccagtaacgt tgattgtcga aaacaaagac 240
tggaaaaatt ggacctccgt gatgtcagta gagccagttc ctgaaaaaca aagaaaatc 300
cgccgcgtca gcaaaccacg tccaggacat gctgatttag tcggtggcat gaaatatcaa 360
catgatgatt tacggaatgt tttagaacgg tcttcggcac gagaaacaac gatgcgtgtg 420
gcgattggtg cggttgctaa aaaactctta gctgaactgg atatccaagt cgctgggcat 480
gtcgcggtat taggtgggat tgaagctacg atccctgaaa atttaacgat tcgtgaaatt 540
caagaacgat ctgaacaatc tgccgttcgc gtattagatc cttccgtaga agaaaaaatg 600
aaagaactaa ttgaccaaac caagaaaaat ggcgatacaa ttggtggggt agtagaagta 660
cttgtgggtg gcgttccagc tggcttaggt agctatgtcc aatgggatcg taaactagat 720
gccaaaattg cgcaagcagt tgtaagcatc aacgcttttta caggtgctga gtttggcatt 780
ggatttgaaa tggcacaacg ccctggtagt caactgatgg acgagattgt ttgggacgaa 840
agtactggtt ataccagaac ttccaacaat ttaggcggtt ttgaaggagg aatgaccaac 900
ggaatgccaa tcatcgttcg tggtgtcatg aaacctattc caacccttta taaaccatta 960
caaagcgtga atattgatac aaaagagcct tataaggcca gtgttgagcg ctctgatagc 1020
acggcggtac cggccgctag cgttgtttgt gaagccgttg ttgcaacgga agtagcaaag 1080
gctatgctcg aaaaatttga tagtgactca tttgaacaaa tgaaagaagc agtgaaacgt 1140
tatcgtctat atactcaaaa cttttaa                                     1167
```

Figure 15I

ORF4

| | | | | | | | | | | | | | | |
|---|---|---|---|---|---|---|---|---|---|---|---|---|---|---|
|Met|Arg|Phe|Ile|Thr|Ala|Gly|Glu|Ser|His|Gly|Pro|Glu|Leu|Thr|Ala|
|1| | | |5| | | | |10| | | | |15|
|Ile|Ile|Glu|Gly|Leu|Pro|Ala|Gly|Leu|Pro|Leu|Ser|Ser|Glu|Glu|Ile|
| | | |20| | | | |25| | | | |30| |
|Asn|Arg|Glu|Leu|Ala|Arg|Arg|Gln|Gly|Gly|Tyr|Gly|Arg|Gly|Gly|Arg|
| | |35| | | | |40| | | | |45| | |
|Met|Lys|Ile|Glu|Lys|Asp|Gln|Val|Arg|Ile|Thr|Ser|Gly|Ile|Arg|His|
| |50| | | | |55| | | | |60| | | |
|Gly|Lys|Thr|Leu|Gly|Ser|Pro|Val|Thr|Leu|Ile|Val|Glu|Asn|Lys|Asp|
|65| | | |70| | | | |75| | | | |80|
|Trp|Lys|Asn|Trp|Thr|Ser|Val|Met|Ser|Val|Glu|Pro|Val|Pro|Glu|Lys|
| | | |85| | | | |90| | | | |95| |
|Gln|Lys|Lys|Ile|Arg|Arg|Val|Ser|Lys|Pro|Arg|Pro|Gly|His|Ala|Asp|
| | |100| | | | |105| | | | |110| | |
|Leu|Val|Gly|Gly|Met|Lys|Tyr|Gln|His|Asp|Asp|Leu|Arg|Asn|Val|Leu|
| | |115| | | | |120| | | | |125| | |
|Glu|Arg|Ser|Ser|Ala|Arg|Glu|Thr|Thr|Met|Arg|Val|Ala|Ile|Gly|Ala|
| |130| | | | |135| | | | |140| | | |
|Val|Ala|Lys|Lys|Leu|Leu|Ala|Glu|Leu|Asp|Ile|Gln|Val|Ala|Gly|His|
|145| | | | |150| | | | |155| | | | |160|
|Val|Ala|Val|Leu|Gly|Gly|Ile|Glu|Ala|Thr|Ile|Pro|Glu|Asn|Leu|Thr|
| | | |165| | | | |170| | | | |175| |
|Ile|Arg|Glu|Ile|Gln|Glu|Arg|Ser|Glu|Gln|Ser|Ala|Val|Arg|Val|Leu|
| | |180| | | | |185| | | | |190| | |
|Asp|Pro|Ser|Val|Glu|Glu|Lys|Met|Lys|Glu|Leu|Ile|Asp|Gln|Thr|Lys|
| |195| | | | |200| | | | |205| | | |
|Lys|Asn|Gly|Asp|Thr|Ile|Gly|Gly|Val|Val|Glu|Val|Leu|Val|Gly|Gly|
| |210| | | | |215| | | | |220| | | |
|Val|Pro|Ala|Gly|Leu|Gly|Ser|Tyr|Val|Gln|Trp|Asp|Arg|Lys|Leu|Asp|
|225| | | | |230| | | | |235| | | | |240|
|Ala|Lys|Ile|Ala|Gln|Ala|Val|Val|Ser|Ile|Asn|Ala|Phe|Thr|Gly|Ala|
| | | |245| | | | |250| | | | |255| |
|Glu|Phe|Gly|Ile|Gly|Phe|Glu|Met|Ala|Gln|Arg|Pro|Gly|Ser|Gln|Leu|
| | |260| | | | |265| | | | |270| | |
|Met|Asp|Glu|Ile|Val|Trp|Asp|Glu|Ser|Thr|Gly|Tyr|Thr|Arg|Thr|Ser|
| |275| | | | |280| | | | |285| | | |
|Asn|Asn|Leu|Gly|Gly|Phe|Glu|Gly|Gly|Met|Thr|Asn|Gly|Met|Pro|Ile|
| |290| | | | |295| | | | |300| | | |
|Ile|Val|Arg|Gly|Val|Met|Lys|Pro|Ile|Pro|Thr|Leu|Tyr|Lys|Pro|Leu|
|305| | | | |310| | | | |315| | | | |320|
|Gln|Ser|Val|Asn|Ile|Asp|Thr|Lys|Glu|Pro|Tyr|Lys|Ala|Ser|Val|Glu|
| | | |325| | | | |330| | | | |335| |
|Arg|Ser|Asp|Ser|Thr|Ala|Val|Pro|Ala|Ala|Ser|Val|Val|Cys|Glu|Ala|
| | |340| | | | |345| | | | |350| | |
|Val|Val|Ala|Thr|Glu|Val|Ala|Lys|Ala|Met|Leu|Glu|Lys|Phe|Asp|Ser|
| | |355| | | | |360| | | | |365| | |
|Asp|Ser|Phe|Glu|Gln|Met|Lys|Glu|Ala|Val|Lys|Arg|Tyr|Arg|Leu|Tyr|
| |370| | | | |375| | | | |380| | | |
|Thr|Gln|Asn|Phe| | | | | | | | | | | | |
|385| | | | | | | | | | | | | | | |

Figure 15J

ORF5

```
atgaagaaac gtattttaat cgtaggatta gggctaatcg ggagttcact ggctttgtgt  60
atcaaaaaag ggcatccaaa cagtgagatt atcggtttcg ataatcaagc ggaggcaact 120
gaatttgcta agaaaacggg tctaattgat gagatagctg aatctttaac aagtggggca 180
agacgagcag agattatttt tctttgttcc ccagttaaag caactttagt acaactagaa 240
gaattaaacc aattatcact agaaactgct ctgatcacag atgtgggtag taccaaggtg 300
gaaattaatc agttagcaac aaagcttaac atgaaaaatt ttattggtgg tcatccaatg 360
gctggttcac ataaatccgg cgtaacagcc gctgatgaac gtttgtttga aaatgcctac 420
tatatttta ccgatgacca tggcgaaaaa aacaaacaga ttcaggagtt acaaacgtta 480
ctaaaaggaa cgcatgcgaa gtttattacg atgcctgcac aggaacatga tgaaattact 540
ggtgctctaa gtcacttgcc acatattgtt gccgcagcgt tagtgaacga aagtcagcaa 600
ctgaatacca cttacctag agcgcagcag ctagcggctg gaggattcag agatattact 660
cgaattgctt cctctgatgc aacgatgtgg acggatattt tattaagcaa tcgcttagta 720
ttattggact tactagaaaa ttggcaaaaa gagatgacta ctgtttgcca atggttaaca 780
gaaaaaatg ccccagctat tcgtaatttt tttgataagg ccaaagaaac acgtgctcaa 840
ttgcctattc ataaagaagg cgcaatccca gctttctatg atctgtttgt tgatgtacca 900
gatcaaccag gaatcattgc tgaaattacg caaatttag gcgaagcgga cctttctctt 960
acaaatatta aaattttaga aacgagagaa gaaatctatg ggattcttca attgtctttt 1020
aaaaatcaac cagactgcca agctgcaaaa caaatttat ctaaaaaaac gaactatacg 1080
tgttacgaaa aataa                                                 1095
```

Figure 15K

ORF5

| | | | | | | | | | | | | | | |
|---|---|---|---|---|---|---|---|---|---|---|---|---|---|---|
| Met 1 | Lys | Lys | Arg | Ile 5 | Leu | Ile | Val | Gly | Leu 10 | Gly | Leu | Ile | Gly | Ser Ser 15 |
| Leu | Ala | Leu | Cys 20 | Ile | Lys | Lys | Gly | His 25 | Pro | Asn | Ser | Glu | Ile 30 | Ile Gly |
| Phe | Asp | Asn 35 | Gln | Ala | Glu | Ala | Thr 40 | Glu | Phe | Ala | Lys | Lys 45 | Thr | Gly Leu |
| Ile | Asp 50 | Glu | Ile | Ala | Glu | Ser 55 | Leu | Thr | Ser | Gly | Ala 60 | Arg | Arg | Ala Glu |
| Ile 65 | Ile | Phe | Leu | Cys | Ser 70 | Pro | Val | Lys | Ala | Thr 75 | Leu | Val | Gln | Leu Glu 80 |
| Glu | Leu | Asn | Gln | Leu 85 | Ser | Leu | Glu | Thr | Ala 90 | Leu | Ile | Thr | Asp | Val Gly 95 |
| Ser | Thr | Lys | Val 100 | Glu | Ile | Asn | Gln | Leu 105 | Ala | Thr | Lys | Leu | Asn 110 | Met Lys |
| Asn | Phe | Ile 115 | Gly | Gly | His | Pro | Met 120 | Ala | Gly | Ser | His | Lys 125 | Ser | Gly Val |
| Thr | Ala 130 | Ala | Asp | Glu | Arg | Leu 135 | Phe | Glu | Asn | Ala | Tyr 140 | Tyr | Ile | Phe Thr |
| Asp 145 | Asp | His | Gly | Glu | Lys 150 | Asn | Lys | Gln | Ile | Gln 155 | Glu | Leu | Gln | Thr Leu 160 |
| Leu | Lys | Gly | Thr | His 165 | Ala | Lys | Phe | Ile | Thr 170 | Met | Pro | Ala | Gln | Glu His 175 |
| Asp | Glu | Ile | Thr 180 | Gly | Ala | Leu | Ser | His 185 | Leu | Pro | His | Ile | Val 190 | Ala Ala |
| Ala | Leu | Val 195 | Asn | Glu | Ser | Gln | Gln 200 | Leu | Asn | Thr | Thr | Tyr 205 | Pro | Arg Ala |
| Gln | Gln 210 | Leu | Ala | Ala | Gly | Gly 215 | Phe | Arg | Asp | Ile | Thr 220 | Arg | Ile | Ala Ser |
| Ser 225 | Asp | Ala | Thr | Met | Trp 230 | Thr | Asp | Ile | Leu | Leu 235 | Ser | Asn | Arg | Leu Val 240 |
| Leu | Leu | Asp | Leu | Leu 245 | Glu | Asn | Trp | Gln | Lys 250 | Glu | Met | Thr | Thr | Val Cys 255 |
| Gln | Trp | Leu | Thr 260 | Glu | Lys | Asn | Ala | Pro 265 | Ala | Ile | Arg | Asn | Phe 270 | Phe Asp |
| Lys | Ala | Lys 275 | Glu | Thr | Arg | Ala | Gln 280 | Leu | Pro | Ile | His | Lys 285 | Glu | Gly Ala |
| Ile | Pro 290 | Ala | Phe | Tyr | Asp | Leu 295 | Phe | Val | Asp | Val | Pro 300 | Asp | Gln | Pro Gly |
| Ile 305 | Ile | Ala | Glu | Ile | Thr 310 | Gln | Ile | Leu | Gly | Glu 315 | Ala | Asp | Leu | Ser Leu 320 |
| Thr | Asn | Ile | Lys | Ile 325 | Leu | Glu | Thr | Arg | Glu 330 | Glu | Ile | Tyr | Gly | Ile Leu 335 |
| Gln | Leu | Ser | Phe 340 | Lys | Asn | Gln | Pro | Asp 345 | Cys | Gln | Ala | Ala | Lys 350 | Gln Ile |
| Leu | Ser | Lys 355 | Lys | Thr | Asn | Tyr | Thr 360 | Cys | Tyr | Glu | Lys | | | |

Figure 15L

ORF6
```
atgagggtgc aactacgtac aaatgtgaag catttacaag ggactctgat ggttcctagc  60
gacaaatcga tttcccatag aagtattatg tttggagcga tttcttctgg aaaaacgacg 120
attacaaatt ttctaagagg cgaagattgt ttaagtacct tagcggcgtt tcgttctttta 180
ggtgtgaaca ttgaagatga cgggacgaca atcaccgttg agggcgagg atttgcaggc 240
ttaaaaaagg cgaagaatac aattgatgtt ggaaattcag ggacaacaat tcgtctgatg 300
ctgggcattt tagctggctg tccctttgaa acgcgcctag ctggtgatgc gtctattgcc 360
aaacgaccaa tgaatcgtgt aatgcttcct ttaaaccaaa tgggagcgga atgtcaaggg 420
gttcagcaaa cggagtttcc gccaatttct attcgcggga ctcaaaattt gcaaccgatt 480
gactacacaa tgcctgttgc aagtgctcaa gttaaatcgg ctattttatt cgccgctttg 540
caagccgagg gcacttctgt agtggttgag aagaaaaga cacgtgatca tacagaagag 600
atgattcgac aatttggtgg gacacttgaa gtagacggta aaaaaattat gttaactgga 660
ccgcaacaat taacaggtca aaatgtggta gttcctggtg atatctcttc tgcagctttc 720
tttttagttg cgggtttagt agtcccagat agcgagatac ttctgaaaaa tgttggctta 780
aatcaaacgc ggacaggtat tttagatgtg attaaaaaca tgggcggttc cgtcactatt 840
ttaaatgaag atgaggccaa tcattctggc gatttacttg taaaaacgag tcaattaaca 900
gctacagaga ttggtggcgc tattatccca cgtttaattg atgagttacc gattattgct 960
ttgttagcta ctcaggctac tggcacgaca atcattcgag atgcagaaga attgaaagtc 1020
aaagaaacca atcggattga tgcagtagcg aaagaattaa caatttttagg cgccgacatc 1080
acgcctactg atgatggctt aattatacat ggaccaactt ctttacatgg tggaagagtt 1140
accagttatg gggatcatcg tatcgggatg atgttacaaa ttgctgcatt acttgtaaaa 1200
gaaggcactg ttgaattaga taaggctgaa gcagtttcag tttcttatcc agcatttttt 1260
gacgacttag aacgtttaag ttgttaa                                   1287
```

Figure 15M

ORF6

| | | | | | | | | | | | | | | |
|---|---|---|---|---|---|---|---|---|---|---|---|---|---|---|
| Met | Arg | Val | Gln | Leu | Arg | Thr | Asn | Val | Lys | His | Leu | Gln | Gly | Thr | Leu |
| 1 | | | | 5 | | | | | 10 | | | | | 15 | |
| Met | Val | Pro | Ser | Asp | Lys | Ser | Ile | Ser | His | Arg | Ser | Ile | Met | Phe | Gly |
| | | | 20 | | | | | 25 | | | | | 30 | | |
| Ala | Ile | Ser | Ser | Gly | Lys | Thr | Thr | Ile | Thr | Asn | Phe | Leu | Arg | Gly | Glu |
| | | | 35 | | | | 40 | | | | | 45 | | | |
| Asp | Cys | Leu | Ser | Thr | Leu | Ala | Ala | Phe | Arg | Ser | Leu | Gly | Val | Asn | Ile |
| | 50 | | | | | 55 | | | | | 60 | | | | |
| Glu | Asp | Asp | Gly | Thr | Thr | Ile | Thr | Val | Glu | Gly | Arg | Gly | Phe | Ala | Gly |
| 65 | | | | | 70 | | | | | 75 | | | | | 80 |
| Leu | Lys | Lys | Ala | Lys | Asn | Thr | Ile | Asp | Val | Gly | Asn | Ser | Gly | Thr | Thr |
| | | | | 85 | | | | | 90 | | | | | 95 | |
| Ile | Arg | Leu | Met | Leu | Gly | Ile | Leu | Ala | Gly | Cys | Pro | Phe | Glu | Thr | Arg |
| | | | | 100 | | | | | 105 | | | | | 110 | |
| Leu | Ala | Gly | Asp | Ala | Ser | Ile | Ala | Lys | Arg | Pro | Met | Asn | Arg | Val | Met |
| | | | 115 | | | | | 120 | | | | | 125 | | |
| Leu | Pro | Leu | Asn | Gln | Met | Gly | Ala | Glu | Cys | Gln | Gly | Val | Gln | Gln | Thr |
| | | | 130 | | | | 135 | | | | | 140 | | | |
| Glu | Phe | Pro | Pro | Ile | Ser | Ile | Arg | Gly | Thr | Gln | Asn | Leu | Gln | Pro | Ile |
| 145 | | | | | 150 | | | | | 155 | | | | | 160 |
| Asp | Tyr | Thr | Met | Pro | Val | Ala | Ser | Ala | Gln | Val | Lys | Ser | Ala | Ile | Leu |
| | | | | 165 | | | | | 170 | | | | | 175 | |
| Phe | Ala | Ala | Leu | Gln | Ala | Glu | Gly | Thr | Ser | Val | Val | Val | Glu | Lys | Glu |
| | | | | 180 | | | | | 185 | | | | | 190 | |
| Lys | Thr | Arg | Asp | His | Thr | Glu | Glu | Met | Ile | Arg | Gln | Phe | Gly | Gly | Thr |
| | | | 195 | | | | | 200 | | | | | 205 | | |
| Leu | Glu | Val | Asp | Gly | Lys | Lys | Ile | Met | Leu | Thr | Gly | Pro | Gln | Gln | Leu |
| 210 | | | | | 215 | | | | | 220 | | | | | |
| Thr | Gly | Gln | Asn | Val | Val | Val | Pro | Gly | Asp | Ile | Ser | Ser | Ala | Ala | Phe |
| 225 | | | | | 230 | | | | | 235 | | | | | 240 |
| Phe | Leu | Val | Ala | Gly | Leu | Val | Val | Pro | Asp | Ser | Glu | Ile | Leu | Leu | Lys |
| | | | | 245 | | | | | 250 | | | | | 255 | |
| Asn | Val | Gly | Leu | Asn | Gln | Thr | Arg | Thr | Gly | Ile | Leu | Asp | Val | Ile | Lys |
| | | | 260 | | | | | 265 | | | | | 270 | | |
| Asn | Met | Gly | Gly | Ser | Val | Thr | Ile | Leu | Asn | Glu | Asp | Glu | Ala | Asn | His |
| | | 275 | | | | | 280 | | | | | 285 | | | |
| Ser | Gly | Asp | Leu | Leu | Val | Lys | Thr | Ser | Gln | Leu | Thr | Ala | Thr | Glu | Ile |
| | 290 | | | | | 295 | | | | | 300 | | | | |
| Gly | Gly | Ala | Ile | Ile | Pro | Arg | Leu | Ile | Asp | Glu | Leu | Pro | Ile | Ile | Ala |
| 305 | | | | | 310 | | | | | 315 | | | | | 320 |
| Leu | Leu | Ala | Thr | Gln | Ala | Thr | Gly | Thr | Thr | Ile | Ile | Arg | Asp | Ala | Glu |
| | | | | 325 | | | | | 330 | | | | | 335 | |
| Glu | Leu | Lys | Val | Lys | Glu | Thr | Asn | Arg | Ile | Asp | Ala | Val | Ala | Lys | Glu |
| | | | 340 | | | | | 345 | | | | | 350 | | |
| Leu | Thr | Ile | Leu | Gly | Ala | Asp | Ile | Thr | Pro | Thr | Asp | Asp | Gly | Leu | Ile |
| | | | 355 | | | | | 360 | | | | | 365 | | |
| Ile | His | Gly | Pro | Thr | Ser | Leu | His | Gly | Gly | Arg | Val | Thr | Ser | Tyr | Gly |
| | | 370 | | | | | 375 | | | | | 380 | | | |
| Asp | His | Arg | Ile | Gly | Met | Met | Leu | Gln | Ile | Ala | Ala | Leu | Leu | Val | Lys |
| 385 | | | | | 390 | | | | | 395 | | | | | 400 |
| Glu | Gly | Thr | Val | Glu | Leu | Asp | Lys | Ala | Glu | Ala | Val | Ser | Val | Ser | Tyr |
| | | | | 405 | | | | | 410 | | | | | 415 | |
| Pro | Ala | Phe | Phe | Asp | Asp | Leu | Glu | Arg | Leu | Ser | Cys | | | | |
| | | | 420 | | | | | 425 | | | | | | | |

Figure 15N

ORF7
```
atggaaagca ttgttttaat tggtttcatg ggtgcgggta aaacaactat cggccaaagt 60
ttggccaata aactgaagat gcctcatctt gatttagata cagcgttaat tgaaaaaata 120
ggacgctcaa ttcctgacta tttcgaaaaa tatggtgaag cagctttccg agaacaggaa 180
acccaacttt taaaggagct gtcaaaaaat acagccgtcc tttcaactgg gggcgggatt 240
gttgtcggac cagaaaatcg tagcttatta aaatcttttc agcaagtgat ttatttacat 300
gcgacaccag aagagctgtt aaaaagaatc acagaagata ctgaaaacca acggcccta 360
gctatagaac gttcttcaaa agaaatcatt actttgtttg agtctcgtaa aaattttat 420
gaagaatgtg cgaagatgac aattgatacg accaatcgct cgccagaaga aattatcaat 480
gaaattctgc aacaattaaa ggagtag                                    507
```

Figure 150

ORF7

| | | | | | | | | | | | | | | |
|---|---|---|---|---|---|---|---|---|---|---|---|---|---|---|
| Met | Glu | Ser | Ile | Val | Leu | Ile | Gly | Phe | Met | Gly | Ala | Gly | Lys | Thr |
| 1 | | | | 5 | | | | | 10 | | | | | 15 |
| Thr | Ile | Gly | Gln | Ser | Leu | Ala | Asn | Lys | Leu | Lys | Met | Pro | His | Leu | Asp |
| | | | 20 | | | | | 25 | | | | | 30 | | |
| Leu | Asp | Thr | Ala | Leu | Ile | Glu | Lys | Ile | Gly | Arg | Ser | Ile | Pro | Asp | Tyr |
| | | 35 | | | | | 40 | | | | | 45 | | | |
| Phe | Glu | Lys | Tyr | Gly | Glu | Ala | Ala | Phe | Arg | Glu | Gln | Glu | Thr | Gln | Leu |
| | 50 | | | | | 55 | | | | | 60 | | | | |
| Leu | Lys | Glu | Leu | Ser | Lys | Asn | Thr | Ala | Val | Leu | Ser | Thr | Gly | Gly | Gly |
| 65 | | | | | 70 | | | | | 75 | | | | | 80 |
| Ile | Val | Val | Gly | Pro | Glu | Asn | Arg | Ser | Leu | Leu | Lys | Ser | Phe | Gln | Gln |
| | | | | 85 | | | | | 90 | | | | | 95 | |
| Val | Ile | Tyr | Leu | His | Ala | Thr | Pro | Glu | Glu | Leu | Leu | Lys | Arg | Ile | Thr |
| | | | 100 | | | | | 105 | | | | | 110 | | |
| Glu | Asp | Thr | Glu | Asn | Gln | Arg | Pro | Leu | Ala | Ile | Glu | Arg | Ser | Ser | Lys |
| | | 115 | | | | | 120 | | | | | 125 | | | |
| Glu | Ile | Ile | Thr | Leu | Phe | Glu | Ser | Arg | Lys | Asn | Phe | Tyr | Glu | Glu | Cys |
| | 130 | | | | | 135 | | | | | 140 | | | | |
| Ala | Lys | Met | Thr | Ile | Asp | Thr | Thr | Asn | Arg | Ser | Pro | Glu | Glu | Ile | Ile |
| 145 | | | | | 150 | | | | | 155 | | | | | 160 |
| Asn | Glu | Ile | Leu | Gln | Gln | Leu | Lys | Glu | | | | | | | |
| | | | | 165 | | | | | | | | | | | |

Figure 15P

ORF8

```
atgaaagttg gttatttagg tccgattggt tcctttacgt acagtgcaac gttggctgct  60
tttcctgaag ctacgttgat gccgtacgca tcgattccag cttgcttgaa agcaattgaa 120
cagcaagaag tggcatggag cattatccca atagaaaaca cgattgaagg aactgttaac 180
gcatcgatag attatttgta tcatcaagcg cagttacctg tccaagcaga gttagtttta 240
ccgattcaac aacaattaat ggtggcaaaa gagaatcaag cgatctggca acaaagtcag 300
aaaattttat cacatccgca agcattagct caatcgcaga tgtttctaga gaaaaacttt 360
ccagaagcga ttttagaagc aacaccttca acagcttacg ccgccaaata cattgcagaa 420
catccagaat tacctttgc agctattgca ccaaaacttt ctgcggaaat gtatgatttg 480
accattgttg aaaaaaatat acaagattta tcggtaaatc aaacccgatt ttgggttctt 540
ggttctgaaa atttagcgat ttctttcccg ctatctgaga aaaaaataac actggcgatt 600
acgatgccaa gtaatgttcc tggctcttta cacaaagtat taagcgtgtt tagttggcga 660
gggattaatc ttagcaaaat agaatcgcgg ccgttgaaaa caaagctagg agagtacttc 720
tttttaatgg acttagtgaa agatcaacca gaaaaattaa ttgaagcagc cttaacagaa 780
ctggaactca ttggtgcaga aataaaaatt ttaggggatt acccgatcta tgttttgtcc 840
acactttaa                                                         849
```

Figure 15Q

ORF8

| | | | | | | | | | | | | | | |
|---|---|---|---|---|---|---|---|---|---|---|---|---|---|---|
| Met | Lys | Val | Gly | Tyr | Leu | Gly | Pro | Ile | Gly | Ser | Phe | Thr | Tyr | Ser | Ala |
| 1 | | | | 5 | | | | | 10 | | | | | 15 |
| Thr | Leu | Ala | Ala | Phe | Pro | Glu | Ala | Thr | Leu | Met | Pro | Tyr | Ala | Ser | Ile |
| | | | 20 | | | | | 25 | | | | | 30 | |
| Pro | Ala | Cys | Leu | Lys | Ala | Ile | Glu | Gln | Gln | Glu | Val | Ala | Trp | Ser | Ile |
| | | 35 | | | | | 40 | | | | | 45 | | |
| Ile | Pro | Ile | Glu | Asn | Thr | Ile | Glu | Gly | Thr | Val | Asn | Ala | Ser | Ile | Asp |
| | 50 | | | | | 55 | | | | | 60 | | | | |
| Tyr | Leu | Tyr | His | Gln | Ala | Gln | Leu | Pro | Val | Gln | Ala | Glu | Leu | Val | Leu |
| 65 | | | | 70 | | | | | 75 | | | | | 80 | |
| Pro | Ile | Gln | Gln | Gln | Leu | Met | Val | Ala | Lys | Glu | Asn | Gln | Ala | Ile | Trp |
| | | | | 85 | | | | | 90 | | | | | 95 | |
| Gln | Gln | Ser | Gln | Lys | Ile | Leu | Ser | His | Pro | Gln | Ala | Leu | Ala | Gln | Ser |
| | | | 100 | | | | | 105 | | | | | 110 | | |
| Gln | Met | Phe | Leu | Glu | Lys | Asn | Phe | Pro | Glu | Ala | Ile | Leu | Glu | Ala | Thr |
| | | 115 | | | | | 120 | | | | | 125 | | | |
| Pro | Ser | Thr | Ala | Tyr | Ala | Ala | Lys | Tyr | Ile | Ala | Glu | His | Pro | Glu | Leu |
| | 130 | | | | | 135 | | | | | 140 | | | | |
| Pro | Phe | Ala | Ala | Ile | Ala | Pro | Lys | Leu | Ser | Ala | Glu | Met | Tyr | Asp | Leu |
| 145 | | | | 150 | | | | | 155 | | | | | 160 | |
| Thr | Ile | Val | Glu | Lys | Asn | Ile | Gln | Asp | Leu | Ser | Val | Asn | Gln | Thr | Arg |
| | | | | 165 | | | | | 170 | | | | | 175 | |
| Phe | Trp | Val | Leu | Gly | Ser | Glu | Asn | Leu | Ala | Ile | Ser | Phe | Pro | Leu | Ser |
| | | | 180 | | | | | 185 | | | | | 190 | | |
| Glu | Lys | Lys | Ile | Thr | Leu | Ala | Ile | Thr | Met | Pro | Ser | Asn | Val | Pro | Gly |
| | | 195 | | | | | 200 | | | | | 205 | | | |
| Ser | Leu | His | Lys | Val | Leu | Ser | Val | Phe | Ser | Trp | Arg | Gly | Ile | Asn | Leu |
| | | 210 | | | | | 215 | | | | | 220 | | | |
| Ser | Lys | Ile | Glu | Ser | Arg | Pro | Leu | Lys | Thr | Lys | Leu | Gly | Glu | Tyr | Phe |
| 225 | | | | 230 | | | | | 235 | | | | | 240 | |
| Phe | Leu | Met | Asp | Leu | Val | Lys | Asp | Gln | Pro | Glu | Lys | Leu | Ile | Glu | Ala |
| | | | 245 | | | | | 250 | | | | | 255 | | |
| Ala | Leu | Thr | Glu | Leu | Glu | Leu | Ile | Gly | Ala | Glu | Ile | Lys | Ile | Leu | Gly |
| | | | 260 | | | | | 265 | | | | | 270 | | |
| Asp | Tyr | Pro | Ile | Tyr | Val | Leu | Ser | Thr | Leu | | | | | | |
| | | 275 | | | | | 280 | | | | | | | | |

SEQUENCE LISTING

<160> NUMBER OF SEQ ID NOS: 47

<210> SEQ ID NO 1
<211> LENGTH: 2267
<212> TYPE: DNA
<213> ORGANISM: Enterococcus faecalis

<400> SEQUENCE: 1

```
gaaattgacc gtaaagtcaa tatttacaac attttaagcc tgaatgcgct aggtacgcta      60
tacgaactgg aaaagatat  gagaaaagcg caagtgtatt acgaaaaatc attacaagaa     120
ttggaacaat ttaaattaga atgttccttg gagcgttgta gaatttatta taattctgct     180
aaattctact cggaaatgaa agactaccaa aaaagtgtca ttttaagcga aaaagggatt     240
cagatttgtc gtgacaaaca ctccatttat ttgctagatt atcttttata tgaaaaagcc     300
tttaacaaac aaatgctcgg ggaagacaca gccgatgact atcgccaagc ctattatttt     360
acacaatttt ttggcaatac ggaagtcctg caatatattg agaaagatat gaaagctttt     420
aatatttcct attaatttaa tcaaaaagcc gataaaagct gaaaactcag tttttaccgg     480
cttttttgaaa aatataggca agttgctttt aaaaatcagc agtcacggtt acgataagca     540
agacgaagta tttaggagga tttaaaaatg aaaagagtaa tatggtttag acgtgattta     600
cgattacagg ataataaagc attagcacac gcgttacaaa attctgcagc tgatgaattg     660
attttattat tccaaatgaa tcctcaacaa tttattcaag aaagtgctaa tcataacgct     720
ttttttgcaa gcttagcctc gttcaaagaa cgaatcgatc aagaggcaca tttacaaatc     780
atggtcggcg aaccattaga tttattttca cgtttgaaaac gcaaattacc cgattggcag     840
gccatttatt ttaatgaaga tacttgtggc tttggggcaa agcgggacca gcaagctatg     900
cgcttttttg aagaaaataa tattcagtct ttctcttttc aagatgccta tttgcatggc     960
tctgaagaaa ttaagaagaa cgatggcagc aagtaccaag tgtttacgcc ctattacaat    1020
aaatggaaag aggcgcctaa agaaacaccg attcctgttt cctatacagc tgaaaaaatt    1080
tttagtgcgt gtcttttttcc agaagaggaa gcagcttatc gtgaacagat tgcgaggatt    1140
cctttaacac actatagtgt cggcgaagaa acagccagaa ggcgcttaaa tactttattt    1200
gatcaaaaac ttcaatccta tgaaaataag cgtgattttc cttatcagga tcaaacgagt    1260
catctgtcta cttttttaag aacgggagaa ctttcgattc gcaccatttg gcaagagctt    1320
gcatctgtgc cttctagctt aagtaaagaa accttcaaaa aagaattagc ttggcgcgac    1380
ttttacaata tgatctatag tgcgtttcca caacaaaaag aggaagctat tcaagaaaaa    1440
tttcgttata ttcaatggac aaatgaccca gaaatgtttg tcagtggcca aaaagggag    1500
acggggtacc ctataattga tgccgcaatg cgacaactga atcaaactgg ttggatgcac    1560
aatcgcttaa gaatgattac tgcctctttt ttagttaaaa atttacacat cgattggcgt    1620
tggggtgaaa aatactttca aaaaatgttg attgactatg atgctgccaa taatatcggt    1680
ggctggcaat gggctgcttc aacaggaacg gacgctgtcc cttattttcg gattttttaat    1740
ccaattatcc agtcaaaaaa atttgataat gacggccagt tcatcaaaaa atatgttcca    1800
gaacttaagc aagtgccaca aaagtatatt catcaaccaa atctaatgaa cgaagcctta    1860
caaacgcaat atcatgtaca tttaggagaa aattatccaa acccattgt cgattatgca    1920
tcaagtaaaa acaaacatt gtttctatat gaagcgagca agaaattca tcaagaaatg    1980
aacaatccaa ggtttcaata aacagtaaac ccaactagct tagcaaacaa cttgtaaggt    2040
```

-continued

| | |
|---|---|
| tagttgggca aattaattag tcgaaagaga agtgcaattt atcggctaaa gttttttatt | 2100 |
| ctattctagt taacataata tacattatac aaagtagagt aaaaagcatt gaaaagcaaa | 2160 |
| caaaaccagt ctttagttta tctagactgg ttttgtcacg tacgttatat aaattatgct | 2220 |
| tgttgcttga tggcttgtgc gacacgtgct ccatattctg gatttac | 2267 |

<210> SEQ ID NO 2
<211> LENGTH: 1434
<212> TYPE: DNA
<213> ORGANISM: Enterococcus faecalis

<400> SEQUENCE: 2

| | |
|---|---|
| atgaaaagag taatatggtt tagacgtgat ttacgattac aggataataa agcattagca | 60 |
| cacgcgttac aaaattctgc agctgatgaa ttgattttat tattccaaat gaatcctcaa | 120 |
| caatttattc aagaaagtgc taatcataac gcttttttg caagcttagc ctcgttcaaa | 180 |
| gaacgaatcg atcaagaggc acatttacaa atcatggtcg gcgaaccatt agatttattt | 240 |
| tcacgtttga aacgcaaatt acccgattgg caggccattt attttaatga agatacttgt | 300 |
| ggctttgggg caaagcggga ccagcaagct atgcgctttt ttgaagaaaa taatattcag | 360 |
| tctttctctt ttcaagatgc ctatttgcat ggctctgaag aaattaagaa gaacgatggc | 420 |
| agcaagtacc aagtgtttac gccctattac aataaatgga agaggcgcc taaagaaaca | 480 |
| ccgattcctg tttcctatac agctgaaaaa attttagtg cgtgtctttt tccagaagag | 540 |
| gaagcagctt atcgtgaaca gattgcgagg attcctttaa cacactatag tgtcggcgaa | 600 |
| gaaacagcca aaggcgctt aaatactttt attgatcaaa acttcaatc ctatgaaaat | 660 |
| aagcgtgatt ttccttatca ggatcaaacg agtcatctgt ctactttttt aagaacggga | 720 |
| gaactttcga ttcgcaccat ttggcaagag cttgcatctg tgccttctag cttaagtaaa | 780 |
| gaaacccttca aaaagaatt agcttggcgc gactttttaca atatgatcta tagtgcgttt | 840 |
| ccacaacaaa aagaggaagc tattcaagaa aaatttcgtt atattcaatg gacaaatgac | 900 |
| ccagaaatgt ttgtcaagtg gcaaaaaggg gagacgggt acccctataat tgatgccgca | 960 |
| atgcgacaac tgaatcaaac tggttggatg cacaatcgct taagaatgat tactgcctct | 1020 |
| ttttagtta aaattttaca catcgattgg cgttggggtg aaaatactt tcaaaaaatg | 1080 |
| ttgattgact atgatgctgc caataatatc ggtggctggc aatgggctgc ttcaacagga | 1140 |
| acggacgctg tcccttattt tcggattttt aatccaatta ccagtcaaa aaatttgat | 1200 |
| aatgacggcc agttcatcaa aaaatatgtt ccagaactta agcaagtgcc acaaaagtat | 1260 |
| attcatcaac caaatctaat gaacgaagcc ttacaaacgc aatatcatgt acatttagga | 1320 |
| gaaaattatc caaacccat tgtcgattat gcatcaagta aaaacaaac attgtttcta | 1380 |
| tatgaagcga gcaaagaaat tcatcaagaa atgaacaatc caaggtttca ataa | 1434 |

<210> SEQ ID NO 3
<211> LENGTH: 477
<212> TYPE: PRT
<213> ORGANISM: Enterococcus faecalis

<400> SEQUENCE: 3

Met Lys Arg Val Ile Trp Phe Arg Arg Asp Leu Arg Leu Gln Asp Asn
1               5                   10                  15

Lys Ala Leu Ala His Ala Leu Gln Asn Ser Ala Ala Asp Glu Leu Ile
            20                  25                  30

-continued

Leu Leu Phe Gln Met Asn Pro Gln Gln Phe Ile Gln Glu Ser Ala Asn
        35                  40                  45

His Asn Ala Phe Phe Ala Ser Leu Ala Ser Phe Lys Glu Arg Ile Asp
    50                  55                  60

Gln Glu Ala His Leu Gln Ile Met Val Gly Glu Pro Leu Asp Leu Phe
65                  70                  75                  80

Ser Arg Leu Lys Arg Lys Leu Pro Asp Trp Gln Ala Ile Tyr Phe Asn
                85                  90                  95

Glu Asp Thr Cys Gly Phe Gly Ala Lys Arg Asp Gln Gln Ala Met Arg
            100                 105                 110

Phe Phe Glu Glu Asn Asn Ile Gln Ser Phe Ser Phe Gln Asp Ala Tyr
        115                 120                 125

Leu His Gly Ser Glu Glu Ile Lys Lys Asn Asp Gly Ser Lys Tyr Gln
    130                 135                 140

Val Phe Thr Pro Tyr Tyr Asn Lys Trp Lys Glu Ala Pro Lys Glu Thr
145                 150                 155                 160

Pro Ile Pro Val Ser Tyr Thr Ala Glu Lys Ile Phe Ser Ala Cys Leu
                165                 170                 175

Phe Pro Glu Glu Glu Ala Ala Tyr Arg Glu Gln Ile Ala Arg Ile Pro
            180                 185                 190

Leu Thr His Tyr Ser Val Gly Glu Glu Thr Ala Arg Arg Arg Leu Asn
        195                 200                 205

Thr Phe Ile Asp Gln Lys Leu Gln Ser Tyr Glu Asn Lys Arg Asp Phe
    210                 215                 220

Pro Tyr Gln Asp Gln Thr Ser His Leu Ser Thr Phe Leu Arg Thr Gly
225                 230                 235                 240

Glu Leu Ser Ile Arg Thr Ile Trp Gln Glu Leu Ala Ser Val Pro Ser
                245                 250                 255

Ser Leu Ser Lys Glu Thr Phe Lys Lys Glu Leu Ala Trp Arg Asp Phe
            260                 265                 270

Tyr Asn Met Ile Tyr Ser Ala Phe Pro Gln Gln Lys Glu Glu Ala Ile
        275                 280                 285

Gln Glu Lys Phe Arg Tyr Ile Gln Trp Thr Asn Asp Pro Glu Met Phe
    290                 295                 300

Val Lys Trp Gln Lys Gly Glu Thr Gly Tyr Pro Ile Ile Asp Ala Ala
305                 310                 315                 320

Met Arg Gln Leu Asn Gln Thr Gly Trp Met His Asn Arg Leu Arg Met
                325                 330                 335

Ile Thr Ala Ser Phe Leu Val Lys Asn Leu His Ile Asp Trp Arg Trp
            340                 345                 350

Gly Glu Lys Tyr Phe Gln Lys Met Leu Ile Asp Tyr Asp Ala Ala Asn
        355                 360                 365

Asn Ile Gly Gly Trp Gln Trp Ala Ala Ser Thr Gly Thr Asp Ala Val
    370                 375                 380

Pro Tyr Phe Arg Ile Phe Asn Pro Ile Ile Gln Ser Lys Lys Phe Asp
385                 390                 395                 400

Asn Asp Gly Gln Phe Ile Lys Lys Tyr Val Pro Glu Leu Lys Gln Val
                405                 410                 415

Pro Gln Lys Tyr Ile His Gln Pro Asn Leu Met Asn Glu Ala Leu Gln
            420                 425                 430

Thr Gln Tyr His Val His Leu Gly Glu Asn Tyr Pro Lys Pro Ile Val
        435                 440                 445

Asp Tyr Ala Ser Ser Lys Lys Gln Thr Leu Phe Leu Tyr Glu Ala Ser

```
                450             455             460
Lys Glu Ile His Gln Glu Met Asn Asn Pro Arg Phe Gln
465             470             475

<210> SEQ ID NO 4
<211> LENGTH: 2543
<212> TYPE: DNA
<213> ORGANISM: Enterococcus faecalis

<400> SEQUENCE: 4 cctttttgaaa atttagatga aggatttgat gtctacgcca ctcaagcctt taatgcgcca      60
gatggtcgtg cacttgcggt cagttggatt gggttgccag aaatcactta cccaagtgat     120
gtggagggtt gggcaaatgg cttaagtctg gttaaagaac tcacaattca aacgggaaa      180
ctatttcaat atccagtttc tgaaacagaa atgcttcgtc aatccgctac tactttatca     240
aatggctgcc atttcttatc tactgcttct tttgaattag aagtggatat tcccaaaaat     300
gagattgctt ttattcggct tttagcgaac gaaacgggtt caaaaggact tttaattaca     360
attgatacga ttcatggtaa aataacccct gatcgaacat tgctggcca atcttttgct     420
gaaaagtatg gcacaattcg tgaaactaaa attaggaaaa ataagtcagt tcagttaact     480
attttttgttg attgctctgt tgcagaaatc tatgtaaata aggtgaaaa acgatgact     540
ggtcgcttct ttccagataa agcgcaacag tatcttcatc tatccaagac ggcaaaagct     600
tgttttttatg agctgaaaa tacgaataat taggaatgat ggtgaatttt gatggtggtt     660
aaattaacgg atgtagcaaa gcttgctggg gtgagcccga caacggtaag ccgcgtgatt     720
aataattatg ttatcttag tcaaaaaaca attgataaag ttcatcaagc gatgggaagaa     780
ttaaattatc aacctaatgg attagccaga agcctccaag gaaaaagtac gcagctgatt     840
ggtttagtct tcccttctgt tagtcatcca ttttttggtg aattaattga aacactggaa     900
agaaagctct tgttcaagg atataaagtg atttttatgtg atagtgaaaa agatccagaa     960
aaagagcgcg cctatttacg aatgctcgct gcaaataaag tggacggtgt aatcactggt    1020
agccataact tagctattaa cgaatatgaa atgttttcac tacctattgt ttccttttgac    1080
cgtttcttgg cacctggcat tccaattgtc tcttcgcaaa actttcaagg gggccaaaaa    1140
gccactgaag cctattttgc aagtggtgca caaaagattg caattattac tggtgctaat    1200
aacacaggcg cacctagcga ttatcgattg gctggttata acaaacaat ggaaaaatat    1260
ggcgcagaaa aaacgattct acaaattgat aatgggacct caacaacatt aaaaaatcta    1320
gaaatcgaac gtttgcttca aaataaaact gtagacggca tcttttgtac agatgatttg    1380
acagcaatta cagttatgaa tattgctcaa aaattgaaga tatccattcc tgaagaatta    1440
aaagtaattg gttatgatgg gacaaaatta atcaaaagaa ttgccccaca actatcaacc    1500
attgtgcagc caatcgacga gatgtgtgac gttatgattg acttactgct tcgtagaatg    1560
aaggatcctg atgttgcact tgaggaaaat tatcctattc cgattcagct atcattgtct    1620
gaatcctgtt aaaaagaca cctttttcagg tgtctttttt tattcttaat tcctcatttg    1680
cctattttcc cttaattcca aagcacagag attaaataat acaacaacat gatccctaca    1740
aatacaccga gcattagtaa acataccac caatttttgg cgctataggt ttcattttta    1800
tttttttcgg ttcgtttccc ggcagcccat ttccataaat cgtaattatt catctctctc    1860
accacctta atgggtttat taacttaagc ctaacacgga atgagagaac ttgaaaacaa    1920
aaggatcacc cgcttatgca atggatgatc cttttttggg cactattctt ctgataaccc    1980
```

| | |
|---|---|
| attattttta ataactgatt ggtaccaata aaaactatct ttttttaatgc gtcgtaaatc | 2040 |
| ttttaactca tggtcttcac gattaacgta aataaaaccg tagcgttttt tgaatccttg | 2100 |
| atgggaactt aaaatatcca tgaccgacca agggcaatag ccaaacaact caacaccgtc | 2160 |
| agaaatagcc gcatgacaag cagcaatatg atcatgcaaa tacgcaattc gataatcatc | 2220 |
| atgaattttt ccgtcctctg ttaggtgatc tggtgtgcct aagccgtttt ctgtaatgat | 2280 |
| taacggcaaa cggtattgac gataataatc atttaaaact aaacgtagac cagttggatc | 2340 |
| aatttgggca ccatacttag aggtttttaa atgttgattt ttttcgattt taaaataacc | 2400 |
| gtatagatca aaatcaatgt cctttctctt cgtacccaat gggtgttgct catctgtcgg | 2460 |
| taaatagcta gcgactaacg tccgataata attaagagcg ataaaatctg gtttagcggc | 2520 |
| tttcaaaatt gcttgatctt ctg | 2543 |

<210> SEQ ID NO 5
<211> LENGTH: 981
<212> TYPE: DNA
<213> ORGANISM: Enterococcus faecalis

<400> SEQUENCE: 5

| | |
|---|---|
| atggtggtta aattaacgga tgtagcaaag cttgctgggg tgagcccgac aacggtaagc | 60 |
| cgcgtgatta taattatgg ttatcttagt caaaaaacaa ttgataaagt tcatcaagcg | 120 |
| atggaagaat taaattatca acctaatgga ttagccagaa gcctccaagg aaaaagtacg | 180 |
| cagctgattg gtttagtctt cccttctgtt agtcatccat tttttggtga attaattgaa | 240 |
| acactggaaa gaaagctctt tgttcaagga tataaagtga ttttatgtga tagtgaaaaa | 300 |
| gatccagaaa aagagcgcgc ctatttacga atgctcgctg caaataaagt ggacggtgta | 360 |
| atcactggta gccataactt agctattaac gaatatgaaa atgtttcact acctattgtt | 420 |
| tcctttgacc gtttcttggc acctggcatt ccaattgtct cttcgcaaaa ctttcaaggg | 480 |
| ggccaaaaag ccactgaagc cttatttgca agtggtgcac aaaagattgc aattattact | 540 |
| ggtgctaata cacaggcgc acctagcgat tatcgattgg ctggttataa acaaacaatg | 600 |
| gaaaaatatg gcgcagaaaa aacgattcta caaattgata tgggacctc aacaacatta | 660 |
| aaaaatctag aaatcgaacg tttgcttcaa aataaaactg tagacggcat cttttgtaca | 720 |
| gatgatttga cagcaattac agttatgaat attgctcaaa aattgaagat atccattcct | 780 |
| gaagaattaa aagtaattgg ttatgatggg acaaaattaa tcaaaagaat tgccccacaa | 840 |
| ctatcaacca ttgtgcagcc aatcgacgag atgtgtgacg ttatgattga cttactgctt | 900 |
| cgtagaatga aggatcctga tgttgcactt gaggaaaatt atcctattcc gattcagcta | 960 |
| tcattgtctg aatcctgtta a | 981 |

<210> SEQ ID NO 6
<211> LENGTH: 326
<212> TYPE: PRT
<213> ORGANISM: Enterococcus faecalis

<400> SEQUENCE: 6

Met Val Val Lys Leu Thr Asp Val Ala Lys Leu Ala Gly Val Ser Pro
1               5                   10                  15

Thr Thr Val Ser Arg Val Ile Asn Asn Tyr Gly Tyr Leu Ser Gln Lys
            20                  25                  30

Thr Ile Asp Lys Val His Gln Ala Met Glu Glu Leu Asn Tyr Gln Pro
        35                  40                  45

```
Asn Gly Leu Ala Arg Ser Leu Gln Gly Lys Ser Thr Gln Leu Ile Gly
 50                  55                  60

Leu Val Phe Pro Ser Val Ser His Pro Phe Gly Glu Leu Ile Glu
 65                  70                  75                  80

Thr Leu Glu Arg Lys Leu Phe Val Gln Gly Tyr Lys Val Ile Leu Cys
                 85                  90                  95

Asp Ser Glu Lys Asp Pro Glu Lys Glu Arg Ala Tyr Leu Arg Met Leu
                100                 105                 110

Ala Ala Asn Lys Val Asp Gly Val Ile Thr Gly Ser His Asn Leu Ala
                115                 120                 125

Ile Asn Glu Tyr Glu Asn Val Ser Leu Pro Ile Val Ser Phe Asp Arg
            130                 135                 140

Phe Leu Ala Pro Gly Ile Pro Ile Val Ser Ser Gln Asn Phe Gln Gly
145                 150                 155                 160

Gly Gln Lys Ala Thr Glu Ala Leu Phe Ala Ser Gly Ala Gln Lys Ile
                165                 170                 175

Ala Ile Ile Thr Gly Ala Asn Asn Thr Gly Ala Pro Ser Asp Tyr Arg
                180                 185                 190

Leu Ala Gly Tyr Lys Gln Thr Met Glu Lys Tyr Gly Ala Glu Lys Thr
                195                 200                 205

Ile Leu Gln Ile Asp Asn Gly Thr Ser Thr Thr Leu Lys Asn Leu Glu
            210                 215                 220

Ile Glu Arg Leu Leu Gln Asn Lys Thr Val Asp Gly Ile Phe Cys Thr
225                 230                 235                 240

Asp Asp Leu Thr Ala Ile Thr Val Met Asn Ile Ala Gln Lys Leu Lys
                245                 250                 255

Ile Ser Ile Pro Glu Glu Leu Lys Val Ile Gly Tyr Asp Gly Thr Lys
                260                 265                 270

Leu Ile Lys Arg Ile Ala Pro Gln Leu Ser Thr Ile Val Gln Pro Ile
            275                 280                 285

Asp Glu Met Cys Asp Val Met Ile Asp Leu Leu Arg Arg Met Lys
290                 295                 300

Asp Pro Asp Val Ala Leu Glu Glu Asn Tyr Pro Ile Pro Ile Gln Leu
305                 310                 315                 320

Ser Leu Ser Glu Ser Cys
                325

<210> SEQ ID NO 7
<211> LENGTH: 3064
<212> TYPE: DNA
<213> ORGANISM: Enterococcus faecalis

<400> SEQUENCE: 7
ctgcggcgtg caagcgattt tgtttatcac gctttgtcgg attgcaggga taccagccaa      60
atggcaatcg ggattatatg tttctacaca ttatacaggc tgtcatgatt gggcacaatt     120
ttatataaaa ccgtacggct ggctctttgc ggatttgtct tttggcggag gtgcttaccg     180
agacggggat agacagcggt ggaatcatta tttcggcaat ttagatgttt ttagaatggt     240
cgcaaatagt gagatccagg cagactttca gccggcaaaa atgcaattgc gtgcagaccc     300
aattgacaac cagcggggag aatttgagta cgaaaatgag gcttgccct acgcatgctt     360
gatagtttcg caagaacggc tttccatgga agagttgccg tttgattgac atagggggg     420
aatagtatga aaaagttaaa aatgatgggg attatgttat tgttagtac ggtcttggta     480
ggttgtggca acagcagaa acaaaaata gacgagaaag caactgagaa aaccagtgtc      540
```

-continued

```
tcgaaaaaag ttttaaattt aatggagaac tcggaaatcg gttcaatgga ttctattttt      600
acacaagatg aagccagtat aacgcacag tccaatgtct ttgaagggtt atatcaattg      660
gatgaaaaag atcaactaat acctgctgct gctaaagaga tgccagaaat ttctgaggat      720
ggcaaacgat ataccattaa actaagagaa gatggcaagt ggtccaatgg tgatgctgta      780
acagccaatt atttcgtttt tgcttggcgt aaattagcga atcccaaaaa ccaagccaat      840 tacttttct tgttagaagg aacgattctg aacggaacag ctattacaaa agaggaaaaa      900 gcaccgagg aattgggtgt caaagcgctt gatgattata ctttggaggt tactttagaa      960
aagcctgtac catatttac gtcgttattg gcattttctc cattttccc acaaaacgaa      1020 gcattcgtga agaaaaagg acaagccat ggcacttcta gtgaaatgat tgtatctaat      1080
ggtccgtttt taatgaaaaa ttgggatcag tcagcgatgt cgtgggattt tgtgcgtaat      1140
ccctactatt acgataaaga aaagtaaaa tcagaaacga ttcattttga agttcttaaa      1200
gaaaccaata ccgtttataa tttgtacgaa tcaggtgaat tagatgtggc tgtcttaaca      1260
ggagattttg ctaaacaaaa tcgagacaac ccagactatg aagcaatcga acggtcaaaa      1320
gtctattcct tacgtttaaa ccaaaaaaga aacgaaaaac catccatttt tgcaaatgag      1380
aatgtccgca aagctttagc ttatgctttg gataaaaaaa gtttagtcga taatatttta      1440
gcagatggct caaagaaaat ttatgggtac attccagaaa aatttgtata acccagaa      1500 acgaatgaag atttcgtca agaagcaggc gctcttgtca aaacagacgc caaaaaagcc      1560
aaagagtatt tagataaagc aaaagcagag ctaaacggag atgtagccat tgaacttctt      1620
tcaagagatg gtgatagtga ccgaaaagtt gctgaattta ccaaggcca gttacaagaa      1680 acgttgcctg gtctcactat taatgtcaaa acagttcctt taataatgc aattgaatta      1740 atgagaaaag gggattatga attgtctgtt ggcatgtggg gacccgatta tcaggatcca      1800
atgactttct tagaaagctc agttagtggt aaccgtatga actattctag cccaacgttt      1860
gatcaactaa ttgaagaagc aacaactaaa tacgcaaatg agcctgaaac tcgttggcaa      1920
acattaatta aagctgaaaa agtattggtg gaagaagatg ccgctttaat tcctttatac      1980
caagaggccc gtagtcagct tgtacgacca ggtgtcaaag gtattcagta tcataacttc      2040
ggtgcaacga gcacatataa gtatgcctat aaagaataaa ttagtgaaca aaagtacctt      2100
tagctgaagg tacttttttt ccgataagag cttcttttt gttaatagtc aacaattaat      2160 aaaaaataa ttgaaaaagg ttgacaaaaa taatgatact cgttagaata agcactgtta      2220
acaaatgaat agcgttttca tgtgactaga taatactagg catggaagaa tttcgtaata      2280
caatgtggtg tacaatggtt acgcaacatg tttaacggga ttgttctatg ctttttttgt      2340
tgttttcact gaaaatgtta gaattacttc tgcagaagag ggtcatttat gaaaattaaa      2400
aaggtgctaa atcaaaatgc tgtacttgtt cttgacgaag acaggagaa agtagctgtc      2460 ggtaaaggcg tcgggtttaa taagactaaa aatgatgtct tatctcgaca attggtggag      2520
cggatgtttg tgatggagcc agaaggactg aaaaaacttc aagtactgct atcacaaatt      2580
gaagacaaat acttttagg agtgaagaaa ttatccaaca tgctgaaacg gtattgggtg      2640
aaaagttgaa tgaacatatt aatattgggt tgagtgatca cattgctttt gcagctgaaa      2700
atattcaaaa taatattatt gttcggaaca agcttttaag tgaaattgag attttatata      2760
gtgaagaatt tgctattgct caatgggctg tagaatattt aacacaaacc ttagagattc      2820
catttagtta tgatgaagcg gggtatattg cgattcatat ccatagtgct cgcagcgggc      2880
```

| gtactgataa tagtaaaagt atccgtgaag ttacaatcgt ttctgaaatt attcatttaa | 2940 |
| tcgagcagga attggctatt gatattcatg atgataaaaa tagtctcagt tattcacgtt | 3000 |
| tggtgaatca tttacgtttg tttattcatc gcttccaaca aaatcaatac gctgttttag | 3060 |
| atga | 3064 |

<210> SEQ ID NO 8
<211> LENGTH: 1653
<212> TYPE: DNA
<213> ORGANISM: Enterococcus faecalis

<400> SEQUENCE: 8

| atgaaaaagt taaaaatgat ggggattatg ttatttgtta gtacggtctt ggtaggttgt | 60 |
| ggcacaacag cagaaacaaa aatagacgag aaagcaactg agaaaaccag tgtctcgaaa | 120 |
| aaagttttaa atttaatgga gaactcggaa atcggttcaa tggattctat ttttacacaa | 180 |
| gatgaagcca gtattaacgc acagtccaat gtctttgaag gttatatca attggatgaa | 240 |
| aaagatcaac taataccctgc tgctgctaaa gagatgccag aaatttctga ggatggcaaa | 300 |
| cgatatacca ttaaactaag agaagatggc aagtggtcca atggtgatgc tgtaacagcc | 360 |
| aatgatttcg ttttttgcttg gcgtaaaatta gcgaatccca aaaaccaagc caattacttt | 420 |
| ttcttgttag aaggaacgat tctgaacgga acagctatta caaagaggaa aaagcacca | 480 |
| gaggaattgg gtgtcaaagc gcttgatgat tatactttgg aggttacttt agaaaagcct | 540 |
| gtaccatatt ttacgtcgtt attggcattt tctccatttt tcccacaaaa cgaagcattc | 600 |
| gtgaaagaaa aaggacaagc ctatggcact tctagtgaaa tgattgtatc taatggtccg | 660 |
| tttttaatga aaaattggga tcagtcagcg atgtcgtggg attttgtgcg taatccctac | 720 |
| tattacgata agaaaaagt aaaatcagaa acgattcatt ttgaagttct taaagaaacc | 780 |
| aataccgttt ataatttgta cgaatcaggt gaattagatg tggctgtctt aacaggagat | 840 |
| tttgctaaac aaaatcgaga caacccagac tatgaagcaa tcgaacggtc aaaagtctat | 900 |
| tccttacgtt taaccaaaa aagaaacgaa aaaccatcca tttttgcaaa tgagaatgtc | 960 |
| cgcaaagctt tagcttatgc tttggataaa aaagtttag tcgataatat tttagcagat | 1020 |
| ggctcaaaag aaatttatgg gtacattcca gaaaaatttg tatataaccc agaaacgaat | 1080 |
| gaagatttc gtcaagaagc aggcgctctt gtcaaaacag acgccaaaaa agccaaagag | 1140 |
| tatttagata agcaaaagc agagctaaac ggagatgtag ccattgaact tctttcaaga | 1200 |
| gatggtgata gtgaccgaaa agttgctgaa tttatccaag gccagttaca agaaacgttg | 1260 |
| cctggtctca ctattaatgt caaaacagtt cctttaaata tgcaattga attaatgaga | 1320 |
| aaaggggatt atgaattgtc tgttggcatg tggggacccg attatcagga tccaatgact | 1380 |
| ttcttagaaa gctcagttag tggtaaccgt atgaactatt ctagcccaac gtttgatcaa | 1440 |
| ctaattgaag aagcaacaac taaatacgca atgagcctg aaactcgttg gcaaacatta | 1500 |
| attaaagctg aaaagtatt ggtggaagaa gatgccgctt taattccttt ataccaagag | 1560 |
| gcccgtagtc agcttgtacg accaggtgtc aaaggtattc agtatcataa cttcggtgca | 1620 |
| acgagcacat ataagtatgc ctataaagaa taa | 1653 |

<210> SEQ ID NO 9
<211> LENGTH: 550
<212> TYPE: PRT
<213> ORGANISM: Enterococcus faecalis

<400> SEQUENCE: 9

```
Met Lys Lys Leu Lys Met Met Gly Ile Met Leu Phe Val Ser Thr Val
  1               5                  10                  15

Leu Val Gly Cys Gly Thr Thr Ala Glu Thr Lys Ile Asp Glu Lys Ala
             20                  25                  30

Thr Glu Lys Thr Ser Val Ser Lys Val Leu Asn Leu Met Glu Asn
         35                  40                  45

Ser Glu Ile Gly Ser Met Asp Ser Ile Phe Thr Gln Asp Glu Ala Ser
     50                  55                  60

Ile Asn Ala Gln Ser Asn Val Phe Glu Gly Leu Tyr Gln Leu Asp Glu
 65              70                  75                      80

Lys Asp Gln Leu Ile Pro Ala Ala Lys Glu Met Pro Glu Ile Ser
                 85                  90                  95

Glu Asp Gly Lys Arg Tyr Thr Ile Lys Leu Arg Glu Asp Gly Lys Trp
             100                 105                 110

Ser Asn Gly Asp Ala Val Thr Ala Asn Asp Phe Val Phe Ala Trp Arg
             115                 120                 125

Lys Leu Ala Asn Pro Lys Asn Gln Ala Asn Tyr Phe Phe Leu Leu Glu
     130                 135                 140

Gly Thr Ile Leu Asn Gly Thr Ala Ile Thr Lys Glu Glu Lys Ala Pro
145                 150                 155                 160

Glu Glu Leu Gly Val Lys Ala Leu Asp Asp Tyr Thr Leu Glu Val Thr
                 165                 170                 175

Leu Glu Lys Pro Val Pro Tyr Phe Thr Ser Leu Leu Ala Phe Ser Pro
             180                 185                 190

Phe Phe Pro Gln Asn Glu Ala Phe Val Lys Glu Lys Gly Gln Ala Tyr
             195                 200                 205

Gly Thr Ser Ser Glu Met Ile Val Ser Asn Gly Pro Phe Leu Met Lys
     210                 215                 220

Asn Trp Asp Gln Ser Ala Met Ser Trp Asp Phe Val Arg Asn Pro Tyr
225                 230                 235                 240

Tyr Tyr Asp Lys Glu Lys Val Lys Ser Glu Thr Ile His Phe Glu Val
             245                 250                 255

Leu Lys Glu Thr Asn Thr Val Tyr Asn Leu Tyr Glu Ser Gly Glu Leu
             260                 265                 270

Asp Val Ala Val Leu Thr Gly Asp Phe Ala Lys Gln Asn Arg Asp Asn
     275                 280                 285

Pro Asp Tyr Glu Ala Ile Glu Arg Ser Lys Val Tyr Ser Leu Arg Leu
     290                 295                 300

Asn Gln Lys Arg Asn Glu Lys Pro Ser Ile Phe Ala Asn Glu Asn Val
305                 310                 315                 320

Arg Lys Ala Leu Ala Tyr Ala Leu Asp Lys Lys Ser Leu Val Asp Asn
             325                 330                 335

Ile Leu Ala Asp Gly Ser Lys Glu Ile Tyr Gly Tyr Ile Pro Glu Lys
             340                 345                 350

Phe Val Tyr Asn Pro Glu Thr Asn Glu Asp Phe Arg Gln Glu Ala Gly
         355                 360                 365

Ala Leu Val Lys Thr Asp Ala Lys Lys Ala Lys Glu Tyr Leu Asp Lys
     370                 375                 380

Ala Lys Ala Glu Leu Asn Gly Asp Val Ala Ile Glu Leu Leu Ser Arg
385                 390                 395                 400

Asp Gly Asp Ser Asp Arg Lys Val Ala Glu Phe Ile Gln Gly Gln Leu
                 405                 410                 415
```

-continued

```
Gln Glu Thr Leu Pro Gly Leu Thr Ile Asn Val Lys Thr Val Pro Leu
                420                 425                 430
Asn Asn Ala Ile Glu Leu Met Arg Lys Gly Asp Tyr Glu Leu Ser Val
            435                 440                 445
Gly Met Trp Gly Pro Asp Tyr Gln Asp Pro Met Thr Phe Leu Glu Ser
    450                 455                 460
Ser Val Ser Gly Asn Arg Met Asn Tyr Ser Ser Pro Thr Phe Asp Gln
465                 470                 475                 480
Leu Ile Glu Glu Ala Thr Thr Lys Tyr Ala Asn Glu Pro Glu Thr Arg
                485                 490                 495
Trp Gln Thr Leu Ile Lys Ala Glu Lys Val Leu Val Glu Glu Asp Ala
            500                 505                 510
Ala Leu Ile Pro Leu Tyr Gln Glu Ala Arg Ser Gln Leu Val Arg Pro
    515                 520                 525
Gly Val Lys Gly Ile Gln Tyr His Asn Phe Gly Ala Thr Ser Thr Tyr
530                 535                 540
Lys Tyr Ala Tyr Lys Glu
545                 550
```

<210> SEQ ID NO 10
<211> LENGTH: 3498
<212> TYPE: DNA
<213> ORGANISM: Enterococcus faecalis

<400> SEQUENCE: 10

```
aatcaatgaa atttaataaa aaagcttagt tagttgcatt cattgttcaa atcggttaca      60
ctaagtaagt aaaaaaatat aatacaaggt tcgtcttcag gggcagggtg taattcccga     120
ccggtggtta tagtccacga ctcgttttta acgattgaat tggtgtaatt ccaataccga     180
cagtatagtc tggataaaga agatagggct tatttgagac gctttttcat cagataatcc     240
tactctattt ttccctgcag aaaaatanggg ttttttttgta tgacaaagaa gcgaatcaaa     300
aagttcgttg aagatgggtc cttaattgga ggatttcaga tgaacaacaa ggtacaaaaa     360
atggtcagca ttgcaatgtt ggccgcaatc ggtacagtat acaatttgt ggcatttccg     420
attatgccgg cgtttagttt tttgaaaatc gattttagtg atattccgat tctactcgga     480
atgttcttgt acggaccgtt agcaggagta attactgctt tgttcgttc gttgctacac     540
ctgttcttaa ccggactagc accgcaaaat atggtgggag atttcgctag ctttttagca     600
agtagtatct tcaccttgcc aatttttat ttctttggta aaagaaaaa tatccgtaca     660
aatcggatag tgggcttagt aagtgggatc ttagccttga caattttcat gagtattgcg     720
aattattttg tcattacacc catttactta caattatatg gtgtgaccac acaacaattt     780
ttaggaacat ctttagcaag ctatgtggcg attggtattg tgccattcaa ccttattaaa     840
ggcctcttag tcagtggtgt ttttctagta ctacatgcga agttattgcc atggctatca     900
aaaaaacaac atactattca gaaaaaaaca ccgttaacaa aataaatgat aaaaaacctg     960
ctgttgaaca atgtttgaca gtgggttttt aaaatttacg cctaaaagaa aagaggttgt    1020
cataatctgt catcattctg ttaaaaaata ctaaaccatc tgcattgtaa ttttaacttt    1080
cccttggtat gatagaaatc atcaaagaaa gaggagtttt cctgagtgaa aaagtgtaaa    1140
aattgtcgtc acgtgaatcg tgatacggag tccttttgtg aagaatgcgg cgctccgcta    1200
atgaatgaat caatgcatca agaggaaaac caagcacaac catcaatgaa taaagggaac    1260
gaatctactc ctctcagatc aaaaagaagc tggatctggg cgtttctttt tgtgttcatc    1320
```

-continued

```
gttcttggag cgggtagcta ttttctcggg acgcattatt tttctaagga acaacaaatt      1380
tcttatttta ttgaagcgat tgagaatggt gatgcccaag aattaagtaa aaaaatgagg      1440
acgaacgagt ctgaatttca agtgaatccg caaagcatta agcctttaat cacttattat      1500
caaaaaaatc caactgagct aaaaaaatta gaaaaagcgc tattaaagga taaaaagtta      1560
catggtttaa ctattcgtga aacaagtcaa acagcatttt tctttcaccg ttatcaattc      1620
attttaacgc ctgtttctgt tcagttaacg acgaatcagc gcggtgtgac gctggcaatg      1680
aacgggcggg aagtgggcac ttccgactca accacttatc aaaaggaatt gggcccctta      1740
gcgccaggac aatatacttt tacagccaca gtgaaagata gcaccggcga acctgttatc      1800
acagaagagt accgtttatt agaagaggaa aattatattt ctagtattcc tttagatttt      1860
aaacgaatga attttgttgt ggaaagcaat ctgccagacg cagatattta tattaatgat      1920
cggaaagttg gtacgctaac gaatggaagc aaaacgattg gccctttgtt ctggtccaaa      1980
gggatgacga ttcaacttaa aaagacgatt aatggagaag aaattcaaac atcaaaagaa      2040
acgattggtg aaaatgattt tgtcgaagcg ctctccgata tccaacgct acaattgaat       2100 tttccgttag ctagcgacta tgatgcccgc aaagcgctag aaaccttta tcaagcattt       2160 gccaaacaag tgaaaagtca tacggatagt acagaatttg ctaaaaaata tctcgttggt      2220
ggggaaaata tcctcaatt tccttctttt atagaagcac ttgaacgatt acgtgaaaag       2280
aaatcgaccg atggttcacc agattttgaa gtgaccatta atacgctaca attggatggt      2340
aaagaaaatt accatgtcaa ttattattta gaagccaaaa attctaaagc aaagaaaat       2400 ggtcttcgtt atgaatggat caatggccta aatgatcaaa ttcatttagt caaagaaccg      2460
ttaaaagaag gacaattaca gtttgtttcg atagatgaac aaaacacttgc ttggctcgaa     2520 aagatactct aagcaaaaat gagtgctaaa ttatttagca ctcattttttg cttatttcta    2580 ttgcacgcgt gggacatttg cggtacgctt ttaacacatt ctcgcgttcg ttttctggaa      2640
taaattgttg tcgagcatgc ggctcgtctt taaaaaggac aatcccatga tcatcataat      2700
caaatatatt aggcgcataa acttgacaaa gtccacaagc aatacatttt tcaggaacta      2760
aacgtgattg cataaacagt gacacatcct atctaaaaga ggtttactat ggaagcaact      2820 tttatttttag cgttattatc tcatggatac aaggtacgtg catcaacttt gtatcatctt     2880
ttaaaaggca acggactag ctctgttttg atttatggtt ttttatatga ttgtttacgg       2940
ttcattggct ggtggccaac gatttccgaa caagcctatt ttcaatttct tgaaaaactt      3000
tcgaaggcga aacaaattca gtatcacgaa gagacaaatg agattcaact aacaaaagaa      3060
gggcaactat ttttaaagga gcaccatttt tcgttgctgg attatcctgc aattgatctt      3120
tatcgttttg gcagaagtga tcgagaaagt tggcaactca ttcaatttgc cgtgcaagtg      3180
acttcatatt tatcatttga ggaaaaacag tatattccac ttttatcaac accgattccg      3240
caactatatt tgaaacgatg gttacaacaa gacaagaaag agcagcgcgt tcaatcaatc      3300
aaagaagaac tgttgcgagg gtttgagtta ctacctgaag cagaaagcga ctatttggtt      3360
gcgcaacttt ctggttatca gcaaactggc aaagttcctc agcaattaac aagccataag      3420
acagctcttg aacagcgttt gtggcacacg caagcggttc atcatttact gcagttgata      3480
atgtacggag gaaattat                                                    3498
```

<210> SEQ ID NO 11
<211> LENGTH: 1332
<212> TYPE: DNA
<213> ORGANISM: Enterococcus faecalis

<400> SEQUENCE: 11

```
atgaatgaat caatgcatca agaggaaaac caagcacaac catcaatgaa taaagggaac      60
gaatctactc ctctcagatc aaaaagaagc tggatctggg cgtttctttt tgtgttcatc     120
gttcttggag cgggtagcta ttttctcggg acgcattatt tttctaagga caacaaatt     180
tcttatttta ttgaagcgat tgagaatggt gatgcccaag aattaagtaa aaaaatgagg     240
acgaacgagt ctgaatttca gtgaatccg caaagcatta agcctttaat cacttattat      300
caaaaaaatc caactgagct aaaaaaatta gaaaagcgc tattaaagga taaaagtta      360
catggtttaa ctattcgtga acaagtcaa acagcatttt tctttcaccg ttatcaattc      420
attttaacgc ctgtttctgt tcagttaacg acgaatcagc gcggtgtgac gctggcaatg     480
aacgggcggg aagtgggcac ttccgactca accacttatc aaaaggaatt gggccccta     540
gcgccaggac aatatacttt tacagccaca gtgaaagata gcaccggcga acctgttatc     600
acagaagagt accgtttatt agaagaggaa aattatattt ctagtattcc tttagattt      660
aaacgaatga attttgttgt ggaaagcaat ctgccagacg cagatattta tattaatgat     720
cggaaagttg gtacgctaac gaatggaagc aaaacgattg gccctttgtt ctggtccaaa     780
gggatgacga ttcaacttaa aaagacgatt aatggagaag aaattcaaac atcaaaagaa     840
acgattggtg aaaatgattt tgtcgaagcg ctctccgata tccaacgct acaattgaat      900
tttccgttag ctagcgacta tgatgcccgc aaagcgctag aacctttta tcaagcattt     960
gccaaacaag tgaaaagtca tacggatagt acagaatttg ctaaaaaata tctcgttggt    1020
ggggaaaata atcctcaatt tccttctttt atagaagcac ttgaacgatt acgtgaaaag    1080
aaatcgaccg atggttcacc agattttgaa gtgaccatta atacgctaca attggatggt    1140
aaagaaaatt accatgtcaa ttattattta gaagccaaaa attctaaagc aaagaaaat    1200
ggtcttcgtt atgaatggat caatggccta aatgatcaaa ttcatttagt caagaaccg    1260
ttaaaagaag gacaattaca gtttgtttcg atagatgaac aaacacttgc ttggctcgaa    1320
aagatactct aa                                                         1332
```

<210> SEQ ID NO 12
<211> LENGTH: 443
<212> TYPE: PRT
<213> ORGANISM: Enterococcus faecalis

<400> SEQUENCE: 12

```
Met Asn Glu Ser Met His Gln Glu Glu Asn Gln Ala Gln Pro Ser Met
  1               5                  10                  15
Asn Lys Gly Asn Glu Ser Thr Pro Leu Arg Ser Lys Arg Ser Trp Ile
             20                  25                  30
Trp Ala Phe Leu Phe Val Phe Ile Val Leu Gly Ala Gly Ser Tyr Phe
         35                  40                  45
Leu Gly Thr His Tyr Phe Ser Lys Glu Gln Gln Ile Ser Tyr Phe Ile
     50                  55                  60
Glu Ala Ile Glu Asn Gly Asp Ala Gln Glu Leu Ser Lys Lys Met Arg
 65                  70                  75                  80
Thr Asn Glu Ser Glu Phe Gln Val Asn Pro Gln Ser Ile Lys Pro Leu
                 85                  90                  95
Ile Thr Tyr Tyr Gln Lys Asn Pro Thr Glu Leu Lys Lys Leu Glu Lys
            100                 105                 110
Ala Leu Leu Lys Asp Lys Lys Leu His Gly Leu Thr Ile Arg Glu Thr
```

```
                 115                 120                 125
Ser Gln Thr Ala Phe Phe His Arg Tyr Gln Phe Ile Leu Thr Pro
    130                 135                 140

Val Ser Val Gln Leu Thr Thr Asn Gln Arg Gly Val Thr Leu Ala Met
145                 150                 155                 160

Asn Gly Arg Glu Val Gly Thr Ser Asp Ser Thr Thr Tyr Gln Lys Glu
                165                 170                 175

Leu Gly Pro Leu Ala Pro Gly Gln Tyr Thr Phe Thr Ala Thr Val Lys
            180                 185                 190

Asp Ser Thr Gly Glu Pro Val Ile Thr Glu Glu Tyr Arg Leu Glu
            195                 200                 205

Glu Glu Asn Tyr Ile Ser Ser Ile Pro Leu Asp Phe Lys Arg Met Asn
210                 215                 220

Phe Val Val Glu Ser Asn Leu Pro Asp Ala Asp Ile Tyr Ile Asn Asp
225                 230                 235                 240

Arg Lys Val Gly Thr Leu Thr Asn Gly Ser Lys Thr Ile Gly Pro Leu
                245                 250                 255

Phe Trp Ser Lys Gly Met Thr Ile Gln Leu Lys Lys Thr Ile Asn Gly
            260                 265                 270

Glu Glu Ile Gln Thr Ser Lys Glu Thr Ile Gly Glu Asn Asp Phe Val
            275                 280                 285

Glu Ala Leu Ser Asp Asn Pro Thr Leu Gln Leu Asn Phe Pro Leu Ala
            290                 295                 300

Ser Asp Tyr Asp Ala Arg Lys Ala Leu Glu Thr Phe Tyr Gln Ala Phe
305                 310                 315                 320

Ala Lys Gln Val Lys Ser His Thr Asp Ser Thr Glu Phe Ala Lys Lys
                325                 330                 335

Tyr Leu Val Gly Gly Glu Asn Asn Pro Gln Phe Pro Ser Phe Ile Glu
            340                 345                 350

Ala Leu Glu Arg Leu Arg Glu Lys Lys Ser Thr Asp Gly Ser Pro Asp
            355                 360                 365

Phe Glu Val Thr Ile Asn Thr Leu Gln Leu Asp Gly Lys Glu Asn Tyr
370                 375                 380

His Val Asn Tyr Tyr Leu Glu Ala Lys Asn Ser Lys Ala Lys Glu Asn
385                 390                 395                 400

Gly Leu Arg Tyr Glu Trp Ile Asn Gly Leu Asn Asp Gln Ile His Leu
                405                 410                 415

Val Lys Glu Pro Leu Lys Glu Gly Gln Leu Gln Phe Val Ser Ile Asp
            420                 425                 430

Glu Gln Thr Leu Ala Trp Leu Glu Lys Ile Leu
            435                 440

<210> SEQ ID NO 13
<211> LENGTH: 3400
<212> TYPE: DNA
<213> ORGANISM: Enterococcus faecalis

<400> SEQUENCE: 13
aatttagata attgacgccg gccgcttcgg caactgtgac aatatcaaag ccagcaaaag    60
ctttttcttt taattcgttc agaaagtcac tcattcctgg catgtttcta ctagcttttg   120
ttactttggc taattgatct gccccatcag caggtaagtt tgtccaagtc aaatctttct   180
taataaaatt aatcgcatct acacgaaaac cagcaattcc tttgtttaac caaaaacgaa   240
tcatttgata gatttctttg cgtagttcag gattttccca atttaaatcc ggctgttttt   300
```

-continued

```
tatgaaaggc atgaaagtag taggcatctt ccccaggtaa ttttttcccaa acactaccac    360 cgaagttaga ccgccaattt gtaggtgctt ctcgtccttc ttttataata taaaagtctc    420
gaaaacgact ttgaggattt tttaaaacat cttgaaacca agcatgttca tcagatgtat    480
ggtttaccac caaatctaaa ataacttttta tgtttcgttt ttttgcttct tcaatgagtt    540
catcgaagtc tgccattgta ccaaaatcgc tagaaatacc ataatagtct gaaatatcat    600
atccattgtc agccattggc gacgggtaca ttggactcag ccaaatcagc gtaattccta    660 aatttttctaa gtaatccagt ttttgaataa tgccttgtaa atcaccaatt ccgtcattat    720
tactatccga aaagctacgt ggataaattt gataggccac ttcttttttgc caccaatttc    780 tgttcattct ggttctcctc actcttaaac tagtcctgtt aatttttttct gtaaccgttt    840 ttacattttg tatgatactc gttttttgcgt aatatgtcaa acgtttatca taaataaatg    900
taaattataa tattcttttg atttaaatag atttatatat gttatacgtt tgacttttttt    960 ctgatttgtt tatactatta gactaactac tattttctaa taaaggagac attacttatg   1020
tcaagcatca tgaaccaatg gacgatgaa ttacgttatg cgccttattc ttcttggaca   1080
tctgctcacc tcgaaaatct aacttctatt atcgcgcaat ctagttggcg ttttaagtat   1140
catattcaac cacagacagg actactaaat gatcccaacg ttttttcgta tttcaataac   1200
cagtggcatt tattttatca agcgtttcct ttcgggagtg ttcacggact aaaaagttgg   1260
gcccacttaa cttcctccga cttaattcac tgggattatg aaggaattgc cctttatccc   1320
gactctgaat atgattctca tggcgtctat tcaggctcag ctttaacaat agataaccaa   1380
ctatgtttat tttatacagg aaatgttcgt gatcaaactt ggcaacgatt tgcatatcaa   1440
aatattgcat ggctgaattc tttaggtgcg atcacaaagg aatcaacacc attcctacct   1500 attgaccca attattcttc ccattttcgt gatccgatgg tatttcctta tcaagaagga   1560
cttgttttat taattggtgc tagtgattta aatggacaag gaaaaattgt ggtctatttt   1620
tctaaagatc gaaatgtaca caattttcat caacttggcg aattgacgtt caccaaccaa   1680
gaattaggct acatggttga atgccccaat ttggtattta ttgatggcca gcctgtctta   1740 ttatttttgcc cacaaggtct atctccatct gtaaaaagtt atcagaatat ctatccgaat   1800
atgtacacat tggccgaaac gtttgatttg gagaatcttt cttttagttca ggctgggcct   1860 tttgaaaatt tagatgaagg atttgatgtc tacgccactc aagcctttaa tgcgccagat   1920
ggtcgtgcac ttgcggtcag ttggattggg ttgccagaaa tcacttaccc aagtgatgtg   1980
gagggttggg caaatggctt aagtctggtt aaagaactca caattcacaa cgggaaacta   2040
tttcaatatc cagtttctga aacagaaatg cttcgtcaat ccgctactac tttatcaaat   2100
ggctgccatt tcttatctac tgcttctttt gaattagaag tggatattcc caaaaatgag   2160 attgcttttta ttcggctttt agcgaacgaa acggggttcaa aaggactttt aattacaatt   2220
gatacgattc atggtaaaat aaccccttgat cgaacatttg ctggccaatc ttttgctgaa   2280
aagtatggca caattcgtga aactaaaatt aggaaaaata agtcagttca gttaactatt   2340
tttgttgatt gctctgttgc agaaatctat gtaaataaag gtgaaaaaac gatgactggt   2400
cgcttctttc cagataaagc gcaacagtat cttcatctat ccaagacggc aaaagcttgt   2460
ttttatgagc tggaaaatac gaataattag gaatgatggt gaattttgat ggtggttaaa   2520
ttaacggatg tagcaaagct tgctgggggtg agcccgacaa cggtaagccg cgtgattaat   2580
aattatggtt atcttagtca aaaacaatt gataaagttc atcaagcgat ggaagaatta   2640
```

| | | | | |
|---|---|---|---|---|
| aattatcaac | ctaatggatt | agccagaagc | ctccaaggaa | aaagtacgca gctgattggt | 2700 |
| ttagtcttcc | cttctgttag | tcatccattt | tttggtgaat | taattgaaac actggaaaga | 2760 |
| aagctctttg | ttcaaggata | taaagtgatt | ttatgtgata | gtgaaaaaga tccagaaaaa | 2820 |
| gagcgcgcct | atttacgaat | gctcgctgca | aataaagtgg | acggtgtaat cactggtagc | 2880 |
| cataacttag | ctattaacga | atatgaaaat | gtttcactac | ctattgtttc ctttgaccgt | 2940 |
| ttcttggcac | ctggcattcc | aattgtctct | tcgcaaaact | ttcaaggggg ccaaaaagcc | 3000 |
| actgaagcct | tatttgcaag | tggtgcacaa | aagattgcaa | ttattactgg tgctaataac | 3060 |
| acaggcgcac | ctagcgatta | tcgattggct | ggttataaac | aaacaatgga aaaatatggc | 3120 |
| gcagaaaaaa | cgattctaca | aattgataat | gggacctcaa | caacattaaa aaatctagaa | 3180 |
| atcgaacgtt | tgcttcaaaa | taaaactgta | gacggcatct | tttgtacaga tgatttgaca | 3240 |
| gcaattacag | ttatgaatat | tgctcaaaaa | ttgaagatat | ccattcctga agaattaaaa | 3300 |
| gtaattggtt | atgatgggac | aaaattaatc | aaaagaattg | ccccacaact atcaaccatt | 3360 |
| gtgcagccaa | tcgacgagat | gtgtgacgtt | atgattgact | | 3400 |

<210> SEQ ID NO 14
<211> LENGTH: 1473
<212> TYPE: DNA
<213> ORGANISM: Enterococcus faecalis

<400> SEQUENCE: 14

| | | | | |
|---|---|---|---|---|
| atgtcaagca | tcatgaacca | atggacggat | gaattacgtt | atgcgcctta ttcttcttgg | 60 |
| acatctgctc | acctcgaaaa | tctaacttct | attatcgcgc | aatctagttg gcgttttaag | 120 |
| tatcatattc | aaccagagac | aggactacta | atgatccca | acggttttc gtatttcaat | 180 |
| aaccagtggc | atttatttta | tcaagcgttt | cctttcggga | gtgttcacgg actaaaaagt | 240 |
| tgggcccact | taacttcctc | cgacttaatt | cactgggatt | atgaaggaat tgccctttat | 300 |
| cccgactctg | aatatgattc | tcatggcgtc | tattcaggct | cagctttaac aatagataac | 360 |
| caactatgtt | tattttatac | aggaaatgtt | cgtgatcaaa | cttggcaacg atttgcatat | 420 |
| caaaatattg | catggctgaa | ttctttaggt | gcgatcacaa | aggaatcaac accattccta | 480 |
| cctattgacc | ccaattattc | ttcccatttt | cgtgatccga | tggtatttcc ttatcaagaa | 540 |
| ggacttgttt | tattaattgg | tgctagtgat | ttaaatggac | aaggaaaaat tgtggtctat | 600 |
| ttttctaaag | atcgaaatgt | acacaatttt | catcaacttg | gcgaattgac gttcaccaac | 660 |
| caagaattag | gctacatggt | tgaatgcccc | aatttggtat | ttattgatgg ccagcctgtc | 720 |
| ttattatttt | gcccacaagg | tctatctcca | tctgtaaaaa | gttatcagaa tatctatccg | 780 |
| aatatgtaca | cattggccga | aacgtttgat | ttggagaatc | tttctttagt tcaggctggg | 840 |
| ccttttgaaa | atttagatga | aggatttgat | gtctacgcca | ctcaagcctt taatgcgcca | 900 |
| gatggtcgtg | cacttgcggt | cagttggatt | gggttgccag | aaatcactta cccaagtgat | 960 |
| gtggagggtt | gggcaaatgg | cttaagtctg | gttaaagaac | tcacaattca acgggaaa | 1020 |
| ctatttcaat | atccagtttc | tgaaacagaa | atgcttcgtc | aatccgctac tactttatca | 1080 |
| aatggctgcc | atttcttatc | tactgcttct | tttgaattag | aagtggatat tcccaaaaat | 1140 |
| gagattgctt | ttattcggct | tttagcgaac | gaaacgggtt | caaaggact tttaattaca | 1200 |
| attgatacga | ttcatggtaa | aataccctt | gatcgaacat | tgctggcca atcttttgct | 1260 |
| gaaaagtatg | gcacaattcg | tgaaactaaa | attaggaaaa | ataagtcagt tcagttaact | 1320 |
| attttttgttg | attgctctgt | tgcagaaatc | tatgtaaata | aaggtgaaaa aacgatgact | 1380 |

-continued

```
ggtcgcttct tccagataaa agcgcaacag tatcttcatc tatccaagac ggcaaaagct   1440
tgtttttatg agctggaaaa tacgaataat tag                                1473
```

<210> SEQ ID NO 15
<211> LENGTH: 490
<212> TYPE: PRT
<213> ORGANISM: Enterococcus faecalis

<400> SEQUENCE: 15

```
Met Ser Ser Ile Met Asn Gln Trp Thr Asp Glu Leu Arg Tyr Ala Pro
1               5                   10                  15

Tyr Ser Ser Trp Thr Ser Ala His Leu Glu Asn Leu Thr Ser Ile Ile
            20                  25                  30

Ala Gln Ser Ser Trp Arg Phe Lys Tyr His Ile Gln Pro Gln Thr Gly
        35                  40                  45

Leu Leu Asn Asp Pro Asn Gly Phe Ser Tyr Phe Asn Asn Gln Trp His
    50                  55                  60

Leu Phe Tyr Gln Ala Phe Pro Phe Gly Ser Val His Gly Leu Lys Ser
65                  70                  75                  80

Trp Ala His Leu Thr Ser Ser Asp Leu Ile His Trp Asp Tyr Glu Gly
                85                  90                  95

Ile Ala Leu Tyr Pro Asp Ser Glu Tyr Asp Ser His Gly Val Tyr Ser
            100                 105                 110

Gly Ser Ala Leu Thr Ile Asp Asn Gln Leu Cys Leu Phe Tyr Thr Gly
        115                 120                 125

Asn Val Arg Asp Gln Thr Trp Gln Arg Phe Ala Tyr Gln Asn Ile Ala
    130                 135                 140

Trp Leu Asn Ser Leu Gly Ala Ile Thr Lys Glu Ser Thr Pro Phe Leu
145                 150                 155                 160

Pro Ile Asp Pro Asn Tyr Ser Ser His Phe Arg Asp Pro Met Val Phe
                165                 170                 175

Pro Tyr Gln Glu Gly Leu Val Leu Ile Gly Ala Ser Asp Leu Asn
            180                 185                 190

Gly Gln Gly Lys Ile Val Val Tyr Phe Ser Lys Asp Arg Asn Val His
        195                 200                 205

Asn Phe His Gln Leu Gly Glu Leu Thr Phe Thr Asn Gln Glu Leu Gly
    210                 215                 220

Tyr Met Val Glu Cys Pro Asn Leu Val Phe Ile Asp Gly Gln Pro Val
225                 230                 235                 240

Leu Leu Phe Cys Pro Gln Gly Leu Ser Pro Ser Val Lys Ser Tyr Gln
                245                 250                 255

Asn Ile Tyr Pro Asn Met Tyr Thr Leu Ala Glu Thr Phe Asp Leu Glu
            260                 265                 270

Asn Leu Ser Leu Val Gln Ala Gly Pro Phe Glu Asn Leu Asp Glu Gly
        275                 280                 285

Phe Asp Val Tyr Ala Thr Gln Ala Phe Asn Ala Pro Asp Gly Arg Ala
    290                 295                 300

Leu Ala Val Ser Trp Ile Gly Leu Pro Glu Ile Thr Tyr Pro Ser Asp
305                 310                 315                 320

Val Glu Gly Trp Ala Asn Gly Leu Ser Leu Val Lys Glu Leu Thr Ile
                325                 330                 335

His Asn Gly Lys Leu Phe Gln Tyr Pro Val Ser Glu Thr Glu Met Leu
            340                 345                 350
```

```
Arg Gln Ser Ala Thr Thr Leu Ser Asn Gly Cys His Phe Leu Ser Thr
        355                 360                 365

Ala Ser Phe Glu Leu Glu Val Asp Ile Pro Lys Asn Glu Ile Ala Phe
    370                 375                 380

Ile Arg Leu Leu Ala Asn Glu Thr Gly Ser Lys Gly Leu Leu Ile Thr
385                 390                 395                 400

Ile Asp Thr Ile His Gly Lys Ile Thr Leu Asp Arg Thr Phe Ala Gly
                405                 410                 415

Gln Ser Phe Ala Glu Lys Tyr Gly Thr Ile Arg Glu Thr Lys Ile Arg
            420                 425                 430

Lys Asn Lys Ser Val Gln Leu Thr Ile Phe Val Asp Cys Ser Val Ala
            435                 440                 445

Glu Ile Tyr Val Asn Lys Gly Glu Lys Thr Met Thr Gly Arg Phe Phe
    450                 455                 460

Pro Asp Lys Ala Gln Gln Tyr Leu His Leu Ser Lys Thr Ala Lys Ala
465                 470                 475                 480

Cys Phe Tyr Glu Leu Glu Asn Thr Asn Asn
                485                 490

<210> SEQ ID NO 16
<211> LENGTH: 2089
<212> TYPE: DNA
<213> ORGANISM: Enterococcus faecalis

<400> SEQUENCE: 16
ccgcggctgt gggtgtatcg ggattggcga gcgcaagaag cgacgctttc ttatttagat      60
tttcggttat atcaaatcca acaaatttgg caagaaaagg agtgagtgtt gttgacatta     120
gaacaagaat tattcactca atttggttac gcagcgttta agcctggtca aaagaagtg      180
attacaaact tacttgacgg tatgaataca ttggctgttt tgccaacagg gactggaaaa     240
tcattgtgtt atcaatttgt gggccagaag ttagagggac taacggtaat tgtttctccc     300
ttactttcgt taatggaaga tcagatgcgt caattacaaa gacaaggaat taaaggtgcg     360
gttgccttaa acagtacgtt acagtattca gaaaagcgtt atattttagc gaaaatgttc     420
caatacgatt atctgttttt aagcccagaa atgcttttgc agcaagaagt acttagtgtg     480
ttacaacgcc aaaaaattgc attatttgtg gtggatgaag cccattgtgt ttatcagtgg     540
ggcgtcgatt ttcgccctga atatagtaaa ttagatctgg tccaaaaaca gctagacttt     600
cctttgacct tggcgttaac tgccacagcg cacccgttg tacagcacgc aattataaaa     660
caattatttt ctcatggcag ctatcaagaa gttctttctt cagtgaatcg aaaaaatatt     720
ggcttgttcg tgaaggaaac gtcagaaaaa gaagaagtgt tactagatta cttatctaaa     780
acggctggta aaatcattat ctattgcgcc acgcgcaaca aaacagaaca atcagtcaa     840
cttattcagg caaaaccag ttttaaggta gcctattatc atgggggctt ggaggctagt     900
gaacgtagtc gcttgcaaga acaatttatt gataatcaaa tcgatattct tgtgcaacg     960
aatgcttttg gatgggaat cgacaaacct gatgttcgtg gagtgattca ttttgatttg    1020
cctgatagct tagaaaatta cctgcaagaa atcgggcgag ctggacgtga tggtcaaaaa    1080
agttgggcgc tattattgta taaaaaaggg gatgaattta ttcatcggtt tttcttagaa    1140
gagacaagag cgaatcgagc gacccttaaaa tcgctgattg aaggagaaga acaagcaggt    1200
ttgctagaaa atgccaccga gttacaacaa aaatgggtcc aaggctattt agccaaggat    1260
tattcttttg aagagctaga gcatcgttta gaggagaaag aaaaagatcg ccaagcacaa    1320
```

-continued

```
ttaagaggga tgctgacgta tattgaaacc acaacctgtc gaagaacgtt gattcaaact    1380
tattttcaag aaccgattgt caaacaatca ccggaaactt gttgtgataa ttgtgcgtta    1440
ttctttgaca tttaccaaga ttcaatagta aaatcgaaca agaccagcaa tcaaaatgaa    1500
gaaggttggc gttctaaatt tctaaaatta tttaaagaac gtgattaatt cattttttta    1560
gtcggcagtt ggcaaaagct atgatataat aacaagcgag agaagtttag gaggaaatta    1620
gcagtgagta aaaggacaa aaagaaaaac caagctcgtg agccatggga acaatcaatt    1680
tatgaacctg atcaaaatgg tggtggttct cgtttagcaa aacgccaaca gcaacgagga    1740
aattcattat ttctaactgt tttagttatt ttgctattat taattattgc cattccaatt    1800
gggactttct tatggatgat gcaagacaag aaaccgaacg aaagtgctag caaaaatagc    1860
cagccatctt cttcattagt ccaatcatca tcaaaagaga agaaaaaaga aagtacgtca    1920
aaatcagtgg aaagctcaga accagcaagc agccaaccag ctgaaaatac aacaccttca    1980
agttcagatg ctgctgcaca gcaacaacag gaccaacaag cacaacaaca gcaacagcaa    2040
caacaagagc agcaacaaca caagaagct caaaatcaac aacagcaac                2089
```

<210> SEQ ID NO 17
<211> LENGTH: 1347
<212> TYPE: DNA
<213> ORGANISM: Enterococcus faecalis

<400> SEQUENCE: 17

```
atgaatacat tggctgtttt gccaacaggg actggaaaat cattgtgtta tcaatttgtg     60
ggccagaagt tagagggact aacggtaatt gtttctccct tactttcgtt aatggaagat    120
cagatgcgtc aattacaaag acaaggaatt aaaggtgcgg ttgccttaaa cagtacgtta    180
cagtattcag aaaagcgtta tattttagcg aaaatgttcc aatacgatta tctgttttta    240
agcccagaaa tgcttttgca gcaagaagta cttagtgtgt tacaacgcca aaaaattgca    300
ttatttgtgg tggatgaagc ccattgtgtt tatcagtggg gcgtcgattt tcgccctgaa    360
tatagtaaat tagatctggt ccaaaaacag ctagactttc ctttgacctt ggcgttaact    420
gccacagcga cacccgttgt acagcacgca attataaaac aattattttc tcatggcagc    480
tatcaagaag ttctttcttc agtgaatcga aaaaatattg gcttgttcgt gaaggaaacg    540
tcagaaaaag aagaagtgtt actagattac ttatctaaaa cggctggtaa atcattatc    600 tattgcgcca cgcgcaacaa aacagaacaa atcagtcaac ttattcaggc aaaaaccagt    660
tttaaggtag cctattatca tgggggcttg gaggctagtg aacgtagtcg cttgcaagaa    720
caatttattg ataatcaaat cgatattctt tgtgcaacga atgcttttgg gatgggaatc    780
gacaaacctg atgttcgtgg agtgattcat tttgatttgc ctgatagctt agaaaattac    840
ctgcaagaaa tcgggcgagc tggacgtgat ggtcaaaaaa gttgggcgct attattgtat    900
aaaaaagggg atgaatttat tcatcggttt tccttagaag agacaagagc gaatcgagcg    960
accttaaaat cgctgattga aggagaagaa caagcaggtt tgctagaaaa tgccaccgag   1020
ttacaacaaa aatgggtcca aggctattta gccaaggatt attctttgga agagctagag   1080
catcgtttag aggagaaaga aaagatcgc caagcacaat taagagggat gctgacgtat   1140
attgaaacca caacctgtcg aagaacgttg attcaaactt attttcaaga accgattgtc   1200
aaacaatcac cggaaacttg ttgtgataat tgtgcgttat tctttgacat ttaccaagat   1260
tcaatagtaa aatcgaacaa gaccagcaat caaaatgaag aaggttggcg ttctaaattt   1320
ctaaaattat ttaaagaacg tgattaa                                       1347
```

<210> SEQ ID NO 18
<211> LENGTH: 448
<212> TYPE: PRT
<213> ORGANISM: Enterococcus faecalis

<400> SEQUENCE: 18

Met Asn Thr Leu Ala Val Leu Pro Thr Gly Thr Gly Lys Ser Leu Cys
1               5                   10                  15

Tyr Gln Phe Val Gly Gln Lys Leu Glu Gly Leu Thr Val Ile Val Ser
            20                  25                  30

Pro Leu Leu Ser Leu Met Glu Asp Gln Met Arg Gln Leu Gln Arg Gln
        35                  40                  45

Gly Ile Lys Gly Ala Val Ala Leu Asn Ser Thr Leu Gln Tyr Ser Glu
    50                  55                  60

Lys Arg Tyr Ile Leu Ala Lys Met Phe Gln Tyr Asp Tyr Leu Phe Leu
65                  70                  75                  80

Ser Pro Glu Met Leu Leu Gln Gln Glu Val Leu Ser Val Leu Gln Arg
                85                  90                  95

Gln Lys Ile Ala Leu Phe Val Val Asp Glu Ala His Cys Val Tyr Gln
            100                 105                 110

Trp Gly Val Asp Phe Arg Pro Glu Tyr Ser Lys Leu Asp Leu Val Gln
        115                 120                 125

Lys Gln Leu Asp Phe Pro Leu Thr Leu Ala Leu Thr Ala Thr Ala Thr
    130                 135                 140

Pro Val Val Gln His Ala Ile Ile Lys Gln Leu Phe Ser His Gly Ser
145                 150                 155                 160

Tyr Gln Glu Val Leu Ser Ser Val Asn Arg Lys Asn Ile Gly Leu Phe
                165                 170                 175

Val Lys Glu Thr Ser Glu Lys Glu Val Leu Leu Asp Tyr Leu Ser
            180                 185                 190

Lys Thr Ala Gly Lys Ile Ile Ile Tyr Cys Ala Thr Arg Asn Lys Thr
    195                 200                 205

Glu Gln Ile Ser Gln Leu Ile Gln Ala Lys Thr Ser Phe Lys Val Ala
210                 215                 220

Tyr Tyr His Gly Gly Leu Glu Ala Ser Glu Arg Ser Arg Leu Gln Glu
225                 230                 235                 240

Gln Phe Ile Asp Asn Gln Ile Asp Ile Leu Cys Ala Thr Asn Ala Phe
                245                 250                 255

Gly Met Gly Ile Asp Lys Pro Asp Val Arg Gly Val Ile His Phe Asp
            260                 265                 270

Leu Pro Asp Ser Leu Glu Asn Tyr Leu Gln Glu Ile Gly Arg Ala Gly
        275                 280                 285

Arg Asp Gly Gln Lys Ser Trp Ala Leu Leu Tyr Lys Lys Gly Asp
    290                 295                 300

Glu Phe Ile His Arg Phe Phe Leu Glu Glu Thr Arg Ala Asn Arg Ala
305                 310                 315                 320

Thr Leu Lys Ser Leu Ile Glu Gly Glu Gln Ala Gly Leu Leu Glu
                325                 330                 335

Asn Ala Thr Glu Leu Gln Gln Lys Trp Val Gln Gly Tyr Leu Ala Lys
            340                 345                 350

Asp Tyr Ser Phe Glu Glu Leu Glu His Arg Leu Glu Glu Lys Glu Lys
        355                 360                 365

Asp Arg Gln Ala Gln Leu Arg Gly Met Leu Thr Tyr Ile Glu Thr Thr

```
            370                 375                 380
Thr Cys Arg Arg Thr Leu Ile Gln Thr Tyr Phe Gln Glu Pro Ile Val
385                 390                 395                 400

Lys Gln Ser Pro Glu Thr Cys Cys Asp Asn Cys Ala Leu Phe Phe Asp
                405                 410                 415

Ile Tyr Gln Asp Ser Ile Val Lys Ser Asn Lys Thr Ser Asn Gln Asn
            420                 425                 430

Glu Glu Gly Trp Arg Ser Lys Phe Leu Lys Leu Phe Lys Glu Arg Asp
            435                 440                 445
```

<210> SEQ ID NO 19
<211> LENGTH: 2096
<212> TYPE: DNA
<213> ORGANISM: Enterococcus faecalis

<400> SEQUENCE: 19

```
tactttagct tctcaaaagc tccatacgag tcaaccttat ttaagtaccc agctcaagga      60
gttggaacgt gaattaggtg cttcattaat tttaagagac aagaaacatt gtcggctttc     120
tccagcaggc gaagtcgtcg ccaagcgaac agaaatgatt tttgcactca ttaaggaagc     180
gcaagaagag attaatgaat tagtgaccca aggatcgaca acgaccattc ggattggaac     240
aaacttaatt gatatagata aagcatttgg agaagtcttg ttgttattta atcaatccta     300
tccgtatgta agtattgatt ttaagtatta ttacgatctt gaaacagcct ggaaacaga     360
tttaattgac attgggattg ggatattttt ggatacctcg attccattag agaaagaatt     420
aatttataca gaaagctatc tcctttgtgt caataaaaat catcctttag cccatgccga     480
tagcgtgacg attgacgaaa ttcgttcttt accttttgct gcatattccg atcaagtata     540
tgaaaaaaaa gtgttcaaac gttgggaacg taaaatcaat tgggaaaatc ggcaaatcgt     600
catcgaactt ccttctcttc atttagtctt agacatggtc aacgagaaa aagcctgtag      660
catccttccc tattcactca ctgatgaact aaacagacgt aacttagttg gtattcctct     720
ggaagatagt ccagaacgag ccatctattt agttcagaat aatcatcacg acattgtga     780
agcacaccgt tatttattcg aacaattacg ttatttattc taggaataga aaaggagga     840
attcccatgg aactatttcg tttacattat tttttagagt tatgcaaagt gaaacaattt     900
actaaagcag ccgaaaattt agcaatttct caagctgcat taagtaagca ataaaaatt      960
cttgaagcaa cgttaggcgc ggaacttttt aatcgccaag gccaaactac caccttaacg    1020
ccagctggat taattttaga aaatattgt tggcgcatca ccaatgagtt ggtctcaatt     1080
gaagaagagc taaagaaat taatcattct tccaaccata tttatgtggc cacttatctc     1140
tgtgatttag aatataaatt gaatgactta ctaatgacaa cattaacgga tcgttcatcc    1200
aacttacaag tccacactat tattacagaa atattcttc aatccttgga acaatggat     1260
gcagatttg gtatttcctt tgctgactta ccattacctg aacatattgg taaaattgat    1320
ttatttacag caaattatca attcatttta agaacgatc atccagcttt ggcaaaagcc    1380
acgacggaag aaatttaaa agaactaaca atgtacccct tcgtccgttt aaataccgaa    1440
ttttccgagc aaaacaaatt aaccaattgg ctagatacta cgttttctaa ttttttctcca   1500
gagaaagtca ttcaagtgga tactctttca cttattactc acttggtgtc tcattccgat    1560
agtttcgcta ttgtccccga atacacaaat attcaacttt tagacaattc gatccataca    1620
ctaacttacc aagaactacc taacgaaac atggcagttt attatttaaa agaacgttac    1680
atgagtcgac aacttcaaca acttttggct gaatgccaaa acaatttca atagtaaaaa    1740
```

```
ccaagactag agcttgtcgg caagcgagtt ccagtcttgg ttttatttg tgttttcagg    1800 tagcggcttc tcttcctttg acaaatccta agaagtgat agccatcact aacgaagtgc    1860
ctccttgact taaaaacgga agcggaatac cttttaacgg caacagtcca atcaccgcac    1920
cgatattctc caccgtttga agaccagcg aaaaatgag ggcgacacag atgtacatac    1980
aaaaacgcga attgctccgc aagccagcta ctaaaacttg ataaaacaag taaaatagaa    2040 gaaaacaac ggtggcactg cccacaaagc cccaggcttc cccgataaaa gtaaaa        2096
```

<210> SEQ ID NO 20
<211> LENGTH: 888
<212> TYPE: DNA
<213> ORGANISM: Enterococcus faecalis

<400> SEQUENCE: 20

```
atggaactat ttcgtttaca ttattttta gagttatgca aagtgaaaca atttactaaa     60
gcagccgaaa atttagcaat ttctcaagct gcattaagta agcaaataaa aattcttgaa    120
gcaacgttag cgcggaact ttttaatcgc caaggccaaa ctaccacctt aacgccagct    180
ggattaattt tagaaaaata ttgttggcgc atcaccaatg agttggtctc aattgaagaa    240
gagctaaaag aaattaatca ttcttccaac catatttatg tggccactta tctctgtgat    300
ttagaatata aattgaatga cttactaatg acaacattaa cggatcgttc atccaactta    360
caagtccaca ctattattac agaaaatatt cttcaatcct tggaaacaat ggatgcagat    420 tttggtatt cctttgctga cttaccatta cctgaacata ttggtaaaat tgatttattt    480
acagcaaatt atcaattcat tttaagaaac gatcatccag ctttggcaaa agccacgacg    540
gaagaaattt taaagaact aacaatgtac cccttcgtcc gtttaaatac cgaattttcc    600
gagcaaaaca aattaaccaa ttggctagat actacgtttt ctaattttc tccagagaaa    660 gtcattcaag tggatactct ttcacttatt actcacttgg tgtctcattc cgatagtttc    720
gctattgtcc ccgaatacac aaatattcaa cttttagaca attcgatcca tacactaact    780
taccaagaac tacctaaacg aaacatggca gtttattatt aaaagaacg ttacatgagt    840 cgacaacttc aacaacttt ggctgaatgc caaaaacaat tcaatag                   888
```

<210> SEQ ID NO 21
<211> LENGTH: 294
<212> TYPE: PRT
<213> ORGANISM: Enterococcus faecalis

<400> SEQUENCE: 21

```
Met Glu Leu Phe Arg Leu His Tyr Phe Leu Glu Leu Cys Lys Val Lys
  1               5                  10                  15

Gln Phe Thr Lys Ala Ala Glu Asn Leu Ala Ile Ser Gln Ala Ala Leu
             20                  25                  30

Ser Lys Gln Ile Lys Ile Leu Glu Ala Thr Leu Gly Ala Glu Leu Phe
         35                  40                  45

Asn Arg Gln Gly Gln Thr Thr Thr Leu Thr Pro Ala Gly Leu Ile Leu
     50                  55                  60

Glu Lys Tyr Cys Trp Arg Ile Thr Asn Glu Leu Val Ser Ile Glu Glu
 65                  70                  75                  80

Glu Leu Lys Glu Ile Asn His Ser Ser Asn His Ile Tyr Val Ala Thr
                 85                  90                  95

Tyr Leu Cys Asp Leu Glu Tyr Lys Leu Asn Asp Leu Leu Met Thr Thr
            100                 105                 110
```

```
Leu Thr Asp Arg Ser Ser Asn Leu Gln Val His Thr Ile Ile Thr Glu
            115                 120                 125

Asn Ile Leu Gln Ser Leu Glu Thr Met Asp Ala Asp Phe Gly Ile Ser
        130                 135                 140

Phe Ala Asp Leu Pro Leu Pro Glu His Ile Gly Lys Ile Asp Leu Phe
145                 150                 155                 160

Thr Ala Asn Tyr Gln Phe Ile Leu Arg Asn Asp His Pro Ala Leu Ala
                165                 170                 175

Lys Ala Thr Thr Glu Glu Ile Leu Lys Glu Leu Thr Met Tyr Pro Phe
            180                 185                 190

Val Arg Leu Asn Thr Glu Phe Ser Glu Gln Asn Lys Leu Thr Asn Trp
        195                 200                 205

Leu Asp Thr Thr Phe Ser Asn Phe Ser Pro Glu Lys Val Ile Gln Val
    210                 215                 220

Asp Thr Leu Ser Leu Ile Thr His Leu Val Ser His Ser Asp Phe Ala
225                 230                 235                 240

Ile Val Pro Glu Tyr Thr Asn Ile Gln Leu Leu Asp Asn Ser Ile His
                245                 250                 255

Thr Leu Thr Tyr Gln Glu Leu Pro Lys Arg Asn Met Ala Val Tyr Tyr
            260                 265                 270

Leu Lys Glu Arg Tyr Met Ser Arg Gln Leu Gln Gln Leu Leu Ala Glu
        275                 280                 285

Cys Gln Lys Gln Phe Gln
    290
```

<210> SEQ ID NO 22
<211> LENGTH: 2340
<212> TYPE: DNA
<213> ORGANISM: Enterococcus faecalis

<400> SEQUENCE: 22

```
acaaaaatta ccttcagaat atgatttagc taaagaatat aactgcagtc gcttgaccat    60
ccgtaaagcg attgatgatt tgatccgcaa aaatattttg gtaaaacgac atggtaaagg   120
tagttatgtg atgtcgcaag cgaaaattca agtggtcgc gctggcttac aaggttttac    180
tgaggcagcc aaagcttacg ggaaaaaaag ccagacagaa gtcatttcct ttgaagaagt   240
agtacatccc gctgagaaaa ttcgggaggc gctccaagta ggcaaaaatg aggcaattta   300
tgaactgatt cgccgccgaa tgttagacgg cgaaccaatg acagttgaaa aaatttattt   360
gccacaggca tacgtacaag gccatacgaa gcaagacttc gagggctctc ttttctgctt   420
aatcgagaag aacgtcgaga ttgcttattc gcatcaagaa attgaagcaa tcttagttga   480
agcggaaatt tcagaattat tgaatgttcc tgtgggccaa ccactttac aagtccactc    540
tatcacctat gcgcttgatg caactcctat tttatatgat gtctctttat atcgagcaga   600
tcggtacacg tttaaaaaca cactgacccg ctatagcccg tctgaaaaca accaagtgga   660
gctaggaggt tcttggaacg aatgaagatc aaagaagaaa tagccgctca aaaagattta   720
tttatatgaag acttaaacaa aattatcgcg attcgaagtg tgaaagggtc gcctaaaaaa   780
gaggcacctt ttggcgaagg accgaaaaga gccttggaag aaacgctgaa acttgcagag   840
cgttatggtt ttcaaactgg gattgtcaat gacgcagttg gctatgcgca tggggaaca    900
gcggaagaat atctgggaat tattggtcat ttagatgtag taccagaagg ttctggttgg   960
tcagtgccgc cctttcaatt aacgaaaaaa atcaacgtt gtatggtag aggaattcta    1020
```

```
gataataaag gtcctatctt ggcttgcctg tatggaatga aattactgaa agaacttggt    1080
taccaaccaa agaaaaccat tcgcttaatg tttggcacgg atgaagaaag tgggagtgga    1140
gatatcccct tatatttaga gaaggaaaac gcacccgttt ttggatttac tccagattgt    1200
aaatatccag tagtttatgg ggagcgaggg attgttaatt atgagatcac aacgaccatc    1260
ccagatgatt caagtgaaca aattggtcag attataggtg atcaagcaaa agaccacgta    1320
cctgatcaat aagtgtggt gattgcggga aaaacaacag caatcacggg aaaacgtgct     1380
ccttccaatg cgccagaact aggcaagaac gcgattactt tattggcaca gaaaattagc    1440
gaggaacagt tagtcaaagg aaatttatta cagtatttcg actggttaac cgctagtttt    1500
cacgaaaagc actatggcga aggagtagct ctggacttta aggatcagga tagtgggcaa    1560
ttgattttaa cgccctatgc gttggaaaaa agaggacagc aattggtgtt atcattggcc    1620
gtgcgttatc ctgtttctat tacagaaaac gaagtaacca cgcagctaac gaaggcacta    1680
tttccagaaa gtgaagtgac cgtcatccgc cgcctcccta gtacgctgtt tccaaaagat    1740
gagcgcaatg ttcaaaaatt aaccaaggtt tatgaacaaa ttactggctt agatgggacg    1800
ccagtcacaa ctacaggtgc tacgtatgct cgctttatgc cgaatatcgt tgcttttggt    1860
ccatcatttc ctggtcaaaa aggcattgcg cataaccaag atgaatatat ggatgaaaaa    1920
gatttactgc ttaatctgga aatctatatg caagcgatga ttgcattaac agaagcataa    1980
aaccaataga agatacacgt atgagaagaa gacaatgtgt ttcgtagagg tcgcatacgt    2040
gtatcttcta tttttctgta taaaatttca ttttcagtat atacaaaaca gtatatacta    2100
gtttataatg gtggagaaat gtaagcgtta acgaaagggc ggatggaaaa tgacttgggg    2160
tgcaattgcg acatggcgga tggcacatga tgggttacta aaagctacag aagaattaca    2220
acaaggaggt gctgcaggca cggccgtgga acaattaatt aaagaagtag aagactatcc    2280
tttttataag tcagtgggct acggcggttt acctaatgag gaagggattt tagaaatgga    2340
```

<210> SEQ ID NO 23
<211> LENGTH: 1299
<212> TYPE: DNA
<213> ORGANISM: Enterococcus faecalis

<400> SEQUENCE: 23

```
atgaagatca agaagaaat agccgctcaa aaagatttat tttatgaaga cttaaacaaa      60
attatcgcga ttcgaagtgt gaaagggtcg cctaaaaaag aggcaccttt tggcgaagga     120
ccgaaaagag ccttggaaga aacgctgaaa cttgcagagc gttatggttt tcaaactggg     180
attgtcaatg acgcagttgg ctatgcgcaa tggggaacag cggaagaata tctgggaatt     240
attggtcatt tagatgtagt accagaaggt tctggttggt cagtgccgcc ctttcaatta     300
acgaaaaaaa atcaacgttt gtatggtaga ggaattctag ataataaagg tcctatcttg     360
gcttgcctgt atggaatgaa attactgaaa gaacttggtt accaaccaaa gaaaaccatt     420
cgcttaatgt tttggcacgga tgaagaaagt gggagtggag atatcccctt atatttagag    480
aaggaaaacg cacccgtttt tggatttact ccagattgta aatatccagt agtttatggg    540
gagcgaggga ttgttaatta tgagatcaca acgaccatcc cagatgattc aagtgaacaa    600
attggtcaga ttataggtga tcaagcaaaa gaccacgtac tgatcaatt aagtgtggtg     660 attgcgggaa aaacaacagc aatcacggga aaacgtgctc cttccaatgc gccagaacta    720
ggcaagaacg cgattacttt attggcacag aaaattagcg aggaacagtt agtcaaagga    780
aatttattac agtatttcga ctggttaacc gctagttttc acgaaaagca ctatggcgaa    840
```

```
ggagtagctc tggactttaa ggatcaggat agtgggcaat tgattttaac gccctatgcg      900
ttggaaaaaa gaggacagca attggtgtta tcattggccg tgcgttatcc tgtttctatt      960
acagaaaacg aagtaaccac gcagctaacg aaggcactat ttccagaaag tgaagtgacc     1020
gtcatccgcc gcctccctag tacgctgttt ccaaagatg agcgcaatgt tcaaaaatta     1080
accaaggttt atgaacaaat tactggctta gatgggacgc cagtcacaac tacaggtgct     1140
acgtatgctc gctttatgcc gaatatcgtt gcttttggtc atcatttcc tggtcaaaaa     1200 ggcattgcgc ataaccaaga tgaatatatg gatgaaaaag atttactgct taatctggaa     1260
atctatatgc aagcgatgat tgcattaaca gaagcataa                            1299
```

<210> SEQ ID NO 24
<211> LENGTH: 432
<212> TYPE: PRT
<213> ORGANISM: Enterococcus faecalis

<400> SEQUENCE: 24

```
Met Lys Ile Lys Glu Glu Ile Ala Ala Gln Lys Asp Leu Phe Tyr Glu
  1               5                  10                  15

Asp Leu Asn Lys Ile Ile Ala Ile Arg Ser Val Lys Gly Ser Pro Lys
             20                  25                  30

Lys Glu Ala Pro Phe Gly Glu Gly Pro Lys Arg Ala Leu Glu Glu Thr
         35                  40                  45

Leu Lys Leu Ala Glu Arg Tyr Gly Phe Gln Thr Gly Ile Val Asn Asp
     50                  55                  60

Ala Val Gly Tyr Ala Gln Trp Gly Thr Ala Glu Glu Tyr Leu Gly Ile
 65                  70                  75                  80

Ile Gly His Leu Asp Val Val Pro Glu Gly Ser Gly Trp Ser Val Pro
                 85                  90                  95

Pro Phe Gln Leu Thr Lys Lys Asn Gln Arg Leu Tyr Gly Arg Gly Ile
            100                 105                 110

Leu Asp Asn Lys Gly Pro Ile Leu Ala Cys Leu Tyr Gly Met Lys Leu
        115                 120                 125

Leu Lys Glu Leu Gly Tyr Gln Pro Lys Lys Thr Ile Arg Leu Met Phe
    130                 135                 140

Gly Thr Asp Glu Glu Ser Gly Ser Gly Asp Ile Pro Leu Tyr Leu Glu
145                 150                 155                 160

Lys Glu Asn Ala Pro Val Phe Gly Phe Thr Pro Asp Cys Lys Tyr Pro
                165                 170                 175

Val Val Tyr Gly Glu Arg Gly Ile Val Asn Tyr Glu Ile Thr Thr Thr
            180                 185                 190

Ile Pro Asp Asp Ser Ser Glu Gln Ile Gly Gln Ile Ile Gly Asp Gln
        195                 200                 205

Ala Lys Asp His Val Pro Asp Gln Leu Ser Val Val Ile Ala Gly Lys
    210                 215                 220

Thr Thr Ala Ile Thr Gly Lys Arg Ala Pro Ser Asn Ala Pro Glu Leu
225                 230                 235                 240

Gly Lys Asn Ala Ile Thr Leu Leu Ala Gln Lys Ile Ser Glu Glu Gln
                245                 250                 255

Leu Val Lys Gly Asn Leu Leu Gln Tyr Phe Asp Trp Leu Thr Ala Ser
            260                 265                 270

Phe His Glu Lys His Tyr Gly Glu Gly Val Ala Leu Asp Phe Lys Asp
        275                 280                 285
```

-continued

```
Gln Asp Ser Gly Gln Leu Ile Leu Thr Pro Tyr Ala Leu Glu Lys Arg
    290                 295                 300

Gly Gln Gln Leu Val Leu Ser Leu Ala Val Arg Tyr Pro Val Ser Ile
305                 310                 315                 320

Thr Glu Asn Glu Val Thr Thr Gln Leu Thr Lys Ala Leu Phe Pro Glu
                325                 330                 335

Ser Glu Val Thr Val Ile Arg Arg Leu Pro Ser Thr Leu Phe Pro Lys
            340                 345                 350

Asp Glu Arg Asn Val Gln Lys Leu Thr Lys Val Tyr Glu Gln Ile Thr
        355                 360                 365

Gly Leu Asp Gly Thr Pro Val Thr Thr Thr Gly Ala Thr Tyr Ala Arg
    370                 375                 380

Phe Met Pro Asn Ile Val Ala Phe Gly Pro Ser Phe Pro Gly Gln Lys
385                 390                 395                 400

Gly Ile Ala His Asn Gln Asp Glu Tyr Met Asp Glu Lys Asp Leu Leu
                405                 410                 415

Leu Asn Leu Glu Ile Tyr Met Gln Ala Met Ile Ala Leu Thr Glu Ala
            420                 425                 430
```

<210> SEQ ID NO 25
<211> LENGTH: 2362
<212> TYPE: DNA
<213> ORGANISM: Enterococcus faecalis

<400> SEQUENCE: 25

```
catttttat taaattacat atttgtaata ggaatttcct gtgaaatgag gtatcctaag      60
aaaggtgata aaacacagag gtaaaggagt gacacgatga gtcgtgtaga tcgttataaa    120
catattcatg aaaaatcgag accagcagag cataaaaaga cctttaatcc ccgaaaatca    180
atgggtgaac atagagaaga agaaccagaa gaactagctg aaagccttca agagccagtt    240
tacgaagaca gctatactga ggacagtcgc agaagtgaga ggcgacatca aacagattca    300
ggtggtggca acggttctga ccaaccaccc cgcggaaaaa agacaagaa accaaaaaag     360
aaacgtaaaa aatcaaaaac aaaacgcttt ttcaaatggc tagtgatcct attgattctg    420
ttatttgcct atagtacagt catgttttta aaggaaaat ctgcagcaga acatgatgac     480
tcgttgcctc aagaaaaagt agaaacattt aatggtgtca aaagtagcaa cggggctaag    540
aatattttaa ttcttggcag cgatacacgt ggggaagatg ctggacgagc cgacacaata    600
atggttctcc aactaaatgg accatcaaaa aaccgaaat taatttcatt tatgcgtgat    660
acattcgtgg acattcctgg tgtcgggccg aataaaatta tgccgcata cgcttatggc    720
ggtgctgaat tggttcgtga aacgttaaaa caaaacttta atttagatac gaaatattat    780
gctaaggtag atttccaatc atttgaaaaa attgttgact ctatgtttcc aaaaggtgtc    840
aaaatcgatg cagaaaaatc actgaattta gatggtgttg atattgaaaa agggcaacag    900
gtcatggatg gacatgtctt acttcaatac gctcgcttta ggatggatga agaaggcgac    960
tttggtcggg ttcgtcgcca caacaagtt atgtcagctg taatgagcca atgaaaaac    1020
ccaatgactt tattaagaac cccagaatca cttgggaaat tagtcggcta tatgtcgaca   1080
gatgtgcctg ttagtttcat gttaacgaat ggaccatcat tgttgattaa ggaaaagca    1140
ggggttgagt cattatcggt tccggtacca gattcttgga attttggtga atcctcttat   1200
gcaggcagta ttttagaagt agatgaacaa aaaaatgctg acgccatcga aaattcctg    1260
aacgaataag gaaagcattt taaatatcc ttttttatgc tatattagaa acaacgtgga    1320
```

-continued

```
aaattagtga acgaggtta caaaatgaaa attgctattg tgacagatag tacagcttat      1380
ttacccgagc gcattaaaga tcatccgaat cttttttgtaa ttcccatccc agtcatttta   1440
gatggaaaaa tatacaacga aggcattgac attgaagcag atgaatatta tgcattgcta    1500
aataatagta aagaatttcc gacgacttca caacctgctt taggagaagt gttagagctt    1560
tacaaatcaa tcgctgaaca agggtacgac accatcatca gcattcatct ttcttcagga    1620
atctctggtt ttgttcatac attgcacgga cttaccgatg aaatcccagg cgttgctttg    1680
tatccatatg actcaaaaat tacaagtatg ccaatgggac acatggtaga agctgcttta    1740
gatttaacag aagaaaaagc cagcttagaa gaaattttttg ccaaattaga tttaattcgt   1800
gacaatacgt atgcatatct aattgtagaa gatctgaaca acttagttcg tggcggtcgc    1860
ttaacgaatg gcgcagcctt gatcgctgga ctattgaaga ttaaacctat cttgactttt    1920
gaagatggaa agattgtatt atttgaaaaa atccgttcaa caagaaaagc ttttgctcgt    1980
gcagaaaaga ttattggtga acgaaacgca gggattgaag caccagttaa actgtatgtg    2040
attcatgcca ataaccgcat cgttgctgaa aaagaacaag caaaattaca aaagctatac    2100
ccaaatgcag aaattgaaat tggtcatttt ggtccagtta tcgggaccca cctaggggaa    2160
aaagcaattg gtttagcgat ttcagctcaa taataaaaga tgagacaaaa gtaaactact    2220
tctgtctcat cttttattct attattttat cgttcgctgg tgttactcag ccgaacactt    2280
tttgtttata agaaaatgta aaattactcc tttttattag aaaatatctt gcaaattaag    2340
caattcctta caaagtaatg ta                                             2362
```

<210> SEQ ID NO 26
<211> LENGTH: 849
<212> TYPE: DNA
<213> ORGANISM: Enterococcus faecalis

<400> SEQUENCE: 26

```
atgaaaattg ctattgtgac agatagtaca gcttatttac ccgagcgcat taagatcat      60 ccgaatcttt ttgtaattcc catcccagtc attttagatg gaaaaatata caacgaaggc    120
attgacattg aagcagatga atattatgca ttgctaaata atagtaaaga atttccgacg    180
acttcacaac tgctttaggg agaagtgtta gagctttaca aatcaatcgc tgaacaaggg    240
tacgacacca tcatcagcat tcatctttct tcaggaatct ctggttttgt tcatacattg    300
cacggactta ccgatgaaat cccaggcgtt gctttgtatc catatgactc aaaaattaca    360
agtatgccaa tgggacacat ggtagaagct gctttagatt taacagaaga aaaagccagc    420
ttagaagaaa ttttttgccaa attagattta attcgtgaca atacgtatgc atatctaatt    480
gtagaagatc tgaacaactt agttcgtggc ggtcgcttaa cgaatggcgc agccttgatc    540
gctggactat tgaagattaa acctatcttg acttttgaag atggaaagat tgtattattt    600
gaaaaaatcc gttcaacaaa gaaagctttt gctcgtgcag aaaagattat tggtgaacga    660
aacgcaggga ttgaagcacc agttaaactg tatgtgattc atgccaataa ccgcatcgtt    720
gctgaaaaag aacaagcaaa attacaaaag ctatacccaa atgcagaaat tgaaattggt    780
cattttggtc cagttatcgg gacccaccta ggggaaaaag caattggttt agcgatttca    840
gctcaataa                                                            849
```

<210> SEQ ID NO 27
<211> LENGTH: 282
<212> TYPE: PRT
<213> ORGANISM: Enterococcus faecalis

<400> SEQUENCE: 27

| | | | | | | | | | | | | | | |
|---|---|---|---|---|---|---|---|---|---|---|---|---|---|---|
|Met|Lys|Ile|Ala|Ile|Val|Thr|Asp|Ser|Thr|Ala|Tyr|Leu|Pro|Glu|Arg|
|1| | | |5| | | | |10| | | | |15| |
|Ile|Lys|Asp|His|Pro|Asn|Leu|Phe|Val|Ile|Pro|Ile|Pro|Val|Ile|Leu|
| | | |20| | | | |25| | | | |30| | |
|Asp|Gly|Lys|Ile|Tyr|Asn|Glu|Gly|Ile|Asp|Ile|Glu|Ala|Asp|Glu|Tyr|
| | | | |35| | | | |40| | | | |45| |
|Tyr|Ala|Leu|Leu|Asn|Asn|Ser|Lys|Glu|Phe|Pro|Thr|Thr|Ser|Gln|Pro|
| |50| | | | |55| | | | |60| | | | |
|Ala|Leu|Gly|Glu|Val|Leu|Glu|Leu|Tyr|Lys|Ser|Ile|Ala|Glu|Gln|Gly|
|65| | | | |70| | | | |75| | | | |80|
|Tyr|Asp|Thr|Ile|Ile|Ser|Ile|His|Leu|Ser|Ser|Gly|Ile|Ser|Gly|Phe|
| | | | |85| | | | |90| | | | |95| |
|Val|His|Thr|Leu|His|Gly|Leu|Thr|Asp|Glu|Ile|Pro|Gly|Val|Ala|Leu|
| | | |100| | | | |105| | | | |110| | |
|Tyr|Pro|Tyr|Asp|Ser|Lys|Ile|Thr|Ser|Met|Pro|Met|Gly|His|Met|Val|
| | | |115| | | | |120| | | | |125| | |
|Glu|Ala|Ala|Leu|Asp|Leu|Thr|Glu|Glu|Lys|Ala|Ser|Leu|Glu|Glu|Ile|
| |130| | | | |135| | | | |140| | | | |
|Phe|Ala|Lys|Leu|Asp|Leu|Ile|Arg|Asp|Asn|Thr|Tyr|Ala|Tyr|Leu|Ile|
|145| | | | |150| | | | |155| | | | |160|
|Val|Glu|Asp|Leu|Asn|Asn|Leu|Val|Arg|Gly|Gly|Arg|Leu|Thr|Asn|Gly|
| | | | |165| | | | |170| | | | |175| |
|Ala|Ala|Leu|Ile|Ala|Gly|Leu|Leu|Lys|Ile|Lys|Pro|Ile|Leu|Thr|Phe|
| | | |180| | | | |185| | | | |190| | |
|Glu|Asp|Gly|Lys|Ile|Val|Leu|Phe|Glu|Lys|Ile|Arg|Ser|Thr|Lys|Lys|
| | | |195| | | | |200| | | | |205| | |
|Ala|Phe|Ala|Arg|Ala|Glu|Lys|Ile|Ile|Gly|Glu|Arg|Asn|Ala|Gly|Ile|
| |210| | | | |215| | | | |220| | | | |
|Glu|Ala|Pro|Val|Lys|Leu|Tyr|Val|Ile|His|Ala|Asn|Asn|Arg|Ile|Val|
|225| | | | |230| | | | |235| | | | |240|
|Ala|Glu|Lys|Glu|Gln|Ala|Lys|Leu|Gln|Lys|Leu|Tyr|Pro|Asn|Ala|Glu|
| | | | |245| | | | |250| | | | |255| |
|Ile|Glu|Ile|Gly|His|Phe|Gly|Pro|Val|Ile|Gly|Thr|His|Leu|Gly|Glu|
| | | |260| | | | |265| | | | |270| | |
|Lys|Ala|Ile|Gly|Leu|Ala|Ile|Ser|Ala|Gln| | | | | | |
| | | |275| | | | |280| | | | | | | |

<210> SEQ ID NO 28
<211> LENGTH: 2203
<212> TYPE: DNA
<213> ORGANISM: Enterococcus faecalis

<400> SEQUENCE: 28

| | | |
|---|---|---|
|gagattatct aaagaaaagt aagcacaatt cgaggtttca atgttttttt caaagggatg|60|
|attttctaga atgtcacaag aaaagatcat tttatagtac tgaaatagtt gaggaatgtc|120|
|ttttcgttta tctgtatcat aaacagcaag caattctttt gctgtaacaa ctaagccagt|180|
|ttcttccaat acttcttttt caatatttc tttaggagag cagccaattt cggcatagcc|240|
|accaggtaat gaccattctt tggtccgtaa atcttcaact aataaaaaac gattctcttt|300|
|ttttatcaaa ccgcgaacat ctactttcgg tgttggataa ccttcttctt tagttaagat|360|
|tttttctaag tcgggcaaga cagtcgcttc gtgtccggtt gcgctaataa gttgtaacgt|420|

```
aagttctcgt agttcttggt aacgttcttg atcaaaagca tctttcccgt aaaaaagacc      480
agcatctgcc aatgctagca accgcttata agtgttcaga taatccatat acgcacgctc      540
ctcatagact taatacgttt agtttaacag aaaaaaataa agaaagggca gatttagcga      600
gaaaaggcgt cgttttaagg aaataaataaa gaataaatga ctaacttaca tttttaaact      660
acctatgcta ttatttaata aaaaagattg ggtatacaat aattttgtta tgtaaacaaa      720
aaggaggttg taaattgaaa gaatttacaa ttataaggga aaaaaatgca gataaaaaga      780
ctcaggcagc acaagaagta ttgtttaatc ttccagaatg gtttggcctt gaaaaagaga      840
cccgcaagta tatcgatata gctagcactt tacctatgtg ggtggcaaag gatgtagaga      900
ataaaatact cggttttata acactttcag aaacaagtaa agatacagta gaaatccatt      960
gtatggcagt taaaaagcgg tatcatcgca aggtatcgg caagttattg atagaaagcg     1020
tggaaacgta ttctaaaaat aactattttt ttattcaagt caaaacagtt gacgaaggaa     1080
attattccgt gtacgatcat actattcgtt tttacgaatc attgggtttt aagcgccttg     1140 aggttttttcc gacattatgg gacgcttgga atccttgttt aatttaatt aaacagttga     1200 tttaatctac aaaggagttt tagtatgtca gtatttatta gagagtgtac cgtcgcagac     1260
gtaccagaat tagaggccat ttgccaagag acttttgcag atacttatgg agatggcgaa     1320
aacgaaaagg atttacaggc acattatgag aggaaattta gtccagcagt tttagaaagc     1380
gaaatcttac ataaagattc gcaatatttc tttgcttttt ataataatga acttgcaggt     1440
tatgtgaaat aaatcacgg tgatgctcag attacctatc aacatccaca agcgttacaa     1500
gttgagcgca tttatattcg taaatctttt aagcgtttag gcttaggcaa acatttgatt     1560
acgaaagcaa ttgaattagc ggaagaagca gaaaaagaga cggtttggtt aggtgtttgg     1620
gaacataatc atccagcgca aaaatttat caatcattgg gcttcgtcaa aacagatgaa     1680
catgattttt atatgggaaa tgaacgccat accgattata caatgacgaa acagttaaaa     1740
gagtcaacgt aaagcaaaaa caaggaaacg gacgcaatga agccgacgat tccttgtttt     1800
tttatcttaa aattgtgaag gagatttttcc ataatatttt ttgataatt tactgaaatg     1860 ataggcatct tcgtaaccaa ccgttttttgc cacttctttg acacttaggg aatcattttt     1920
cagcaattct ttcgcatggt ttaagcggat ttgaattaaa taattgattg gcccaacgcc     1980
tgtggccgct ttaaaggttt tcgacaaata agtcggggtc acatatagca tttcagctaa     2040
ctgttccaaa gtaatttctt cgtcatggtg cgtttccaga taataaatcg tatgattgac     2100
taaatttcgt tttcttttttt ccgttttcga tagccgagtt tcaatttttat tttcttgatc     2160 aactgctaag cttcttaaaa tatagaccaa tagttcaata act                        2203
```

<210> SEQ ID NO 29
<211> LENGTH: 528
<212> TYPE: DNA
<213> ORGANISM: Enterococcus faecalis

<400> SEQUENCE: 29

```
atgtcagtat ttattagaga gtgtaccgtc gcagacgtac cagaattaga ggccatttgc       60
caagagactt ttgcagatac ttatggagat ggcgaaaacg aaaaggattt acaggcacat      120
tatgagagga aatttagtcc agcagtttta gaaagcgaaa tcttacataa agattcgcaa      180
tatttctttg cttttttataa taatgaactt gcaggttatg tgaaattaaa tcacggtgat      240
gctcagatta cctatcaaca tccacaagcg ttacaagttg agcgcattta tattcgtaaa      300
tcttttaagc gtttaggctt aggcaaacat ttgattacga aagcaattga attagcggaa      360
```

```
gaagcagaaa aagagacggt ttggttaggt gtttgggaac ataatcatcc agcgcaaaaa    420
ttttatcaat cattgggctt cgtcaaaaca gatgaacatg atttttatat gggaaatgaa    480
cgccataccg attatacaat gacgaaacag ttaaaagagt caacgtaa                 528
```

```
<210> SEQ ID NO 30
<211> LENGTH: 175
<212> TYPE: PRT
<213> ORGANISM: Enterococcus faecalis

<400> SEQUENCE: 30
```

```
Met Ser Val Phe Ile Arg Glu Cys Thr Val Ala Asp Val Pro Glu Leu
 1               5                  10                  15

Glu Ala Ile Cys Gln Glu Thr Phe Ala Asp Thr Tyr Gly Asp Gly Glu
            20                  25                  30

Asn Glu Lys Asp Leu Gln Ala His Tyr Glu Arg Lys Phe Ser Pro Ala
        35                  40                  45

Val Leu Glu Ser Glu Ile Leu His Lys Asp Ser Gln Tyr Phe Phe Ala
    50                  55                  60

Phe Tyr Asn Asn Glu Leu Ala Gly Tyr Val Lys Leu Asn His Gly Asp
65                  70                  75                  80

Ala Gln Ile Thr Tyr Gln His Pro Gln Ala Leu Gln Val Glu Arg Ile
                85                  90                  95

Tyr Ile Arg Lys Ser Phe Lys Arg Leu Gly Leu Gly Lys His Leu Ile
           100                 105                 110

Thr Lys Ala Ile Glu Leu Ala Glu Glu Ala Glu Lys Glu Thr Val Trp
       115                 120                 125

Leu Gly Val Trp Glu His Asn His Pro Ala Gln Lys Phe Tyr Gln Ser
   130                 135                 140

Leu Gly Phe Val Lys Thr Asp Glu His Asp Phe Tyr Met Gly Asn Glu
145                 150                 155                 160

Arg His Thr Asp Tyr Thr Met Thr Lys Gln Leu Lys Glu Ser Thr
                165                 170                 175
```

```
<210> SEQ ID NO 31
<211> LENGTH: 8347
<212> TYPE: DNA
<213> ORGANISM: Enterococcus faecalis
<220> FEATURE:
<221> NAME/KEY: CDS
<222> LOCATION: (162)...(1028)
<220> FEATURE:
<221> NAME/KEY: CDS
<222> LOCATION: (1065)...(2090)
<220> FEATURE:
<221> NAME/KEY: CDS
<222> LOCATION: (2113)...(3189)
<220> FEATURE:
<221> NAME/KEY: CDS
<222> LOCATION: (3191)...(4357)
<220> FEATURE:
<221> NAME/KEY: CDS
<222> LOCATION: (4391)...(5485)
<220> FEATURE:
<221> NAME/KEY: CDS
<222> LOCATION: (5492)...(6778)
<220> FEATURE:
<221> NAME/KEY: CDS
<222> LOCATION: (6795)...(7304)
<220> FEATURE:
<221> NAME/KEY: CDS
<222> LOCATION: (7312)...(8160)

<400> SEQUENCE: 31
```

-continued

```
ccatgtagat ttaagaaaat ctatagtggc ttttatattg cttttttgta gggtattcac        60
tgtagatttt tcttaaaatt tactgtgaat atccttttg tttggccaaa aattaggatt        120
tcagaaactt actaaaaaaa tttcgtaaag gagcacacag g atg aaa gaa ata act       176
                                             Met Lys Glu Ile Thr
                                               1               5
```

| | | | | | | | | | | | | | | | | |
|---|---|---|---|---|---|---|---|---|---|---|---|---|---|---|---|---|
| gga | gcc | act | cgt | tta | gct | ggg | cta | ttc | gcg | aaa | ccc | agc | caa | cac | agt | 224 |
| Gly | Ala | Thr | Arg | Leu | Ala | Gly | Leu | Phe | Ala | Lys | Pro | Ser | Gln | His | Ser | |
| | | | 10 | | | | | 15 | | | | | 20 | | | |
| att | tca | ccg | ttg | att | cat | aat | aca | gca | ttt | caa | aat | tta | gga | gtt | gat | 272 |
| Ile | Ser | Pro | Leu | Ile | His | Asn | Thr | Ala | Phe | Gln | Asn | Leu | Gly | Val | Asp | |
| | | | 25 | | | | | 30 | | | | | 35 | | | |
| gct | cgg | tat | ctg | gcg | ttt | gac | gtt | gga | caa | gag | aca | ttg | cca | caa | gca | 320 |
| Ala | Arg | Tyr | Leu | Ala | Phe | Asp | Val | Gly | Gln | Glu | Thr | Leu | Pro | Gln | Ala | |
| | | | 40 | | | | | 45 | | | | | 50 | | | |
| att | gaa | gcg | att | cga | acg | ttt | cac | atg | tta | ggg | gcc | aac | tta | tca | atg | 368 |
| Ile | Glu | Ala | Ile | Arg | Thr | Phe | His | Met | Leu | Gly | Ala | Asn | Leu | Ser | Met | |
| | | | 55 | | | | | 60 | | | | | 65 | | | |
| ccc | aat | aaa | gtg | gcg | gct | gta | agt | tat | atg | gat | gaa | cta | agt | cct | acc | 416 |
| Pro | Asn | Lys | Val | Ala | Ala | Val | Ser | Tyr | Met | Asp | Glu | Leu | Ser | Pro | Thr | |
| 70 | | | | | 75 | | | | | 80 | | | | | 85 | |
| gct | caa | ctg | gtt | ggc | gca | att | aat | acg | att | gtc | aac | aaa | gat | gga | aaa | 464 |
| Ala | Gln | Leu | Val | Gly | Ala | Ile | Asn | Thr | Ile | Val | Asn | Lys | Asp | Gly | Lys | |
| | | | | 90 | | | | | 95 | | | | | 100 | | |
| ctt | tac | gga | gac | agc | acg | gat | ggt | act | ggt | ttt | atg | tgg | agt | ttg | aaa | 512 |
| Leu | Tyr | Gly | Asp | Ser | Thr | Asp | Gly | Thr | Gly | Phe | Met | Trp | Ser | Leu | Lys | |
| | | | | 105 | | | | | 110 | | | | | 115 | | |
| gag | aaa | aag | gtt | gac | gtt | ttt | cag | aat | aaa | atg | acc | atc | tta | gga | aca | 560 |
| Glu | Lys | Lys | Val | Asp | Val | Phe | Gln | Asn | Lys | Met | Thr | Ile | Leu | Gly | Thr | |
| | | | | 120 | | | | | 125 | | | | | 130 | | |
| ggt | ggt | gca | gcc | tta | tca | atc | att | gcc | caa | gct | gct | tta | gat | ggc | gtg | 608 |
| Gly | Gly | Ala | Ala | Leu | Ser | Ile | Ile | Ala | Gln | Ala | Ala | Leu | Asp | Gly | Val | |
| | | | | 135 | | | | | 140 | | | | | 145 | | |
| aaa | gaa | atc | gcc | gtt | tac | aac | agg | aaa | agc | gcg | ggc | ttt | aac | gac | agt | 656 |
| Lys | Glu | Ile | Ala | Val | Tyr | Asn | Arg | Lys | Ser | Ala | Gly | Phe | Asn | Asp | Ser | |
| 150 | | | | | 155 | | | | | 160 | | | | | 165 | |
| caa | aaa | aaa | ctg | gca | aat | ttc | act | gaa | cga | acc | aac | tgt | gta | att | cat | 704 |
| Gln | Lys | Lys | Leu | Ala | Asn | Phe | Thr | Glu | Arg | Thr | Asn | Cys | Val | Ile | His | |
| | | | | 170 | | | | | 175 | | | | | 180 | | |
| tta | aac | gat | tta | gcg | gat | act | gaa | aaa | cta | gca | aaa | gat | gtt | gct | gaa | 752 |
| Leu | Asn | Asp | Leu | Ala | Asp | Thr | Glu | Lys | Leu | Ala | Lys | Asp | Val | Ala | Glu | |
| | | | | 185 | | | | | 190 | | | | | 195 | | |
| agc | gtc | ttg | tta | gtt | aat | gca | acg | agt | gtg | ggt | atg | cat | cca | cat | gcg | 800 |
| Ser | Val | Leu | Leu | Val | Asn | Ala | Thr | Ser | Val | Gly | Met | His | Pro | His | Ala | |
| | | | | 200 | | | | | 205 | | | | | 210 | | |
| cat | agt | agt | cct | ata | gaa | aat | tat | gca | atg | att | caa | ccg | aag | tta | ttt | 848 |
| His | Ser | Ser | Pro | Ile | Glu | Asn | Tyr | Ala | Met | Ile | Gln | Pro | Lys | Leu | Phe | |
| | 215 | | | | | 220 | | | | | 225 | | | | | |
| gtg | tat | gat | gct | att | tat | aat | ccc | aga | gaa | aca | cag | tta | tta | aaa | gaa | 896 |
| Val | Tyr | Asp | Ala | Ile | Tyr | Asn | Pro | Arg | Glu | Thr | Gln | Leu | Leu | Lys | Glu | |
| 230 | | | | | 235 | | | | | 240 | | | | | 245 | |
| gcc | cgt | tta | cgt | ggt | gca | gaa | aca | agc | aac | ggc | ttg | gac | atg | cta | ctt | 944 |
| Ala | Arg | Leu | Arg | Gly | Ala | Glu | Thr | Ser | Asn | Gly | Leu | Asp | Met | Leu | Leu | |
| | | | | 250 | | | | | 255 | | | | | 260 | | |
| tat | caa | ggc | gct | gct | gct | ttt | gaa | caa | tgg | aca | gga | caa | aaa | atg | cct | 992 |
| Tyr | Gln | Gly | Ala | Ala | Ala | Phe | Glu | Gln | Trp | Thr | Gly | Gln | Lys | Met | Pro | |
| | | | | 265 | | | | | 270 | | | | | 275 | | |
| gta | tca | gtc | gta | aaa | cgt | aaa | att | gaa | aat | aga | taa | aaagagcgcc | | | | 1038 |
| Val | Ser | Val | Val | Lys | Arg | Lys | Ile | Glu | Asn | Arg | * | | | | | |
| | | | | 280 | | | | | 285 | | | | | | | |

```
                                                            -continued gtttaaaggc atgaggagag aatata atg atc gta att atg aaa gaa aat gca    1091
                            Met Ile Val Ile Met Lys Glu Asn Ala
                            290                 295 acc gaa aag caa atg aaa caa gtc att gat tta gta aca ggt gca ggc    1139
Thr Glu Lys Gln Met Lys Gln Val Ile Asp Leu Val Thr Gly Ala Gly
            300                 305                 310 tta act act caa aca agt caa gat aat gga aaa aca gtg ata ggc ttg    1187
Leu Thr Thr Gln Thr Ser Gln Asp Asn Gly Lys Thr Val Ile Gly Leu
    315                 320                 325 att ggt gat aca gaa aaa tta gtt gaa gca gag tta aca gca tta gaa    1235
Ile Gly Asp Thr Glu Lys Leu Val Glu Ala Glu Leu Thr Ala Leu Glu
330                 335                 340                 345 ggc gtg gag aaa agt gtc cgc att tcg ttg tct tac aaa cta acg agt    1283
Gly Val Glu Lys Ser Val Arg Ile Ser Leu Ser Tyr Lys Leu Thr Ser
                350                 355                 360 cgt tta ttt cat cca gag aat aca gtg gtt gat gtg aac ggt gtt aaa    1331
Arg Leu Phe His Pro Glu Asn Thr Val Val Asp Val Asn Gly Val Lys
            365                 370                 375 atc ggt gac ggc agt atg acc atg atg gcg ggc cct tgt tca atc gaa    1379
Ile Gly Asp Gly Ser Met Thr Met Met Ala Gly Pro Cys Ser Ile Glu
    380                 385                 390 agc tta gat cag att cgc gaa tgt gcg cga att gct aaa gct gga ggt    1427
Ser Leu Asp Gln Ile Arg Glu Cys Ala Arg Ile Ala Lys Ala Gly Gly
395                 400                 405 gca aca att tta cga ggt ggt gca ttc aaa cct aga acg tcg cca tac    1475
Ala Thr Ile Leu Arg Gly Gly Ala Phe Lys Pro Arg Thr Ser Pro Tyr
410                 415                 420                 425 gct ttc caa gga cta gaa gaa gaa gga cta aaa tac att cgc caa gcg    1523
Ala Phe Gln Gly Leu Glu Glu Glu Gly Leu Lys Tyr Ile Arg Gln Ala
                430                 435                 440 gct gat gaa tta gat atg caa gtc att aca gaa gtg atg gat gaa gcg    1571
Ala Asp Glu Leu Asp Met Gln Val Ile Thr Glu Val Met Asp Glu Ala
            445                 450                 455 aat tta gaa ctt gtc gca aaa tac agt gac att tta caa atc ggt gcg    1619
Asn Leu Glu Leu Val Ala Lys Tyr Ser Asp Ile Leu Gln Ile Gly Ala
    460                 465                 470 cgc aac atg caa aat ttc aag tta tta caa gcg gtt ggt aaa act gga    1667
Arg Asn Met Gln Asn Phe Lys Leu Leu Gln Ala Val Gly Lys Thr Gly
475                 480                 485 aaa cct att ggc tta aaa cgc ggg att gct ggt acg att gat gaa tgg    1715
Lys Pro Ile Gly Leu Lys Arg Gly Ile Ala Gly Thr Ile Asp Glu Trp
490                 495                 500                 505 cta aac gca gct gaa tac att gct gcg caa gga aat ttc aat gtg atc    1763
Leu Asn Ala Ala Glu Tyr Ile Ala Ala Gln Gly Asn Phe Asn Val Ile
                510                 515                 520 ttc att gaa cgt ggg att cgt acg tac gaa acc gct acg cgc aat aca    1811
Phe Ile Glu Arg Gly Ile Arg Thr Tyr Glu Thr Ala Thr Arg Asn Thr
            525                 530                 535 ctt gat tta agt gcg gtg cct tta att aaa aaa tta agt cat ttt cca    1859
Leu Asp Leu Ser Ala Val Pro Leu Ile Lys Lys Leu Ser His Phe Pro
    540                 545                 550 att att gtt gat ccg agt cat ggt gtt ggt atc tgg gat tta gta ccg    1907
Ile Ile Val Asp Pro Ser His Gly Val Gly Ile Trp Asp Leu Val Pro
555                 560                 565 cca atg gcc cga gca ggt gtt gct tca ggt gcg gac ggc ttg att gta    1955
Pro Met Ala Arg Ala Gly Val Ala Ser Gly Ala Asp Gly Leu Ile Val
570                 575                 580                 585 gaa att cat cca gat cca gcg aat gcg tgg tca gat ggg cca caa tcc    2003
Glu Ile His Pro Asp Pro Ala Asn Ala Trp Ser Asp Gly Pro Gln Ser
```

-continued 590              595              600
ttg aat gaa aaa act tac cta cgt atg atg aaa gaa gtt cat atc atc        2051
Leu Asn Glu Lys Thr Tyr Leu Arg Met Met Lys Glu Val His Ile Ile
            605              610              615 gaa aaa gca atg aaa gaa att aat gct tta gaa gat tag taaagacaga         2100
Glu Lys Ala Met Lys Glu Ile Asn Ala Leu Glu Asp *
            620              625 ggagtagagg ac atg aaa tta acc gta acg tta cct aca cat tca tat gat     2151
              Met Lys Leu Thr Val Thr Leu Pro Thr His Ser Tyr Asp
                       630              635              640 tta acc atc gaa aca ggt gcc tta gat aaa att ggc acc tgg gta cgt        2199
Leu Thr Ile Glu Thr Gly Ala Leu Asp Lys Ile Gly Thr Trp Val Arg
            645              650              655 agc ctg tgg cag cca caa cgg gta gcg att att acc gat gaa acg gtg        2247
Ser Leu Trp Gln Pro Gln Arg Val Ala Ile Ile Thr Asp Glu Thr Val
            660              665              670 aat aaa tta tat ggc gca gct gtt gag aaa gaa ttg caa gct gct ggt        2295
Asn Lys Leu Tyr Gly Ala Ala Val Glu Lys Glu Leu Gln Ala Ala Gly
675              680              685              690 ttt gaa aca tca ttg att gct gta gcg gca ggt gaa caa agt aag agc        2343
Phe Glu Thr Ser Leu Ile Ala Val Ala Ala Gly Glu Gln Ser Lys Ser
                 695              700              705 ctc gaa ata gct caa ctg ctt tat gat ttt tta gcg gaa cag caa ttg        2391
Leu Glu Ile Ala Gln Leu Leu Tyr Asp Phe Leu Ala Glu Gln Gln Leu
            710              715              720 act cga agt gat ggt cta att gct tta ggt gga ggc gtt gtg gga gat        2439
Thr Arg Ser Asp Gly Leu Ile Ala Leu Gly Gly Gly Val Val Gly Asp
            725              730              735 cta gct gga ttt gtc gct tca acc tat atg cgc ggt att cac ttt ttg        2487
Leu Ala Gly Phe Val Ala Ser Thr Tyr Met Arg Gly Ile His Phe Leu
            740              745              750 caa gta cca aca acc tta ctg gca caa gta gat agt agc att gga ggt        2535
Gln Val Pro Thr Thr Leu Leu Ala Gln Val Asp Ser Ser Ile Gly Gly
755              760              765              770 aaa aca gcg gtt aat act aaa aaa gcc aaa aat ctt gtc ggt act ttt        2583
Lys Thr Ala Val Asn Thr Lys Lys Ala Lys Asn Leu Val Gly Thr Phe
                 775              780              785 gcc caa cca gat ggg gtt tta att gat cct aat aca ctt aaa aca tta        2631
Ala Gln Pro Asp Gly Val Leu Ile Asp Pro Asn Thr Leu Lys Thr Leu
            790              795              800 gaa cct aga cgt gtg cgt gaa gga att gca gaa att gta aaa tca gca        2679
Glu Pro Arg Arg Val Arg Glu Gly Ile Ala Glu Ile Val Lys Ser Ala
            805              810              815 gct atc gct gat gtt gaa ttg tgg cac cgt tta tcc tct ttg gaa aat        2727
Ala Ile Ala Asp Val Glu Leu Trp His Arg Leu Ser Ser Leu Glu Asn
820              825              830 gaa caa gat tta gtg gca cat gca gaa gaa att atc acg gcc tgt tgc        2775
Glu Gln Asp Leu Val Ala His Ala Glu Glu Ile Ile Thr Ala Cys Cys
835              840              845              850 aag att aaa cgt gat gtc gtc gaa gaa gat gaa tta gat ttg ggc tta        2823
Lys Ile Lys Arg Asp Val Val Glu Glu Asp Glu Leu Asp Leu Gly Leu
            855              860              865 cgt ttg att ctg aat ttt ggg cat acg atc ggc cac gca tta gaa aat        2871
Arg Leu Ile Leu Asn Phe Gly His Thr Ile Gly His Ala Leu Glu Asn
            870              875              880 aca gct ggt tac ggg gtg att gct cac ggt gaa ggc gtt tct tta gga        2919
Thr Ala Gly Tyr Gly Val Ile Ala His Gly Glu Gly Val Ser Leu Gly
            885              890              895 atg att caa ata act caa gtc gca gaa caa caa ggg ctt tcc cca ctt        2967

```
                                                        -continued

Met Ile Gln Ile Thr Gln Val Ala Glu Gln Gln Gly Leu Ser Pro Leu
    900             905                 910 ggg act acc caa gag ttg gtc acc atg cta gaa aag ttc cat tta cca      3015
Gly Thr Thr Gln Glu Leu Val Thr Met Leu Glu Lys Phe His Leu Pro
915             920                 925                 930 gta acc aca gat cgt tgg tca gaa gaa cgt ctc tat caa gca att aca      3063
Val Thr Thr Asp Arg Trp Ser Glu Glu Arg Leu Tyr Gln Ala Ile Thr
                935                 940                 945 cat gat aaa aaa aca cgt ggg gga cag att aaa atc att gtc tta gaa      3111
His Asp Lys Lys Thr Arg Gly Gly Gln Ile Lys Ile Ile Val Leu Glu
        950                 955                 960 aaa att ggt caa gcg aaa att gtc tct tta cca acg gaa gaa att cga      3159
Lys Ile Gly Gln Ala Lys Ile Val Ser Leu Pro Thr Glu Glu Ile Arg
    965                 970                 975 gca ttt tta aac aga gaa gga gga att taa g atg cgc ttt att aca gca    3208
Ala Phe Leu Asn Arg Glu Gly Gly Ile  *   Met Arg Phe Ile Thr Ala
980             985                      990 ggc gaa tca cat gga cct gaa tta act gct att att gaa ggc tta cca      3256
Gly Glu Ser His Gly Pro Glu Leu Thr Ala Ile Ile Glu Gly Leu Pro
    995             1000                1005 gcc ggc ttg cct tta agt agc gaa gag att aac cga gaa tta gca aga      3304
Ala Gly Leu Pro Leu Ser Ser Glu Glu Ile Asn Arg Glu Leu Ala Arg
1010            1015                1020                1025 cgt caa ggc ggt tac ggt cgt ggg gga cgg atg aaa att gaa aaa gac      3352
Arg Gln Gly Gly Tyr Gly Arg Gly Gly Arg Met Lys Ile Glu Lys Asp
                1030                1035                1040 caa gta cgt att act tcg ggt att cgg cat ggt aaa aca ctt ggc tca      3400
Gln Val Arg Ile Thr Ser Gly Ile Arg His Gly Lys Thr Leu Gly Ser
            1045                1050                1055 cca gta acg ttg att gtc gaa aac aaa gac tgg aaa aat tgg acc tcc      3448
Pro Val Thr Leu Ile Val Glu Asn Lys Asp Trp Lys Asn Trp Thr Ser
        1060                1065                1070 gtg atg tca gta gag cca gtt cct gaa aaa caa aag aaa atc cgc cgc      3496
Val Met Ser Val Glu Pro Val Pro Glu Lys Gln Lys Lys Ile Arg Arg
    1075                1080                1085 gtc agc aaa cca cgt cca gga cat gct gat tta gtc ggt ggc atg aaa      3544
Val Ser Lys Pro Arg Pro Gly His Ala Asp Leu Val Gly Gly Met Lys
1090                1095                1100                1105 tat caa cat gat gat tta cgg aat gtt tta gaa cgg tct tcg gca cga      3592
Tyr Gln His Asp Asp Leu Arg Asn Val Leu Glu Arg Ser Ser Ala Arg
                1110                1115                1120 gaa aca acg atg cgt gtg gcg att ggt gcg gtt gct aaa aaa ctc tta      3640
Glu Thr Thr Met Arg Val Ala Ile Gly Ala Val Ala Lys Lys Leu Leu
            1125                1130                1135 gct gaa ctg gat atc caa gtc gct ggg cat gtc gcg gta tta ggt ggg      3688
Ala Glu Leu Asp Ile Gln Val Ala Gly His Val Ala Val Leu Gly Gly
        1140                1145                1150 att gaa gct acg atc cct gaa aat tta acg att cgt gaa att caa gaa      3736
Ile Glu Ala Thr Ile Pro Glu Asn Leu Thr Ile Arg Glu Ile Gln Glu
    1155                1160                1165 cga tct gaa caa tct gcc gtt cgc gta tta gat cct tcc gta gaa gaa      3784
Arg Ser Glu Gln Ser Ala Val Arg Val Leu Asp Pro Ser Val Glu Glu
1170                1175                1180                1185 aaa atg aaa gaa cta att gac caa acc aag aaa aat ggc gat aca att      3832
Lys Met Lys Glu Leu Ile Asp Gln Thr Lys Lys Asn Gly Asp Thr Ile
                1190                1195                1200 ggt ggg gta gta gaa gta ctt gtg ggt ggc gtt cca gct ggc tta ggt      3880
Gly Gly Val Val Glu Val Leu Val Gly Gly Val Pro Ala Gly Leu Gly
            1205                1210                1215
```

-continued

| | |
|---|---|
| agc tat gtc caa tgg gat cgt aaa cta gat gcc aaa att gcg caa gca<br>Ser Tyr Val Gln Trp Asp Arg Lys Leu Asp Ala Lys Ile Ala Gln Ala<br>        1220                        1225                 1230 | 3928 |
| gtt gta agc atc aac gct ttt aca ggt gct gag ttt ggc att gga ttt<br>Val Val Ser Ile Asn Ala Phe Thr Gly Ala Glu Phe Gly Ile Gly Phe<br>        1235                        1240                 1245 | 3976 |
| gaa atg gca caa cgc cct ggt agt caa ctg atg gac gag att gtt tgg<br>Glu Met Ala Gln Arg Pro Gly Ser Gln Leu Met Asp Glu Ile Val Trp<br>1250                        1255                    1260                1265 | 4024 |
| gac gaa agt act ggt tat acc aga act tcc aac aat tta ggc ggt ttt<br>Asp Glu Ser Thr Gly Tyr Thr Arg Thr Ser Asn Asn Leu Gly Gly Phe<br>                1270                        1275                 1280 | 4072 |
| gaa gga gga atg acc aac gga atg cca atc atc gtt cgt ggt gtc atg<br>Glu Gly Gly Met Thr Asn Gly Met Pro Ile Ile Val Arg Gly Val Met<br>        1285                        1290                 1295 | 4120 |
| aaa cct att cca acc ctt tat aaa cca tta caa agc gtg aat att gat<br>Lys Pro Ile Pro Thr Leu Tyr Lys Pro Leu Gln Ser Val Asn Ile Asp<br>1300                        1305                    1310 | 4168 |
| aca aaa gag cct tat aag gcc agt gtt gag cgc tct gat agc acg gcg<br>Thr Lys Glu Pro Tyr Lys Ala Ser Val Glu Arg Ser Asp Ser Thr Ala<br>                1315                        1320                 1325 | 4216 |
| gta ccg gcc gct agc gtt gtt tgt gaa gcc gtt gtt gca acg gaa gta<br>Val Pro Ala Ala Ser Val Val Cys Glu Ala Val Val Ala Thr Glu Val<br>1330                        1335                    1340                1345 | 4264 |
| gca aag gct atg ctc gaa aaa ttt gat agt gac tca ttt gaa caa atg<br>Ala Lys Ala Met Leu Glu Lys Phe Asp Ser Asp Ser Phe Glu Gln Met<br>                1350                        1355                 1360 | 4312 |
| aaa gaa gca gtg aaa cgt tat cgt cta tat act caa aac ttt taa<br>Lys Glu Ala Val Lys Arg Tyr Arg Leu Tyr Thr Gln Asn Phe  *<br>1365                        1370                    1375 | 4357 |
| tggaagaaag tcgcaagtat atggagggaa aaa atg aag aaa cgt att tta atc<br>                                              Met Lys Lys Arg Ile Leu Ile<br>                                                              1380 | 4411 |
| gta gga tta ggg cta atc ggg agt tca ctg gct ttg tgt atc aaa aaa<br>Val Gly Leu Gly Leu Ile Gly Ser Ser Leu Ala Leu Cys Ile Lys Lys<br>        1385                        1390                 1395 | 4459 |
| ggg cat cca aac agt gag att atc ggt ttc gat aat caa gcg gag gca<br>Gly His Pro Asn Ser Glu Ile Ile Gly Phe Asp Asn Gln Ala Glu Ala<br>        1400                        1405                 1410 | 4507 |
| act gaa ttt gct aag aaa acg ggt cta att gat gag ata gct gaa tct<br>Thr Glu Phe Ala Lys Lys Thr Gly Leu Ile Asp Glu Ile Ala Glu Ser<br>1415                        1420                    1425                1430 | 4555 |
| tta aca agt ggg gca aga cga gca gag att att ttt ctt tgt tcc cca<br>Leu Thr Ser Gly Ala Arg Arg Ala Glu Ile Ile Phe Leu Cys Ser Pro<br>                1435                        1440                 1445 | 4603 |
| gtt aaa gca act tta gta caa cta gaa gaa tta aac caa tta tca cta<br>Val Lys Ala Thr Leu Val Gln Leu Glu Glu Leu Asn Gln Leu Ser Leu<br>1450                        1455                    1460 | 4651 |
| gaa act gct ctg atc aca gat gtg ggt agt acc aag gtg gaa att aat<br>Glu Thr Ala Leu Ile Thr Asp Val Gly Ser Thr Lys Val Glu Ile Asn<br>                1465                        1470                 1475 | 4699 |
| cag tta gca aca aag ctt aac atg aaa aat ttt att ggt ggt cat cca<br>Gln Leu Ala Thr Lys Leu Asn Met Lys Asn Phe Ile Gly Gly His Pro<br>1480                        1485                    1490 | 4747 |
| atg gct ggt tca cat aaa tcc ggc gta aca gcc gct gat gaa cgt ttg<br>Met Ala Gly Ser His Lys Ser Gly Val Thr Ala Ala Asp Glu Arg Leu<br>1495                        1500                    1505                1510 | 4795 |
| ttt gaa aat gcc tac tat att ttt acc gat gac cat ggc gaa aaa aac<br>Phe Glu Asn Ala Tyr Tyr Ile Phe Thr Asp Asp His Gly Glu Lys Asn<br>                1515                        1520                 1525 | 4843 |

-continued

| | |
|---|---|
| aaa cag att cag gag tta caa acg tta cta aaa gga acg cat gcg aag<br>Lys Gln Ile Gln Glu Leu Gln Thr Leu Leu Lys Gly Thr His Ala Lys<br>          1530                     1535                     1540 | 4891 |
| ttt att acg atg cct gca cag gaa cat gat gaa att act ggt gct cta<br>Phe Ile Thr Met Pro Ala Gln Glu His Asp Glu Ile Thr Gly Ala Leu<br>        1545                     1550                     1555 | 4939 |
| agt cac ttg cca cat att gtt gcc gca gcg tta gtg aac gaa agt cag<br>Ser His Leu Pro His Ile Val Ala Ala Ala Leu Val Asn Glu Ser Gln<br>1560                     1565                     1570 | 4987 |
| caa ctg aat acc act tac cct aga gcg cag cag cta gcg gct gga gga<br>Gln Leu Asn Thr Thr Tyr Pro Arg Ala Gln Gln Leu Ala Ala Gly Gly<br>1575                 1580                     1585                     1590 | 5035 |
| ttc aga gat att act cga att gct tcc tct gat gca acg atg tgg acg<br>Phe Arg Asp Ile Thr Arg Ile Ala Ser Ser Asp Ala Thr Met Trp Thr<br>                 1595                     1600                     1605 | 5083 |
| gat att tta tta agc aat cgc tta gta tta ttg gac tta cta gaa aat<br>Asp Ile Leu Leu Ser Asn Arg Leu Val Leu Leu Asp Leu Leu Glu Asn<br>        1610                     1615                     1620 | 5131 |
| tgg caa aaa gag atg act act gtt tgc caa tgg tta aca gaa aaa aat<br>Trp Gln Lys Glu Met Thr Thr Val Cys Gln Trp Leu Thr Glu Lys Asn<br>1625                 1630                     1635 | 5179 |
| gcc cca gct att cgt aat ttt ttt gat aag gcc aaa gaa aca cgt gct<br>Ala Pro Ala Ile Arg Asn Phe Phe Asp Lys Ala Lys Glu Thr Arg Ala<br>        1640                     1645                     1650 | 5227 |
| caa ttg cct att cat aaa gaa ggc gca atc cca gct ttc tat gat ctg<br>Gln Leu Pro Ile His Lys Glu Gly Ala Ile Pro Ala Phe Tyr Asp Leu<br>1655                 1660                     1665                     1670 | 5275 |
| ttt gtt gat gta cca gat caa cca gga atc att gct gaa att acg caa<br>Phe Val Asp Val Pro Asp Gln Pro Gly Ile Ile Ala Glu Ile Thr Gln<br>                 1675                     1680                     1685 | 5323 |
| att tta ggc gaa gcg gac ctt tct ctt aca aat att aaa att tta gaa<br>Ile Leu Gly Glu Ala Asp Leu Ser Leu Thr Asn Ile Lys Ile Leu Glu<br>        1690                     1695                     1700 | 5371 |
| acg aga gaa gaa atc tat ggg att ctt caa ttg tct ttt aaa aat caa<br>Thr Arg Glu Glu Ile Tyr Gly Ile Leu Gln Leu Ser Phe Lys Asn Gln<br>                 1705                     1710                     1715 | 5419 |
| cca gac tgc caa gct gca aaa caa att tta tct aaa aaa acg aac tat<br>Pro Asp Cys Gln Ala Ala Lys Gln Ile Leu Ser Lys Lys Thr Asn Tyr<br>        1720                     1725                     1730 | 5467 |
| acg tgt tac gaa aaa taa gaggtg atg agg gtg caa cta cgt aca aat<br>Thr Cys Tyr Glu Lys *       Met Arg Val Gln Leu Arg Thr Asn<br>1735                                          1740                     1745 | 5515 |
| gtg aag cat tta caa ggg act ctg atg gtt cct agc gac aaa tcg att<br>Val Lys His Leu Gln Gly Thr Leu Met Val Pro Ser Asp Lys Ser Ile<br>        1750                     1755                     1760 | 5563 |
| tcc cat aga agt att atg ttt gga gcg att tct tct gga aaa acg acg<br>Ser His Arg Ser Ile Met Phe Gly Ala Ile Ser Ser Gly Lys Thr Thr<br>                 1765                     1770                     1775 | 5611 |
| att aca aat ttt cta aga ggc gaa gat tgt tta agt acc tta gcg gcg<br>Ile Thr Asn Phe Leu Arg Gly Glu Asp Cys Leu Ser Thr Leu Ala Ala<br>1780                 1785                     1790                     1795 | 5659 |
| ttt cgt tct tta ggt gtg aac att gaa gat gac ggg acg aca atc acc<br>Phe Arg Ser Leu Gly Val Asn Ile Glu Asp Asp Gly Thr Thr Ile Thr<br>                 1800                     1805                     1810 | 5707 |
| gtt gag ggg cga gga ttt gca ggc tta aaa aag gcg aag aat aca att<br>Val Glu Gly Arg Gly Phe Ala Gly Leu Lys Lys Ala Lys Asn Thr Ile<br>        1815                     1820                     1825 | 5755 |
| gat gtt gga aat tca ggg aca aca att cgt ctg atg ctg ggc att tta<br>Asp Val Gly Asn Ser Gly Thr Thr Ile Arg Leu Met Leu Gly Ile Leu | 5803 |

```
                1830                1835                1840
gct ggc tgt ccc ttt gaa acg cgc cta gct ggt gat gcg tct att gcc    5851
Ala Gly Cys Pro Phe Glu Thr Arg Leu Ala Gly Asp Ala Ser Ile Ala
    1845                1850                1855 aaa cga cca atg aat cgt gta atg ctt cct tta aac caa atg gga gcg    5899
Lys Arg Pro Met Asn Arg Val Met Leu Pro Leu Asn Gln Met Gly Ala
1860                1865                1870                1875 gaa tgt caa ggg gtt cag caa acg gag ttt ccg cca att tct att cgc    5947
Glu Cys Gln Gly Val Gln Gln Thr Glu Phe Pro Pro Ile Ser Ile Arg
                1880                1885                1890 ggg act caa aat ttg caa ccg att gac tac aca atg cct gtt gca agt    5995
Gly Thr Gln Asn Leu Gln Pro Ile Asp Tyr Thr Met Pro Val Ala Ser
            1895                1900                1905 gct caa gtt aaa tcg gct att tta ttc gcc gct ttg caa gcc gag ggc    6043
Ala Gln Val Lys Ser Ala Ile Leu Phe Ala Ala Leu Gln Ala Glu Gly
        1910                1915                1920 act tct gta gtg gtt gag aaa gaa aag aca cgt gat cat aca gaa gag    6091
Thr Ser Val Val Val Glu Lys Glu Lys Thr Arg Asp His Thr Glu Glu
    1925                1930                1935 atg att cga caa ttt ggt ggg aca ctt gaa gta gac ggt aaa aaa att    6139
Met Ile Arg Gln Phe Gly Gly Thr Leu Glu Val Asp Gly Lys Lys Ile
1940                1945                1950                1955 atg tta act gga ccg caa caa tta aca ggt caa aat gtg gta gtt cct    6187
Met Leu Thr Gly Pro Gln Gln Leu Thr Gly Gln Asn Val Val Val Pro
                1960                1965                1970 ggt gat atc tct tct gca gct ttc ttt tta gtt gcg ggt tta gta gtc    6235
Gly Asp Ile Ser Ser Ala Ala Phe Phe Leu Val Ala Gly Leu Val Val
            1975                1980                1985 cca gat agc gag ata ctt ctg aaa aat gtt ggc tta aat caa acg cgg    6283
Pro Asp Ser Glu Ile Leu Leu Lys Asn Val Gly Leu Asn Gln Thr Arg
        1990                1995                2000 aca ggt att tta gat gtg att aaa aac atg ggc ggt tcc gtc act att    6331
Thr Gly Ile Leu Asp Val Ile Lys Asn Met Gly Gly Ser Val Thr Ile
    2005                2010                2015 tta aat gaa gat gag gcc aat cat tct ggc gat tta ctt gta aaa acg    6379
Leu Asn Glu Asp Glu Ala Asn His Ser Gly Asp Leu Leu Val Lys Thr
2020                2025                2030                2035 agt caa tta aca gct aca gag att ggt ggc gct att atc cca cgt tta    6427
Ser Gln Leu Thr Ala Thr Glu Ile Gly Gly Ala Ile Ile Pro Arg Leu
                2040                2045                2050 att gat gag tta ccg att att gct ttg tta gct act cag gct act ggc    6475
Ile Asp Glu Leu Pro Ile Ile Ala Leu Leu Ala Thr Gln Ala Thr Gly
            2055                2060                2065 acg aca atc att cga gat gca gaa gaa ttg aaa gtc aaa gaa acc aat    6523
Thr Thr Ile Ile Arg Asp Ala Glu Glu Leu Lys Val Lys Glu Thr Asn
        2070                2075                2080 cgg att gat gca gta gcg aaa gaa tta aca att tta ggc gcc gac atc    6571
Arg Ile Asp Ala Val Ala Lys Glu Leu Thr Ile Leu Gly Ala Asp Ile
    2085                2090                2095 acg cct act gat gat ggc tta att ata cat gga cca act tct tta cat    6619
Thr Pro Thr Asp Asp Gly Leu Ile Ile His Gly Pro Thr Ser Leu His
2100                2105                2110                2115 ggt gga aga gtt acc agt tat ggg gat cat cgt atc ggg atg atg tta    6667
Gly Gly Arg Val Thr Ser Tyr Gly Asp His Arg Ile Gly Met Met Leu
                2120                2125                2130 caa att gct gca tta ctt gta aaa gaa ggc act gtt gaa tta gat aag    6715
Gln Ile Ala Ala Leu Leu Val Lys Glu Gly Thr Val Glu Leu Asp Lys
            2135                2140                2145 gct gaa gca gtt tca gtt tct tat cca gca ttt ttt gac gac tta gaa    6763
```

-continued

```
                Ala Glu Ala Val Ser Val Ser Tyr Pro Ala Phe Phe Asp Asp Leu Glu
                    2150                2155                2160 cgt tta agt tgt taa cgaaggagga taacga acc atg gaa agc att gtt tta      6815
Arg Leu Ser Cys *                      Thr Met Glu Ser Ile Val Leu
    2165                                       2170 att ggt ttc atg ggt gcg ggt aaa aca act atc ggc caa agt ttg gcc        6863
Ile Gly Phe Met Gly Ala Gly Lys Thr Thr Ile Gly Gln Ser Leu Ala
2175            2180                2185                2190 aat aaa ctg aag atg cct cat ctt gat tta gat aca gcg tta att gaa        6911
Asn Lys Leu Lys Met Pro His Leu Asp Leu Asp Thr Ala Leu Ile Glu
                2195                2200                2205 aaa ata gga cgc tca att cct gac tat ttc gaa aaa tat ggt gaa gca        6959
Lys Ile Gly Arg Ser Ile Pro Asp Tyr Phe Glu Lys Tyr Gly Glu Ala
                    2210                2215                2220 gct ttc cga gaa cag gaa acc caa ctt tta aag gag ctg tca aaa aat        7007
Ala Phe Arg Glu Gln Glu Thr Gln Leu Leu Lys Glu Leu Ser Lys Asn
                        2225                2230                2235 aca gcc gtc ctt tca act ggg ggc ggg att gtt gtc gga cca gaa aat        7055
Thr Ala Val Leu Ser Thr Gly Gly Gly Ile Val Val Gly Pro Glu Asn
    2240                2245                2250 cgt agc tta tta aaa tct ttt cag caa gtg att tat tta cat gcg aca        7103
Arg Ser Leu Leu Lys Ser Phe Gln Gln Val Ile Tyr Leu His Ala Thr
2255            2260                2265                2270 cca gaa gag ctg tta aaa aga atc aca gaa gat act gaa aac caa cgg        7151
Pro Glu Glu Leu Leu Lys Arg Ile Thr Glu Asp Thr Glu Asn Gln Arg
                2275                2280                2285 ccc tta gct ata gaa cgt tct tca aaa gaa atc att act ttg ttt gag        7199
Pro Leu Ala Ile Glu Arg Ser Ser Lys Glu Ile Ile Thr Leu Phe Glu
                    2290                2295                2300 tct cgt aaa aat ttt tat gaa gaa tgt gcg aag atg aca att gat acg        7247
Ser Arg Lys Asn Phe Tyr Glu Glu Cys Ala Lys Met Thr Ile Asp Thr
                        2305                2310                2315 acc aat cgc tcg cca gaa gaa att atc aat gaa att ctg caa caa tta        7295
Thr Asn Arg Ser Pro Glu Glu Ile Ile Asn Glu Ile Leu Gln Gln Leu
    2320                2325                2330 aag gag tag agaaacg atg aaa gtt ggt tat tta ggt ccg att ggt tcc        7344
Lys Glu *           Met Lys Val Gly Tyr Leu Gly Pro Ile Gly Ser
2335                        2340                2345 ttt acg tac agt gca acg ttg gct gct ttt cct gaa gct acg ttg atg        7392
Phe Thr Tyr Ser Ala Thr Leu Ala Ala Phe Pro Glu Ala Thr Leu Met
            2350                2355                2360 ccg tac gca tcg att cca gct tgc ttg aaa gca att gaa cag caa gaa        7440
Pro Tyr Ala Ser Ile Pro Ala Cys Leu Lys Ala Ile Glu Gln Gln Glu
        2365                2370                2375 gtg gca tgg agc att atc cca ata gaa aac acg att gaa gga act gtt        7488
Val Ala Trp Ser Ile Ile Pro Ile Glu Asn Thr Ile Glu Gly Thr Val
2380            2385                2390                2395 aac gca tcg ata gat tat ttg tat cat caa gcg cag tta cct gtc caa        7536
Asn Ala Ser Ile Asp Tyr Leu Tyr His Gln Ala Gln Leu Pro Val Gln
                2400                2405                2410 gca gag tta gtt tta ccg att caa caa caa tta atg gtg gca aaa gag        7584
Ala Glu Leu Val Leu Pro Ile Gln Gln Gln Leu Met Val Ala Lys Glu
                    2415                2420                2425 aat caa gcg atc tgg caa caa agt cag aaa att tta tca cat ccg caa        7632
Asn Gln Ala Ile Trp Gln Gln Ser Gln Lys Ile Leu Ser His Pro Gln
                        2430                2435                2440 gca tta gct caa tcg cag atg ttt cta gag aaa aac ttt cca gaa gcg        7680
Ala Leu Ala Gln Ser Gln Met Phe Leu Glu Lys Asn Phe Pro Glu Ala
    2445                2450                2455
```

|   |   |
|---|---|
| att tta gaa gca aca cct tca aca gct tac gcc gcc aaa tac att gca<br>Ile Leu Glu Ala Thr Pro Ser Thr Ala Tyr Ala Ala Lys Tyr Ile Ala<br>2460                    2465                  2470                  2475 | 7728 |
| gaa cat cca gaa tta cct ttt gca gct att gca cca aaa ctt tct gcg<br>Glu His Pro Glu Leu Pro Phe Ala Ala Ile Ala Pro Lys Leu Ser Ala<br>                    2480                  2485                  2490 | 7776 |
| gaa atg tat gat ttg acc att gtt gaa aaa aat ata caa gat tta tcg<br>Glu Met Tyr Asp Leu Thr Ile Val Glu Lys Asn Ile Gln Asp Leu Ser<br>2495                    2500                  2505 | 7824 |
| gta aat caa acc cga ttt tgg gtt ctt ggt tct gaa aat tta gcg att<br>Val Asn Gln Thr Arg Phe Trp Val Leu Gly Ser Glu Asn Leu Ala Ile<br>                    2510                  2515                  2520 | 7872 |
| tct ttc ccg cta tct gag aaa aaa ata aca ctg gcg att acg atg cca<br>Ser Phe Pro Leu Ser Glu Lys Lys Ile Thr Leu Ala Ile Thr Met Pro<br>2525                    2530                  2535 | 7920 |
| agt aat gtt cct ggc tct tta cac aaa gta tta agc gtg ttt agt tgg<br>Ser Asn Val Pro Gly Ser Leu His Lys Val Leu Ser Val Phe Ser Trp<br>2540                    2545                  2550                  2555 | 7968 |
| cga ggg att aat ctt agc aaa ata gaa tcg cgg ccg ttg aaa aca aag<br>Arg Gly Ile Asn Leu Ser Lys Ile Glu Ser Arg Pro Leu Lys Thr Lys<br>                    2560                  2565                  2570 | 8016 |
| cta gga gag tac ttc ttt tta atg gac tta gtg aaa gat caa cca gaa<br>Leu Gly Glu Tyr Phe Phe Leu Met Asp Leu Val Lys Asp Gln Pro Glu<br>2575                    2580                  2585 | 8064 |
| aaa tta att gaa gca gcc tta aca gaa ctg gaa ctc att ggt gca gaa<br>Lys Leu Ile Glu Ala Ala Leu Thr Glu Leu Glu Leu Ile Gly Ala Glu<br>                    2590                  2595                  2600 | 8112 |
| ata aaa att tta ggg gat tac ccg atc tat gtt ttg tcc aca ctt taa<br>Ile Lys Ile Leu Gly Asp Tyr Pro Ile Tyr Val Leu Ser Thr Leu *<br>2605                    2610                  2615 | 8160 |
| agagttaaaa atgaaaatga agcttactta ttagataaag tgagtttcat tttttattaa | 8220 |
| attacatatt tgtaatagga atttcctgtg aaatgaggta tcctaagaaa ggtgataaaa | 8280 |
| cacagaggta aaggagtgac acgatgagtc gtgtagatcg ttataaacat attcatgaaa | 8340 |
| tcttttc | 8347 |

<210> SEQ ID NO 32
<211> LENGTH: 867
<212> TYPE: DNA
<213> ORGANISM: Enterococcus faecalis

<400> SEQUENCE: 32

|   |   |
|---|---|
| atgaaagaaa taactggagc cactcgttta gctgggctat tcgcgaaacc cagccaacac | 60 |
| agtatttcac cgttgattca taatacagca tttcaaaatt taggagttga tgctcggtat | 120 |
| ctggcgtttg acgttggaca agagacattg ccacaagcaa ttgaagcgat tcgaacgttt | 180 |
| cacatgttag gggccaactt atcaatgccc aataaagtgg cggctgtaag ttatatggat | 240 |
| gaactaagtc ctaccgctca actggttggc gcaattaata cgattgtcaa caaagatgga | 300 |
| aaactttacg gagacagcac ggatggtact ggttttatgt ggagtttgaa agagaaaaag | 360 |
| gttgacgttt ttcagaataa aatgaccatc ttaggaacag gtggtgcagc cttatcaatc | 420 |
| attgcccaag ctgctttaga tggcgtgaaa gaaatcgccg tttacaacag gaaaagcgcg | 480 |
| ggctttaacg acagtcaaaa aaaactggca aatttcactg aacgaaccaa ctgtgtaatt | 540 |
| catttaaacg atttagcgga tactgaaaaa ctagcaaaag atgttgctga agcgtcttg | 600 |
| ttagttaatg caacgagtgt gggtatgcat ccacatgcgc atagtagtcc tatagaaaat | 660 |
| tatgcaatga ttcaaccgaa gttatttgtg tatgatgcta tttataatcc cagagaaaca | 720 |

| | |
|---|---|
| cagttattaa aagaagcccg tttacgtggt gcagaaacaa gcaacggctt ggacatgcta | 780 |
| ctttatcaag gcgctgctgc ttttgaacaa tggacaggac aaaaaatgcc tgtatcagtc | 840 |
| gtaaaacgta aaattgaaaa tagataa | 867 |

<210> SEQ ID NO 33
<211> LENGTH: 1026
<212> TYPE: DNA
<213> ORGANISM: Enterococcus faecalis

<400> SEQUENCE: 33

| | |
|---|---|
| atgatcgtaa ttatgaaaga aaatgcaacc gaaaagcaaa tgaaacaagt cattgattta | 60 |
| gtaacaggtg caggcttaac tactcaaaca agtcaagata atggaaaaac agtgataggc | 120 |
| ttgattggtg atacagaaaa attagttgaa gcagagttaa cagcattaga aggcgtggag | 180 |
| aaaagtgtcc gcatttcgtt gtcttacaaa ctaacgagtc gtttatttca tccagagaat | 240 |
| acagtggttg atgtgaacgg tgttaaaatc ggtgacggca gtatgaccat gatggcgggc | 300 |
| ccttgttcaa tcgaaagctt agatcagatt cgcgaatgtg cgcgaattgc taaagctgga | 360 |
| ggtgcaacaa ttttacgagg tggtgcattc aaacctagaa cgtcgccata cgctttccaa | 420 |
| ggactagaag aagaaggact aaaatacatt cgccaagcgg ctgatgaatt agatatgcaa | 480 |
| gtcattacag aagtgatgga tgaagcgaat ttagaacttg tcgcaaaata cagtgacatt | 540 |
| ttacaaatcg gtgcgcgcaa catgcaaaat ttcaagttat tacaagcggt tggtaaaact | 600 |
| ggaaaaccta ttggcttaaa acgcgggatt gctggtacga ttgatgaatg gctaaacgca | 660 |
| gctgaataca ttgctgcgca aggaaatttc aatgtgatct tcattgaacg tgggattcgt | 720 |
| acgtacgaaa ccgctacgcg caatacactt gatttaagtg cggtgccttt aattaaaaaa | 780 |
| ttaagtcatt ttccaattat tgttgatccg agtcatggtg ttggtatctg ggatttagta | 840 |
| ccgccaatgg cccgagcagg tgttgcttca ggtgcggacg gcttgattgt agaaattcat | 900 |
| ccagatccag cgaatgcgtg gtcagatggg ccacaatcct tgaatgaaaa aacttaccta | 960 |
| cgtatgatga agaagttca tatcatcgaa aaagcaatga agaaattaa tgctttagaa | 1020 |
| gattag | 1026 |

<210> SEQ ID NO 34
<211> LENGTH: 1077
<212> TYPE: DNA
<213> ORGANISM: Enterococcus faecalis

<400> SEQUENCE: 34

| | |
|---|---|
| atgaaattaa ccgtaacgtt acctacacat tcatatgatt taaccatcga acaggtgcc | 60 |
| ttagataaaa ttggcacctg gtacgtagc ctgtggcagc cacaacgggt agcgattatt | 120 |
| accgatgaaa cggtgaataa attatatggc gcagctgttg agaaagaatt gcaagctgct | 180 |
| ggttttgaaa catcattgat tgctgtagcg gcaggtgaac aaagtaagag cctcgaaata | 240 |
| gctcaactgc tttatgattt tttagcggaa cagcaattga ctcgaagtga tggtctaatt | 300 |
| gctttaggtg gaggcgttgt gggagatcta gctggatttg tcgcttcaac ctatatgcgc | 360 |
| ggtattcact ttttgcaagt accaacaacc ttactggcac aagtagatag tagcattgga | 420 |
| ggtaaaacag cggttaatac taaaaaagcc aaaaatcttg tcggtacttt tgcccaacca | 480 |
| gatgggggtt taattgatcc taatacactt aaaacattag aacctagacg tgtgcgtgaa | 540 |
| ggaattgcag aaattgtaaa atcagcagct atcgctgatg ttgaattgtg gcaccgttta | 600 |

-continued

```
tcctctttgg aaaatgaaca agatttagtg gcacatgcag aagaaattat cacggcctgt    660
tgcaagatta acgtgatgt cgtcgaagaa gatgaattag atttgggctt acgtttgatt    720
ctgaattttg ggcatacgat cggccacgca ttagaaaata cagctggtta cgggtgatt    780 gctcacggtg aaggcgtttc tttaggaatg attcaaataa ctcaagtcgc agaacaacaa    840
gggctttccc cacttgggac tacccaagag ttggtcacca tgctagaaaa gttccattta    900
ccagtaacca cagatcgttg gtcagaagaa cgtctctatc aagcaattac acatgataaa    960
aaaacacgtg ggggacagat taaaatcatt gtcttagaaa aaattggtca agcgaaaatt   1020
gtctctttac caacggaaga aattcgagca ttttaaaca gagaaggagg aatttaa      1077
```

<210> SEQ ID NO 35
<211> LENGTH: 1167
<212> TYPE: DNA
<213> ORGANISM: Enterococcus faecalis

<400> SEQUENCE: 35

```
atgcgcttta ttacagcagg cgaatcacat ggacctgaat taactgctat tattgaaggc    60
ttaccagccg gcttgccttt aagtagcgaa gagattaacc gagaattagc aagacgtcaa   120
ggcggttacg gtcgtggggg acggatgaaa attgaaaaag accaagtacg tattacttcg   180
ggtattcggc atggtaaaac acttggctca ccagtaacgt tgattgtcga aacaaagac    240 tggaaaaatt ggacctccgt gatgtcagta gagccagttc ctgaaaaaca aagaaaatc    300 cgccgcgtca gcaaaccacg tccaggacat gctgatttag tcggtggcat gaaatatcaa   360
catgatgatt tacggaatgt tttagaacgg tcttcggcac gagaaacaac gatgcgtgtg   420
gcgattggtg cggttgctaa aaaactctta gctgaactgg atatccaagt cgctgggcat   480
gtcgcggtat taggtgggat tgaagctacg atccctgaaa atttaacgat tcgtgaaatt   540
caagaacgat ctgaacaatc tgccgttcgc gtattagatc cttccgtaga agaaaaaatg   600
aaagaactaa ttgaccaaac caagaaaaat ggcgataaa ttggtggggt agtagaagta    660
cttgtgggtg gcgttccagc tggcttaggt agctatgtcc aatgggatcg taaactagat   720
gccaaaattg cgcaagcagt tgtaagcatc aacgcttta caggtgctga gtttggcatt   780
ggatttgaaa tggcacaacg ccctggtagt caactgatgg acgagattgt ttgggacgaa   840
agtactggtt ataccagaac ttccaacaat ttaggcggtt ttgaaggagg aatgaccaac   900
ggaatgccaa tcatcgttcg tggtgtcatg aaacctattc caaccctta taaaccatta   960 caaagcgtga atattgatac aaaagagcct tataaggcca gtgttgagcg ctctgatagc   1020
acggcggtac cggccgctag cgttgtttgt gaagccgttg ttgcaacgga gtagcaaag   1080 gctatgctcg aaaaatttga tagtgactca tttgaacaaa tgaaagaagc agtgaaacgt   1140
tatcgtctat atactcaaaa cttttaa                                       1167
```

<210> SEQ ID NO 36
<211> LENGTH: 1095
<212> TYPE: DNA
<213> ORGANISM: Enterococcus faecalis

<400> SEQUENCE: 36

```
atgaagaaac gtattttaat cgtaggatta gggctaatcg ggagttcact ggctttgtgt    60
atcaaaaaag ggcatccaaa cagtgagatt atcggtttcg ataatcaagc ggaggcaact   120
gaatttgcta agaaaacggg tctaattgat gagatagctg aatctttaac aagtggggca   180
agacgagcag agattatttt tctttgttcc ccagttaaag caactttagt acaactagaa   240
```

| | |
|---|---|
| gaattaaacc aattatcact agaaactgct ctgatcacag atgtgggtag taccaaggtg | 300 |
| gaaattaatc agttagcaac aaagcttaac atgaaaaatt ttattggtgg tcatccaatg | 360 |
| gctggttcac ataaatccgg cgtaacagcc gctgatgaac gtttgtttga aaatgcctac | 420 |
| tatattttta ccgatgacca tggcgaaaaa acaaacaga ttcaggagtt acaaacgtta | 480 |
| ctaaaaggaa cgcatgcgaa gtttattacg atgcctgcac aggaacatga tgaaattact | 540 |
| ggtgctctaa gtcacttgcc acatattgtt gccgcagcgt tagtgaacga aagtcagcaa | 600 |
| ctgaatacca cttaccctag agcgcagcag ctagcggctg gaggattcag agatattact | 660 |
| cgaattgctt cctctgatgc aacgatgtgg acggatattt tattaagcaa tcgcttagta | 720 |
| ttattggact tactagaaaa ttggcaaaaa gagatgacta ctgtttgcca atggttaaca | 780 |
| gaaaaaaatg ccccagctat tcgtaatttt tttgataagg ccaaagaaac acgtgctcaa | 840 |
| ttgcctattc ataagaagg cgcaatccca gctttctatg atctgtttgt tgatgtacca | 900 |
| gatcaaccag gaatcattgc tgaaattacg caaattttag gcgaagcgga cctttctctt | 960 |
| acaaatatta aaattttaga aacgagagaa gaaatctatg ggattcttca attgtctttt | 1020 |
| aaaaatcaac cagactgcca agctgcaaaa caaattttat ctaaaaaaac gaactatacg | 1080 |
| tgttacgaaa aataa | 1095 |

<210> SEQ ID NO 37
<211> LENGTH: 1287
<212> TYPE: DNA
<213> ORGANISM: Enterococcus faecalis

<400> SEQUENCE: 37

| | |
|---|---|
| atgagggtgc aactacgtac aaatgtgaag catttacaag ggactctgat ggttcctagc | 60 |
| gacaaatcga tttcccatag aagtattatg tttggagcga tttcttctgg aaaaacgacg | 120 |
| attacaaatt ttctaagagg cgaagattgt ttaagtacct tagcggcgtt tcgttctttta | 180 |
| ggtgtgaaca ttgaagatga cgggacgaca atcaccgttg aggggcgagg atttgcaggc | 240 |
| ttaaaaaagg cgaagaatac aattgatgtt ggaaattcag ggacaacaat tcgtctgatg | 300 |
| ctgggcattt tagctggctg tccctttgaa acgcgcctag ctggtgatgc gtctattgcc | 360 |
| aaacgaccaa tgaatcgtgt aatgcttcct ttaaaccaaa tgggagcgga atgtcaaggg | 420 |
| gttcagcaaa cggagtttcc gccaatttct attcgcggga ctcaaaattt gcaaccgatt | 480 |
| gactacacaa tgcctgttgc aagtgctcaa gttaaatcgg ctattttatt cgccgctttg | 540 |
| caagccgagg gcacttctgt agtggttgag aaagaaaaga cacgtgatca tacagaagag | 600 |
| atgattcgac aatttggtgg gacacttgaa gtagacggta aaaaaattat gttaactgga | 660 |
| ccgcaacaat taacaggtca aaatgtggta gttcctggtg atatctcttc tgcagctttc | 720 |
| ttttagttg cgggttttagt agtcccagat agcgagatac ttctgaaaaa tgttggctta | 780 |
| aatcaaacgc ggacaggtat tttagatgtg attaaaaaca tgggcggttc cgtcactatt | 840 |
| ttaaatgaag atgaggccaa tcattctggc gatttacttg taaaaacgag tcaattaaca | 900 |
| gctacagaga ttggtggcgc tattatccca cgtttaattg atgagttacc gattattgct | 960 |
| ttgttagcta ctcaggctac tggcacgaca atcattcgag atgcagaaga attgaaagtc | 1020 |
| aaagaaacca atcggattga tgcagtagcg aaagaattaa caattttagg cgccgacatc | 1080 |
| acgcctactg atgatggctt aattatacat ggaccaactt cttttcatgg tggaagagtt | 1140 |
| accagttatg gggatcatcg tatcgggatg atgttacaaa ttgctgcatt acttgtaaaa | 1200 |

```
gaaggcactg ttgaattaga taaggctgaa gcagtttcag tttcttatcc agcattttt      1260 gacgacttag aacgtttaag ttgttaa                                          1287

<210> SEQ ID NO 38
<211> LENGTH: 507
<212> TYPE: DNA
<213> ORGANISM: Enterococcus faecalis

<400> SEQUENCE: 38
atggaaagca ttgttttaat tggtttcatg ggtgcgggta aacaactat cggccaaagt        60 ttggccaata aactgaagat gcctcatctt gatttagata cagcgttaat tgaaaaata       120 ggacgctcaa ttcctgacta tttcgaaaaa tatggtgaag cagctttccg agaacaggaa      180
acccaacttt taaaggagct gtcaaaaaat acagccgtcc tttcaactgg ggcgggatt       240 gttgtcggac cagaaaatcg tagcttatta aaatcttttc agcaagtgat ttatttacat      300
gcgacaccag aagagctgtt aaaaagaatc acagaagata ctgaaaacca acggcccta      360 gctatagaac gttcttcaaa agaaatcatt actttgtttg agtctcgtaa aaatttttat      420
gaagaatgtg cgaagatgac aattgatacg accaatcgct cgccagaaga aattatcaat     480
gaaattctgc aacaattaaa ggagtag                                          507

<210> SEQ ID NO 39
<211> LENGTH: 849
<212> TYPE: DNA
<213> ORGANISM: Enterococcus faecalis

<400> SEQUENCE: 39
atgaaagttg ttatttaagg tccgattggt tcctttacgt acagtgcaac gttggctgct       60
tttcctgaag ctacgttgat gccgtacgca tcgattccag cttgcttgaa agcaattgaa      120
cagcaagaag tggcatggag cattatccca atagaaaaca cgattgaagg aactgttaac      180
gcatcgatag attatttgta tcatcaagcg cagttacctg tccaagcaga gttagttta       240 ccgattcaac aacaattaat ggtggcaaaa gagaatcaag cgatctggca acaaagtcag      300
aaaattttat cacatccgca agcattagct caatcgcaga tgtttctaga gaaaaacttt      360
ccagaagcga tttagaagc aacaccttca acagcttacg ccgccaaata cattgcagaa      420
catccagaat tacctttgtc agctattgca ccaaaacttt ctgcggaaat gtatgatttg      480
accattgttg aaaaaatat acaagattta tcggtaaatc aaacccgatt ttgggttctt       540
ggttctgaaa atttagcgat ttctttcccg ctatctgaga aaaaaataac actggcgatt      600
acgatgccaa gtaatgttcc tggctctta cacaaagtat taagcgtgtt tagttggcga      660
gggattaatc ttagcaaaat agaatcgcgg ccgttgaaaa caaagctagg agagtacttc      720 ttttaatgg acttagtgaa agatcaacca gaaaaattaa ttgaagcagc cttaacagaa      780
ctggaactca ttggtgcaga ataaaaaatt ttagggatt acccgatcta tgttttgtcc      840
acactttaa                                                              849

<210> SEQ ID NO 40
<211> LENGTH: 288
<212> TYPE: PRT
<213> ORGANISM: Enterococcus faecalis

<400> SEQUENCE: 40

Met Lys Glu Ile Thr Gly Ala Thr Arg Leu Ala Gly Leu Phe Ala Lys
     1               5                   10                  15
```

-continued

```
Pro Ser Gln His Ser Ile Ser Pro Leu Ile His Asn Thr Ala Phe Gln
            20                  25                  30

Asn Leu Gly Val Asp Ala Arg Tyr Leu Ala Phe Asp Val Gly Gln Glu
        35                  40                  45

Thr Leu Pro Gln Ala Ile Glu Ala Ile Arg Thr Phe His Met Leu Gly
 50                  55                  60

Ala Asn Leu Ser Met Pro Asn Lys Val Ala Val Ser Tyr Met Asp
 65                  70                  75                  80

Glu Leu Ser Pro Thr Ala Gln Leu Val Gly Ala Ile Asn Thr Ile Val
                85                  90                  95

Asn Lys Asp Gly Lys Leu Tyr Gly Asp Ser Thr Asp Gly Thr Gly Phe
            100                 105                 110

Met Trp Ser Leu Lys Glu Lys Val Asp Val Phe Gln Asn Lys Met
            115                 120                 125

Thr Ile Leu Gly Thr Gly Ala Ala Leu Ser Ile Ile Ala Gln Ala
    130                 135                 140

Ala Leu Asp Gly Val Lys Glu Ile Ala Val Tyr Asn Arg Lys Ser Ala
145                 150                 155                 160

Gly Phe Asn Asp Ser Gln Lys Lys Leu Ala Asn Phe Thr Glu Arg Thr
                165                 170                 175

Asn Cys Val Ile His Leu Asn Asp Leu Ala Asp Thr Glu Lys Leu Ala
            180                 185                 190

Lys Asp Val Ala Glu Ser Val Leu Leu Val Asn Ala Thr Ser Val Gly
        195                 200                 205

Met His Pro His Ala His Ser Ser Pro Ile Glu Asn Tyr Ala Met Ile
    210                 215                 220

Gln Pro Lys Leu Phe Val Tyr Asp Ala Ile Tyr Asn Pro Arg Glu Thr
225                 230                 235                 240

Gln Leu Leu Lys Glu Ala Arg Leu Arg Gly Ala Glu Thr Ser Asn Gly
                245                 250                 255

Leu Asp Met Leu Leu Tyr Gln Gly Ala Ala Ala Phe Glu Gln Trp Thr
            260                 265                 270

Gly Gln Lys Met Pro Val Ser Val Val Lys Arg Lys Ile Glu Asn Arg
        275                 280                 285
```

<210> SEQ ID NO 41
<211> LENGTH: 341
<212> TYPE: PRT
<213> ORGANISM: Enterococcus faecalis

<400> SEQUENCE: 41

```
Met Ile Val Ile Met Lys Glu Asn Ala Thr Glu Lys Gln Met Lys Gln
 1               5                  10                  15

Val Ile Asp Leu Val Thr Gly Ala Gly Leu Thr Thr Gln Thr Ser Gln
            20                  25                  30

Asp Asn Gly Lys Thr Val Ile Gly Leu Ile Gly Asp Thr Glu Lys Leu
        35                  40                  45

Val Glu Ala Glu Leu Thr Ala Leu Glu Gly Val Glu Lys Ser Val Arg
 50                  55                  60

Ile Ser Leu Ser Tyr Lys Leu Thr Ser Arg Leu Phe His Pro Glu Asn
 65                  70                  75                  80

Thr Val Val Asp Val Asn Gly Val Lys Ile Gly Asp Gly Ser Met Thr
                85                  90                  95

Met Met Ala Gly Pro Cys Ser Ile Glu Ser Leu Asp Gln Ile Arg Glu
            100                 105                 110
```

-continued

```
Cys Ala Arg Ile Ala Lys Ala Gly Gly Ala Thr Ile Leu Arg Gly Gly
            115                 120                 125

Ala Phe Lys Pro Arg Thr Ser Pro Tyr Ala Phe Gln Gly Leu Glu Glu
        130                 135                 140

Glu Gly Leu Lys Tyr Ile Arg Gln Ala Ala Asp Glu Leu Asp Met Gln
145                 150                 155                 160

Val Ile Thr Glu Val Met Asp Glu Ala Asn Leu Glu Leu Val Ala Lys
                165                 170                 175

Tyr Ser Asp Ile Leu Gln Ile Gly Ala Arg Asn Met Gln Asn Phe Lys
            180                 185                 190

Leu Leu Gln Ala Val Gly Lys Thr Gly Lys Pro Ile Gly Leu Lys Arg
        195                 200                 205

Gly Ile Ala Gly Thr Ile Asp Glu Trp Leu Asn Ala Ala Glu Tyr Ile
    210                 215                 220

Ala Ala Gln Gly Asn Phe Asn Val Ile Phe Ile Glu Arg Gly Ile Arg
225                 230                 235                 240

Thr Tyr Glu Thr Ala Thr Arg Asn Thr Leu Asp Leu Ser Ala Val Pro
                245                 250                 255

Leu Ile Lys Lys Leu Ser His Phe Pro Ile Ile Val Asp Pro Ser His
            260                 265                 270

Gly Val Gly Ile Trp Asp Leu Val Pro Met Ala Arg Ala Gly Val
        275                 280                 285

Ala Ser Gly Ala Asp Gly Leu Ile Val Glu Ile His Pro Asp Pro Ala
        290                 295                 300

Asn Ala Trp Ser Asp Gly Pro Gln Ser Leu Asn Glu Lys Thr Tyr Leu
305                 310                 315                 320

Arg Met Met Lys Glu Val His Ile Ile Glu Lys Ala Met Lys Glu Ile
                325                 330                 335

Asn Ala Leu Glu Asp
            340

<210> SEQ ID NO 42
<211> LENGTH: 358
<212> TYPE: PRT
<213> ORGANISM: Enterococcus faecalis

<400> SEQUENCE: 42

Met Lys Leu Thr Val Thr Leu Pro Thr His Ser Tyr Asp Leu Thr Ile
 1                5                  10                  15

Glu Thr Gly Ala Leu Asp Lys Ile Gly Thr Trp Val Arg Ser Leu Trp
            20                  25                  30

Gln Pro Gln Arg Val Ala Ile Ile Thr Asp Glu Thr Val Asn Lys Leu
        35                  40                  45

Tyr Gly Ala Ala Val Glu Lys Glu Leu Gln Ala Ala Gly Phe Glu Thr
    50                  55                  60

Ser Leu Ile Ala Val Ala Ala Gly Glu Gln Ser Lys Ser Leu Glu Ile
65                  70                  75                  80

Ala Gln Leu Leu Tyr Asp Phe Leu Ala Glu Gln Leu Thr Arg Ser
                85                  90                  95

Asp Gly Leu Ile Ala Leu Gly Gly Gly Val Val Gly Asp Leu Ala Gly
            100                 105                 110

Phe Val Ala Ser Thr Tyr Met Arg Gly Ile His Phe Leu Gln Val Pro
        115                 120                 125

Thr Thr Leu Leu Ala Gln Val Asp Ser Ser Ile Gly Gly Lys Thr Ala
```

```
                130                 135                 140
Val Asn Thr Lys Lys Ala Lys Asn Leu Val Gly Thr Phe Ala Gln Pro
145                 150                 155                 160

Asp Gly Val Leu Ile Asp Pro Asn Thr Leu Lys Thr Leu Glu Pro Arg
                165                 170                 175

Arg Val Arg Glu Gly Ile Ala Glu Ile Val Lys Ser Ala Ala Ile Ala
            180                 185                 190

Asp Val Glu Leu Trp His Arg Leu Ser Ser Leu Glu Asn Glu Gln Asp
                195                 200                 205

Leu Val Ala His Ala Glu Glu Ile Ile Thr Ala Cys Cys Lys Ile Lys
            210                 215                 220

Arg Asp Val Val Glu Glu Asp Glu Leu Asp Leu Gly Leu Arg Leu Ile
225                 230                 235                 240

Leu Asn Phe Gly His Thr Ile Gly His Ala Leu Glu Asn Thr Ala Gly
                245                 250                 255

Tyr Gly Val Ile Ala His Gly Glu Gly Val Ser Leu Gly Met Ile Gln
                260                 265                 270

Ile Thr Gln Val Ala Glu Gln Gln Gly Leu Ser Pro Leu Gly Thr Thr
        275                 280                 285

Gln Glu Leu Val Thr Met Leu Glu Lys Phe His Leu Pro Val Thr Thr
    290                 295                 300

Asp Arg Trp Ser Glu Glu Arg Leu Tyr Gln Ala Ile Thr His Asp Lys
305                 310                 315                 320

Lys Thr Arg Gly Gly Gln Ile Lys Ile Val Leu Glu Lys Ile Gly
                325                 330                 335

Gln Ala Lys Ile Val Ser Leu Pro Thr Glu Glu Ile Arg Ala Phe Leu
            340                 345                 350

Asn Arg Glu Gly Gly Ile
            355

<210> SEQ ID NO 43
<211> LENGTH: 388
<212> TYPE: PRT
<213> ORGANISM: Enterococcus faecalis

<400> SEQUENCE: 43

Met Arg Phe Ile Thr Ala Gly Glu Ser His Gly Pro Glu Leu Thr Ala
 1               5                  10                  15

Ile Ile Glu Gly Leu Pro Ala Gly Leu Pro Leu Ser Ser Glu Glu Ile
            20                  25                  30

Asn Arg Glu Leu Ala Arg Arg Gln Gly Gly Tyr Gly Arg Gly Gly Arg
        35                  40                  45

Met Lys Ile Glu Lys Asp Gln Val Arg Ile Thr Ser Gly Ile Arg His
50                  55                  60

Gly Lys Thr Leu Gly Ser Pro Val Thr Leu Ile Val Glu Asn Lys Asp
65                  70                  75                  80

Trp Lys Asn Trp Thr Ser Val Met Ser Val Glu Pro Val Pro Glu Lys
                85                  90                  95

Gln Lys Lys Ile Arg Arg Val Ser Lys Pro Arg Pro Gly His Ala Asp
            100                 105                 110

Leu Val Gly Gly Met Lys Tyr Gln His Asp Asp Leu Arg Asn Val Leu
        115                 120                 125

Glu Arg Ser Ser Ala Arg Glu Thr Thr Met Arg Val Ala Ile Gly Ala
    130                 135                 140
```

-continued

```
Val Ala Lys Lys Leu Leu Ala Glu Leu Asp Ile Gln Val Ala Gly His
145                 150                 155                 160

Val Ala Val Leu Gly Gly Ile Glu Ala Thr Ile Pro Glu Asn Leu Thr
                165                 170                 175

Ile Arg Glu Ile Gln Glu Arg Ser Glu Gln Ser Ala Val Arg Val Leu
            180                 185                 190

Asp Pro Ser Val Glu Glu Lys Met Lys Glu Leu Ile Asp Gln Thr Lys
        195                 200                 205

Lys Asn Gly Asp Thr Ile Gly Gly Val Val Glu Val Leu Val Gly Gly
210                 215                 220

Val Pro Ala Gly Leu Gly Ser Tyr Val Gln Trp Asp Arg Lys Leu Asp
225                 230                 235                 240

Ala Lys Ile Ala Gln Ala Val Val Ser Ile Asn Ala Phe Thr Gly Ala
                245                 250                 255

Glu Phe Gly Ile Gly Phe Glu Met Ala Gln Arg Pro Gly Ser Gln Leu
            260                 265                 270

Met Asp Glu Ile Val Trp Asp Glu Ser Thr Gly Tyr Thr Arg Thr Ser
        275                 280                 285

Asn Asn Leu Gly Gly Phe Glu Gly Gly Met Thr Asn Gly Met Pro Ile
290                 295                 300

Ile Val Arg Gly Val Met Lys Pro Ile Pro Thr Leu Tyr Lys Pro Leu
305                 310                 315                 320

Gln Ser Val Asn Ile Asp Thr Lys Glu Pro Tyr Lys Ala Ser Val Glu
                325                 330                 335

Arg Ser Asp Ser Thr Ala Val Pro Ala Ala Ser Val Val Cys Glu Ala
            340                 345                 350

Val Val Ala Thr Glu Val Ala Lys Ala Met Leu Glu Lys Phe Asp Ser
        355                 360                 365

Asp Ser Phe Glu Gln Met Lys Glu Ala Val Lys Arg Tyr Arg Leu Tyr
    370                 375                 380

Thr Gln Asn Phe
385

<210> SEQ ID NO 44
<211> LENGTH: 364
<212> TYPE: PRT
<213> ORGANISM: Enterococcus faecalis

<400> SEQUENCE: 44

Met Lys Lys Arg Ile Leu Ile Val Gly Leu Gly Leu Ile Gly Ser Ser
1               5                   10                  15

Leu Ala Leu Cys Ile Lys Lys Gly His Pro Asn Ser Glu Ile Ile Gly
                20                  25                  30

Phe Asp Asn Gln Ala Glu Ala Thr Glu Phe Ala Lys Lys Thr Gly Leu
            35                  40                  45

Ile Asp Glu Ile Ala Glu Ser Leu Thr Ser Gly Ala Arg Arg Ala Glu
        50                  55                  60

Ile Ile Phe Leu Cys Ser Pro Val Lys Ala Thr Leu Val Gln Leu Glu
65                  70                  75                  80

Glu Leu Asn Gln Leu Ser Leu Glu Thr Ala Leu Ile Thr Asp Val Gly
                85                  90                  95

Ser Thr Lys Val Glu Ile Asn Gln Leu Ala Thr Lys Leu Asn Met Lys
            100                 105                 110

Asn Phe Ile Gly Gly His Pro Met Ala Gly Ser His Lys Ser Gly Val
        115                 120                 125
```

-continued

```
Thr Ala Ala Asp Glu Arg Leu Phe Glu Asn Ala Tyr Tyr Ile Phe Thr
        130                 135                 140

Asp Asp His Gly Glu Lys Asn Lys Gln Ile Gln Glu Leu Gln Thr Leu
145                 150                 155                 160

Leu Lys Gly Thr His Ala Lys Phe Ile Thr Met Pro Ala Gln Glu His
                165                 170                 175

Asp Glu Ile Thr Gly Ala Leu Ser His Leu Pro His Ile Val Ala Ala
                180                 185                 190

Ala Leu Val Asn Glu Ser Gln Gln Leu Asn Thr Thr Tyr Pro Arg Ala
            195                 200                 205

Gln Gln Leu Ala Ala Gly Gly Phe Arg Asp Ile Thr Arg Ile Ala Ser
        210                 215                 220

Ser Asp Ala Thr Met Trp Thr Asp Ile Leu Leu Ser Asn Arg Leu Val
225                 230                 235                 240

Leu Leu Asp Leu Leu Glu Asn Trp Gln Lys Glu Met Thr Thr Val Cys
                245                 250                 255

Gln Trp Leu Thr Glu Lys Asn Ala Pro Ala Ile Arg Asn Phe Phe Asp
            260                 265                 270

Lys Ala Lys Glu Thr Arg Ala Gln Leu Pro Ile His Lys Glu Gly Ala
        275                 280                 285

Ile Pro Ala Phe Tyr Asp Leu Phe Val Asp Val Pro Asp Gln Pro Gly
290                 295                 300

Ile Ile Ala Glu Ile Thr Gln Ile Leu Gly Glu Ala Asp Leu Ser Leu
305                 310                 315                 320

Thr Asn Ile Lys Ile Leu Glu Thr Arg Glu Glu Ile Tyr Gly Ile Leu
                325                 330                 335

Gln Leu Ser Phe Lys Asn Gln Pro Asp Cys Gln Ala Ala Lys Gln Ile
            340                 345                 350

Leu Ser Lys Lys Thr Asn Tyr Thr Cys Tyr Glu Lys
        355                 360
```

<210> SEQ ID NO 45
<211> LENGTH: 428
<212> TYPE: PRT
<213> ORGANISM: Enterococcus faecalis

<400> SEQUENCE: 45

```
Met Arg Val Gln Leu Arg Thr Asn Val Lys His Leu Gln Gly Thr Leu
1               5                   10                  15

Met Val Pro Ser Asp Lys Ser Ile Ser His Arg Ser Ile Met Phe Gly
                20                  25                  30

Ala Ile Ser Ser Gly Lys Thr Thr Ile Thr Asn Phe Leu Arg Gly Glu
            35                  40                  45

Asp Cys Leu Ser Thr Leu Ala Ala Phe Arg Ser Leu Gly Val Asn Ile
        50                  55                  60

Glu Asp Asp Gly Thr Thr Ile Thr Val Glu Gly Arg Gly Phe Ala Gly
65                  70                  75                  80

Leu Lys Lys Ala Lys Asn Thr Ile Asp Val Gly Asn Ser Gly Thr Thr
                85                  90                  95

Ile Arg Leu Met Leu Gly Ile Leu Ala Gly Cys Pro Phe Glu Thr Arg
                100                 105                 110

Leu Ala Gly Asp Ala Ser Ile Ala Lys Arg Pro Met Asn Arg Val Met
            115                 120                 125

Leu Pro Leu Asn Gln Met Gly Ala Glu Cys Gln Gly Val Gln Gln Thr
```

```
                130                 135                 140
Glu Phe Pro Pro Ile Ser Ile Arg Gly Thr Gln Asn Leu Gln Pro Ile
145                 150                 155                 160

Asp Tyr Thr Met Pro Val Ala Ser Ala Gln Val Lys Ser Ala Ile Leu
                165                 170                 175

Phe Ala Ala Leu Gln Ala Glu Gly Thr Ser Val Val Glu Lys Glu
                180                 185                 190

Lys Thr Arg Asp His Thr Glu Glu Met Ile Arg Gln Phe Gly Gly Thr
                195                 200                 205

Leu Glu Val Asp Gly Lys Lys Ile Met Leu Thr Gly Pro Gln Gln Leu
210                 215                 220

Thr Gly Gln Asn Val Val Pro Gly Asp Ile Ser Ser Ala Ala Phe
225                 230                 235                 240

Phe Leu Val Ala Gly Leu Val Val Pro Asp Ser Glu Ile Leu Leu Lys
                245                 250                 255

Asn Val Gly Leu Asn Gln Thr Arg Thr Gly Ile Leu Asp Val Ile Lys
                260                 265                 270

Asn Met Gly Gly Ser Val Thr Ile Leu Asn Glu Asp Glu Ala Asn His
                275                 280                 285

Ser Gly Asp Leu Leu Val Lys Thr Ser Gln Leu Thr Ala Thr Glu Ile
                290                 295                 300

Gly Gly Ala Ile Ile Pro Arg Leu Ile Asp Glu Leu Pro Ile Ile Ala
305                 310                 315                 320

Leu Leu Ala Thr Gln Ala Thr Gly Thr Thr Ile Ile Arg Asp Ala Glu
                325                 330                 335

Glu Leu Lys Val Lys Glu Thr Asn Arg Ile Asp Ala Val Ala Lys Glu
                340                 345                 350

Leu Thr Ile Leu Gly Ala Asp Ile Thr Pro Thr Asp Gly Leu Ile
                355                 360                 365

Ile His Gly Pro Thr Ser Leu His Gly Gly Arg Val Thr Ser Tyr Gly
                370                 375                 380

Asp His Arg Ile Gly Met Met Leu Gln Ile Ala Ala Leu Leu Val Lys
385                 390                 395                 400

Glu Gly Thr Val Glu Leu Asp Lys Ala Glu Ala Val Ser Val Ser Tyr
                405                 410                 415

Pro Ala Phe Phe Asp Asp Leu Glu Arg Leu Ser Cys
                420                 425

<210> SEQ ID NO 46
<211> LENGTH: 168
<212> TYPE: PRT
<213> ORGANISM: Enterococcus faecalis

<400> SEQUENCE: 46

Met Glu Ser Ile Val Leu Ile Gly Phe Met Gly Ala Gly Lys Thr Thr
1               5                   10                  15

Ile Gly Gln Ser Leu Ala Asn Lys Leu Lys Met Pro His Leu Asp Leu
                20                  25                  30

Asp Thr Ala Leu Ile Glu Lys Ile Gly Arg Ser Ile Pro Asp Tyr Phe
            35                  40                  45

Glu Lys Tyr Gly Glu Ala Ala Phe Arg Glu Gln Glu Thr Gln Leu Leu
        50                  55                  60

Lys Glu Leu Ser Lys Asn Thr Ala Val Leu Ser Thr Gly Gly Gly Ile
65                  70                  75                  80
```

```
Val Val Gly Pro Glu Asn Arg Ser Leu Leu Lys Ser Phe Gln Gln Val
            85                  90                  95

Ile Tyr Leu His Ala Thr Pro Glu Glu Leu Leu Lys Arg Ile Thr Glu
            100                 105                 110

Asp Thr Glu Asn Gln Arg Pro Leu Ala Ile Glu Arg Ser Ser Lys Glu
            115                 120                 125

Ile Ile Thr Leu Phe Glu Ser Arg Lys Asn Phe Tyr Glu Glu Cys Ala
            130                 135                 140

Lys Met Thr Ile Asp Thr Thr Asn Arg Ser Pro Glu Glu Ile Ile Asn
145                 150                 155                 160

Glu Ile Leu Gln Gln Leu Lys Glu
            165

<210> SEQ ID NO 47
<211> LENGTH: 282
<212> TYPE: PRT
<213> ORGANISM: Enterococcus faecalis

<400> SEQUENCE: 47

Met Lys Val Gly Tyr Leu Gly Pro Ile Gly Ser Phe Thr Tyr Ser Ala
1               5                   10                  15

Thr Leu Ala Ala Phe Pro Glu Ala Thr Leu Met Pro Tyr Ala Ser Ile
            20                  25                  30

Pro Ala Cys Leu Lys Ala Ile Glu Gln Gln Glu Val Ala Trp Ser Ile
            35                  40                  45

Ile Pro Ile Glu Asn Thr Ile Glu Gly Thr Val Asn Ala Ser Ile Asp
        50                  55                  60

Tyr Leu Tyr His Gln Ala Gln Leu Pro Val Gln Ala Glu Leu Val Leu
65                  70                  75                  80

Pro Ile Gln Gln Gln Leu Met Val Ala Lys Glu Asn Gln Ala Ile Trp
            85                  90                  95

Gln Gln Ser Gln Lys Ile Leu Ser His Pro Gln Ala Leu Ala Gln Ser
            100                 105                 110

Gln Met Phe Leu Glu Lys Asn Phe Pro Glu Ala Ile Leu Glu Ala Thr
            115                 120                 125

Pro Ser Thr Ala Tyr Ala Ala Lys Tyr Ile Ala Glu His Pro Glu Leu
            130                 135                 140

Pro Phe Ala Ala Ile Ala Pro Lys Leu Ser Ala Glu Met Tyr Asp Leu
145                 150                 155                 160

Thr Ile Val Glu Lys Asn Ile Gln Asp Leu Ser Val Asn Gln Thr Arg
            165                 170                 175

Phe Trp Val Leu Gly Ser Glu Asn Leu Ala Ile Ser Phe Pro Leu Ser
            180                 185                 190

Glu Lys Lys Ile Thr Leu Ala Ile Thr Met Pro Ser Asn Val Pro Gly
            195                 200                 205

Ser Leu His Lys Val Leu Ser Val Phe Ser Trp Arg Gly Ile Asn Leu
            210                 215                 220

Ser Lys Ile Glu Ser Arg Pro Leu Lys Thr Lys Leu Gly Glu Tyr Phe
225                 230                 235                 240

Phe Leu Met Asp Leu Val Lys Asp Gln Pro Glu Lys Leu Ile Glu Ala
            245                 250                 255
```

-continued

```
Ala Leu Thr Glu Leu Glu Leu Ile Gly Ala Glu Ile Lys Ile Leu Gly
            260                 265                 270

Asp Tyr Pro Ile Tyr Val Leu Ser Thr Leu
            275                 280
```

US 7,186,816 B2

PHOTOLYASE NUCLEIC ACIDS

CROSS-REFERENCE TO RELATED APPLICATIONS

This application is a continuation of International Application No. PCT/US02/22979, filed Jul. 18, 2002, which was published in English under PCT Article 21(2), which claims the benefit of U.S. Provisional Application 60/306,212, filed Jul. 18, 2001.

BACKGROUND OF THE INVENTION

The invention relates to virulence factors and methods for identifying drugs that inhibit pathogen infections.

The gram-positive pathogens in the genus *Enterococcus* are an increasingly problematic source of nosocomial infections, in part due to multi-drug resistance. *Enterococcus* can cause diseases such as bacteremia and endocarditis. These pathogens can also infect the urinary tract and skin wounds in immunocompromised individuals. Infection can be fatal if the bacteria cannot be neutralized.

Despite their increasing prevalence as infectious agents, little is known about how these bacteria cause disease. Only cytolysin and aggregation substance have been studied rigorously enough to be established as virulence factors in mammalian models of *Enterococcus faecalis* pathogenesis. Other virulence factors, such as certain proteases, are believed to contribute to pathogenesis, but have not been studied adequately in mammalian model systems.

One reason that little is known about Enterococcal virulence factors is that the model systems used to study these bacteria, the favorite being a rabbit model of endocarditis, are expensive and unwieldy. Using a mammalian model system to screen for these virulence factors would be virtually impossible. Accordingly, there exists a need for straightforward, inexpensive, and reliable methods to identify Enterococcal virulence factors. Also needed, are easy, accurate screening methods that would greatly simplify the drug discovery process aimed at identifying molecules that inhibit Enterococcal pathogenicity or promote host resistance to this pathogen.

SUMMARY OF THE INVENTION

The invention provides a novel approach to identifying Enterococcal virulence factors and for identifying compounds for treating bacterial pathogenesis. The invention further provides novel Enterococcal virulence factors, which serve as targets for drug discovery.

In one aspect, the invention features a method for identifying an Enterococcal virulence factor. The method, in general, involves the steps of: (a) exposing a nematode to a mutagenized Enterococcal pathogen; (b) determining whether the Enterococcal mutant infects the nematode, a reduction of disease in the nematode relative to that caused by the non-mutagenized Enterococcal pathogen indicating a mutation in an Enterococcal virulence factor; and (c) using the mutation as a marker for identifying the Enterococcal virulence factor. In preferred embodiments, the Enterococcal pathogen is *Enterococcus faecalis* (e.g., *Enterococcus faecalis* strain V583) and the nematode is *Caenorhabditis elegans* (e.g., a wild-type or mutant worm). In other preferred embodiments, the method utilizes an Enterococcal/*C. elegans* killing assay.

In another aspect, the invention features a method of identifying a compound that inhibits pathogenicity of an Enterococcal pathogen. The method, in general, involves the steps of: (a) providing a nematode infected with an Enterococcal pathogen; (b) contacting the infected nematode with a test compound; and (c) determining whether the test compound inhibits the pathogenicity of the Enterococcal pathogen in the nematode. In preferred embodiments, the Enterococcal pathogen is *Enterococcus faecalis* (e.g., *Enterococcus faecalis* strain V583) and the nematode is *Caenorhabditis elegans* (e.g., a wild-type or mutant worm). Preferably, the test compound is provided in a compound library. In other preferred embodiments the test compound is a small organic compound; or is a peptide, peptidomimetic, or antibody or fragment thereof. In still other preferred embodiments, the in inhibition of pathogenicity is measured by an Enterococcal/*C. elegans* is killing assay.

In yet another aspect, the invention features an isolated nematode (e.g., *Caenorhabditis elegans*), that includes an isolated Enterococcal pathogen. In preferred embodiments, the Enterococcal pathogen is *Enterococcus faecalis, Enterococcus faecalis* strain V583, *Enterococcus faecium*, or is a mutated Enterococcal pathogen.

In addition, we have identified and characterized a number of nucleic acid molecules and polypeptides that are involved in conferring pathogenicity and virulence to a pathogen. This discovery therefore provides a basis for drug-screening assays aimed at evaluating and identifying "anti-virulence" agents which are capable of blocking pathogenicity and virulence of a pathogen, e.g., by selectively switching pathogen gene expression on or off, or which inactivate or inhibit the activity of a polypeptide which is involved in the pathogenicity of a microbe. Drugs that target these molecules are useful as such anti-virulence agents.

Accordingly, the invention further features an isolated nucleic acid molecule including a sequence substantially identical to any one of the nucleic acid sequences encoding photolyase (FIG. 5A) (SEQ ID NO:2), ScrR (FIG. 6A) (SEQ ID NO:5), OppA (FIG. 7A) (SEQ ID NO:8), TcaA (FIG. 8A).(SEQ ID NO:11), ScrB (FIG. 9A) (SEQ ID NO:14), RecQ (FIG. 10A) (SEQ ID NO:17), LysR family of positive regulators (FIG. 11A) (SEQ ID NO:20), XAA-His dipeptidase (carnosinase) (FIG. 12A) (SEQ ID NO:23), SacU (FIG. 13A) (SEQ ID NO:26), Pai1 (FIG. 14A) (SEQ ID NO:29), or ORFs 1–8 of the shikimate amino acid biosynthetic gene cluster (FIGS. 15A, 15B, 15D, 15F, 15H, 15J, 15L, 15N, and 15P) (SEQ ID NOS:32–39). Preferably, the isolated nucleic acid molecule includes any of the above-described sequences or a fragment thereof; and is derived from a pathogen (e.g., from a bacterial pathogen such as *Enterococcus*). Additionally, the invention includes a vector and a cell, each of which includes at least one of the isolated nucleic acid molecules of the invention; and a method of producing a recombinant polypeptide involving providing a cell transformed with a nucleic acid molecule of the invention positioned for expression in the cell, culturing the transformed cell under conditions for expressing the nucleic acid molecule, and isolating a recombinant polypeptide. The invention further features recombinant polypeptides produced by such expression of an isolated nucleic acid molecule of the invention, and substantially pure antibodies that specifically recognize and bind to such recombinant polypeptides.

In an another aspect, the invention features a substantially pure polypeptide including an amino acid sequence that is substantially identical to the amino acid sequence of photolyase (FIG. 5B) (SEQ ID NO:3), ScrR (FIG. 6B) (SEQ ID NO:6), OppA (FIG. 7B) (SEQ ID NO:9), TcaA (FIG. 8B) (SEQ ID NO:12), ScrB (FIG. 9B) (SEQ ID NO:15), RecQ (FIG. 10B) (SEQ ID NO:18), LysR family of positive regulators (FIG. 11B) (SEQ ID NO:21), XAA-His dipeptidase (camosinase) (FIG. 12B) (SEQ ID NO:24), SacU (FIG. 13B) (SEQ ID NO:27), Pai1 (FIG. 14B) (SEQ ID NO:30), or ORFs 1–8 of the shikimate amino acid biosynthetic gene cluster (FIGS. 15A, 15C, 15E, 15G, 15I, 15K, 15M, 15O, and 15Q) (SEQ ID NO:40–47). Preferably, the substantially pure polypeptide includes any of the above-described sequences of a fragment thereof; and is derived from a pathogen (e.g., from a bacterial pathogen such as *Enterococcus*).

In yet another related aspect, the invention features a method for identifying a compound which is capable of decreasing the expression of a pathogenic virulence factor (e.g., at the transcriptional or post-transcriptional levels), involving (a) providing a pathogenic cell expressing any one of the isolated nucleic acid molecules of the invention; and (b) contacting the pathogenic cell with a candidate compound, a decrease in expression of the nucleic acid molecule following contact with the candidate compound identifying a compound which decreases the expression of a pathogenic virulence factor. In preferred embodiments, the pathogenic cell infects a mammal (e.g., a human).

In yet another related aspect, the invention features a method for identifying a compound which binds a polypeptide, involving (a) contacting a candidate compound with a substantially pure polypeptide including any one of the amino acid sequences of the invention under conditions that allow binding; and (b) detecting binding of the candidate compound to the polypeptide.

In addition, the invention features a method of treating a pathogenic infection in a mammal, involving (a) identifying a mammal having a pathogenic infection; and (b) administering to the mammal a therapeutically effective amount of a composition which inhibits the expression or activity of a polypeptide encoded by any one of the nucleic acid molecules of the invention. In preferred embodiments, the pathogen is *Enterococcus*.

In yet another aspect, the invention features a method of treating a pathogenic infection in a mammal, involving (a) identifying a mammal having a pathogenic infection; and (b) administering to the mammal a therapeutically effective amount of a composition which binds and inhibits a polypeptide encoded by any one of the amino acid sequences of the invention. In preferred embodiments, the pathogenic infection is caused by *Enterococcus*.

The invention further features compounds or combinations of compounds used to treat or prevent microbial infections.

By "virulence factor" is meant a cellular component (e.g., a protein such as a transcription factor or a molecule) without which a pathogen is incapable of causing disease or infection in a eukaryotic host organism (e.g., a nematode or mammal). Such components are involved in the adaptation of the bacteria to a host (e.g., a nematode host), establishment of a bacterial infection, maintenance of a bacterial infection, and generation of the damaging effects of the infection to the host organism. Further, the phrase includes components that act directly on host tissue, as well as components which regulate the activity or production of other pathogenesis factors.

By "infection" or "infected" is meant an invasion or colonization of a host animal (e.g., nematode) by pathogenic bacteria that is damaging to the host.

By "inhibits pathogenicity of an Enterococcal pathogen" is meant the ability of a test compound to decrease, suppress, attenuate, diminish, arrest, or stabilize the development or progression of an Enterococcal-mediated disease or infection in a eukaryotic host organism. Preferably, such inhibition decreases pathogenicity by at least 5%, more preferably by at least 25%, and most preferably by at least 50% or more, as compared to symptoms in the absence of the test compound in any appropriate pathogenicity assay (for example, those assays described herein). In one particular example, inhibition may be measured by monitoring pathogenic symptoms in a nematode infected with an Enterococcal pathogen exposed to a test compound or extract, a decrease in the level of pathogenic symptoms relative to the level of symptoms in the host organism not exposed to the compound indicating compound-mediated inhibition of the Enterococcal pathogen.

By "isolated nucleic acid molecule" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By "polypeptide" is meant any chain of amino acids, regardless of length or post-translational modification (for example, glycosylation or phosphorylation).

By a "substantially pure polypeptide" is meant a polypeptide of the invention that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. A substantially pure polypeptide of the invention may be obtained, for example, by extraction from a natural source (for example, a pathogen); by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "substantially identical" is meant a polypeptide or nucleic acid molecule exhibiting at least 25% identity to a reference amino acid sequence (for example, any one of the amino acid sequences described herein) or nucleic acid sequence (for example, any one of the nucleic acid sequences described herein). Preferably, such a sequence is at least 30%, 35%, 40%, 45%, 50%, 55%, 60%, 65%, 70%, or 75% identical at the amino acid or nucleic acid level to the sequence used for comparison, more preferably 80%, or 85% and most preferably 90% or even 95% to 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "transformed cell" is meant a cell into which (or into an ancestor of which) has been introduced, by means of recombinant DNA techniques, a DNA molecule encoding (as used herein) a polypeptide of the invention.

By "positioned for expression" is meant that the DNA molecule is positioned adjacent to a DNA sequence which directs transcription and translation of the sequence (i.e., facilitates the production of, for example, a recombinant polypeptide of the invention, or an RNA molecule).

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody. A purified antibody of the invention may be obtained, for example, by affinity chromatography using a recombinantly-produced polypeptide of the invention and standard techniques.

By "specifically binds" is meant a compound or antibody which recognizes and binds a polypeptide of the invention but which does not substantially recognize and bind other molecules in a sample, for example, a biological sample, which naturally includes a polypeptide of the invention.

By "derived from" is meant isolated from or having the sequence of a naturally-occurring sequence (e.g., a cDNA, genomic DNA, synthetic, or combination thereof).

The present invention provides a number of advantages. For example, the invention facilitates the identification of novel targets and therapeutic approaches for preparing therapeutic agents active on Enterococcal virulence factors and genes. The invention also provides long awaited advantages over a wide variety of standard screening methods used for distinguishing and evaluating the efficacy of a compound against Enterococcal pathogens. In one particular example, the screening methods described herein allow for the simultaneous evaluation of host toxicity as well as anti-Enterococcal potency in a simple in vivo screen. Moreover, the methods of the invention allow one to evaluate the ability of a compound to inhibit Enterococcal pathogenesis, and, at the same time, to evaluate the ability of the compound to stimulate and strengthen a host's response to Enterococcal pathogenic attack.

Accordingly, the methods of the invention provide a straightforward means to identify compounds that are both safe for use in eukaryotic host organisms (i.e., compounds which do not adversely affect the normal development and physiology of the organism) and efficacious against Enterococcal pathogenic microbes. In addition, the methods of the invention provide a route for analyzing virtually any number of compounds for anti-Enterococcal pathogenic effect with high-volume throughput, high sensitivity, and low complexity. The methods are also relatively inexpensive to perform and enable the analysis of small quantities of active substances found in either purified or crude extract form. Furthermore, the methods disclosed herein provide a means for identifying anti-pathogenic compounds which have the capability of crossing eukaryotic cell membranes and which maintain therapeutic efficacy in an in vivo method of administration. In addition, the above-described methods of screening are suitable for both known and unknown compounds and compound libraries.

Other features and advantages of the invention will be apparent from the following description of the preferred embodiments thereof, and from the claims.

BRIEF DESCRIPTION OF THE DRAWINGS

FIG. 5A shows the nucleic acid sequence of the Enterococcal virulence factor photolyase including the upstream and downstream untranslated regions (SEQ ID NO:1). The photolyase open reading frame (ORF) nucleic acid sequence (SEQ ID NO:2) extends from the start codon (ATG) to the stop (TAA) codon. The start and stop codons are indicated by highlighting.

FIG. 5B shows the amino acid sequence of the Enterococcal virulence factor photolyase (SEQ ID NO:3).

FIG. 6A shows the nucleic acid sequence of the Enterococcal virulence factor ScrR including the upstream and downstream untranslated regions (SEQ ID NO:4). The ScrR ORF nucleic acid sequence (SEQ ID NO:5) extends from the start codon (ATG) to the stop (TAA) codon. The start and stop codons are indicated by highlighting.

FIG. 6B shows the amino acid sequence of the Enterococcal virulence factor ScrR (SEQ ID NO:6).

FIG. 7A shows the nucleic acid sequence of the Enterococcal virulence factor OppA including the upstream and downstream untranslated regions (SEQ ID NO:7). The OppA ORF nucleic acid sequence (SEQ ID NO:8) extends from the start codon (ATG) to the stop (TAA) codon. The start and stop codons are indicated by highlighting.

FIG. 7B shows the amino acid sequence of the Enterococcal virulence factor OppA (SEQ ID NO:9).

FIG. 8A shows the nucleic acid sequence of an Enterococcal virulence factor, which is predicted to be a membrane protein related to TcaA, including the upstream and downstream untranslated regions (SEQ ID NO:10). The TcaA ORF nucleic acid sequence (SEQ ID NO:11) extends from the start codon (ATG) to the stop (TAA) codon. The start and stop codons are indicated by highlighting.

FIG. 8B shows the amino acid sequence of an Enterococcal virulence factor which is predicted to be a membrane protein related to TcaA (SEQ ID NO:12).

FIG. 9A shows the nucleic acid sequence of the Enterococcal virulence factor ScrB including the upstream and downstream untranslated regions (SEQ ID NO:13). The ScrB ORF nucleic acid sequence (SEQ ID NO:14) extends from the start codon (ATG) to the stop (TAG) codon. The start and stop codons are indicated by highlighting.

FIG. 9B shows the amino acid sequence of the Enterococcal virulence factor ScrB (SEQ ID NO:15).

FIG. 10A shows the nucleic acid sequence of the Enterococcal virulence factor RecQ including the upstream and downstream untranslated regions (SEQ ID NO:16). The RecQ ORF nucleic acid sequence (SEQ ID NO:17) extends from the start codon (ATG) to the stop (TAA) codon. The start and stop codons are indicated by highlighting.

FIG. 10B shows the amino acid sequence of the Enterococcal virulence factor RecQ (SEQ ID NO:18).

FIG. 11A shows the nucleic acid sequence of an Enterococcal virulence factor, which is a member of the LysR family of positive regulators, including the upstream and downstream untranslated regions (SEQ ID NO:19). The LysR ORF nucleic acid sequence (SEQ ID NO:20) extends from the start codon (ATG) to the stop (TAG) codon. The start and stop codons are indicated by highlighting.

FIG. 11B shows the amino acid sequence (SEQ ID NO:21) of an Enterococcal virulence factor which is a member of the LysR family of positive regulators.

FIG. 12A shows the nucleic acid sequence of the Enterococcal virulence factor XAA-His dipeptidase (carnosinase) including the upstream and downstream untranslated regions (SEQ ID NO:22). The dipeptidase ORF nucleic acid sequence (SEQ ID NO:23) extends from the start codon (ATG) to the stop (TAA) codon. The start and stop codons are indicated by highlighting.

FIG. 12B shows the amino acid sequence (SEQ ID NO:24) of the Enterococcal virulence factor XAA-His dipeptidase (carnosinase).

FIG. 13A shows the nucleic acid sequence of the Enterococcal virulence factor SacU including the upstream and downstream untranslated regions (SEQ ID NO:25). The SacU ORF nucleic acid sequence (SEQ ID NO:26) extends from the start codon (ATG) to the stop (TAA) codon. The start and stop codons are indicated by highlighting.

FIG. 13B shows the amino acid sequence (SEQ ID NO:27) of the Enterococcal virulence factor SacU.

FIG. 14A shows the nucleic acid sequence of the Enterococcal virulence factor Pai1 including the upstream and downstream untranslated regions (SEQ ID NO:28). The Pai1 ORF nucleic acid sequence (SEQ ID NO:29) extends from the start codon (ATG) to the stop (TAA) codon. The start and stop codons are indicated by highlighting.

FIG. 14B shows the amino acid sequence (SEQ ID NO:30) of the Enterococcal virulence factor Pai1.

FIG. 15A shows the nucleic acid sequence (SEQ ID NO:31) of an Enterococcal amino acid biosynthetic gene cluster that includes ORF1–ORF8 and the intergenic regions. ORF1 is from nucleotide 162–1028 (SEQ ID NO:32); ORF2 is from nucleotide 1065–2090 (SEQ ID NO:33); ORF3 is from nucleotide 2113–3189 (SEQ ID NO:34); ORF4 is from nucleotide 3191–4357 (SEQ ID NO:35); ORF5 is from nucleotide 4391–5485 (SEQ ID NO:36); ORF6 is from nucleotide 5492–6778 (SEQ ID NO:37); ORF7 is from nucleotide 6795–7304 (SEQ ID NO:38); and ORF8 is from nucleotide 7312–8160 (SEQ ID NO:39).

FIG. 15B shows the nucleic acid sequence of ORF1 (SEQ ID NO:32).

FIG. 15C shows the amino acid sequence of ORF1 (SEQ ID NO:40).

FIG. 15D shows the nucleic acid sequence of ORF2 (SEQ ID NO:33).

FIG. 15E shows the amino acid sequence of ORF2 (SEQ ID NO:41).

FIG. 15F shows the nucleic acid sequence of ORF3 (SEQ ID NO:34).

FIG. 15G shows the amino acid sequence of ORF3 (SEQ ID NO:42).

FIG. 15H shows the nucleic acid sequence of ORF4 (SEQ ID NO:35).

FIG. 15I shows the amino acid sequence of ORF4 (SEQ ID NO:43).

FIG. 15J shows the nucleic acid sequence of ORF5 (SEQ ID NO:36).

FIG. 15K shows the amino acid sequence of ORF5 (SEQ ID NO:44).

FIG. 15L shows the nucleic acid sequence of ORF6 (SEQ ID NO:37).

FIG. 15M shows the amino acid sequence of ORF6 (SEQ ID NO:45).

FIG. 15N shows the nucleic acid sequence of ORF7 (SEQ ID NO:38).

FIG. 15O shows the amino acid sequence of ORF7 (SEQ ID NO:46).

FIG. 15P shows the nucleic acid sequence of ORF8 (SEQ ID NO:39).

FIG. 15Q shows the amino acid sequence of ORF8 (SEQ ID NO:47).

Figure 1:
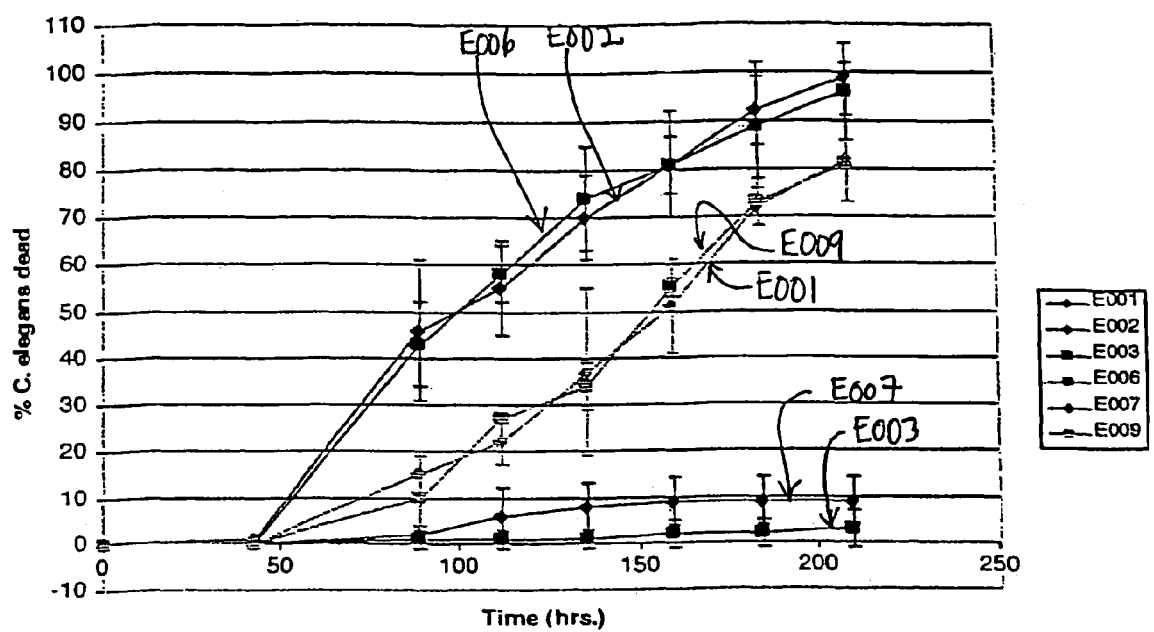
FIG. 1 shows *C. elegans* killing by Enterococcal strains, E001, E002, E003, E006, E007, and E009.

Below we describe experimental evidence demonstrating that *Enterococcus* causes disease in the nematode *C. elegans*, and that *C. elegans* feeding on lawns of *Enterococcus faecalis* die over the course of a few days as a result of a pathogenic process. Data is also presented demonstrating that at least one known *E. faecalis* virulence factor, cytolysin, required for maximum virulence in mammalian models. enhances the killing of *C. elegans*, validating the use of a *C. elegans* host as a model for mammalian pathogenesis. The Enterococcal/*C. elegans* killing assay described herein therefore provides a useful system for identifying novel Enterococcal virulence factors, as well as for identifying compounds that either inhibit Enterococcal pathogenicity, promote a host's resistance to the pathogen, or both. Exemplary virulence factors identified in these assays are also disclosed. The following experimental examples are intended to illustrate, not limit, the scope of the claimed invention.

*C. elegans*/Enterococcus Killing Assays

To monitor *Enterococcus*-mediated killing, *C. elegans* assays were carried out as follows. Brain heart infusion (BHI) agar medium (Difco) was autoclaved and poured into 35 mm tissue culture plates (Fisher). Appropriate antibiotics were added to the medium before pouring that prevented growth of *E. coli*, but allowed growth of the particular *Enterococcus* strains being tested. For strains E001, E002, E003, E006 and E009, 12.5 µg/ml tetracycline was used. For strain V583, 200 µg/ml gentamycin was used. For strain E007, 50 µg/ml ampicillin was used. For strains OG1 and OG1 (pAD1), 250 µg/ml of spectinomycin was used. For strain OG1 (pCF10), 250 µg/ml spectinomycin and 12.5 µg/ml tetracycline were used. For strains FA2-2, FA2-2 (pAM714), and FA2-2 (pAM771), 50 µg/ml gentamycin was used.

Bacterial lawns of *Enterococcus* were prepared as follows. On the tissue culture plate, 2 ml of BHI was inoculated with a single colony of the appropriate strain, grown at 37° C. for four to five hours, and 10 µl of the culture was plated on each plate. The plates were incubated at 37° C. overnight, and then brought to room temperature for two to five hours. Thirty *C. elegans*, at the L4 larval stage, were then placed on the lawn from a plate of OP50 *E. coli*. The plates were incubated at 25° C., and the number of worms found dead compared to the total number of plated worms was counted at approximately-twenty-four hour intervals. Each experimental condition in the following experiments was done in triplicate and repeated at least twice.

*C. elegans* Killing by Enterococcal Clinical Isolates

Six different strains of *Enterococcus* were obtained from the clinical microbiology laboratory at Massachusetts General Hospital (Boston, Mass.) and were designated E001, E002, E003, E006, E007, and E009. Standard clinical methods were used to identify strains E003 and E007 as *Enterococcus faecalis*, and strains E001, E002, E006, and E009 as *Enterococcus faecalis*. In general, *Enterococcus faecalis* causes approximately 80–90% of the Enterococcal infections in humans, and *Enterococcus faecium* causes approximately 10–20%.

Using the above-described killing assay protocol, the percentage of *C. elegans* dead as a function of time feeding on each of the *Enterococcus* strains was determined. As shown in FIG. 1, clinical isolates E002 and E006 were found to kill *C. elegans* most quickly, with a $LT_{50}$ of about 100 hours. E001 and E009 killed more slowly, with a $LT_{50}$ of about 150 hours. E003 and E007 did not cause any significant killing of *C. elegans*. These data suggest that *Enterococcus faecalis*, but not *Enterococcus faecium*, can kill *C. elegans*. Also, the differences between different strains of *Enterococcus faecalis* suggested that there might be identifiable genetic differences that caused the observed range in killing efficiency.

*C. elegans* Killing by *Enterococcus faecalis* strain V583

Strain V583 is a vancomycin-resistant clinical isolate of *E. faecalis*. It was first described in the late 1980's when vancomycin resistance emerged as a problem among Enterococcal infections. The genome of *E. faecalis* strain V583 is currently being sequenced by TIGR (The Institute for Genomic Research). The sequence is publicly available at tigr.org.

Figure 2:
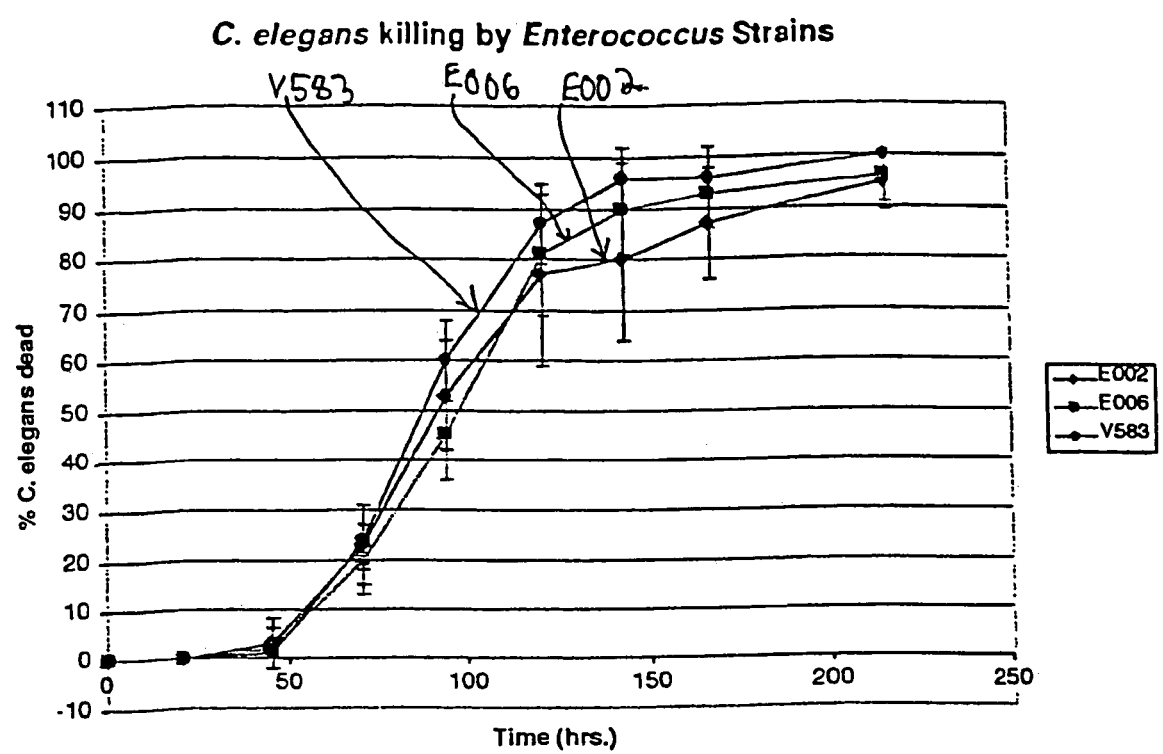
FIG. 2 shows *C. elegans* killing by *Enterococcus* strains E002, E006, and V583.

FIG. 2 shows the killing of *C. elegans* by strains E002, E006, and V583. In comparison to E002 and E006, *E. faecalis* strain V583 was found to kill just as effectively with a $LT_{50}$ of about 100 hours (FIG. 2).

*C. elegans* Killing by Isogenic *Enterococcus faecalis* Expressing Different Known Virulence Factors

*E. faecalis* contains a number of naturally occurring conjugative plasmids. Two such plasmids, called pAD1 (Jett et al., *Clinical Microbiol. Rev.* 7:462–478, 1994) and pCF10 (Leonard et al., *Proc. Natl. Acad. Sci.* 93:260–264, 1996) are well studied. A strain that does not have a particular plasmid (recipient) releases a peptide signal called a pheromone which, in turn, causes a strain that does contain the plasmid (donor) to produce aggregation substance (AS) on its surface. AS binds to *Enterococcus* binding substance (EBS) on the recipient, forming a mating aggregate which allows a copy of the plasmid to be conjugatively transferred from the donor to the recipient.

In addition to its role in plasmid conjugation, AS is also thought to play a role in pathogenesis by helping *E. faecalis* bind to host tissues. For example, strains producing AS bound more tightly to pig renal tubular cells than strains that did not produce AS. The genes for producing AS are located on both pAD1 and pCF10.

In addition to AS, cytolysin (Cy1) is another virulence factor that is capable of lysing both eukaryotic and other prokaryotic cells. The cytolysin operon is present on pAD1, but not pCF10. When both AS and Cy1 are expressed in rabbit endocarditis models, there is a significant increase in mortality.

Figure 3:
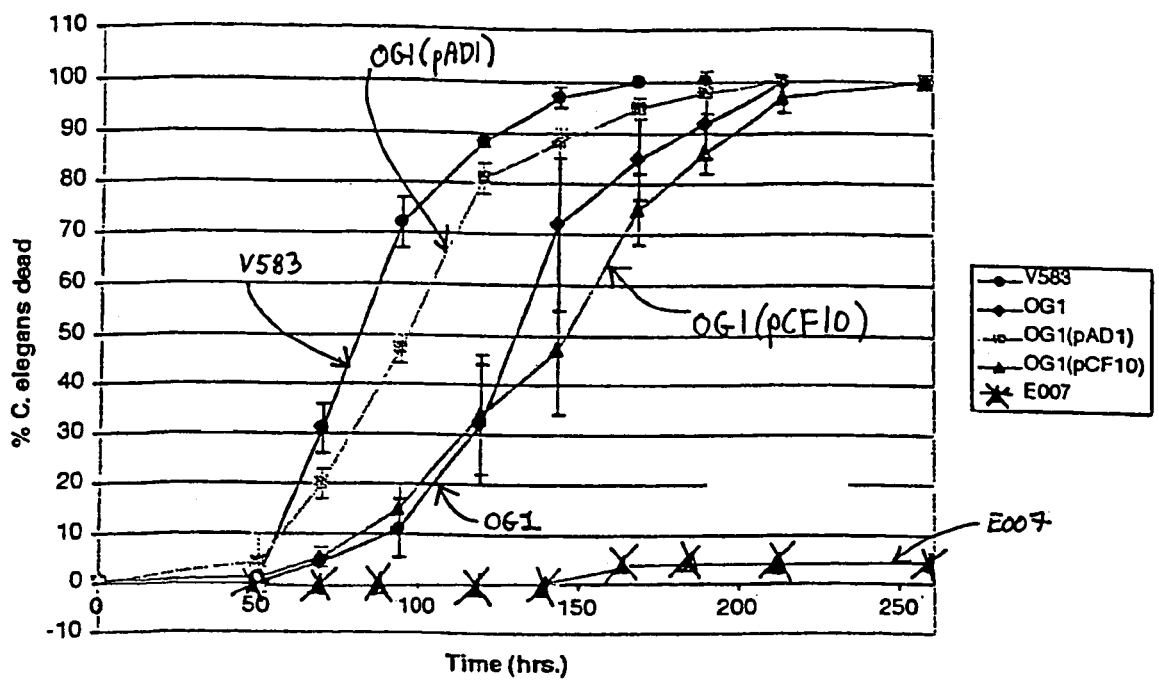
FIG. 3 shows *C. elegans* killing by *Enterococcus* strains V583, OG1, OG1 (pAD1), OG1 (pCF10), and E007.

To examine the role of AS and Cy1 in nematode infection, isogenic strains of *E. faecalis* that were plasmid-free (strain OG1), harbored a plasmid containing genes for both AS and Cy1 (strain OG1 containing pAD1), or harbored a plasmid containing only the gene for AS (strain OG1 containing pCF10) were examined in the above-described killing assay. *E. faecalis* strains V583 and E007 were used as controls. Results of these experiments are shown in FIG. 3.

Strain OG1 containing pAD1 was found to kill *C. elegans* significantly faster than strain OG1 or strain OG1 with pCF10. These results appear to indicate that cytolysin contributes to pathogenesis in *C. elegans*, but that aggregation substance has little or no effect.

*C. elegans* Killing by Isogenic *Enterococcus* Strains Containing Conjugative Plasmids: pAD1 vs. pAD1-cy1

Figure 4:
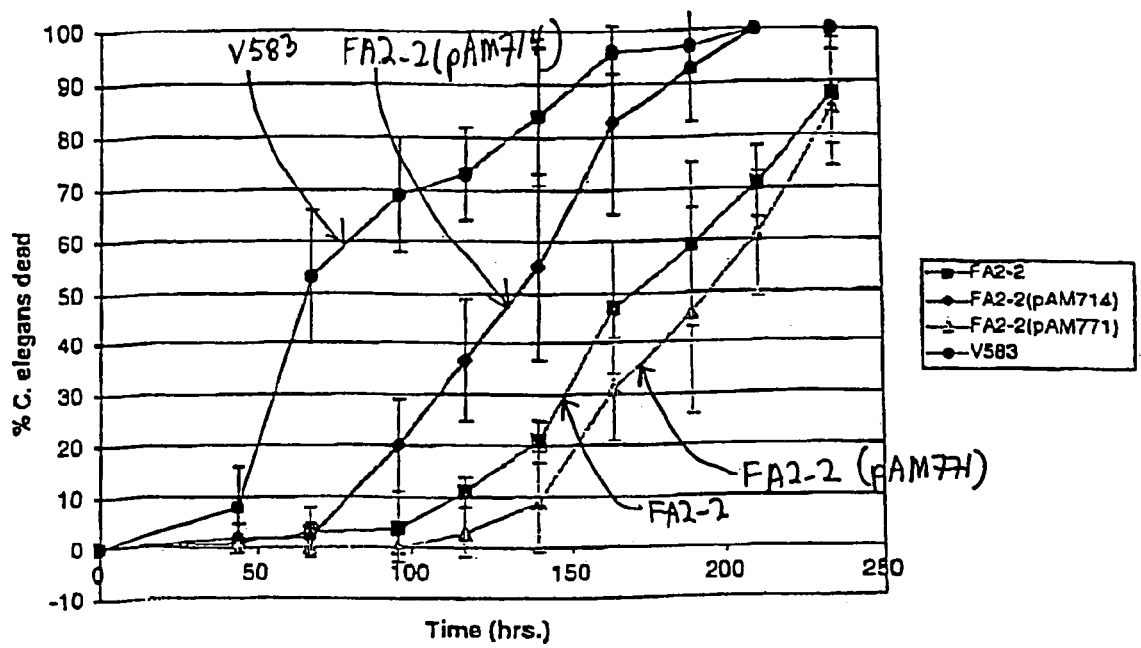
FIG. 4 shows *C. elegans* is killing by *Enterococcus* strains FA2-2, FA2-2 (pAM714), FA2-2(pAM771), and V583 containing plasmids pAD1 or pAD1-cy1.

To examine whether the virulence factor, cytolysin, is responsible for the faster killing of the *C. elegans*, the killing rates of isogenic *E. faecalis* strains containing different mutations in pAD1 (Ike et al., *J. Bacteriol.* 172:155–163, 1990) were examined. As shown in FIG. 4, the strain containing wild-type pAD1 (FA2-2 containing pAM714) was found to kill *C. elegans* faster than the plasmid-free strain or the strain containing pAD1 with a deletion in the promoter of the cytolysin operon (FA2-2 containing pAM771). These data indicated that the virulence factor, cytolysin, caused faster killing of *C. elegans*.

To summarize, we have developed a new pathogen/host model system employing *E. faecalis* and *C. elegans*. We have shown that different strains of *E. faecalis* kill *C. elegans* at different rates and that *E. faecium* does not cause significant mortality. The sequenced strain of *E. faecalis* kills very effectively making it an ideal choice for mutagenesis studies. The known mammalian virulence factor, cytolysin, was also found to increase the rate of killing, suggesting that *C. elegans* is a valid model host for studying mammalian pathogenesis by *E. faecalis*. This model system provides a potentially valuable tool for identifying novel *E. faecalis* virulence factors, and for developing a better understanding of this problematic pathogen.

Nematode Screening Systems for Identifying Enteroccocal Virulence Factors

Based on the results described above showing that *E. faecalis* virulence factor is involved in pathogenicity of *C. elegans*, we have developed a method for identifying virulence determinants important for pathogenicity of *Enterococcus*. The screen, in general, utilizes the above-described Enterococcal/nematode killing assays and exploits the ability to readily screen thousands of randomly generated Enterococcal mutants. In addition to using wild-type host worms in the killing assays, mutants that are constipated or defecation defective, such as aex-2 and unc-25, mutants that are grinding defective, such as phm-2 and eat-14, and specific ABC transporter mutants such as pgp-4 and mrp-1 may be utilized as well.

In general, a strain of *Enterococcus* is mutated according to standard methods known in the art and then subsequently evaluated for its ability to induce disease in the nematode host organism. A mutagenized pathogen found to have diminished pathogenicity or which is rendered non-pathogenic is useful in the method of the invention. Such mutant pathogens are then used for identifying host-dependent or host-independent virulence factors responsible for pathogenicity according to methods known in the art.

The following is a working example of a virulence factor nematode screening system that utilizes the human clinical isolate *E. faecalis* strain V583 found to be infectious in the *C. elegans* nematode feeding model. Strain V583 is a vancomycin-resistant variety of *E. faecalis*, which contains plasmids amounting to an estimated 100 kb. It contains a set of seven genes spanning about 7 kb which contribute to its resistance to the vancomycin antibiotic. The advantage of using a nematode as a host for studying this mammalian pathogen is the relative simplicity of identifying non-pathogenic *Enterococcus* mutants in the nematode.

In one preferred working example, in which survival is monitored., four to eight *C. elegans* worms (e.g., L4 larvae) are placed on a lawn of mutagenized *E. faecalis* strain V583, and survival is monitored after approximately one hundred to two hundred hours according to the methods described herein. An *Enterococcus* pathogen, such as *E. faecalis* strain V583, is mutated according to any standard procedure, e.g., standard in vivo or in vito insertional/transponson mutagenesis methods (see, e.g., Ike et al., *J. Bacteriol*. 172:155–63, 1990; Munkenbeck et al., *Plasmid* 24:57–67, 1990; Kleckner et al., *J. Mol. Biol*. 116:125, 1977). Other methods are also available, e.g., chemical mutagenesis, or directed mutagenesis of DNA. After approximately one hundred to one hundred fifty hours, very few or no live worms are found on a plate seeded with wild-type pathogenic *E. faecalis* strain V583, whereas on a plate with mutagenized *E. faecalis* strain V583, increased survival (e.g., as determined by an increased $LT_{50}$) of the worms is observed. Thus, the ability of worms to grow in the presence of mutated *E. faecalis* strain V583 is an indication that a gene responsible for pathogenicity has been inactivated. The positions of the inactivating mutations are then identified using standard methods, (e.g., by polymerase chain reaction and sequencing of insertion/transposon junctions or by mapping), leading to the cloning and identification of the mutated virulence factor(s) (e.g., by nucleotide sequencing).

In another working example, in which survival and reproduction is monitored, two *C. elegans* worms (e.g., L4 hermaphrodite larvae) are placed on a lawn of mutagenized *E. faecalis* strain V583, and worm progeny is monitored. Strain V583 is mutated according to standard methods. After approximately one hundred to one hundred fifty hours, very few or no live worms are found on a plate seeded with wild-type, pathogenic *E. faecalis* strain V583, whereas on a plate with the V583 mutant, hundreds or thousands of live progeny of the initial two hermaphrodite worms are present. Thus, the ability of worms to grow and reproduce in the presence of mutated V583 is taken as an indication that a gene responsible for pathogenicity has been inactivated. The mutated-virulence factor is then identified using standard methods.

Enterococcal Virulence Factors

Using the aforementioned screening assays, several novel Enterococcal virulence factors have been identified.

Nucleic acids encoding the Enterococcal virulence factors of the present invention were first identified using the following Enterococcal/nematode screening assay. To make a transposon library, OG1RF was transformed with pTV1-OK, which is a temperature sensitive vector containing the erythromycin-resistant transposon Tn917. A 50 ml culture from a single transformant was then grown in Brain-Heart Infusion (BHI) media at the nonselective temperature of 28° C. to mid-log phase. The culture was then plated on BHI agar plates containing erythromycin and transposants selected for at the selective temperature of 42° C. to select against the plasmid backbone and for chromosomal transposon insertions. The individual transposants were picked, grown in individual wells of a 384-well plate and then frozen at −80° C. to form the library. To screen how well these mutants killed *C. elegans* relative to wildtype OG1RF, transposon mutants were picked from the library, grown in liquid BHI media, and then plated as a lawn on 35 mm BHI-agar plates. Eight young adult nematodes were placed onto the *E. faecalis* lawn. The number of *C. elegans* alive at day two and day six were counted. Those mutants, causing significantly less death than average, were assayed again. In the second assay, each mutant was assayed in duplicate. The number of *C. elegans* alive was counted daily for six days. Mutants resulting in a significantly attenuated phenotype were assayed a third time in which each mutant was tested in triplicate using thirty worms. We sequenced the DNA flanking the transposon insertions of mutants that still displayed an attenuated phenotype. To do this we cultured mutants of interest in BHI media. The cultures were then boiled, solid material was removed by centrifugation, and the supernatant was used as the starting material for polymerase chain reaction (PCR) amplification of the genes of interest. For the PCR amplification, primers homologous to the transposon sequence and an arbitrary primer were utilized. The resulting material was next used in a second round of PCR with a second primer homologous to the transposon sequence and a primer homologous to the non-randomized sequence of the arbitrary primer. The resulting product was then sequenced and the DNA sequence flanking the transposon determined. The characterization of the identified virulence factors now follows.

Photolyase

A nucleic acid sequence (SEQ ID NO:2) (FIG. 5A) encoding a photolyase of *Enterococcus faecalis* was identified from a mutant found to have decreased virulence in the above-described screening assay using a computer search for amino acid sequence alignments. First, the sequence information obtained by sequencing the region flanking the transposon insertion was used to query the *E. faecalis* unfinished genome sequence (available publicly at www.tigr.org). We found that the transposon had inserted within a large ORF. The ORF of interest was then blasted against the NCBI database of all publicly available sequences using the blastx program, which translates the queried sequence and then searches against the protein database. By this method we identified an ORF that was related to photolyase of *Bacillus firmus*. The *E. faecalis* photolyase mutant was also tested using an in vivo mouse peritonitis assay and found to display an attenuated virulence phenotype.

In one embodiment, the invention encompasses a polypeptide that includes the photolyase amino acid sequence (SEQ ID NO:3) shown in FIG. 5B. Enterococcal photolyase is 476 amino acids and shares significant amino acid identity to photolyases of other bacteria. In particular, *E. faecalis* photolyase and *Bacillus firmus* photolyase share 43% identity and 61% similarity. A fragment of SEQ ID NO:1 from about nucleotide 568 to nucleotide 1998 is useful as a hybridization probe. Photolyases are generally thought to be involved in the repair of light-damaged DNA.

The invention also encompasses Enterococcal photolyase variants. One preferred photolyase variant is one that has at least about 60%, more preferably at least 75%, and most preferably at least 90% amino acid sequence identity to the photolyase amino acid sequence.

ScrR

A nucleic acid sequence (SEQ ID NO:5) (FIG. 6A) encoding ScrR of Enterococcus faecalis was identified from a mutant found to have decreased virulence in the above-described screening assay using a computer search for amino acid sequence alignments. The sequence analysis was done as described for photolyase (above). The ORF the transposon inserted into was found to have high similarity to scrR (the gene for the sucrose operon repressor) of various different bacterial species.

In one embodiment, the invention encompasses a polypeptide comprising the ScrR amino acid sequence (SEQ ID NO:6) shown in FIG. 6B. Enterococcal ScrR is 325 amino acids in length and has very high identity to other ScrR sequences from other bacteria. For example, *E. faecalis* ScrR shares 52% similarity with Streptococcus mutants ScrR. A fragment of SEQ ID NO:4 from about nucleotide 662 to nucleotide 1629 is useful as a hybridization probe. ScrR functions to repress expression of the enzymes that degrade sucrose when no sucrose is available.

The invention also encompasses Enterococcal ScrR variants. One preferred ScrR variant is one that has at least about 60%, more preferably at least 75%, and most preferably at least 90% amino acid sequence identity to the ScrR amino acid sequence.

OppA

A nucleic acid sequence (SEQ ID NO:8) (FIG. 7A) encoding an OppA-like protein of *Enterococcus faecalis* was identified from a mutant found to have decreased virulence in the above-described screening assay using a computer search for amino acid sequence alignments. The sequence analysis was done as described for photolyase (above). The sequence was found to have high similarity to OppA of *Listeria monocytogenes* and other bacterial peptide binding proteins.

In one embodiment, the invention encompasses a polypeptide that includes the OppA amino acid sequence (SEQ ID NO:9) shown in FIG. 7B. Enterococcal OppA is 550 amino acids in length. The *E. faecalis* OppA protein shares 42% identity and 63% similarity to OppA of *Listeria monocytogenes*. A fragment of SEQ ID NO:7 from about nucleotide 421 to nucleotide 696 is useful as a hybridization probe. OppA of *Listeria monocytogenes* mediates the transport of oligopeptides and mutants in this gene are inhibited in intracellular survival and growth when infecting mice.

The invention also encompasses Enterococcal OppA variants. One preferred. OppA variant is one that has at least about 60%, more preferably at least 75%, and most preferably at least 90% amino acid sequence identity to the OppA amino acid sequence.

TcaA

A nucleic acid sequence (SEQ ID NO:11) (FIG. 8A) encoding a TcaA-like protein of *Enterococcus faecalis* was identified from a mutant found to have decreased virulence in the above-described screening assay using a computer search for amino acid sequence alignments. The sequence analysis was done as described for photolyase (above). The sequence was not strongly homologous to any proteins in the database. It had weak similarity to the TcaA protein of *Staphylococcus aureus* and several other known and hypothetical proteins that share the feature of being membrane-associated. In one embodiment, the invention encompasses a polypeptide that includes the TcaA-like amino acid sequence (SEQ ID NO:12) shown in FIG. 8B. Enterococcal TcaA-like protein is 443 amino acids in length and shares 20% identity and 36% similarity to *S. aureus* TcaA. A fragment of SEQ ID NO:10 from about nucleotide 1201 to nucleotide 2532 is useful as a hybridization probe. Mutations in *S. aureus* TcaA are associated with increased resistance to the antibiotic teicoplanin.

The invention also encompasses Enterococcal TcaA variants. One preferred TcaA variant is one that has at least about 60%, more preferably at least 75%, and most preferably at least 90% amino acid sequence identity to the TcaA amino acid sequence.

ScrB

A nucleic acid sequence (SEQ ID NO:14) (FIG. 9A) encoding an ScrB of *Enterococcus faecalis* was identified from a mutant found to have decreased virulence in the above-described screening assay using a computer search for amino acid sequence alignments. The sequence analysis was done as described for photolyase (above). The protein sequence was strongly homologous to bacterial sucrose-6-phosphate hydrolases encoded by ScrB genes in other species. The *E. faecalis* ScrB mutant was also tested using an in vivo mouse peritonitis assay and found to display an attenuated virulence phenotype.

In one embodiment, the invention encompasses a polypeptide that includes the ScrB amino acid sequence (SEQ ID NO:15) shown in FIG. 9B. Enterococcal ScrB is 490 amino acids in length. It is highly homologous to other bacterial sucrases; for example it shares 48% identity and 64% similarity with ScrB of *Streptococcus sobrinus*. A fragment of SEQ ID NO:13 from about nucleotide 1018 to nucleotide 2487 is useful as a hybridization probe. Sucrose-6-phosphate hydrolases breakdown sucrose.

The invention also encompasses Enterococcal ScrB variants. One preferred ScrB variant is one that has at least about 60%, more preferably at least 75%, and most preferably at least 90% amino acid sequence identity to the ScrB amino acid sequence.

RecQ

A nucleic acid sequence (SEQ ID NO:17) (FIG. 10A) encoding a RecQ of *Enterococcus faecalis* was identified from a mutant found to have decreased virulence in the above-described screening assay using a computer search for amino acid sequence alignments. The sequence analysis was done as described for photolyase (above). The protein sequence was most homologous to the ATP-dependent helicase RecQ of various bacterial species. The *E. faecalis* RecQ mutant was also tested using an in vivo mouse peritonitis assay and found to display an attenuated virulence phenotype.

In one embodiment, the invention encompasses a polypeptide that includes the RecQ amino acid sequence (SEQ ID NO:18) shown in FIG. 10B. Enterococcal RecQ is 448 amino acids in length. It was most homologous to RecQ of *Bacillus subtilis* with which it shares 37% identity and 56% similarity. RecQ is thought to unwind DNA during DNA repair processes. It has, for example, been shown to be involved in homologous recombination during pilin antigenic variation of the pathogen *Neisseria gonorrhoeae*. A fragment of SEQ ID NO:16 from about nucleotide 202 to nucleotide 1545 is useful as a hybridization probe.

The invention also encompasses Enterococcal RecQ variants. One preferred RecQ variant is one that has at least about 60%, more preferably at least 75%, and most preferably at least 90% amino acid sequence identity to the RecQ amino acid sequence.

LysR

A nucleic acid sequence (SEQ ID NO:20) (FIG. 11A) encoding a positive regulator of the LysR family of *Enterococcus faecalis* was identified from a mutant found to have decreased virulence in the above-described screening assay using a computer search for amino acid sequence alignments. The sequence analysis was done as described for photolyase (above). The sequence was homologous to a family of positive regulators from various bacterial species which include CynR and LysR among others.

In one embodiment, the invention encompasses a polypeptide that includes the LysR-like amino acid sequence (SEQ ID NO:21) shown in FIG. 11B. The Enterococcal LysR family member is 318 amino acids in length. The protein is most homologous to the CynR (a LysR-like regulator) from *Escherichia coli* with 27% identity and 48% similarity. These regulators are thought to positively regulate transcription of the operons they control under the appropriate conditions. A fragment of SEQ ID NO:19 from about nucleotide 847 to nucleotide 1800 is useful as a hybridization probe.

The invention also encompasses Enterococcal variants of this protein. One preferred variant is one that has at least about 60%, more preferably at least 75%, and most preferably at least 90% amino acid sequence identity to the LysR-like amino acid sequence.

Dipeptidase

A nucleic acid sequence (SEQ ID NO:23) (FIG. 12A) encoding a dipeptidase of *Enterococcus faecalis* was identified from a mutant found to have decreased virulence in the above-described screening assay using a computer search for amino acid sequence alignments. The sequence analysis was done as described for photolyase (above). Specifically the dipeptidase appeared most closely related to bacterial carnosinases, which cleave aminoacyl-histidine dipeptides.

In one embodiment, the invention encompasses a polypeptide that includes the dipeptidase amino acid sequence (SEQ ID NO:24) shown in FIG. 12B. This Enterococcal dipeptidase is 432 amino acids in length. The dipeptidase is most homologous to *Lactobacillus helveticus* carnosinase with 32% identity and 48% similarity. A fragment of SEQ ID NO:22 from about nucleotide 682 to nucleotide 1977 is useful as a hybridization probe.

The invention also encompasses Enterococcal dipeptidase variants. One preferred dipeptidase variant is one that has at least about 60%, more preferably at least 75%, and most preferably at least 90% amino acid sequence identity to the dipeptidase amino acid sequence.

SacU

A nucleic acid sequence (SEQ ID NO:26) (FIG. 13A) encoding a SacU of *Enterococcus faecalis* was identified from a mutant found to have decreased virulence in the above-described screening assay using a computer search for amino acid sequence alignments. The sequence analysis was done as described for photolyase (above). The protein was most homologous to SacU, a two-component regulator of saccharolytic enzyme induction.

In one embodiment the invention encompasses a polypeptide that includes the SacU amino acid sequence (SEQ ID NO:27) shown in, FIG. 13B. Enterococcal SacU is 282 amino acids in length. The protein is most homologous to *Bacillus subtilis* SacU with 37% identity and 57% similarity. A fragment of SEQ ID NO:25 from about nucleotide 1345 to nucleotide 2190 is useful as a hybridization probe.

The invention also encompasses Enterococcal SacU variants. One preferred SacU variant is one that has at least about 60%, more preferably at least 75%, and most preferably at least 90% amino acid sequence identity to the SacU amino acid sequence.

Pai1

A nucleic acid sequence (SEQ ID NO:29) (FIG. 14A) encoding Pai1 of *Enterococcus faecalis* was identified from a mutant found to have decreased virulence in the above-described screening assay using a computer search for amino acid sequence alignments. The sequence analysis was done as described for photolyase (above). The protein was most homologous to Pai1, of various bacterial species, which is a negative transcriptional regulator. The *E. faecalis* Pai1 mutant was also tested using an in vivo mouse peritonitis assay and found to display an attenuated virulence phenotype.

In one embodiment, the invention encompasses a polypeptide that includes the Pai1 amino acid sequence (SEQ ID NO:30) shown in FIG. 14B. Enterococcal Pai1 is 176 amino acids in length. The protein was most homologous to *Bacillus subtilis* Pai1 with 40% identity and 61% similarity. Pai1 affects sporulation and degradative-enzyme production in *Bacillus subtilis*. A fragment of SEQ ID NO:28 from about nucleotide 1225 to nucleotide 1749 is useful as a hybridization probe.

The invention also encompasses Enterococcal Pai1 variants. One preferred Pai1 variant is one that has at least about 60%, more preferably at least 75%, and most preferably at least 90% amino acid sequence identity to the Pai1 amino acid sequence.

Aromatic Amino Acid Biosynthetic Gene Cluster

A nucleic acid sequence (SEQ ID NO:31) encoding the aromatic amino acid biosynthetic gene cluster of *Enterococcus faecalis* (shown in FIG. 15A) was identified from a mutant found to have decreased virulence in the above-described screening assay using a computer search for amino acid sequence alignments. First we blasted the sequence information obtained by sequencing the region flanking the transposon insertion against the *E. faecalis* unfinished genome sequence (available publicly at www.tigr.org). This search provided us with an exact match to our queried sequence and also gave us the DNA sequence upstream and downstream to this sequence. We then used this sequence to identify open reading frames (ORF's) existing within the sequence. We found that the transposon had inserted within the promoter region of a large operon containing eight ORFs. The operon of interest was then blasted against the NCBI database of all publicly available sequences using the blastx program, which translates the queried sequence and then searches against the protein database. This search revealed that the *E. faecalis* aromatic biosynthesis gene cluster functions in virulence.

The first ORF nucleic acid sequence (SEQ ID NO:32) is aroE, shown in FIG. 15B (from nucleotide 162–1028 of SEQ ID NO:11), which encodes the predicted amino acid sequence (SEQ ID NO:40) (shown in FIG. 15C) of shikimate 5-dehydrogenase, a 288 amino acid polypeptide that catalyzes the fourth step in the biosynthesis of chorismate within the aromatic amino acid biosynthetic pathway.

The second ORF nucleic acid sequence (SEQ ID NO:33) is aroF, shown in FIG. 15D (from nucleotide 1065–2090 of SEQ ID NO:11), which encodes the predicted amino acid sequence (SEQ ID NO:41) (FIG. 15E) of phospho-2-dehydro-3-deoxyheptonate adolase, a 341 amino acid polypeptide that catalyzes the first step in the biosynthesis of chorismate within the aromatic amino acid biosynthetic pathway.

The third ORF nucleic acid sequence (SEQ ID NO:34) is aroB, shown in FIG. 15F (from nucleotide 2113–3189 of SEQ ID NO:11), which encodes the predicted amino acid sequence (SEQ ID NO:42) (FIG. 15G) of dehydroquinate synthase, a 358 amino acid polypeptide that catalyzes the second step in the biosynthesis of chorismate within the aromatic amino acid biosynthetic pathway.

The fourth ORF nucleic acid sequence (SEQ ID NO:35) is aroC, shown in FIG. 15H (from nucleotide 3191–4357 of SEQ ID NO:11), which encodes the predicted amino acid sequence (SEQ ID NO:43) (FIG. 15I) of chorismate synthase, a 388 amino acid polypeptide that catalyzes the seventh step in the biosynthesis of chorismate within the aromatic amino acid biosynthetic pathway.

The fifth ORF nucleic acid sequence (SEQ ID NO:36) is tyrA, shown in FIG. 15J from nucleotide 4391–5485, which encodes the predicted amino acid sequence (SEQ ID NO:44) (FIG. 15K) of chorismate mutase, a 364 amino acid polypeptide that is involved in tyrosine biosynthesis.

The sixth ORF nucleic acid sequence (SEQ ID NO:37), shown in FIG. 15L, is aroA (from nucleotide 5492–6778 of SEQ ID NO:11), which encodes the predicted amino acid sequence (SEQ ID NO:45) (FIG. 15M) of phosphoshikimate 1-carboxyvinyltransferase, a 428 amino acid polypeptide that catalyzes the sixth step in the biosynthesis of chorismate within the aromatic amino acid biosynthetic pathway.

The seventh ORF nucleic acid sequence (SEQ ID NO:38), shown in FIG. 15N (from nucleotide 6795–7304 of SEQ ID NO:11) encodes the predicted amino acid sequence (SEQ ID NO:46) shown in FIG. 15O of shikimate kinase, a 169 amino acid polypeptide. This protein was identified as being related to the *Lactococcus lactis* shikimate kinase, having 40% identity and 63% similarity. Shikimate kinase, like the other proteins encoded by this operon, is involved in aminoacid biosynthesis.

The eighth ORF nucleic acid sequence (SEQ ID NO:39) shown in FIG. 15P (from nucleotide 7312–8160 of SEQ ID NO:11) is pheA which encodes the predicted amino acid sequence (SEQ ID NO:47) of prephenate dehydratase, a 282 amino acid polypeptide involved in L-phenylalanine biosynthesis.

Isolation of Additional Virulence Genes

Based on the nucleotide and amino acid sequences described herein, the isolation of additional coding sequences of virulence factors from virtually any Enterococcal pathogen is made possible using standard strategies and techniques that are well known in the art. In addition, any pathogenic cell can serve as the nucleic acid source for the molecular cloning of any of the virulence genes described herein, and these sequences are identified as ones encoding a protein exhibiting pathogenicity-associated structures, properties, or activities. Examples of pathogenic bacteria include, without limitation, *Aerobacter, Aeromonas, Acinetobacter, Agrobacterium, Bacillus, Bacteroides, Bartonella, Bortella, Brucella, Calymmatobacterium, Campylobacter, Citrobacter, Clostridium, Cornyebacterium, Enterobacter, Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio,* and *Yersinia.*

In one particular example of such an isolation technique, any one of the nucleotide sequences described herein may be used, together with conventional screening methods of nucleic acid hybridization screening. Such hybridization techniques and screening procedures are well known to those skilled in the art and are described, for example, in Benton and Davis (*Science* 196:180, 1977); Grunstein and Hogness (*Proc. Natl. Acad. Sci.*, USA 72:3961, 1975); Ausubel et al. (*Current Protocols in Molecular Biology*, Wiley Interscience, New York, 1997); Berger and Kimmel (supra); and Sambrook et al., *Molecular Cloning: A Laboratory Manual*, Cold Spring Harbor Laboratory Press, New York. In one particular example, all or part of the nucleic acid sequence of photolyase (FIG. 5A), ScrR (FIG. 6A), OppA (FIG. 7A), TcaA (FIG. 8A), ScrB (FIG. 9A), RecQ (FIG. 10A), LysR family of positive regulators (FIG. 11A), XAA-His dipeptidase (carnosinase)(FIG. 12A), SacU (FIG. 13A), Pai1 (FIG. 14A), and ORFs 1–8 of the shikimate amino acid biosynthetic gene cluster (FIG. 15A), may be used as a probe to screen a recombinant plant DNA library for genes having sequence identity to these genes. Hybridizing sequences are detected by plaque or colony hybridization according to standard methods.

Alternatively, using all or a portion of the amino acid sequence, one may readily design specific oligonucleotide probes, including degenerate oligonucleotide probes (i.e., a mixture of all possible coding sequences for a given amino acid sequence). These oligonucleotides may be based upon the sequence of either DNA strand and any appropriate portion of the sequence of the described protein(s). General methods for designing and preparing such probes are provided, for example, in Ausubel et al. (supra), and Berger and Kimmel, *Guide to Molecular Cloning Techniques*, 1987, Academic Press, New York. These oligonucleotides are useful for gene isolation, either through their use as probes capable of hybridizing to complementary sequences or as primers for various amplification techniques, for example, polymerase chain reaction (PCR) cloning strategies. If desired, a combination of different, detectably-labelled oligonucleotide probes may be used for the screening of a recombinant DNA library. Such libraries are prepared according to methods well known in the art, for example, as described in Ausubel et al., (supra), or they may be obtained from commercial sources.

As discussed above, sequence specific oligonucleotides may also be used as primers in amplification cloning strategies, for example, using PCR. PCR methods are well known in the art and are described, for example, in PCR Technology, Erlich, ed., Stockton Press, London, 1989; *PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, nucleotide sequences may be isolated using the PCR "RACE" technique, or Rapid Amplification of cDNA Ends (see, e.g., Innis et al. (supra)). By this method, oligonucleotide primers based on a desired sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci.* USA 85:8998, 1988.

Partial virulence sequences, e.g., sequence tags, are also useful as hybridization probes for identifying full-length sequences, as well as for screening databases for identifying previously unidentified related virulence genes. Confirmation of a sequence's relatedness to a pathogenicity polypeptide may be accomplished by a variety of conventional methods including, but not limited to, functional complementation assays and sequence comparison of the gene and its expressed product. In addition, the activity of the gene product may be evaluated according to any of the techniques described herein, for example, the functional or immunological properties of its encoded product.

Once an appropriate sequence is identified, it is cloned according to standard methods and may be used, for example, for screening compounds that reduce the virulence of a pathogen.

Polypeptide Expression

In general, polypeptides of the invention may be produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains which express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once the recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short peptide fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful peptide fragments or analogs (described herein).

Antibodies

To generate antibodies, a coding sequence for a polypeptide of the invention may be expressed as a C-terminal fusion with glutathione S-transferase (GST) (Smith et al., Gene 67:31–40, 1988). The fusion protein is purified on glutathione-Sepharose beads, eluted with glutathione, cleaved with thrombin (at the engineered cleavage site), and purified to the degree necessary for immunization of rabbits. Primary immunizations are carried out with Freund's complete adjuvant and subsequent immunizations with Freund's incomplete adjuvant. Antibody titres are monitored by Western blot and immunoprecipitation analyses using the thrombin-cleaved protein fragment of the GST fusion protein. Immune sera are affinity purified using CNBr-Sepharose-coupled protein. Antiserum specificity is determined using a panel of unrelated GST proteins.

As an alternate or adjunct immunogen to GST fusion proteins, peptides corresponding to relatively unique immunogenic regions of a polypeptide of the invention may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using the polypeptide expressed as a GST fusion protein.

Alternatively, monoclonal antibodies which specifically bind any one of the polypeptides of the invention are prepared according to standard hybridoma technology (see, e.g., Kohler et al., *Nature* 256:495, 1975; Kohler et al., *Eur. J. Immumunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra). Once produced, monoclonal antibodies are also tested for specific recognition by Western blot or immunoprecipitation analysis (by the methods described in Ausubel et al., supra). Antibodies which specifically recognize the polypeptide of the invention are considered to be useful in the invention; such antibodies may be used, e.g., in an immunoassay. Alternatively monoclonal antibodies may be prepared using the polypeptide of the invention described above and a phage display library (Vaughan et al., *Nature Biotech.* 14:309–314, 1996).

Preferably, antibodies of the invention are produced using fragments of the polypeptide of the invention which lie outside generally conserved regions and appear likely to be antigenic, by criteria such as high frequency of charged residues. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

Antibodies against any of the polypeptides described herein may be employed to treat bacterial infections.

Mouse Pathogenicity Screening Assays

To further evaluate the virulence of Enterococcal mutants identified in the above-described nematode screening assays, mouse pathogenicity/mortality studies are performed as follows. Female ICR Mice (Taconic, Germantown, N.Y. or Charles River, Wilmington, Mass.) weighing 20 to 30 grams and housed 5 per cage, are used for evaluating the virulence of Enterococcal mutants. Mice, in groups of 6–10, are injected intraperitoneally with mutant bacteria in sterile rat fecal extracts (SRFE) as described below. The survival of mice receiving mutant bacteria is then compared to the survival of animals receiving an equal inoculum of wild-type bacteria (e.g., without a mutation). All animals have access to chow and water ad libitum throughout an experiment.

An exemplary bacterial inoculum is prepared as follows. *Enterococcus faecalis* OG1RF or Enterococcal mutants are grown overnight in BHI broth at 37° C. with gentle shaking. The cells are harvested by centrifugation, washed once with 0.9% saline, and then are resuspended in saline to an optical density of 2.2 to 2.8 at 600 nm. CFUs (colony-forming units) of cells suspensions are determined by plating serial dilutions onto BHI agar plates. Serial dilutions are prepared in saline and mixed with SRFE to the desired inoculum. For the preparation of SRFE, rat feces are dried, crushed, mixed with a volume of sterile distilled water three times that of the feces, and autoclaved. The resultant slurry is centrifuged, and the fecal extracts are removed aseptically. The extracts are then autoclaved and mixed with an enterococcal culture. Each inoculum is then diluted to a final 35% SRFE to yield the desired final inoculum.

Using a 25-gauge needle, mice are injected intraperitoneally with a 1 ml inoculum containing approximately $5 \times 10^8$ to $1 \times 10^9$ colony forming units of *E. faecalis* or an Enterococcal mutant. After injection the animals are returned to their cages and monitored every eight hours for seven days. Surviving animals are then sacrificed and examined by autopsy. Control mice injected intraperitoneally with 1 ml of sterile SRFE are also examined.

Upon autopsy, bacteria are recovered from the kidneys or spleens under aseptic conditions. Peritoneal fluid and abdominal abscesses are also sampled for evaluation. Serial dilutions of the peritoneal fluid are prepared and 0.1 ml of each dilution is spread on agar plates for colony counts. Plates are then incubated under aerobic conditions for up to four days. BHI plates containing rifampin (for culturing Enterococcal wild-type *Enterococcus* OG1RF) or rifampin and erythromycin (for culturing Enterococcal mutants) are used for selection. Results are expressed, for example, by Kaplan-Meier curves and log rank test using STATA software (StataCorp. 1999. Stata Statistical Software: Release 6.0. College Station, Tex.: Stata Corporation).

Mutants showing a statistically significant difference or a statistical trend ($P \leq 0.20$) compared to the wild-type are, if desired, evaluated a second time. Mutants identified as having reduced virulence are taken as being useful in the invention.

Compound Screening Assays

As discussed above, our experimental results demonstrated that Enterococcal virulence factors are involved in pathogenicity of the nematode, *C. elegans*. Based on this discovery we have also developed a screening procedure for identifying therapeutic compounds (e.g., anti-pathogenicity pharmaceuticals) which can be used to inhibit the ability of the Enterococcal pathogen to cause infection. In general, the method involves screening any number of compounds for therapeutically-active agents by employing the Enterococcal/nematode killing system described herein. Based on our demonstration that these pathogens infect and kill *C. elegans*, it will be readily understood that a compound which interferes with the pathogenicity of *Enterococcus* in a nematode also provides an effective therapeutic agent in a mammal (e.g., a human patient). Whereas most antibiotics currently in medical use are either bactericidal or bacteriostatic, thus favoring resistant strains or mutants, the compounds identified in the screening procedures described herein do not kill the bacteria but instead render them non-pathogenic. Moreover, since the screening procedures of the invention are performed in vivo, it is also unlikely that the identified compounds will be highly toxic to the host organism.

Accordingly, the methods of the invention simplify the evaluation, identification, and development of active agents such as drugs for the treatment of pathogenic diseases caused by Enterococcal microbes.

In addition, we have identified a number of enterococcal virulence factors that are involved in pathogenicity and that may therefore be used to screen for compounds that reduce the virulence of that organism, as well as other microbial pathogens. For example, the invention provides methods of screening compounds to identify those which enhance (agonist) or block (antagonist) the action of a polypeptide or the gene expression of a nucleic acid sequence of the invention. The method of screening may involve high-throughput techniques.

Any number of methods are available for carrying out such screening assays. According to one approach, candidate compounds are added at varying concentrations to the culture medium of pathogenic cells expressing one of the nucleic acid sequences of the invention. Gene expression is then measured, for example, by standard Northern blot analysis (Ausubel et al., supra), using any appropriate fragment prepared from the nucleic acid molecule as a hybridization probe. The level of gene expression in the presence of the candidate compound is compared to the level measured in a control culture medium lacking the candidate molecule. A compound which promotes a decrease in the expression of the pathogenicity factor is considered useful in the invention; such a molecule may be used, for example, as a therapeutic to combat the pathogenicity of an infectious organism.

If desired, the effect of candidate compounds may, in the alternative, be measured at the level of polypeptide production using the same general approach and standard immunological techniques such as Western blotting or immunoprecipitation with an antibody specific for a pathogenicity factor. For example, immunoassays may be used to detect or monitor the expression of at least one of the polypeptides of the invention in a pathogenic organism. Polyclonal or monoclonal antibodies (produced as described above) which are capable of binding to such a polypeptide may be used in any standard immunoassay format (e.g., ELISA, Western blot, or RIA assay) to measure the level of the pathogenicity polypeptide. A compound which promotes a decrease in the expression of the pathogenicity polypeptide is considered particularly useful. Again, such a molecule may be used, for example, as a therapeutic to combat the pathogenicity of an infectious organism.

Alternatively, or in addition, candidate compounds may be screened for those which specifically bind to and inhibit a pathogenicity polypeptide of the invention. The efficacy of such a candidate compound is dependent upon its ability to interact with the pathogenicity polypeptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate pathogenicity may be assayed by any standard assays (e.g., those described herein).

In one particular example, a candidate compound that binds to a pathogenicity polypeptide may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the pathogenicity polypeptide is identified on the basis of its ability to bind to the pathogenicity polypeptide and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography). In addition, these candidate compounds may be tested for their ability to render a pathogen less virulent (e.g., as described herein). Compounds isolated by this approach may also be used, for example, as therapeutics to treat or prevent the onset of a pathogenic infection, disease, or both. Compounds which are identified as binding to pathogenicity polypeptides with an affinity constant less than or equal to 10 mM are considered particularly useful in the invention.

Potential antagonists include organic molecules, peptides, peptide mimetics, polypeptides, and antibodies that bind to a nucleic acid sequence or polypeptide of the invention and thereby inhibit or extinguish its activity. Potential antagonists also include small molecules that bind to and occupy the binding site of the polypeptide thereby preventing binding to cellular binding molecules, such that normal biological activity is prevented. Other potential antagonists include antisense molecules.

Each of the DNA sequences provided herein may also be used in the discovery and development of antipathogenic compounds (e.g., antibiotics). The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, or inhibitor of the invention to interfere with the initial physical interaction between a pathogen and mammalian host responsible for infection. In particular the molecules of the invention may be used: in the prevention of adhesion and colonization of bacteria to mammalian extracellular matrix proteins; to extracellular matrix proteins in wounds; to block mammalian cell invasion; or to block the normal progression of pathogenesis.

The antagonists and agonists of the invention may be employed, for instance, to inhibit and treat a variety of bacterial infections.

Optionally, compounds identified in any of the above-described assays may be confirmed as useful in conferring protection against the development of a pathogenic infection in any standard animal model (e.g., the mouse peritonitis assay described herein) and, if successful, may be used as anti-pathogen therapeutics (e.g, antibiotics).

In general, the chemical screening methods of the invention provide a straightforward means for selecting natural product extracts or compounds of interest from a large population which are further evaluated and condensed to a few active and selective materials. Constituents of this pool are then purified and evaluated in the methods of the invention to determine their anti-pathogenic activity.

Test Extracts and Compounds

In general, novel anti-pathogenic drugs are identified from large libraries of both natural product or synthetic (or semi-synthetic) extracts or chemical libraries according to methods known in the art. The screening method of the present invention is appropriate and useful for testing compounds from a variety of sources for possible anti-pathogenic activity. The initial screens may be performed using a diverse library of compounds, but the method is suitable for a variety of other compounds and compound libraries. Such compound libraries can be combinatorial libraries, natural product libraries, or other small molecule libraries. In addition, compounds from commercial sources can be tested, as well as commercially available analogs of identified inhibitors.

For example, those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to have anti-pathogenic activity, further fractionation of the positive lead extract is necessary to isolate chemical constituents responsible for the observed effect. Thus, the goal of the extraction, fractionation, and purification process is the careful characterization and identification of a chemical entity within the crude extract having anti-pathogenic activity. Methods of fractionation and purification of such heterogenous extracts are known in the art. If desired, compounds shown to be useful agents for the treatment of pathogenicity are chemically modified according to methods known in the art.

Since many of the compounds in libraries such as combinatorial and natural products libraries, as well as in natural products preparations, are not characterized, the screening methods of this invention provide novel compounds which are active as inhibitors or inducers in the particular screens, in addition to identifying known compounds which are active in the screens. Therefore, this invention includes such novel compounds, as well as the use of both novel and known compounds in pharmaceutical compositions and methods of treating.

Exemplary High Throughput Screening Systems

To evaluate the efficacy of a molecule or compound in promoting host resistance to, or inhibiting pathogenicity of *Enterococcus*, a number of high throughput assays may be utilized.

For example, to enable mass screening of large quantities of natural products, extracts, or compounds in an efficient and systematic fashion, *Caenorhabditis elegans*, (e.g., L4 hermaphrodite larvae or a mutant worm such as aex-2, unc-25, phm-2, eat-14, pgp-4, or mrp-1), are cultured in wells of a microtiter plate, facilitating the semiautomation of manipulations and full automation of data collection. As is discussed above, *E. faecalis* infects and kills *C. elegans*. If *E. faecalis* has diminished pathogenicity, then L4 worms live, develop into adult hermaphrodites, and produce thousands of live progeny. Accordingly, if *C. elegans* is incubated with the pathogen, the worms will die, unless a compound is present to reduce *E. faecalis* pathogenicity. The presence of such live progeny is easily detected using a variety of methods, including visual screening with standard microscopes.

To evaluate the ability of a test compound or extract to promote a host's resistance to a pathogen or to repress pathogenicity of a pathogen, a test compound or extract is inoculated at an appropriate dosage into an appropriate agar medium (e.g., BHI or M17 (Difco)) seeded with an appropriate amount of an overnight culture of a pathogen, e.g., *E. faecalis*. If desired, various concentrations of the test compound or extract can be inoculated to assess dosage effect on both the host and the pathogen. Control wells are inoculated with non-pathogenic bacteria (negative control) or a pathogen in the absence of a test compound or extract (positive control). Plates are then incubated twenty-four hours at 37° C. to facilitate the growth of the pathogen. Microtiter dishes are subsequently cooled to 25° C., and two *C. elegans* L4 hermaphrodite larva are added to the plate and incubated at 25° C., the upper limit for normal physiological integrity of *C. elegans*. At an appropriate time interval, e.g., one hundred to two hundred hours, wells are examined for surviving worms, the presence of progeny, or both, e.g., by visual screening or monitoring motion of worms using a motion detector.

In another working example, *Enterococcus*-mediated killing of *C. elegans* is carried out as follows. Brain heart infusion (BHI) agar medium (Difco) is autoclaved and poured into 35 mm tissue culture plates (Fisher). Appropriate antibiotics are added to the medium before pouring to prevent growth of *E. coli*, but allow for the growth of the particular *Enterococcus* strains being tested. A test compound or compound library is also added to the medium. On the tissue culture plate, 2 ml of BHI is inoculated with a single colony of the appropriate strain, grown at 37° C. for four to five hours, and 10 µl of the culture is plated on each plate. The plates are incubated at 37° C. overnight, and then brought to room temperature for two to five hours. Thirty *C. elegans*, at the L4 larval stage, are then placed on the lawn from a plate of OP50 *E. coli*. The plates are incubated at 25° C., and the number of worms found dead compared to the total number of plated worms are then counted at approximately twenty-four hour intervals. Each experimental condition is done in triplicate and repeated at least twice. At an appropriate time interval plates are examined for surviving worms.

Comparative studies between treated and control worms (or larvae) are used to determine the relative efficacy of the test molecule or compound in promoting the host's resistance to the pathogen or inhibiting the virulence of the pathogen. A test compound which effectively stimulates, boosts, enhances, increases, or promotes the host's resistance to the pathogen or which inhibits, inactivates, suppresses, represses, or controls pathogenicity of the pathogen, and does not significantly adversely affect the normal physiology, reproduction, or development of the worms is considered useful in the invention.

Vaccines

The invention also includes vaccine compositions or formulations including the polypeptides or nucleic acid sequences of the invention. For example, the polypeptides of the invention may be used as an antigen for vaccination of a host to produce specific antibodies which protect against invasion or infection or both of bacteria. The invention therefore includes a vaccine formulation which includes an immunogenic recombinant polypeptide of the invention together with a suitable carrier. For example, the invention also includes a vaccine formulation which includes an immunogenic recombinant protein of the invention together with a suitable carrier.

Use

The methods of the invention provide a simple means for identifying Enterococcal virulence factors and compounds capable of either inhibiting pathogenicity or enhancing an organism's resistance capabilities to such pathogens. Accordingly, a chemical entity discovered to have medicinal value using the methods described herein are useful as either drugs, or as information for structural modification of existing anti-pathogenic compounds, e.g., by rational drug design.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections which provide continuous, sustained levels of the drug in the patient. Treatment of human patients or other animals will be carried out using a therapeutically effective amount of an anti-pathogenic agent in a physiologically-acceptable carrier. In the context of treating a bacterial infection a "therapeutically effective amount" or "pharmaceutically effective amount" indicates an amount of an antibacterial agent, e.g., as disclosed for this invention, which has a therapeutic effect. This generally refers to the inhibition, to some extent, of the normal cellular functioning of bacterial cells (e.g., Enterococcal cells) causing or contributing to a bacterial infection.

The dose of antibacterial agent which is useful as a treatment is a "therapeutically effective amount." Thus, as used herein, a therapeutically effective amount means an amount of an antibacterial agent which produces the desired therapeutic effect as judged by clinical trial results, standard animal models of infection, or both. This amount can be routinely determined by one skilled in the art and will vary depending upon several factors, such as the particular bacterial strain involved and the particular antibacterial agent used. This amount can further depend on the patient's height, weight, sex, age, and renal and liver function or other medical history. For these purposes, a therapeutic effect is one which relieves to some extent one or more of the symptoms of the infection and includes curing an infection.

The compositions containing antibacterial agents of virulence factors or genes can be administered for prophylactic or therapeutic treatments, or both. In therapeutic applications, the compositions are administered to a patient already suffering from an infection from bacteria (similarly for infections by other microbes), in an amount sufficient to cure or at least partially arrest the symptoms of the infection. An amount adequate to accomplish this is defined as "therapeutically effective amount." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to, or otherwise at risk of, a particular infection. Such an amount is defined to be a "prophylactically effective amount." In this use, the precise amounts again depend on the patient's state of health, weight, and the like. However, generally, a suitable effective dose will be in the range of 0.1 to 10000 milligrams (mg) per recipient per day, preferably in the range of 10–5000 mg per day. The desired dosage is preferably presented in one, two, three, four, or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 25 mg/kg of patient body weight, between about one to four times per day.

Suitable carriers and their formulation are described, for example, in Remington's Pharmaceutical Sciences by E. W. Martin. The amount of the anti-pathogenic agent to be administered varies depending upon the manner of administration, the age and body weight of the patient, and with the type of disease and extensiveness of the disease. Generally, amounts will be in the range of those used for other agents used in the treatment of other microbial diseases, although in certain instances lower amounts will be needed because of the increased specificity of the compound. A compound is administered at a dosage that inhibits microbial proliferation.

Combination Therapy

The invention further features a method for treating a patient having a bacterial infection, for example, an Enterococcal infection, by administering to the patient an antibacterial combination therapy that includes a compound identified as modulating expression, at the transcriptional, post-transcriptional, translational, or post-translational levels, of a polynucleotide having at least 50% identity to any of the polynucleotides described herein (or that is substantially identical to a polynucleotide described herein) and one or more antibiotics, including, but not limited to, amikacin, aminoglicosides (e.g., tobramycin), aztreonam, carbenicillin, cephalosporines (e.g., ceftazidime or cefipime), chloramphenicol, gentamicin, levofloxacin, meropenem, piperacillin, tazobactam, tetracycline, vancomycin, and quinolones (e.g., ciprofloxacin), simultaneously or within a period of time (e.g., 14 to 21 days) sufficient to inhibit the growth of the bacteria.

Preferably, the compound and antibiotic are administered within fifteen days of each other, more preferably within five or ten days of each other, and most preferably within twenty-four hours of each other or even simultaneously.

In a related aspect, the invention also features a method for treating a patient having an Enterococcal infection. In this method, a patient is administered (a) a first compound (e.g., a compound that modulates the expression a polynucleotide or polypeptide described herein), and (b) one or more antibiotics (such as amikacin, aminoglicosides (e.g., tobramycin), aztreonam, carbenicillin, cephalosporines (e.g., ceftazidime or cefipime), chloramphenicol, gentamicin, levofloxacin, meropenem, piperacillin, tazobactam, tetracycline, and quinolones (e.g., ciprofloxacin)). If desired, the therapy includes administration of two antibiotics according to standard methods known in the art. Such dual antibiotic combinations most preferably include high-dose tobramycin plus meropenem, meropenem plus ciprofloxacin, or tobramycin (4 µg/ml), or cefipime. Other preferred combinations include piperacillin plus tazobactam, or piperacillin plus ciprofloxacin. The antibiotic and compound combination therapy are preferably administered simultaneously or within a period of time sufficient to inhibit the growth of the bacteria.

In any of the foregoing treatments, the compound and antibiotic included in the combination therapy are preferably administered to the patient as part of a pharmaceutical composition that also includes a pharmaceutically acceptable carrier. Preferred modes of administration include intramuscular, intravenous, inhalation, and oral administration, or a combination thereof.

The antibacterial combinations of the invention can also be part of a pharmaceutical kit. Preferably, the first compound (e.g., a compound identified as modulating expression, at the transcriptional, post-transcriptional, translational, or post-translation levels, of a polynucleotide or polypeptide having at least 50% identity to any one of the polynucleotide or polypeptide sequences described herein (or that is substantially identical to any one of the polynucleotides or polypeptides described herein)) and the second compound, an antibiotic, are formulated together or separately and in individual dosage amounts.

Combination therapy may be provided wherever antibiotic treatment is performed: at home, the doctor's office, a clinic, a hospital's outpatient department, or a hospital. Treatment generally begins at a hospital so that the doctor can observe the therapy's effects closely and make any adjustments that are needed. The duration of the combination therapy depends on the kind of bacteria being treated, the age and condition of the patient, the stage and type of the patient's bacterial infection, and how the patient's body responds to the treatment. Drug administration may be performed at different intervals (e.g., daily, weekly, or monthly) and the administration of each agent can be determined individually. Combination therapy may be given in on-and-off cycles that include rest periods so that the patient's body has a chance to build healthy new cells and regain its strength.

All publications and patents mentioned in this specification are herein incorporated by reference to the same extent as if each individual publication or patent was specifically and individually indicated to be incorporated by reference.

What is claimed is:

1. An isolated nucleic acid molecule comprising the sequence of SEQ ID NO:2.

2. A vector or host cell comprising the isolated nucleic acid molecule of claim 1.

* * * * *